(12) United States Patent
Vaillancourt et al.

(10) Patent No.: US 8,415,310 B2
(45) Date of Patent: Apr. 9, 2013

(54) ISOXAZOLINE DERIVATIVES AS ANTIPARASITIC AGENTS

(75) Inventors: Valerie A. Vaillancourt, Portage, MI (US); Nathan Anthony Logan Chubb, Richland, MI (US); Michael Curtis, Portage, MI (US); William Howson, Richland, MI (US); Graham M. Kyne, Portage, MI (US); Sanjay Menon, Kalamazoo, MI (US); Susan M. K. Sheehan, Galesburg, MI (US); Donald J. Skalitzky, Kalamazoo, MI (US); John A. Wendt, Mattawan, MI (US)

(73) Assignee: AH USA 42 LLC, New York, NY (US)

( * ) Notice: Subject to any disclaimer, the term of this patent is extended or adjusted under 35 U.S.C. 154(b) by 117 days.

(21) Appl. No.: 13/197,826

(22) Filed: Aug. 4, 2011

(65) Prior Publication Data

US 2012/0035122 A1   Feb. 9, 2012

Related U.S. Application Data

(60) Provisional application No. 61/371,014, filed on Aug. 5, 2010, provisional application No. 61/445,221, filed on Feb. 22, 2011, provisional application No. 61/451,888, filed on Mar. 11, 2011, provisional application No. 61/486,831, filed on May 17, 2011, provisional application No. 61/490,811, filed on May 27, 2011.

(51) Int. Cl.
| | |
|---|---|
| *A61K 31/422* | (2006.01) |
| *A61K 31/401* | (2006.01) |
| *A61K 31/7048* | (2006.01) |
| *A61K 31/4439* | (2006.01) |
| *A61P 33/00* | (2006.01) |
| *C07D 413/14* | (2006.01) |

(52) U.S. Cl.
USPC .............. 514/30; 514/210.18; 514/210.2; 544/238

(58) Field of Classification Search ............ None
See application file for complete search history.

(56) References Cited

U.S. PATENT DOCUMENTS

| | | | |
|---|---|---|---|
| 7,897,630 | B2 | 3/2011 | Lahm et al. |
| 7,947,715 | B2 | 5/2011 | Mita et al. |
| 2010/0144808 | A1 | 6/2010 | Mita et al. |
| 2010/0179194 | A1 | 7/2010 | Mihara et al. |
| 2010/0249191 | A1 | 9/2010 | Coqueron et al. |
| 2011/0009438 | A1 | 1/2011 | Mita et al. |

FOREIGN PATENT DOCUMENTS

| | | |
|---|---|---|
| WO | 2007/075459 | 7/2007 |
| WO | 2007/105814 | 9/2007 |
| WO | 2008/019760 | 2/2008 |
| WO | 2008/122375 | 10/2008 |
| WO | 2009/035004 | 3/2009 |
| WO | 2009/051956 | 4/2009 |
| WO | 2009/080250 | 7/2009 |
| WO | 2009/005015 | 8/2009 |
| WO | 2010/020521 | 2/2010 |
| WO | 2010/020522 | 2/2010 |
| WO | 2010/070068 | 6/2010 |
| WO | 2010/072602 | 7/2010 |
| WO | 2010/079077 | 7/2010 |

OTHER PUBLICATIONS

PCT International Search Report, PCT/IB2011/053355, mailed Oct. 19, 2011.

*Primary Examiner* — Kamal Saeed
(74) *Attorney, Agent, or Firm* — Paul M. Misiak

(57) ABSTRACT

This invention recites isoxazoline substituted azetidine derivatives of Formula (1)

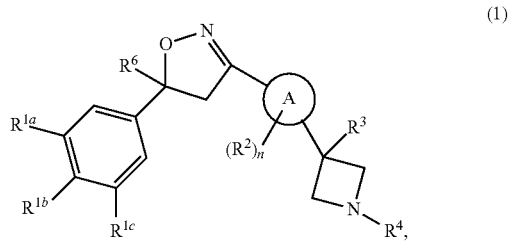

stereoisomers thereof, veterinarily acceptable salts thereof, compositions thereof, and their use as a parasiticide in mammals and birds. $R^{1a}$, $R^{1b}$, $R^{1c}$, $R^2$, $R^3$, $R^4$, $R^6$, and n are as described herein.

19 Claims, No Drawings

ISOXAZOLINE DERIVATIVES AS ANTIPARASITIC AGENTS

CROSS-REFERENCE TO RELATED APPLICATIONS

This application claims benefit of priority from pending U.S. Provisional Application Ser. No. 61/371,014, filed Aug. 5, 2010; U.S. Provisional Application Ser. No. 61/445,221, filed Feb. 22, 2011; U.S. Provisional Application Ser. No. 61/451,888, filed Mar. 11, 2011; U.S. Provisional Application Ser. No. 61/486,831, filed May 17, 2011; and U.S. Provisional Application Ser. No. 61/490,811, filed May 27, 2011.

FIELD OF THE INVENTION

This invention relates to isoxazoline derivatives having parasiticidal activity. The compounds of interest are isoxazoline derivatives substituted with phenyl-azetidines, naphthyl-azetidines, or heteroaryl azetidines. The invention also relates to compositions and methods of use thereof.

BACKGROUND

There is a need for improved antiparasitic agents for use with mammals, and in particular there is a need for improved insecticides and acaricides. Furthermore there is a need for improved topical and oral products with convenient administration and which contain one or more of such antiparasitic agents which can be used to effectively treat ectoparasites, such as insects (e.g., fleas, lice, and flies) and acarids (e.g., mites and ticks). Such products would be particularly useful for the treatment of companion animals, such as cats, dogs, llamas, and horses, and livestock, such as cattle, bison, swine, sheep, and goats.

The compounds currently available for insecticidal and acaricidal treatment of companion animals and livestock do not always demonstrate good activity, good speed of action, or a long duration of action. Most treatments contain hazardous chemicals that can have serious consequences, including lethality from accidental ingestion. Persons applying these agents are generally advised to limit their exposure. Pet collars and tags have been utilized to overcome some problems, but these are susceptible to chewing, ingestion, and subsequent toxicological affects to the mammal. Thus, current treatments achieve varying degrees of success which depend partly on toxicity, method of administration, and efficacy. Currently, some agents are actually becoming ineffective due to parasitic resistance.

Isoxazoline derivatives have been disclosed in the art as having insecticidal and acaricidal activity. For example, WO2007/105814 (US2009/0156643), WO2008/122375, and WO2009/035004 recite certain alkylene linked amides. Further, WO2007/075459 discloses phenyl isoxazolines substituted with 5- to 6-membered heterocycles. However, none of these citations exemplify an isoxazoline substituted phenyl azetidine, nor does the prior art indicate that such compounds would be useful against a spectrum of parasitic species, regardless of morphological lifecycle stages, in animals.

Despite the availability of effective, broad spectrum antiparasitic agents, there remains a need for a safer, convenient, efficacious, and environmentally friendly product that will overcome the ever-present threat of resistance development.

The present invention overcomes one or more of the various disadvantages of, or improves upon, the properties of existing compounds. In particular the present invention develops new isoxazoline substituted phenyl azetidines which demonstrate such properties.

SUMMARY

The present invention provides Formula (1) and Formula (XX) compounds, stereoisomers thereof, pharmaceutical or veterinarily acceptable salts thereof, which act as parasiticides, in particular, ectoparasiticides; therefore may be used to treat acarids and insect infection and infestation in animals. In addition, the invention contemplates the control and prevention endoparasites in animals. The present invention also contemplates the control and treatment of tick borne diseases, for example, Lyme disease, canine and bovine anaplasmosis, canine ehrlichiosis, canine rickettsiosis, canine and bovine babesiosis, epizootic bovine abortion, and theileriosis. Thus, according to the invention, there is provided a compound of Formula (1)

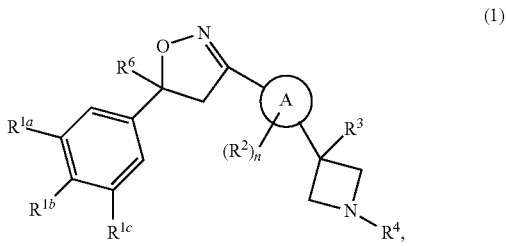

(1)

wherein

A is phenyl, naphthyl, or heteroaryl where said heteroaryl contains 1 to 4 heteroatoms each independently selected from N, O and S;

$R^{1a}$, $R^{1b}$, and $R^{1c}$ are each independently hydrogen, halo, hydroxyl, cyano, nitro, $C_1$-$C_6$alkyl, $C_1$-$C_6$haloalkyl, $C_1$-$C_6$alkoxy, $C_0$-$C_3$alkyl$C_3$-$C_6$cycloalkyl, $C_1$-$C_6$haloalkoxy, —C(O)NH$_2$, —SF$_5$, or —S(O)$_p$R;

$R^2$ is halo, cyano, $C_1$-$C_6$alkyl, $C_1$-$C_6$haloalkyl, nitro, hydroxyl, —C(O)NR$^a$R$^b$, $C_2$-$C_6$alkenyl, $C_2$-$C_6$alkynyl, —S(O)$_p$R, or —OR;

$R^3$ is hydrogen, halo, hydroxyl, cyano, $C_1$-$C_6$alkyl, $C_1$-$C_6$haloalkyl, $C_0$-$C_3$alkyl$C_3$-$C_6$cycloalkyl, —C(O)NH$_2$, nitro, —SC(O)R, —C(O)NR$^a$R$^b$, $C_0$-$C_3$alkylNR$^a$R$^4$, —NR$^a$NR$^b$R$^4$, —NR$^a$OR$^b$, —ONR$^a$R$^b$, N$_3$, —NHR$^4$, —OR, or —S(O)$_p$R;

$R^4$ is hydrogen, $C_1$-$C_6$alkyl, $C_0$-$C_6$alkyl$C_3$-$C_6$cycloalkyl, —C(O)R$^5$, —C(S)R$^5$, —C(O)NR$^a$R$^5$, —C(O)C(O)NR$^a$R$^5$, —S(O)$_p$R$^c$, —S(O)$_2$NR$^a$R$^5$, —C(NR$^7$)R$^5$, —C(NR$^7$)NR$^a$R$^5$, $C_0$-$C_6$alkylphenyl, $C_0$-$C_6$alkylheteroaryl, or $C_0$-$C_6$alkylheterocycle;

$R^5$ is hydrogen, $C_1$-$C_6$alkyl, $C_2$-$C_6$alkenyl, $C_0$-$C_6$alkyl$C_3$-$C_6$cycloalkyl, $C_0$-$C_6$alkylphenyl, $C_0$-$C_6$alkylheteroaryl, or $C_0$-$C_6$alkylheterocycle;

$R^6$ is cyano, $C_1$-$C_6$alkyl, $C_1$-$C_6$haloalkyl, —C(O)NR$^a$R$^b$, $C_2$-$C_6$alkenyl, $C_2$-$C_6$alkynyl, $C_2$-$C_6$haloalkenyl, or $C_2$-$C_6$haloalkynyl;

$R^7$ is hydrogen, $C_1$-$C_6$alkyl, hydroxyl, cyano, nitro, —S(O)$_p$R$^c$, or $C_1$-$C_6$alkoxy;

R is $C_1$-$C_6$alkyl or $C_3$-$C_6$cycloalkyl each optionally substituted by at least one halo;

$R^a$ is hydrogen, $C_1$-$C_6$alkyl, or $C_0$-$C_3$alkyl$C_3$-$C_6$cycloalkyl; wherein the alkyl and alkylcycloalkyl is optionally substituted by cyano or at least one halo substituent;

$R^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each optionally substituted, where chemically possible, with at least one substituent selected from hydroxyl, cyano, halo, or —S(O)$_p$R;

$R^c$ is $C_1$-$C_6$alkyl, $C_1$-$C_6$haloalkyl, $C_1$-$C_6$haloalkyl$C_3$-$C_6$cycloalkyl, $C_0$-$C_3$alkyl$C_3$-$C_6$cycloalkyl, $C_0$-$C_3$alkylphenyl, $C_0$-$C_3$alkylheteroaryl, or $C_0$-$C_3$alkylheterocycle each optionally substituted with at least one substituent selected from cyano, halo, hydroxyl, oxo, $C_1$-$C_6$alkoxy, $C_1$-$C_6$haloalkoxy, $C_1$-$C_6$haloalkyl, —S(O)$_p$R, —SH, —S(O)$_p$NR$^a$R$^b$, —NR$^a$R$^b$, —NR$^a$C(O)R$^b$, —SC(O)R$^b$, —SCN, or —C(O)NR$^a$R$^b$;

each of $R^4$ and $R^5$ $C_1$-$C_6$alkyl or $C_0$-$C_6$alkyl$C_3$-$C_6$cycloalkyl can be optionally and independently substituted by at least one substituent selected from cyano, halo, hydroxyl, oxo, $C_1$-$C_6$alkoxy, $C_1$-$C_6$haloalkoxy, $C_1$-$C_6$haloalkyl, —S(O)$_p$R$^c$, —SH, —S(O)$_p$NR$^a$R$^b$, —NR$^a$R$^b$, —NR$^a$C(O)R$^b$, —SC(O)R$^c$, —SCN, or —C(O)NR$^a$R$^b$; and wherein $R^4$ and $R^5$ $C_0$-$C_6$alkylphenyl, $C_0$-$C_6$alkylheteroaryl, or $C_0$-$C_6$alkylheterocycle moiety can be further optionally substituted with at least one substituent selected from cyano, halo, oxo, =S, =NR$^7$, hydroxyl, $C_1$-$C_6$alkoxy, $C_1$-$C_6$alkyl, $C_1$-$C_6$haloalkyl, —SH, —S(O)$_p$R, and $C_1$-$C_6$haloalkoxy;

n is the integer 0, 1, or 2, and when n is 2, each $R^2$ may be identical or different from each other; and p is the integer 0, 1, or 2;

stereoisomers thereof, and pharmaceutically or veterinarily acceptable salts thereof.

In another aspect of the invention, A is phenyl, naphthyl, pyridinyl, pyrimidinyl, pyrazolyl, imidazolyl pyrrolyl, furanyl, thiophenyl, triazolyl, tetrazolyl, thiazolyl, isoxazolyl, oxazolyl, oxadiazolyl, thiadiazolyl, pyridazinyl, pyrazinyl, benzofuranyl, benzothiophenyl, indolyl, benzimidazolyl, indazolyl, benzotriazolyl, thieno[2,3-c]pyridine, thieno[3,2-b]pyridine, and benzo[1,2,5]thiadiazole. In another aspect of the invention, A is phenyl, naphthyl, pyridinyl, pyrimidinyl, pyrazolyl, triazolyl, tetrazolyl, thiazolyl, isoxazolyl, benzofuranyl, benzothiophenyl, indolyl, and benzo[1,2,5]thiadiazole. In another aspect of the invention, A is phenyl, naphthyl, pyridinyl, pyrazolyl, triazolyl, isoxazolyl, benzofuranyl, and benzo[1,2,5]thiadiazole. In another aspect of the invention, A is phenyl, naphthyl, pyridinyl, pyrazolyl, and benzo[1,2,5]thiadiazole. In another aspect of the invention, A is phenyl, pyridinyl, naphthyl, or benzo[1,2,5]thiadiazole. In another aspect of the invention A is phenyl or pyridinyl. In another aspect of the invention A is phenyl. In another aspect of the invention A is pyridinyl. In another aspect of the invention, A is naphthyl. In yet another aspect of the invention, A is benzo[1,2,5]thiadiazole.

In another aspect of the invention are compounds of Formula (2), (3), (4), (5), and (6)

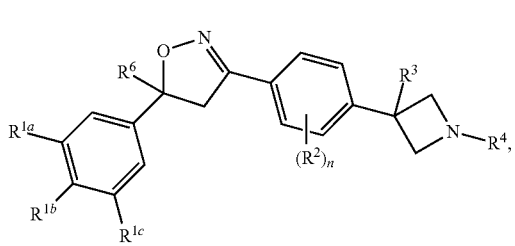
(2)

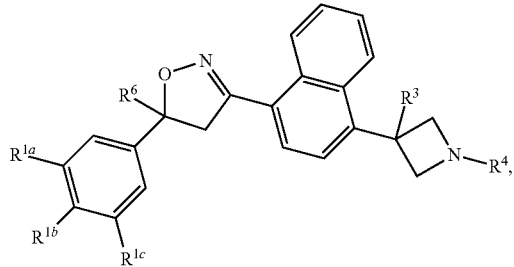
(3)

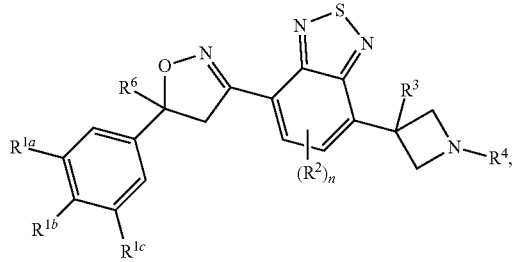
(4)

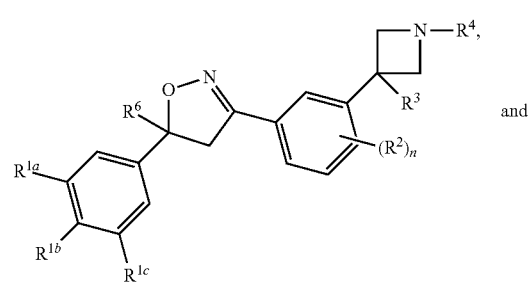
(5)
and

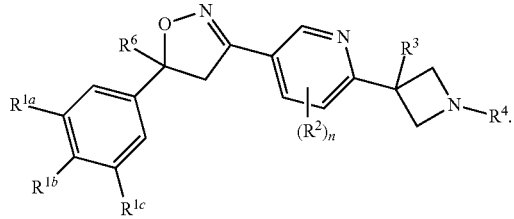
(6)

In yet another aspect of the invention are compounds of Formula (2a), (2b), (2c), (2d), (2e), (2f), (3a), (4a), (4b), (5a), (6a), and (6b).

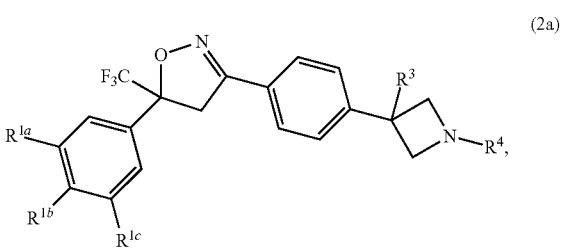
(2a)

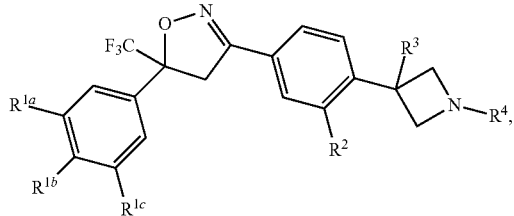
(2b)
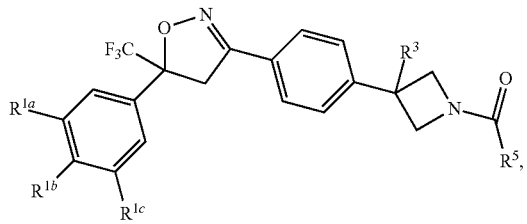
(2c)
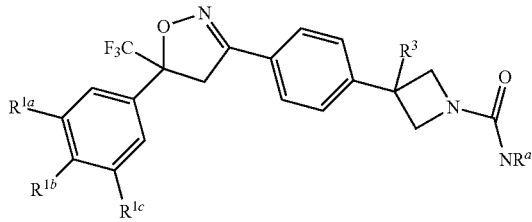
(2d)
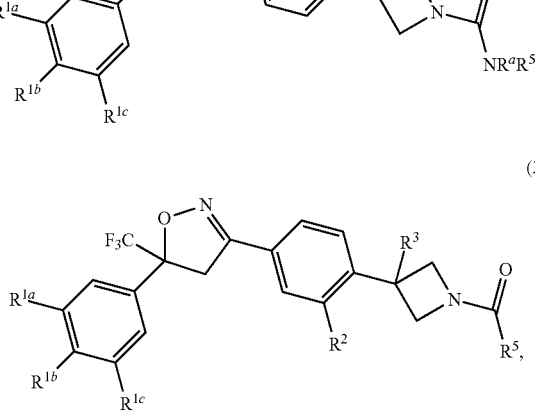
(2e)
(2f)
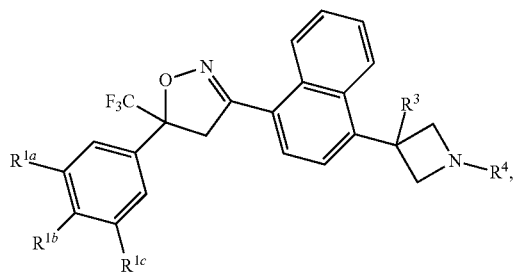
(3a)
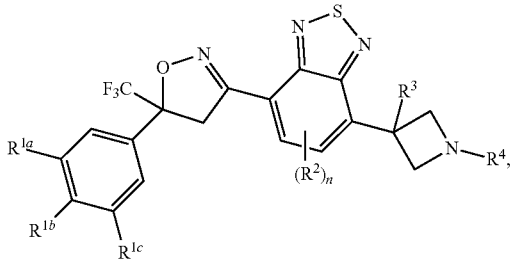
(4a)
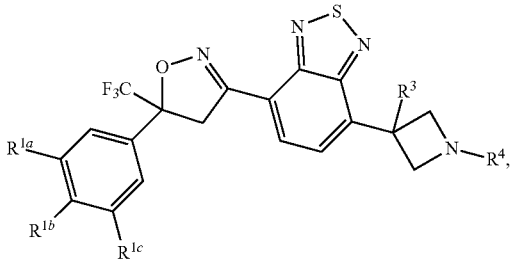
(4b)
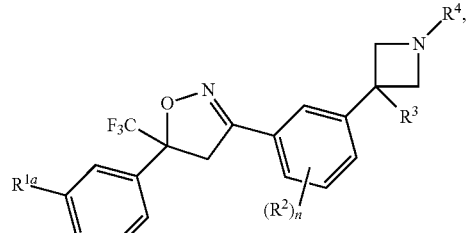
(5a)
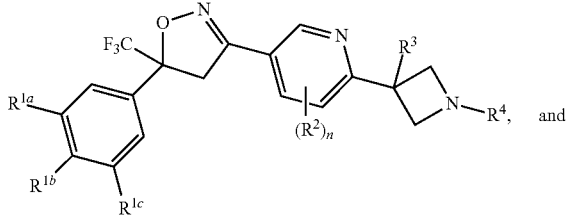
(6a)
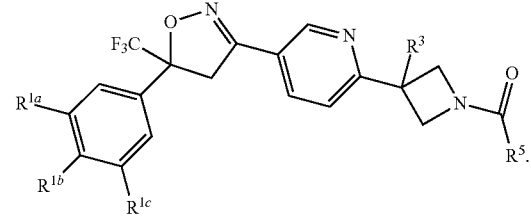
(6b)
In yet another aspect of the invention are compounds of Formula (2a), (2b), (2c), (2d), (6a), and (6b).

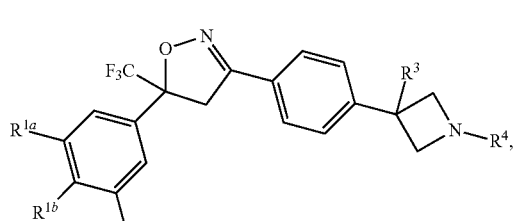
(2a)
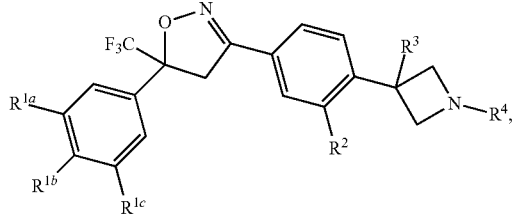
(2b)
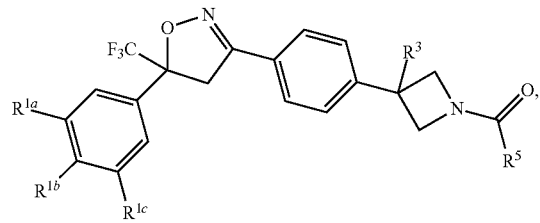
(2c)
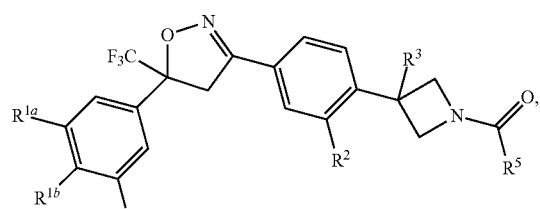
(2d)
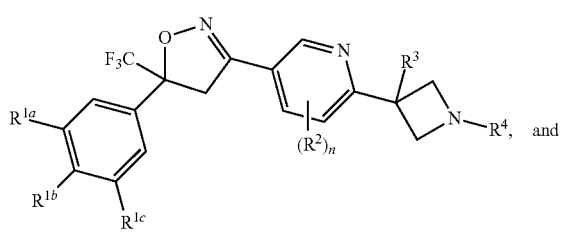
(6a)
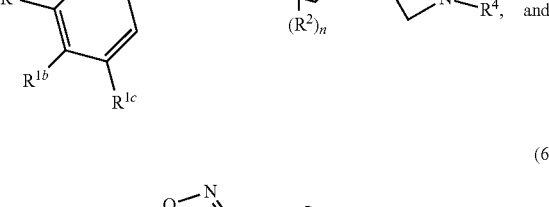
(6b)
In yet another aspect of the invention are compounds of Formula (2a)
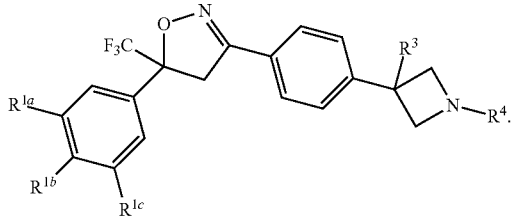
(2a)
In yet another aspect of the invention are compounds of Formula (2b)
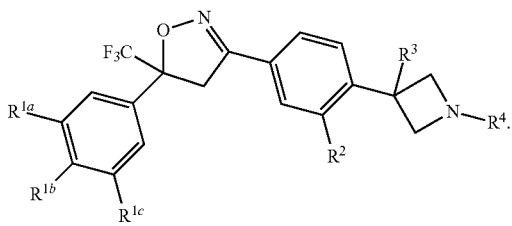
(2b)
In yet another aspect of the invention are compounds of Formula (2c)
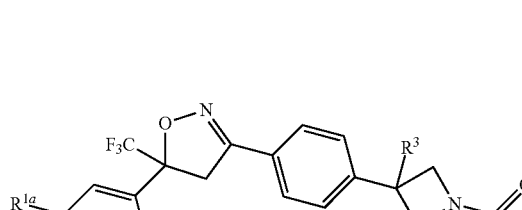
(2c)
In yet another aspect of the invention are compounds of Formula (2d)
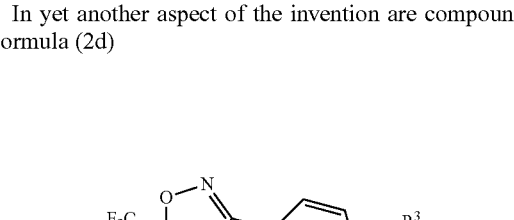
(2d)
In yet another aspect of the invention are compounds of Formula (6a)

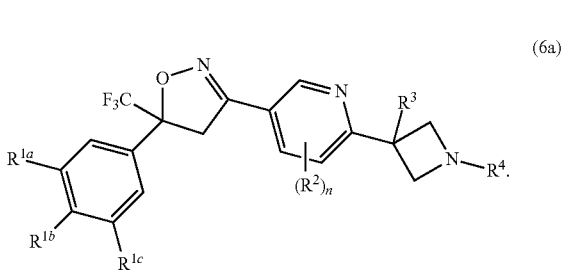

In yet another aspect of the invention are compounds of Formula (6b)

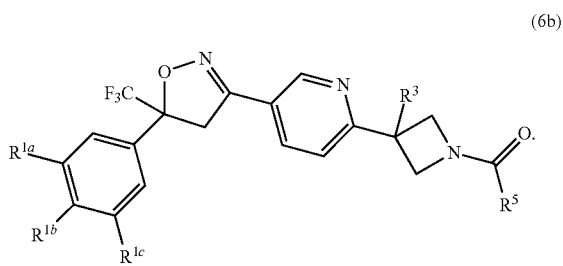

In another aspect of the invention, each of $R^{1a}$, $R^{1b}$, and $R^{1c}$ are independently selected from hydrogen, halo, hydroxyl, cyano, $C_1$-$C_6$alkyl, $C_1$-$C_6$haloalkyl, $C_0$-$C_3$alkyl$C_3$-$C_6$cycloalkyl, —S(O)$_p$R, and —SF$_5$. In yet another aspect of the invention, each of $R^{1a}$, $R^{1b}$, and $R^{1c}$ are independently selected from hydrogen, halo, hydroxyl, cyano, $C_1$-$C_6$ haloalkyl, and $C_0$-$C_3$alkyl$C_3$-$C_6$cycloalkyl. In yet another aspect of the invention, each of $R^{1a}$, $R^{1b}$, and $R^{1c}$ are independently selected from hydrogen, halo, hydroxyl, cyano, and $C_1$-$C_6$ haloalkyl. In yet another aspect of the invention, each of $R^{1a}$, $R^{1b}$, and $R^{1c}$ are independently selected from hydrogen, fluoro, chloro, bromo, cyano, and $C_1$-$C_6$ haloalkyl. In yet another aspect of the invention, each of $R^{1a}$, $R^{1b}$, and $R^{1c}$ are independently selected from hydrogen, fluoro, chloro, bromo, and $C_1$-$C_6$ haloalkyl. In yet another aspect of the invention, each of $R^{1a}$, $R^{1b}$, and $R^{1c}$ are independently selected from hydrogen, fluoro, chloro, bromo, and —CF$_3$. In yet another aspect of the invention, each of $R^{1a}$, $R^{1b}$, and $R^{1c}$ are independently selected from hydrogen, fluoro, chloro, and —CF$_3$.

In yet another aspect of the invention, the integer n of $(R^2)_n$ is 2. When the integer n is 2, then each $R^2$ may be identical or different from each other. In yet another aspect of the invention, the integer n of $(R^2)_n$ is 1. In yet another aspect of the invention, the integer n of $(R^2)_n$ is 0.

In yet another aspect of the invention, $R^2$ is selected from halo, cyano, $C_1$-$C_6$alkyl, $C_1$-$C_6$haloalkyl, hydroxyl, —C(O)NR$^a$R$^b$, $C_2$-$C_6$alkenyl, or —OR. In yet another aspect of the invention, $R^2$ is selected from halo, cyano, $C_1$-$C_6$alkyl, $C_1$-$C_6$haloalkyl, hydroxyl, —C(O)NR$^a$R$^b$, or —OR. In yet another aspect of the invention, $R^2$ is selected from halo, cyano, $C_1$-$C_6$alkyl, —C(O)NR$^a$R$^b$, or hydroxyl. In yet another aspect of the invention, $R^2$ is selected from halo, cyano, —C(O)NR$^a$R$^b$, or hydroxyl. In yet another aspect of the invention, $R^2$ is selected from cyano or —C(O)NR$^a$R$^b$, or hydroxyl. In yet another aspect of the invention, $R^2$ is selected from cyano. In yet another aspect of the invention, $R^2$ is selected from —C(O)NR$^a$R$^b$.

In another aspect of the invention, $R^3$ is hydrogen, halo, hydroxyl, cyano, $C_1$-$C_6$alkyl, $C_1$-$C_6$haloalkyl, $C_0$-$C_3$alkyl$C_3$-$C_6$cycloalkyl, —C(O)NH$_2$, —SC(O)R, —C(O)NR$^a$R$^b$, $C_0$-$C_3$alkylNR$^a$R$^4$, —NR$^a$NR$^b$R$^4$, —NR$^a$OR$^b$, —ONR$^a$R$^b$, N$_3$, —NHR$^4$, —OR, or —S(O)$_p$R. In yet another aspect of the invention, $R^3$ is hydrogen, halo, hydroxyl, cyano, $C_1$-$C_6$alkyl, $C_1$-$C_6$haloalkyl, $C_0$-$C_3$alkyl$C_3$-$C_6$cycloalkyl, —C(O)NH$_2$, —C(O)NR$^a$R$^b$, $C_0$-$C_3$alkylNR$^a$R$^4$, —NR$^a$NR$^b$R$^4$, —NR$^a$OR$^b$, —ONR$^a$R$^b$, N$_3$, —NHR$^4$, or —S(O)$_p$R. In yet another aspect of the invention, $R^3$ is hydrogen, halo, hydroxyl, cyano, $C_1$-$C_6$alkyl, $C_1$-$C_6$haloalkyl, $C_0$-$C_3$alkyl$C_3$-$C_6$cycloalkyl, —C(O)NH$_2$, —C(O)NR$^a$R$^b$, $C_0$-$C_3$alkylNR$^a$R$^4$, —NR$^a$NR$^b$R$^4$, —NHR$^4$, N$_3$, or —S(O)$_p$R. In yet another aspect of the invention, $R^3$ is hydrogen, halo, hydroxyl, cyano, $C_1$-$C_6$alkyl, $C_1$-$C_6$haloalkyl, $C_0$-$C_3$alkyl$C_3$-$C_6$cycloalkyl, —C(O)NH$_2$, —C(O)NR$^a$R$^b$, —NHR$^4$, N$_3$, or —S(O)$_p$R. In yet another aspect of the invention, $R^3$ is hydrogen, halo, hydroxyl, cyano, $C_1$-$C_6$alkyl, $C_1$-$C_6$haloalkyl, $C_0$-$C_3$alkyl$C_3$-$C_6$cycloalkyl, —C(O)NH$_2$, or N$_3$. In yet another aspect of the invention, $R^3$ is hydrogen, halo, hydroxyl, cyano, $C_1$-$C_6$alkyl, $C_1$-$C_6$haloalkyl, or N$_3$. In yet another aspect of the invention, $R^3$ is hydrogen, halo, hydroxyl, cyano, $C_1$-$C_6$alkyl, or N$_3$. In yet another aspect of the invention, $R^3$ is hydrogen, halo, hydroxyl, cyano, or N$_3$. In yet another aspect of the invention, $R^3$ is hydrogen, fluoro, chloro, bromo, N$_3$, hydroxyl, or cyano. In yet another aspect of the invention, $R^3$ is hydrogen, fluoro, chloro, N$_3$, hydroxyl, or cyano. In yet another aspect of the invention, $R^3$ is hydrogen. In yet another aspect of the invention, $R^3$ is fluoro. In yet another aspect of the invention, $R^3$ is chloro. In yet another aspect of the invention, $R^3$ is hydroxyl. In yet another aspect of the invention, $R^3$ is cyano. In yet another aspect of the invention, $R^3$ is N$_3$.

In another aspect of the invention, $R^4$ is $C_1$-$C_6$alkyl, $C_0$-$C_6$alkyl$C_3$-$C_6$cycloalkyl, —C(O)R$^5$, —C(S)R$^5$, —C(O)NR$^a$R$^5$, —C(O)C(O)NR$^a$R$^5$, —S(O)$_p$R$^c$, —S(O)$_2$NR$^a$R$^5$, —C(NR$^7$)R$^5$, —C(NR$^7$)NR$^a$R$^5$, $C_0$-$C_6$alkylheteroaryl, or $C_0$-$C_6$alkylheterocycle; wherein each of $R^4$ and $R^5$ $C_1$-$C_6$alkyl or $C_0$-$C_6$alkyl$C_3$-$C_6$cycloalkyl can be optionally and independently substituted as described herein, and wherein each of $R^a$, $R^c$, $R^4$ and $R^5$ substituents can be optionally and independently substituted as described herein. In yet another aspect of the invention, $R^4$ is —C(O)R$^5$, —C(O)NR$^a$R$^5$, —S(O)$_p$R$^c$, —C(S)R$^5$, —S(O)$_2$NR$^a$R$^5$, —C(NR$^7$)R$^5$, or —C(NR$^7$)NR$^a$R$^5$, and wherein each of $R^a$, $R^c$, and $R^5$ substituents can be optionally and independently substituted as described herein. In yet another aspect of the invention, $R^4$ is —C(O)R$^5$, or —C(O)NR$^a$R$^5$, and wherein each of $R^a$ and $R^5$ substituents can be optionally and independently substituted as described herein.

In yet another aspect of the invention, when $R^4$ is —C(O)R$^5$, then $R^5$ is hydrogen, $C_1$-$C_6$alkyl, $C_0$-$C_6$alkyl$C_3$-$C_6$cycloalkyl, $C_0$-$C_6$alkylphenyl, $C_0$-$C_6$alkylheteroaryl, or $C_0$-$C_6$alkylheterocycle, wherein said $R^5$ $C_1$-$C_6$alkyl or $C_0$-$C_6$alkyl$C_3$-$C_6$cycloalkyl can be optionally and independently substituted by at least one substituent selected from cyano, halo, hydroxyl, oxo, $C_1$-$C_6$alkoxy, $C_1$-$C_6$haloalkoxy, $C_1$-$C_6$haloalkyl, —S(O)$_p$R$^c$, —SH, —S(O)$_p$NR$^a$R$^b$, —NR$^a$R$^b$, —NR$^a$C(O)R$^b$, —SC(O)R$^c$, —SCN, or —C(O)NR$^a$R$^b$, where said $R^5$ $C_0$-$C_6$alkylphenyl, $C_0$-$C_6$alkylheteroaryl, or $C_0$-$C_6$alkylheterocycle moiety can be further optionally substituted with at least one substituent selected from cyano, halo, hydroxyl, $C_1$-$C_0$alkoxy, $C_1$-$C_6$alkyl, $C_1$-$C_6$haloalkyl, —SH, —S(O)$_p$R, and $C_1$-$C_6$haloalkoxy. The $R^a$ and $R^c$ substituents are also optionally substituted with at least one substituent as defined herein.

In yet another aspect of the invention, when $R^4$ is —C(O)R$^5$, then $R^5$ is hydrogen, $C_1$-$C_6$alkyl, $C_0$-$C_6$alkyl$C_3$-$C_6$cycloalkyl, or $C_0$-$C_6$alkylheteroaryl, where said $C_0$-$C_6$alkyl$C_3$-$C_6$cycloalkyl or $C_0$-$C_6$alkylheteroaryl moieties are optionally substituted as defined herein.

In yet another aspect of the invention, when $R^4$ is —C(O)$R^5$, then $R^5$ is methyl, ethyl, propyl, isopropyl, isobutyl, n-butyl, t-butyl, cyclopropyl, cyclobutyl, cyclopentyl, —CH$_2$-cyclopropyl, —CH$_2$-cyclobutyl, —CH$_2$-cyclopentyl, —(CH$_2$)$_2$-cyclopropyl, —(CH$_2$)$_2$-cyclobutyl, —(CH$_2$)$_2$-cyclopentyl, pyrazolyl, —CH$_2$-pyrazolyl, —(CH$_2$)$_2$-pyrazolyl, pyridinyl, —CH$_2$-pyridinyl, —(CH$_2$)$_2$-pyridinyl, wherein the alkyl (for example, methyl, ethyl, and propyl), cycloalkyl (for example, cyclopropyl and cyclobutyl) or alkylcycloalkyl (for example, —CH$_2$-cyclopropyl and —(CH$_2$)$_2$-cyclobutyl) can be optionally and independently substituted as defined herein.

In yet another aspect of the invention, when $R^4$ is —C(O)$R^5$, then $R^5$ is methyl, ethyl, propyl, isopropyl, isobutyl, n-butyl, t-butyl, cyclopropyl, cyclobutyl, cyclopentyl, —CH$_2$-cyclopropyl, —CH$_2$-cyclobutyl, —CH$_2$-cyclopentyl, —(CH$_2$)$_2$-cyclopropyl, —(CH$_2$)$_2$-cyclobutyl, —(CH$_2$)$_2$-cyclopentyl, pyrazolyl, —CH$_2$-pyrazolyl, —(CH$_2$)$_2$-pyrazolyl, pyridinyl, —CH$_2$-pyridinyl, —(CH$_2$)$_2$-pyridinyl, wherein the alkyl (for example, methyl, ethyl, and propyl), cycloalkyl (for example, cyclopropyl and cyclobutyl) or alkylcycloalkyl (for example, —CH$_2$-cyclopropyl and —(CH$_2$)$_2$-cyclobutyl) can be optionally and independently substituted by at least one substituent selected from cyano, halo, hydroxyl, oxo, methoxy, —CF$_3$, ethoxy, —S(O)$_p$R, —SCH$_3$, —SCH$_2$CH$_3$, —NH$_2$, —NHCH$_3$, —NHCH$_2$CH$_3$, —NH(CH$_2$)$_2$CH$_3$, —NHcyclopropyl, —NHcyclobutyl, —NHCH$_2$cyclopropyl, —NHCH$_2$cyclobutyl, —NR$^a$C(O)R$^b$, or —C(O)NH$_2$.

In yet another aspect of the invention, when $R^4$ is —C(O)$R^5$, then $R^5$ is methyl, ethyl, propyl, isopropyl, isobutyl, cyclopropyl, cyclobutyl, cyclopentyl, —CH$_2$-cyclopropyl, —CH$_2$-cyclobutyl, —CH$_2$-cyclopentyl, pyrazolyl, —CH$_2$-pyrazolyl, pyridinyl, —CH$_2$-pyridinyl, wherein the alkyl (for example, methyl, ethyl, and isopropyl), cycloalkyl (for example, cyclopropyl and cyclobutyl) or alkylcycloalkyl (for example, —CH$_2$-cyclopropyl) can be optionally and independently substituted by at least one substituent selected from cyano, halo, hydroxyl, oxo, —CF$_3$, S(O)$_p$R, methoxy, ethoxy, —SCH$_3$, —NH$_2$, —NHCH$_3$, —NHCH$_2$CH$_3$, —NHcyclopropyl, —NHcyclobutyl, —NHC(O)H, or —C(O)NH$_2$.

In yet another aspect of the invention, when $R^4$ is —C(O)$R^5$, then $R^5$ is methyl, ethyl, propyl, isopropyl, isobutyl, cyclopropyl, cyclobutyl, cyclopentyl, —CH$_2$-cyclopropyl, —CH$_2$-cyclobutyl, —CH$_2$-cyclopentyl, pyrazolyl, —CH$_2$-pyrazolyl, pyridinyl, —CH$_2$-pyridinyl, wherein the alkyl (for example, methyl, ethyl, and isopropyl), cycloalkyl (for example, cyclopropyl and cyclobutyl) or alkylcycloalkyl (for example, —CH$_2$cyclopropyl) can be optionally and independently substituted by at least one substituent selected from cyano, halo, hydroxyl, oxo, —CF$_3$, methoxy, —SCH$_3$, S(O)$_p$R, —NH$_2$, —NHCH$_3$, —NHCH$_2$CH$_3$, —NHcyclopropyl, —NHC(O)H, or —C(O)NH$_2$.

In yet another aspect of the invention, when $R^4$ is —C(O)$R^5$, then $R^5$ is oxetane, thiatane, azetidine, tetrahydrofuran, tetrahydrothiophene, pyrrolidine, —CH$_2$-oxetane, —CH$_2$-thiatane, —CH$_2$-azetidine, or —CH$_2$-tetrahydrofuran, each of which are optionally substituted as defined herein. In yet another aspect of the invention, when $R^4$ is —C(O)$R^5$, then $R^5$ is oxetane, thiatane, azetidine, tetrahydrofuran, tetrahydrothiophene, —CH$_2$-oxetane, —CH$_2$-thiatane, or —CH$_2$-azetidine, each of which are optionally substituted as defined herein. In yet another aspect of the invention, when $R^4$ is —C(O)$R^5$, then $R^5$ is oxetane, thiatane, azetidine, —CH$_2$-oxetane, —CH$_2$-thiatane, or —CH$_2$-azetidine, each of which are optionally substituted as defined herein. In yet another aspect of the invention, when $R^4$ is —C(O)$R^5$, then $R^5$ is oxetane, thiatane, or azetidine, each of which are optionally substituted as defined herein. In yet another aspect of the invention, when $R^4$ is —C(O)$R^5$, then $R^5$ is —CH$_2$-oxetane, —CH$_2$-thiatane, or —CH$_2$-azetidine, each of which are optionally substituted as defined herein.

In yet another aspect of the invention, when $R^4$ is —C(O)$R^5$, then $R^5$ is pyrazole, imidazole, isoxazole, oxazole, isothiazole, thiazole, triazole, pyridine, pyridazine, pyrazine, or pyrimidine, each of the which are optionally substituted as defined herein.

In yet another aspect of the invention, when $R^4$ is —C(O)$R^5$, then $R^5$ is $C_1$-$C_6$alkyl, $C_2$-$C_6$alkenyl, or $C_0$-$C_6$alkyl$C_3$-$C_6$cycloalkyl, wherein each of $C_1$-$C_6$alkyl or $C_0$-$C_6$alkyl$C_3$-$C_6$cycloalkyl is optionally substituted with at least one substituent selected from cyano, halo, hydroxyl, —S(O)$_p$R$^c$, $C_1$-$C_6$alkoxy, —S(O)$_p$NR$^a$R$^b$, or —SC(O)R$^c$; pyrazole, pyridine, oxazole, pyridazine, triazole, azetidine, thiatane, wherein each heterocycle and heteroaryl moiety are optionally substituted further with at least one substituent selected from fluoro, hydroxyl, methyl, and oxo; where p, R$^a$, R$^b$, and R$^c$ are as defined herein.

In yet another aspect of the invention, when $R^4$ is —C(O)NR$^a$R$^5$, then R$^a$ is hydrogen, methyl, ethyl, propyl, isopropyl, cyclopropyl, cyclobutyl, cyclopentyl, —CH$_2$-cyclopropyl, —CH$_2$-cyclobutyl, —CH$_2$-cyclopentyl, —(CH$_2$)$_2$-cyclopropyl, —(CH$_2$)$_2$-cyclobutyl, or —(CH$_2$)$_2$-cyclopentyl; wherein the alkyl (for example methyl and propyl), cycloalkyl (for example, cyclopropyl and cyclopentyl), or the alkylcycloalkyl (for example, —CH$_2$-cyclopropyl, —CH$_2$-cyclopentyl, and —(CH$_2$)$_2$cyclobutyl) are optionally substituted by cyano or at least one halo substituent; and R$^5$ is as defined herein.

In yet another aspect of the invention, when $R^4$ is —C(O)NR$^a$R$^5$, then R$^a$ is hydrogen, methyl, ethyl, propyl, isopropyl, cyclopropyl, cyclobutyl, cyclopentyl, —CH$_2$-cyclopropyl, —CH$_2$-cyclobutyl, —CH$_2$-cyclopentyl; wherein the alkyl (for example methyl and propyl), cycloalkyl (for example, cyclopropyl and cyclopentyl), or the alkylcycloalkyl (for example, —CH$_2$-cyclopropyl and —CH$_2$-cyclopentyl) are optionally substituted by cyano or at least one halo substituent; and R$^5$ is as defined herein.

In yet another aspect of the invention, when $R^4$ is —C(O)NR$^a$R$^5$, then R$^a$ is hydrogen or methyl and R$^5$ is selected from hydrogen, methyl, ethyl, propyl, cyclopropyl, and $C_0$-$C_6$alkylheterocycle, wherein the alkyl and alkylheterocycle moiety are each optionally substituted as described herein.

In yet another aspect of the invention, when $R^4$ is —S(O)$_p$R$^c$, the integer p is 2, and R$^c$ is as defined herein, and said R$^c$ substituent is optionally substituted with at least one substituent as defined herein. In yet another aspect of the invention, when $R^4$ is —S(O)$_p$R$^c$, the integer p is 2, R$^c$ is $C_1$-$C_6$alkyl optionally substituted with at least one substituent as defined herein. In yet another aspect of the invention, when $R^4$ is —S(O)$_p$R$^c$, the integer p is 2, R$^c$ is $C_1$-$C_6$alkyl optionally substituted with at least one substituent selected from cyano or halo. In yet another aspect of the invention, when $R^4$ is —S(O)$_p$R$^c$, the integer p is 2, and R$^c$ is $C_1$-$C_6$alkyl. In yet another aspect of the invention, when $R^4$ is —S(O)$_p$R$^c$, the integer p is 2, and R$^c$ is methyl, ethyl, propyl, or isopropyl. In yet another aspect of the invention, when $R^4$ is —S(O)$_p$R$^c$, the integer p is 2, and R$^c$ is methyl or ethyl.

In yet another aspect of the invention, $R^6$ is cyano, $C_1$-$C_6$alkyl, $C_1$-$C_6$haloalkyl, or —C(O)NH$_2$. In yet another aspect of the invention, $R^6$ is cyano, $C_1$-$C_6$alkyl, or $C_1$-$C_6$haloalkyl. In yet another aspect of the invention, $R^6$ is cyano, methyl, ethyl, or $C_1$-$C_6$haloalkyl. In yet another aspect of the invention, $R^6$ is cyano, methyl, or $C_1$-$C_6$haloalkyl. In yet another aspect of the invention, $R^6$ is cyano or $C_1$-$C_6$haloalkyl. In yet another aspect of the invention, $R^6$ is $C_1$-$C_6$haloalkyl. In yet another aspect of the invention, $R^6$ is —$CF_3$, —$CHF_2$, —$CH_2F$, and —$CF_2Cl$. In yet another aspect of the invention, $R^6$ is —$CF_3$, —$CHF_2$, and —$CH_2F$. In yet another aspect of the invention, $R^6$ is —$CF_3$.

In yet another aspect of the invention, R is methyl, ethyl, propyl, isopropyl, cyclopropyl, cyclobutyl, or cyclopentyl. In yet another aspect of the invention, R is methyl, ethyl, isopropyl, cyclopropyl, or cyclobutyl.

In yet another aspect of the invention, $R^a$ is hydrogen, methyl, ethyl, propyl, isopropyl, or isobutyl, each alkyl moiety is optionally substituted as defined herein. In yet another aspect of the invention, $R^a$ is hydrogen, methyl, ethyl, propyl, or isopropyl, each alkyl moiety is optionally substituted as defined herein. In yet another aspect of the invention, $R^a$ is hydrogen, methyl, or ethyl, each alkyl is optionally substituted as defined herein.

In yet another aspect of the invention, $R^a$ is hydrogen, methyl, ethyl, propyl, isopropyl, isobutyl, cyclopropyl, cyclobutyl, cyclopentyl, —$CH_2$-cyclopropyl, or —$CH_2$-cyclobutyl, each alkyl, cycloalkyl, and alkylcycloalkyl moiety is optionally substituted as defined herein. In yet another aspect of the invention, $R^a$ is hydrogen, methyl, ethyl, propyl, isopropyl, cyclopropyl, cyclobutyl, —$CH_2$-cyclopropyl, or —$CH_2$-cyclobutyl, each alkyl, cycloalkyl, and alkylcycloalkyl moiety is optionally substituted as defined herein. In yet another aspect of the invention, $R^a$ is hydrogen, methyl, ethyl, isopropyl, cyclopropyl, cyclobutyl, —$CH_2$-cyclopropyl, or —$CH_2$-cyclobutyl, each alkyl, cycloalkyl, and alkylcycloalkyl moiety is optionally substituted as defined herein.

In another aspect of the invention, $R^b$ is hydrogen, $C_1$-$C_6$alkyl, $C_3$-$C_6$cycloalkyl, $C_0$-$C_3$alkylphenyl, or $C_0$-$C_3$alkylheteroaryl. In yet another aspect of the invention, $R^b$ is hydrogen, $C_1$-$C_6$alkyl, $C_3$-$C_6$cycloalkyl, or $C_0$-$C_3$alkylheteroaryl. In yet another aspect of the invention, $R^b$ is hydrogen, $C_1$-$C_6$alkyl, or $C_3$-$C_6$cycloalkyl. In yet another aspect of the invention, $R^b$ is hydrogen, methyl, ethyl, isopropyl, propyl, isobutyl, cyclopropyl, or cyclobutyl.

In another aspect of the invention, are Formula (1) compounds selected from:

1-(3-fluoro-3-(4-(5-(3,4,5-trichlorophenyl)-5-(trifluoromethyl)-4,5-dihydroisoxazol-3-yl)phenyl)azetidin-1-yl)ethanone;

cyclopropyl(3-fluoro-3-(4-(5-(3,4,5-trichlorophenyl)-5-(trifluoromethyl)-4,5-dihydroisoxazol-3-yl)phenyl)azetidin-1-yl)methanone;

3-fluoro-N-methyl-3-(4-(5-(3,4,5-trichlorophenyl)-5-(trifluoromethyl)-4,5-dihydroisoxazol-3-yl)phenyl)azetidine-1-carboxamide;

N-ethyl-3-fluoro-3-(4-(5-(3,4,5-trichlorophenyl)-5-(trifluoromethyl)-4,5-dihydroisoxazol-3-yl)phenyl)azetidine-1-carboxamide;

N-cyclopropyl-3-fluoro-3-(4-(5-(3,4,5-trichlorophenyl)-5-(trifluoromethyl)-4,5-dihydroisoxazol-3-yl)phenyl)azetidine-1-carboxamide;

cyclopropyl(3-(4-(5-(3,5-dichlorophenyl)-5-(trifluoromethyl)-4,5-dihydroisoxazol-3-yl)phenyl)-3-fluoroazetidin-1-yl)methanone;

1-(3-(4-(5-(3,5-dichlorophenyl)-5-(trifluoromethyl)-4,5-dihydroisoxazol-3-yl)phenyl)-3-fluoroazetidin-1-yl)-2-methylpropan-1-one;

3-(4-(5-(3,5-dichlorophenyl)-5-(trifluoromethyl)-4,5-dihydroisoxazol-3-yl)phenyl)-3-fluoro-N-methylazetidine-1-carboxamide;

3-(4-(5-(3,5-dichlorophenyl)-5-(trifluoromethyl)-4,5-dihydroisoxazol-3-yl)phenyl)-N-ethyl-3-fluoroazetidine-1-carboxamide;

N-cyclopropyl-3-(4-(5-(3,5-dichlorophenyl)-5-(trifluoromethyl)-4,5-dihydroisoxazol-3-yl)phenyl)-3-fluoroazetidine-1-carboxamide;

1-(3-(4-(5-(3,5-dichloro-4-fluorophenyl)-5-(trifluoromethyl)-4,5-dihydroisoxazol-3-yl)phenyl)-3-fluoroazetidin-1-yl)propan-1-one;

1-(3-(4-(5-(3,5-dichloro-4-fluorophenyl)-5-(trifluoromethyl)-4,5-dihydroisoxazol-3-yl)phenyl)-3-fluoroazetidin-1-yl)butan-1-one;

2-cyclopropyl-1-(3-(4-(5-(3,5-dichloro-4-fluorophenyl)-5-(trifluoromethyl)-4,5-dihydroisoxazol-3-yl)phenyl)-3-fluoroazetidin-1-yl)ethanone;

3-(3-(4-(5-(3,5-dichloro-4-fluorophenyl)-5-(trifluoromethyl)-4,5-dihydroisoxazol-3-yl)phenyl)-3-fluoroazetidin-1-yl)-3-oxopropanenitrile;

1-(3-(4-(5-(3,5-dichloro-4-fluorophenyl)-5-(trifluoromethyl)-4,5-dihydroisoxazol-3-yl)phenyl)-3-fluoroazetidin-1-yl)-2-(methylthio)ethanone;

1-(3-(4-(5-(3,5-dichloro-4-fluorophenyl)-5-(trifluoromethyl)-4,5-dihydroisoxazol-3-yl)phenyl)-3-fluoroazetidin-1-yl)-2-methoxyethanone;

cyclobutyl(3-(4-(5-(3,5-dichloro-4-fluorophenyl)-5-(trifluoromethyl)-4,5-dihydroisoxazol-3-yl)phenyl)-3-fluoroazetidin-1-yl)methanone;

1-(3-(4-(5-(3,5-dichloro-4-fluorophenyl)-5-(trifluoromethyl)-4,5-dihydroisoxazol-3-yl)phenyl)-3-fluoroazetidin-1-yl)-2-methylpropan-1-one;

1-(3-(4-(5-(3,5-dichloro-4-fluorophenyl)-5-(trifluoromethyl)-4,5-dihydroisoxazol-3-yl)phenyl)-3-fluoroazetidin-1-yl)-3,3,3-trifluoropropan-1-one;

N-cyclopropyl-3-(4-(5-(3,5-dichloro-4-fluorophenyl)-5-(trifluoromethyl)-4,5-dihydroisoxazol-3-yl)phenyl)-3-fluoroazetidine-1-carboxamide;

3-(4-(5-(3,5-dichloro-4-fluorophenyl)-5-(trifluoromethyl)-4,5-dihydroisoxazol-3-yl)phenyl)-3-fluoro-N-methylazetidine-1-carboxamide;

3-(4-(5-(3,5-dichloro-4-fluorophenyl)-5-(trifluoromethyl)-4,5-dihydroisoxazol-3-yl)phenyl)-N-ethyl-3-fluoroazetidine-1-carboxamide;

3-(4-(5-(3,5-dichloro-4-fluorophenyl)-5-(trifluoromethyl)-4,5-dihydroisoxazol-3-yl)phenyl)-3-fluoroazetidine-1-carboxamide;

cyclopropyl(3-(4-(5-(3,4-dichloro-5-(trifluoromethyl)phenyl)-5-(trifluoromethyl)-4,5-dihydroisoxazol-3-yl)phenyl)-3-hydroxyazetidin-1-yl)methanone;

cyclobutyl(3-(4-(5-(3,4-dichloro-5-(trifluoromethyl)phenyl)-5-(trifluoromethyl)-4,5-dihydroisoxazol-3-yl)phenyl)-3-hydroxyazetidin-1-yl)methanone;

3-(4-(5-(3,4-dichloro-5-(trifluoromethyl)phenyl)-5-(trifluoromethyl)-4,5-dihydroisoxazol-3-yl)phenyl)-3-fluoro-N-methylazetidine-1-carboxamide;

3-(4-(5-(3,4-dichloro-5-(trifluoromethyl)phenyl)-5-(trifluoromethyl)-4,5-dihydroisoxazol-3-yl)phenyl)-N-ethyl-3-fluoroazetidine-1-carboxamide;

N-cyclopropyl-3-(4-(5-(3,4-dichloro-5-(trifluoromethyl)phenyl)-5-(trifluoromethyl)-4,5-dihydroisoxazol-3-yl)phenyl)-3-fluoroazetidine-1-carboxamide;

3-(4-(5-(3,4-dichloro-5-(trifluoromethyl)phenyl)-5-(trifluoromethyl)-4,5-dihydroisoxazol-3-yl)phenyl)-N-ethyl-3-hydroxyazetidine-1-carboxamide;

N-cyclopropyl-3-(4-(5-(3,4-dichloro-5-(trifluoromethyl)phenyl)-5-(trifluoromethyl)-4,5-dihydroisoxazol-3-yl)phenyl)-3-hydroxyazetidine-1-carboxamide;

3-(4-(5-(3,5-bis(trifluoromethyl)phenyl)-5-(trifluoromethyl)-4,5-dihydroisoxazol-3-yl)phenyl)-3-fluoro-N-methylazetidine-1-carboxamide;

3-(4-(5-(3,5-bis(trifluoromethyl)phenyl)-5-(trifluoromethyl)-4,5-dihydroisoxazol-3-yl)phenyl)-N-ethyl-3-fluoroazetidine-1-carboxamide;

3-(4-(5-(3,5-bis(trifluoromethyl)phenyl)-5-(trifluoromethyl)-4,5-dihydroisoxazol-3-yl)phenyl)-N-cyclopropyl-3-fluoroazetidine-1-carboxamide;

3-(4-(5-(3,5-bis(trifluoromethyl)phenyl)-5-(trifluoromethyl)-4,5-dihydroisoxazol-3-yl)phenyl)-N-cyclopropyl-3-hydroxyazetidine-1-carboxamide;

3-(4-(5-(3-chloro-5-(trifluoromethyl)phenyl)-5-(trifluoromethyl)-4,5-dihydroisoxazol-3-yl)phenyl)-N-ethyl-3-hydroxyazetidine-1-carboxamide;

3-(4-(5-(3-chloro-5-(trifluoromethyl)phenyl)-5-(trifluoromethyl)-4,5-dihydroisoxazol-3-yl)phenyl)-N-ethyl-3-fluoroazetidine-1-carboxamide;

3-(4-(5-(3-chloro-5-(trifluoromethyl)phenyl)-5-(trifluoromethyl)-4,5-dihydroisoxazol-3-yl)phenyl)-N-cyclopropyl-3-fluoroazetidine-1-carboxamide;

3-(4-(5-(3-chloro-5-(trifluoromethyl)phenyl)-5-(trifluoromethyl)-4,5-dihydroisoxazol-3-yl)phenyl)-3-fluoro-N-methylazetidine-1-carboxamide;

1-(3-(4-(5-(3,5-Dichlorophenyl)-5-(trifluoromethyl)-4,5-dihydroisoxazol-3-yl)phenyl)-3-fluoroazetidin-1-yl)ethanone;

cyclopropyl(3-(4-(5-(3,5-dichloro-4-fluorophenyl)-5-(trifluoromethyl)-4,5-dihydroisoxazol-3-yl)phenyl)-3-fluoroazetidin-1-yl)methanone;

2-Cyclopropyl-1-(3-(4-(5-(3,5-dichlorophenyl)-5-(trifluoromethyl)-4,5-dihydroisoxazol-3-yl)phenyl)-3-fluoroazetidin-1-yl)ethanone;

3-(3-(4-(5-(3,5-Dichlorophenyl)-5-(trifluoromethyl)-4,5-dihydroisoxazol-3-yl)phenyl)-3-fluoroazetidin-1-yl)-3-oxopropanenitrile;

1-(3-(4-(5-(3,5-Dichlorophenyl)-5-(trifluoromethyl)-4,5-dihydroisoxazol-3-yl)phenyl)-3-fluoroazetidin-1-yl)-3,3,3-trifluoropropan-1-one;

1-(3-(4-(5-(3,5-Dichlorophenyl)-5-(trifluoromethyl)-4,5-dihydroisoxazol-3-yl)phenyl)-3-fluoroazetidin-1-yl)-2-methoxyethanone;

1-(3-(4-(5-(3,5-Dichlorophenyl)-5-(trifluoromethyl)-4,5-dihydroisoxazol-3-yl)phenyl)-3-fluoroazetidin-1-yl)propan-1-one;

1-(3-(4-(5-(3,5-Dichlorophenyl)-5-(trifluoromethyl)-4,5-dihydroisoxazol-3-yl)phenyl)-3-fluoroazetidin-1-yl)butan-1-one;

5-[3,5-bis(trifluoromethyl)phenyl]-3-{4-[1-(cyclobutylcarbonyl)-3-fluoroazetidin-3-yl]phenyl}-5-(trifluoromethyl)-4,5-dihydroisoxazole;

5-[3,5-bis(trifluoromethyl)phenyl]-3-{4-[1-(cyclopropylcarbonyl)-3-fluoroazetidin-3-yl]phenyl}-5-(trifluoromethyl)-4,5-dihydroisoxazole;

5-[3,5-bis(trifluoromethyl)phenyl]-3-[4-(3-fluoro-1-isobutyrylazetidin-3-yl)phenyl]-5-(trifluoromethyl)-4,5-dihydroisoxazole;

3-[4-(1-butyryl-3-fluoroazetidin-3-yl)phenyl]-5-[3-chloro-5-(trifluoromethyl)phenyl]-5-(trifluoromethyl)-4,5-dihydroisoxazole;

5-[3-chloro-5-(trifluoromethyl)phenyl]-3-[4-(3-fluoro-1-propionylazetidin-3-yl)phenyl]-5-(trifluoromethyl)-4,5-dihydroisoxazole;

3-[4-(1-acetyl-3-fluoroazetidin-3-yl)phenyl]-5-[3-chloro-5-(trifluoromethyl)phenyl]-5-(trifluoromethyl)-4,5-dihydroisoxazole;

3-[3-(4-{5-[3-chloro-5-(trifluoromethyl)phenyl]-5-(trifluoromethyl)-4,5-dihydroisoxazol-3-yl}phenyl)-3-fluoroazetidin-1-yl]-3-oxopropanenitrile;

1-[(3-{4-[5-(3,5-dichlorophenyl)-5-(trifluoromethyl)-4,5-dihydroisoxazol-3-yl]phenyl}-3-fluoroazetidin-1-yl)carbonyl]cyclopropanol;

1-[(3-{4-[5-(3,5-dichloro-4-fluorophenyl)-5-(trifluoromethyl)-4,5-dihydroisoxazol-3-yl]phenyl}-3-fluoroazetidin-1-yl)carbonyl]cyclopropanol;

3-{-4-[3-fluoro-1-(methoxyacetyl)azetidin-3-yl]phenyl}-5-(3,4,5-trichlorophenyl)-5-(trifluoromethyl)-4,5-dihydroisoxazole;

3-(4-{5-[3,4-dichloro-5-(trifluoromethyl)phenyl]-5-(trifluoromethyl)-4,5-dihydroisoxazol-3-yl}phenyl)-1-isobutyrylazetidin-3-ol;

1-butyryl-3-(4-{5-[3,4-dichloro-5-(trifluoromethyl)phenyl]-5-(trifluoromethyl)-4,5-dihydroisoxazol-3-yl}phenyl)azetidin-3-ol;

5-[3,5-bis(trifluoromethyl)phenyl]-3-{4-[1-(cyclopropylacetyl)-3-fluoroazetidin-3-yl]phenyl}-5-(trifluoromethyl)-4,5-dihydroisoxazole;

2-[3-(4-{5-[3,5-bis(trifluoromethyl)phenyl]-5-(trifluoromethyl)-4,5-dihydroisoxazol-3-yl}phenyl)-3-fluoroazetidin-1-yl]-2-oxoethanol;

5-[3-chloro-5-(trifluoromethyl)phenyl]-3-(4-{3-fluoro-1-[(methylthio)acetyl]azetidin-3-yl}phenyl)-5-(trifluoromethyl)-4,5-dihydroisoxazole;

5-[3-chloro-5-(trifluoromethyl)phenyl]-3-{4-[1-(cyclobutylcarbonyl)-3-fluoroazetidin-3-yl]phenyl}-5-(trifluoromethyl)-4,5-dihydroisoxazole;

3-[3-(4-{5-[3,4-dichloro-5-(trifluoromethyl)phenyl]-5-(trifluoromethyl)-4,5-dihydroisoxazol-3-yl}phenyl)-3-fluoroazetidin-1-yl]-3-oxopropanamide;

3-[3-(4-{5-[3,4-dichloro-5-(trifluoromethyl)phenyl]-5-(trifluoromethyl)-4,5-dihydroisoxazol-3-yl}phenyl)-3-fluoroazetidin-1-yl]-3-oxopropanamide;

1-[(3-fluoro-3-{4-[5-(3,4,5-trichlorophenyl)-5-(trifluoromethyl)-4,5-dihydroisoxazol-3-yl]phenyl}azetidin-1-yl)carbonyl]cyclopropanol;

5-(3,5-dichlorophenyl)-3-{-4-[3-fluoro-1-(3-methylbutanoyl)azetidin-3-yl]phenyl}-5-(trifluoromethyl)-4,5-dihydroisoxazole;

3-(4-{3-fluoro-1-[(methylthio)acetyl]azetidin-3-yl}phenyl)-5-(3,4,5-trichlorophenyl)-5-(trifluoromethyl)-4,5-dihydroisoxazole;

3-{4-[5-(3,5-dichloro-4-fluorophenyl)-5-(trifluoromethyl)-4,5-dihydroisoxazol-3-yl]phenyl}-1-propionylazetidin-3-ol;

5-[3-chloro-5-(trifluoromethyl)phenyl]-3-{4-[1-(cyclopropylcarbonyl)-3-fluoroazetidin-3-yl]phenyl}-5-(trifluoromethyl)-4,5-dihydroisoxazole;

5-(3,5-dichloro-4-fluorophenyl)-3-{-4-[3-fluoro-1-(1H-pyrazol-3-ylcarbonyl)azetidin-3-yl]phenyl}-5-(trifluoromethyl)-4,5-dihydroisoxazole;

4-{2-[3-(4-{5-[3,5-bis(trifluoromethyl)phenyl]-5-(trifluoromethyl)-4,5-dihydroisoxazol-3-yl}phenyl)-3-fluoroazetidin-1-yl]-2-oxoethyl}pyridine;

5-[3-chloro-5-(trifluoromethyl)phenyl]-3-{4-[1-(cyclopropylacetyl)-3-fluoroazetidin-3-yl]phenyl}-5-(trifluoromethyl)-4,5-dihydroisoxazole;

5-[3,4-dichloro-5-(trifluoromethyl)phenyl]-3-[4-(3-fluoro-1-propionylazetidin-3-yl)phenyl]-5-(trifluoromethyl)-4,5-dihydroisoxazole;

3-{4-[1-(cyclopropylcarbonyl)-3-fluoroazetidin-3-yl]phenyl}-5-[3,4-dichloro-5-(trifluoromethyl)phenyl]-5-(trifluoromethyl)-4,5-dihydroisoxazole;

3-[4-(1-acetyl-3-fluoroazetidin-3-yl)phenyl]-5-[3,4-dichloro-5-(trifluoromethyl)phenyl]-5-(trifluoromethyl)-4,5-dihydroisoxazole;

5-[3,4-dichloro-5-(trifluoromethyl)phenyl]-3-[4-(3-fluoro-1-isobutyrylazetidin-3-yl)phenyl]-5-(trifluoromethyl)-4,5-dihydroisoxazole;

3-[3-(4-{5-[3,4-dichloro-5-(trifluoromethyl)phenyl]-5-(trifluoromethyl)-4,5-dihydroisoxazol-3-yl}phenyl)-3-fluoroazetidin-1-yl]-3-oxopropanenitrile;

4-[(3-fluoro-3-{4-[5-(3,4,5-trichlorophenyl)-5-(trifluoromethyl)-4,5-dihydroisoxazol-3-yl]phenyl}azetidin-1-yl)carbonyl]pyridine;

5-[3,5-bis(trifluoromethyl)phenyl]-3-[4-(3-fluoro-1-propionylazetidin-3-yl)phenyl]-5-(trifluoromethyl)-4,5-dihydroisoxazole;

3-{4-[1-(cyclopentylcarbonyl)-3-fluoroazetidin-3-yl]phenyl}-5-[3,4-dichloro-5-(trifluoromethyl)phenyl]-5-(trifluoromethyl)-4,5-dihydroisoxazole;

5-[3,4-dichloro-5-(trifluoromethyl)phenyl]-3-(4-{3-fluoro-1-[(methylthio)acetyl]azetidin-3-yl}phenyl)-5-(trifluoromethyl)-4,5-dihydroisoxazole;

1-(cyclopropylcarbonyl)-3-{4-[5-(3,5-dichloro-4-fluorophenyl)-5-(trifluoromethyl)-4,5-dihydroisoxazol-3-yl]phenyl}azetidin-3-ol;

(3-(2-bromo-4-(5-(3,4,5-trichlorophenyl)-5-(trifluoromethyl)-4,5-dihydroisoxazol-3-yl)phenyl)-3-fluoroazetidin-1-yl)(cyclopropyl)methanone;

2-(1-(cyclopropanecarbonyl)-3-fluoroazetidin-3-yl)-5-(5-(3,4,5-trichlorophenyl)-5-(trifluoromethyl)-4,5-dihydroisoxazol-3-yl)benzonitrile;

5-[3-chloro-5-(trifluoromethyl)phenyl]-3-(4-(3-fluoro-1-(methylsulfonyl)azetidin-3-yl)phenyl)-5-(trifluoromethyl)-4,5-dihydroisoxazole;

3-(2-bromo-4-(5-(3,4,5-trichlorophenyl)-5-(trifluoromethyl)-4,5-dihydroisoxazol-3-yl)phenyl)-1-(cyclopropanecarbonyl)azetidine-3-carbonitrile;

1-(cyclopropanecarbonyl)-3-(4-(5-(3,4,5-trichlorophenyl)-5-(trifluoromethyl)-4,5-dihydroisoxazol-3-yl)phenyl)azetidine-3-carbonitrile;

1-(3-(4-(5-(3,5-dichlorophenyl)-5-(trifluoromethyl)-4,5-dihydroisoxazol-3-yl)phenyl)azetidin-1-yl)-2-methylpropan-1-one;

2-methyl-1-(3-(4-(5-(3,4,5-trichlorophenyl)-5-(trifluoromethyl)-4,5-dihydroisoxazol-3-yl)phenyl)azetidin-1-yl)propan-1-one;

Cyclopropyl(3-(4-(5-(3,5-dichlorophenyl)-5-(trifluoromethyl)-4,5-dihydroisoxazol-3-yl)phenyl)azetidin-1-yl)methanone;

Cyclopropyl(3-(4-(5-(3,4,5-trichlorophenyl)-5-(trifluoromethyl)-4,5-dihydroisoxazol-3-yl)phenyl)azetidin-1-yl)methanone;

1-(3-(4-(5-(3,5-dichlorophenyl)-5-(trifluoromethyl)-4,5-dihydroisoxazol-3-yl)phenyl)azetidin-1-yl)ethanone;

1-(3-(4-(5-(3,4,5-trichlorophenyl)-5-(trifluoromethyl)-4,5-dihydroisoxazol-3-yl)phenyl)azetidin-1-yl)ethanone;

1-isobutyryl-3-{4-[5-(3,4,5-trichlorophenyl)-5-(trifluoromethyl)-4,5-dihydroisoxazol-3-yl]phenyl}azetidin-3-ol;

3-{-4-[3-fluoro-1-(3,3,3-trifluoropropanoyl)azetidin-3-yl]phenyl}-5-(3,4,5-trichlorophenyl)-5-(trifluoromethyl)-4,5-dihydroisoxazole;

3-{4-[1-(cyclopropylacetyl)-3-fluoroazetidin-3-yl]phenyl}-5-(3,4,5-trichlorophenyl)-5-(trifluoromethyl)-4,5-dihydroisoxazole;

3-[4-(1-butyryl-3-fluoroazetidin-3-yl)phenyl]-5-(3,4,5-trichlorophenyl)-5-(trifluoromethyl)-4,5-dihydroisoxazole;

3-[4-(3-fluoro-1-isobutyrylazetidin-3-yl)phenyl]-5-(3,4,5-trichlorophenyl)-5-(trifluoromethyl)-4,5-dihydroisoxazole;

3-[4-(3-fluoro-1-propionylazetidin-3-yl)phenyl]-5-(3,4,5-trichlorophenyl)-5-(trifluoromethyl)-4,5-dihydroisoxazole;

5-[3-chloro-5-(trifluoromethyl)phenyl]-3-[4-(3-fluoro-1-isobutyrylazetidin-3-yl)phenyl]-5-(trifluoromethyl)-4,5-dihydroisoxazole;

2-[3-(4-{5-[3-chloro-5-(trifluoromethyl)phenyl]-5-(trifluoromethyl)-4,5-dihydroisoxazol-3-yl}phenyl)-3-fluoroazetidin-1-yl]-2-oxoethanol;

5-[3-chloro-5-(trifluoromethyl)phenyl]-3-{4-[1-(cyclopentylcarbonyl)-3-fluoroazetidin-3-yl]phenyl}-5-(trifluoromethyl)-4,5-dihydroisoxazole;

3-[4-(1-butyryl-3-fluoroazetidin-3-yl)phenyl]-5-[3,4-dichloro-5-(trifluoromethyl)phenyl]-5-(trifluoromethyl)-4,5-dihydroisoxazole;

5-(3,5-dichlorophenyl)-3-[4-(1-propionylazetidin-3-yl)phenyl]-5-(trifluoromethyl)-4,5-dihydroisoxazole;

1-[(3-{4-[5-(3,5-dichlorophenyl)-5-(trifluoromethyl)-4,5-dihydroisoxazol-3-yl]phenyl}azetidin-1-yl)carbonyl]cyclopropanol;

5-(3,5-dichlorophenyl)-3-{4-[1-(methoxyacetyl)azetidin-3-yl]phenyl}-5-(trifluoromethyl)-4,5-dihydroisoxazole;

3-{4-[1-(cyclopropylacetyl)azetidin-3-yl]phenyl}-5-[3,4-dichloro-5-(trifluoromethyl)phenyl]-5-(trifluoromethyl)-4,5-dihydroisoxazole;

3-[4-(1-acetylazetidin-3-yl)phenyl]-5-[3,4-dichloro-5-(trifluoromethyl)phenyl]-5-(trifluoromethyl)-4,5-dihydroisoxazole;

5-[3,4-dichloro-5-(trifluoromethyl)phenyl]-3-[4-(1-propionylazetidin-3-yl)phenyl]-5-(trifluoromethyl)-4,5-dihydroisoxazole;

3-[4-(1-butyrylazetidin-3-yl)phenyl]-5-[3-chloro-5-(trifluoromethyl)phenyl]-5-(trifluoromethyl)-4,5-dihydroisoxazole;

3-[4-(1-butyrylazetidin-3-yl)phenyl]-5-[3,4-dichloro-5-(trifluoromethyl)phenyl]-5-(trifluoromethyl)-4,5-dihydroisoxazole;

2-[3-(4-{5-[3,4-dichloro-5-(trifluoromethyl)phenyl]-5-(trifluoromethyl)-4,5-dihydroisoxazol-3-yl}phenyl)azetidin-1-yl]-2-oxoethanol;

1-{[3-(4-{5-[3,4-dichloro-5-(trifluoromethyl)phenyl]-5-(trifluoromethyl)-4,5-dihydroisoxazol-3-yl}phenyl)azetidin-1-yl]carbonyl}cyclopropanol;

5-[3,4-dichloro-5-(trifluoromethyl)phenyl]-3-(4-{1-[(methylthio)acetyl]azetidin-3-yl}phenyl)-5-(trifluoromethyl)-4,5-dihydroisoxazole;

5-[3-chloro-5-(trifluoromethyl)phenyl]-3-{4-[1-(cyclopropylacetyl)azetidin-3-yl]phenyl}-5-(trifluoromethyl)-4,5-dihydroisoxazole;

5-[3-chloro-5-(trifluoromethyl)phenyl]-3-{4-[1-(methoxyacetyl)azetidin-3-yl]phenyl}-5-(trifluoromethyl)-4,5-dihydroisoxazole;

3-[3-(4-{5-[3,4-dichloro-5-(trifluoromethyl)phenyl]-5-(trifluoromethyl)-4,5-dihydroisoxazol-3-yl}phenyl)azetidin-1-yl]-3-oxopropanenitrile;

1-{[3-(4-{5-[3-chloro-5-(trifluoromethyl)phenyl]-5-(trifluoromethyl)-4,5-dihydroisoxazol-3-yl}phenyl)azetidin-1-yl]carbonyl}cyclopropanol;

5-[3,4-dichloro-5-(trifluoromethyl)phenyl]-3-{4-[1-(methoxyacetyl)azetidin-3-yl]phenyl}-5-(trifluoromethyl)-4,5-dihydroisoxazole;

5-[3-chloro-5-(trifluoromethyl)phenyl]-3-[4-(1-propionylazetidin-3-yl)phenyl]-5-(trifluoromethyl)-4,5-dihydroisoxazole;

3-[4-(1-butyrylazetidin-3-yl)phenyl]-5-(3,4,5-trichlorophenyl)-5-(trifluoromethyl)-4,5-dihydroisoxazole;

5-[3-chloro-5-(trifluoromethyl)phenyl]-3[4-(1-isobutyrylazetidin-3-yl)phenyl]-5-(trifluoromethyl)-4,5-dihydroisoxazole;

1-[(3-{4-[5-(3,4,5-trichlorophenyl)-5-(trifluoromethyl)-4,5-dihydroisoxazol-3-yl]phenyl}azetidin-1-yl)carbonyl]cyclopropanol;

3-[4-(1-propionylazetidin-3-yl)phenyl]-5-(3,4,5-trichlorophenyl)-5-(trifluoromethyl)-4,5-dihydroisoxazole;

3-(4-{1-[(methylthio)acetyl]azetidin-3-yl}phenyl)-5-(3,4,5-trichlorophenyl)-5-(trifluoromethyl)-4,5-dihydroisoxazole;

3-{4-[1-(methoxyacetyl)azetidin-3-yl]phenyl}-5-(3,4,5-trichlorophenyl)-5-(trifluoromethyl)-4,5-dihydroisoxazole;

3-{4-[1-(cyclopropylacetyl)azetidin-3-yl]phenyl}-5-(3,4,5-trichlorophenyl)-5-(trifluoromethyl)-4,5-dihydroisoxazole;

5-(3,5-dichloro-4-fluorophenyl)-3-(4-{1-[(methylthio)acetyl]azetidin-3-yl}phenyl)-5-(trifluoromethyl)-4,5-dihydroisoxazole;

5-(3,5-dichloro-4-fluorophenyl)-3-{4-[1-(methoxyacetyl)azetidin-3-yl]phenyl}-5-(trifluoromethyl)-4,5-dihydroisoxazole;

1-[(3-{4-[5-(3,5-dichloro-4-fluorophenyl)-5-(trifluoromethyl)-4,5-dihydroisoxazol-3-yl]phenyl}azetidin-1-yl)carbonyl]cyclopropanol;

5-(3,5-dichloro-4-fluorophenyl)-3-[4-(1-propionylazetidin-3-yl)phenyl]-5-(trifluoromethyl)-4,5-dihydroisoxazole;

5-(3,5-dichloro-4-fluorophenyl)-3-[4-(1-isobutyrylazetidin-3-yl)phenyl]-5-(trifluoromethyl)-4,5-dihydroisoxazole;

5-(3,5-dichloro-4-fluorophenyl)-3-(4-{1-[(3,3-difluoroazetidin-1-yl)carbonyl]-3-fluoroazetidin-3-yl}phenyl)-5-(trifluoromethyl)-4,5-dihydroisoxazole;

3-{4-[5-(3,5-dichloro-4-fluorophenyl)-5-(trifluoromethyl)-4,5-dihydroisoxazol-3-yl]phenyl}-1-(3,3,3-trifluoropropanoyl)azetidin-3-ol;

5-[3,4-dichloro-5-(trifluoromethyl)phenyl]-3-{-4-[3-fluoro-1-(3,3,3-trifluoropropanoyl)azetidin-3-yl]phenyl}-5-(trifluoromethyl)-4,5-dihydroisoxazole;

5-(3,5-dichloro-4-fluorophenyl)-3-(4-{3-fluoro-1-[(4-methyl-1,3-oxazol-5-yl)carbonyl]azetidin-3-yl}phenyl)-5-(trifluoromethyl)-4,5-dihydroisoxazole;

N-[2-(3-{4-[5-(3,5-dichloro-4-fluorophenyl)-5-(trifluoromethyl)-4,5-dihydroisoxazol-3-yl]phenyl}-3-fluoroazetidin-1-yl)-2-oxoethyl]formamide;

4-[(3-{4-[5-(3,5-dichloro-4-fluorophenyl)-5-(trifluoromethyl)-4,5-dihydroisoxazol-3-yl]phenyl}-3-fluoroazetidin-1-yl)carbonyl]pyridazine;

1-[2-(3-{4-[5-(3,5-dichloro-4-fluorophenyl)-5-(trifluoromethyl)-4,5-dihydroisoxazol-3-yl]phenyl}-3-fluoroazetidin-1-yl)-2-oxoethyl]-1H-1,2,4-triazole;

5-(3,5-dichloro-4-fluorophenyl)-3-(4-{3-fluoro-1-[(methylsulfonyl)acetyl]azetidin-3-yl}phenyl)-5-(trifluoromethyl)-4,5-dihydroisoxazole;

5-(3,5-dichloro-4-fluorophenyl)-3-{-4-[3-fluoro-1-(1H-pyrazol-1-ylacetyl)azetidin-3-yl]phenyl}-5-(trifluoromethyl)-4,5-dihydroisoxazole;

5-(3,5-dichloro-4-fluorophenyl)-3-{-4-[3-fluoro-1-(1,3-oxazol-5-ylcarbonyl)azetidin-3-yl]phenyl}-5-(trifluoromethyl)-4,5-dihydroisoxazole;

5-(3,5-dichloro-4-fluorophenyl)-3-{4-[1-(2,2-difluoropropanoyl)-3-fluoroazetidin-3-yl]phenyl}-5-(trifluoromethyl)-4,5-dihydroisoxazole;

1-{[3-(4-{5-[3,4-dichloro-5-(trifluoromethyl)phenyl]-5-(trifluoromethyl)-4,5-dihydroisoxazol-3-yl}phenyl)-3-fluoroazetidin-1-yl]carbonyl}azetidin-3-ol;

1-(3-{4-[5-(3,5-dichloro-4-fluorophenyl)-5-(trifluoromethyl)-4,5-dihydroisoxazol-3-yl]phenyl}-3-fluoroazetidin-1-yl)-2-methyl-1-oxopropan-2-ol;

3-[4-(1-but-3-enoyl-3-fluoroazetidin-3-yl)phenyl]-5-(3,5-dichloro-4-fluorophenyl)-5-(trifluoromethyl)-4,5-dihydroisoxazole;

2-(3-{4-[5-(3,5-dichloro-4-fluorophenyl)-5-(trifluoromethyl)-4,5-dihydroisoxazol-3-yl]phenyl}-3-fluoroazetidin-1-yl)-N,N-dimethyl-2-oxoethanesulfonamide;

5-(3,5-dichloro-4-fluorophenyl)-3-[4-(3-fluoro-1-{[(trifluoromethyl)thio]acetyl}azetidin-3-yl)phenyl]-5-(trifluoromethyl)-4,5-dihydroisoxazole;

5-(3,5-dichloro-4-fluorophenyl)-3-{-4-[3-fluoro-1-(2-methoxypropanoyl)azetidin-3-yl]phenyl}-5-(trifluoromethyl)-4,5-dihydroisoxazole;

5-(3,5-dichloro-4-fluorophenyl)-3-(4-{1-[(2,2-difluorocyclopropyl)carbonyl]-3-fluoroazetidin-3-yl}phenyl)-5-(trifluoromethyl)-4,5-dihydroisoxazole;

3-(3-{4-[5-(3,5-dichloro-4-fluorophenyl)-5-(trifluoromethyl)-4,5-dihydroisoxazol-3-yl]phenyl}-3-fluoroazetidin-1-yl)-2-methyl-3-oxopropan-1-ol;

(2S)-4-(3-{4-[5-(3,5-dichloro-4-fluorophenyl)-5-(trifluoromethyl)-4,5-dihydroisoxazol-3-yl]phenyl}-3-fluoroazetidin-1-yl)-4-oxobutan-2-ol;

4-(3-{4-[5-(3,5-dichloro-4-fluorophenyl)-5-(trifluoromethyl)-4,5-dihydroisoxazol-3-yl]phenyl}-3-fluoroazetidin-1-yl)-4-oxobutan-2-ol;

3-{-4-[3-chloro-1-(cyclopropylcarbonyl)azetidin-3-yl]phenyl}-5-(3,5-dichloro-4-fluorophenyl)-5-(trifluoromethyl)-4,5-dihydroisoxazole;

3-{-4-[3-chloro-1-(cyclopropylcarbonyl)azetidin-3-yl]phenyl}-5-[3,4-dichloro-5-(trifluoromethyl)phenyl]-5-(trifluoromethyl)-4,5-dihydroisoxazole;

5-(3-chlorophenyl)-3-{4-[1-(cyclopropylcarbonyl)-3-fluoroazetidin-3-yl]phenyl}-5-(trifluoromethyl)-4,5-dihydroisoxazole;

3-{4-[5-(3-chloro-4,5-difluorophenyl)-5-(trifluoromethyl)-4,5-dihydroisoxazol-3-yl]phenyl}-1-(cyclopropylcarbonyl)-azetidin-3-ol;

3-{4-[1-(cyclopropylcarbonyl)-3-fluoroazetidin-3-yl]phenyl}-5-[3,4-difluoro-5-(trifluoromethyl)phenyl]-5-(trifluoromethyl)-4,5-dihydroisoxazole;

(2S)-1-(3-{4-[5-(3,5-dichloro-4-fluorophenyl)-5-(trifluoromethyl)-4,5-dihydroisoxazol-3-yl]phenyl}-3-fluoroazetidin-1-yl)-1-oxopropan-2-ol;

(2R)-1-(3-{4-[5-(3,5-dichloro-4-fluorophenyl)-5-(trifluoromethyl)-4,5-dihydroisoxazol-3-yl]phenyl}-3-fluoroazetidin-1-yl)-1-oxopropan-2-ol;

(2S)-4-(3-{4-[5-(3,5-dichloro-4-fluorophenyl)-5-(trifluoromethyl)-4,5-dihydroisoxazol-3-yl]phenyl}-3-fluoroazetidin-1-yl)-4-oxobutan-2-ol;

5-(3,5-dichloro-4-fluorophenyl)-3-(4-{3-fluoro-1-[(methylsulfinyl)acetyl]azetidin-3-yl}phenyl)-5-(trifluoromethyl)-4,5-dihydroisoxazole;

3-{4[3-azido-1-(cyclopropylcarbonyl)azetidin-3-yl]phenyl}-5-(3,4,5-trichlorophenyl)-5-(trifluoromethyl)-4,5-dihydroisoxazole;

3-[4-(3-azido-1-propionylazetidin-3-yl)phenyl]-5-(3,4,5-trichlorophenyl)-5-(trifluoromethyl)-4,5-dihydroisoxazole;

S-[2-(3-{4-[5-(3,5-dichloro-4-fluorophenyl)-5-(trifluoromethyl)-4,5-dihydroisoxazol-3-yl]phenyl}-3-fluoroazetidin-1-yl)-2-oxoethyl]ethanethioate;

5-(3-fluorophenyl)-3-[4-(3-fluoro-1-propionylazetidin-3-yl) phenyl]-5-(trifluoromethyl)-4,5-dihydroisoxazole;
5-(3-chlorophenyl)-3-[4-(3-fluoro-1-propionylazetidin-3-yl)phenyl]-5-(trifluoromethyl)-4,5-dihydroisoxazole;
5-(3,4-dichlorophenyl)-3-[4-(3-fluoro-1-propionylazetidin-3-yl)phenyl]-5-(trifluoromethyl)-4,5-dihydroisoxazole;
3-{4-[1-(cyclopropylcarbonyl)-3-fluoroazetidin-3-yl]phenyl}-5-(trifluoromethyl)-5-[3-(trifluoromethyl)phenyl]-4,5-dihydroisoxazole;
5-(3-chloro-5-fluorophenyl)-3-{4-[1-(cyclopropylcarbonyl)-3-fluoroazetidin-3-yl]phenyl}-5-(trifluoromethyl)-4,5-dihydroisoxazole;
3-{4-[1-(cyclopropylcarbonyl)-3-fluoroazetidin-3-yl]phenyl}-5-(3,4-difluorophenyl)-5-(trifluoromethyl)-4,5-dihydroisoxazole;
1-(3-(4-(5-(3,5-dichloro-4-fluorophenyl)-5-(trifluoromethyl)-4,5-dihydroisoxazol-3-yl)phenyl)-3-fluoroazetidin-1-yl)-3,3,3-trifluoropropan-1-one;
3-{4-[1-(azetidin-1-ylcarbonyl)-3-fluoroazetidin-3-yl]phenyl}-5-(3,5-dichlorophenyl)-5-(trifluoromethyl)-4,5-dihydroisoxazole;
3-{4-[1-(azetidin-1-ylcarbonyl)-3-fluoroazetidin-3-yl]phenyl}-5-(3,4,5-trichlorophenyl)-5-(trifluoromethyl)-4,5-dihydroisoxazole;
3-{4-[1-(azetidin-1-ylcarbonyl)-3-fluoroazetidin-3-yl]phenyl}-5-(3,5-dichloro-4-fluorophenyl)-5-(trifluoromethyl)-4,5-dihydroisoxazole;
1-(cyclopropylcarbonyl)-3-{4-[(5R)-5-[3,4-dichloro-5-(trifluoromethyl)phenyl]-5-(trifluoromethyl)-4,5-dihydroisoxazol-3-yl]phenyl}azetidin-3-ol;
5-(3,5-dichloro-4-fluorophenyl)-3-[4-(3-fluoro-1-isobutyrylazetidin-3-yl)phenyl]-5-(trifluoromethyl)-4,5-dihydroisoxazole;
{[2-(3-{4-[5-(3,5-dichloro-4-fluorophenyl)-5-(trifluoromethyl)-4,5-dihydroisoxazol-3-yl]phenyl}-3-fluoroazetidin-1-yl)-2-oxoethyl]sulfonyl}acetonitrile;
1-(3-{4-[5-(3,5-Dichloro-4-fluoro-phenyl)-5-trifluoromethyl-4,5-dihydro-isoxazol-3-yl]-phenyl}-3-fluoro-azetidin-1-yl)-3-methanesulfonyl-propan-1-one;
1-(3-{4-[5-(3,5-Dichloro-4-fluoro-phenyl)-5-trifluoromethyl-4,5-dihydro-isoxazol-3-yl]-phenyl}-3-fluoro-azetidin-1-yl)-2-(2,2,2-trifluoro-ethanesulfonyl)-ethanone;
2-(3-{4-[5-(3,5-Dichloro-4-fluoro-phenyl)-5-trifluoromethyl-4,5-dihydro-isoxazol-3-yl]-phenyl}-3-fluoro-azetidin-1-yl)-2-oxo-ethanesulfonic acid dimethylamide;
2-Benzenesulfonyl-1-(3-{4-[5-(3,5-dichloro-4-fluoro-phenyl)-5-trifluoromethyl-4,5-dihydro-isoxazol-3-yl]-phenyl}-3-fluoro-azetidin-1-yl)-ethanone;
1-(3-{4-[5-(3,5-Dichloro-4-fluoro-phenyl)-5-trifluoromethyl-4,5-dihydro-isoxazol-3-yl]-phenyl}-3-fluoro-azetidin-1-yl)-2-methanesulfonyl-propan-1-one;
cyclopropanecarboxylic acid (1-cyclopropanecarbonyl-3-{4-[5-(3,4-dichloro-5-trifluoromethyl-phenyl)-5-trifluoromethyl-4,5-dihydro-isoxazol-3-yl]-phenyl}-azetidin-3-yl)-amide;
(3-Amino-3-{4-[5-(3,4-dichloro-5-trifluoromethyl-phenyl)-5-trifluoromethyl-4,5-dihydro-isoxazol-3-yl]-phenyl}-azetidin-1-yl)-cyclopropyl-methanone;
3-fluoro-3-{4-[5-(3,4,5-trichlorophenyl)-5-(trifluoromethyl)-4,5-dihydroisoxazol-3-yl]phenyl}azetidine-1-carboxamide;
N-cyclopropyl-3-{4-[5-(3,4,5-trichlorophenyl)-5-(trifluoromethyl)-4,5-dihydroisoxazol-3-yl]phenyl}azetidine-1-carboxamide;
N-cyclopropyl-3-{4-[5-(3,5-dichlorophenyl)-5-(trifluoromethyl)-4,5-dihydroisoxazol-3-yl]phenyl}azetidine-1-carboxamide;
3-(4-{5-[3,4-dichloro-5-(trifluoromethyl)phenyl]-5-(trifluoromethyl)-4,5-dihydroisoxazol-3-yl}phenyl)-3-hydroxy-N-propylazetidine-1-carboxamide;
3-(4-{5-[3,4-dichloro-5-(trifluoromethyl)phenyl]-5-(trifluoromethyl)-4,5-dihydroisoxazol-3-yl}phenyl)-3-hydroxy-N,N-dimethylazetidine-1-carboxamide;
N-ethyl-3-{4-[5-(3,4,5-trichlorophenyl)-5-(trifluoromethyl)-4,5-dihydroisoxazol-3-yl]phenyl}azetidine-1-carboxamide;
3-{4-[5-(3,5-dichloro-4-fluorophenyl)-5-(trifluoromethyl)-4,5-dihydroisoxazol-3-yl]phenyl}-N-methylazetidine-1-carboxamide;
3-(4-{5-[3,4-dichloro-5-(trifluoromethyl)phenyl]-5-(trifluoromethyl)-4,5-dihydroisoxazol-3-yl}phenyl)-N-methylazetidine-1-carboxamide;
3-{4-[5-(3,5-dichlorophenyl)-5-(trifluoromethyl)-4,5-dihydroisoxazol-3-yl]phenyl}-N-ethylazetidine-1-carboxamide;
3-{4-[5-(3,5-dichloro-4-fluorophenyl)-5-(trifluoromethyl)-4,5-dihydroisoxazol-3-yl]phenyl}-N-ethylazetidine-1-carboxamide;
3-(4-{5-[3-chloro-5-(trifluoromethyl)phenyl]-5-(trifluoromethyl)-4,5-dihydroisoxazol-3-yl}phenyl)-N-methylazetidine-1-carboxamide;
3-(4-{5-[3-chloro-5-(trifluoromethyl)phenyl]-5-(trifluoromethyl)-4,5-dihydroisoxazol-3-yl}phenyl)-N-cyclopropylazetidine-1-carboxamide;
N-cyclopropyl-3-{4-[5-(3,5-dichloro-4-fluorophenyl)-5-(trifluoromethyl)-4,5-dihydroisoxazol-3-yl] phenyl}azetidine-1-carboxamide;
N-cyclopropyl-3-(4-{5-[3,4-dichloro-5-(trifluoromethyl) phenyl]-5-(trifluoromethyl)-4,5-dihydroisoxazol-3-yl}phenyl)azetidine-1-carboxamide;
3-(4-{5-[3,4-dichloro-5-(trifluoromethyl)phenyl]-5-(trifluoromethyl)-4,5-dihydroisoxazol-3-yl}phenyl)-3-fluoro-N-(2,2,2-trifluoroethyl)azetidine-1-carboxamide;
3-fluoro-N,N-dimethyl-3-{4-[5-(3,4,5-trichlorophenyl)-5-(trifluoromethyl)-4,5-dihydroisoxazol-3-yl] phenyl}azetidine-1-carboxamide;
3-(4-{5-[3,4-dichloro-5-(trifluoromethyl)phenyl]-5-(trifluoromethyl)-4,5-dihydroisoxazol-3-yl}phenyl)-3-fluoro-N,N-dimethylazetidine-1-carboxamide;
3-(4-{5-[3,4-dichloro-5-(trifluoromethyl)phenyl]-5-(trifluoromethyl)-4,5-dihydroisoxazol-3-yl}phenyl)-3-fluoro-N-(3,3,3-trifluoropropyl)azetidine-1-carboxamide;
3-(4-{5-[3,4-dichloro-5-(trifluoromethyl)phenyl]-5-(trifluoromethyl)-4,5-dihydroisoxazol-3-yl}phenyl)-3-fluoro-N-oxetan-3-ylazetidine-1-carboxamide;
3-azido-N,N-dimethyl-3-{4-[5-(3,4,5-trichlorophenyl)-5-(trifluoromethyl)-4,5-dihydroisoxazol-3-yl] phenyl}azetidine-1-carboxamide;
2-[1-(cyclopropylcarbonyl)-3-fluoroazetidin-3-yl]-5-[5-(3,5-dichloro-4-fluorophenyl)-5-(trifluoromethyl)-4,5-dihydroisoxazol-3-yl]benzonitrile;
2-(1-acetyl-3-fluoroazetidin-3-yl)-5-[5-(3,5-dichloro-4-fluorophenyl)-5-(trifluoromethyl)-4,5-dihydroisoxazol-3-yl]benzonitrile;
5-[5-(3,5-dichloro-4-fluorophenyl)-5-(trifluoromethyl)-4,5-dihydroisoxazol-3-yl]-2-[3-fluoro-1-(3,3,3-trifluoropropanoyl)azetidin-3-yl]benzonitrile;
5-[5-(3,5-dichloro-4-fluorophenyl)-5-(trifluoromethyl)-4,5-dihydroisoxazol-3-yl]-2-(3-fluoro-1-propionylazetidin-3-yl)benzonitrile;
5-[5-(3,5-dichloro-4-fluorophenyl)-5-(trifluoromethyl)-4,5-dihydroisoxazol-3-yl]-2-(3-fluoro-1-isobutyrylazetidin-3-yl)benzonitrile;

5-[5-(3,5-dichloro-4-fluorophenyl)-5-(trifluoromethyl)-4,5-dihydroisoxazol-3-yl]-2-(3-fluoro-1-glycoloylazetidin-3-yl)benzonitrile;

2-(1-butyryl-3-fluoroazetidin-3-yl)-5-[5-(3,5-dichloro-4-fluorophenyl)-5-(trifluoromethyl)-4,5-dihydroisoxazol-3-yl]benzonitrile;

2-[1-(cyclobutylcarbonyl)-3-fluoroazetidin-3-yl]-5-[5-(3,5-dichloro-4-fluorophenyl)-5-(trifluoromethyl)-4,5-dihydroisoxazol-3-yl]benzonitrile;

2-[1-(cyclopentylcarbonyl)-3-fluoroazetidin-3-yl]-5-[5-(3,5-dichloro-4-fluorophenyl)-5-(trifluoromethyl)-4,5-dihydroisoxazol-3-yl]benzonitrile;

5-[5-(3,5-dichloro-4-fluorophenyl)-5-(trifluoromethyl)-4,5-dihydroisoxazol-3-yl]-2-[3-fluoro-1-(methoxyacetyl)azetidin-3-yl]benzonitrile;

2-[1-(cyclopropylacetyl)-3-fluoroazetidin-3-yl]-5-[5-(3,5-dichloro-4-fluorophenyl)-5-(trifluoromethyl)-4,5-dihydroisoxazol-3-yl]benzonitrile;

5-[5-(3,5-dichloro-4-fluorophenyl)-5-(trifluoromethyl)-4,5-dihydroisoxazol-3-yl]-2-(3-fluoro-1-pentanoylazetidin-3-yl)benzonitrile;

5-[5-(3,5-dichloro-4-fluorophenyl)-5-(trifluoromethyl)-4,5-dihydroisoxazol-3-yl]-2-{3-fluoro-1-[(methylthio)acetyl]-azetidin-3-yl}benzonitrile;

2-[1-(cyclopropylcarbonyl)-3-fluoroazetidin-3-yl]-5-[5-(3,4,5-trichlorophenyl)-5-(trifluoromethyl)-4,5-dihydroisoxazol-3-yl]pyridine;

(3-(4-(5-(3,5-dichloro-4-fluorophenyl)-5-(trifluoromethyl)-4,5-dihydroisoxazol-3-yl)phenyl)-3-fluoroazetidin-1-yl)(1-oxidothietan-3-yl)methanone;

(3-(4-(5-(3,5-dichloro-4-fluorophenyl)-5-(trifluoromethyl)-4,5-dihydroisoxazol-3-yl)phenyl)-3-fluoroazetidin-1-yl)(1,1-dioxidothietan-3-yl)methanone;

1-(3-(4-(5-(3,5-dichloro-4-fluorophenyl)-5-(trifluoromethyl)-4,5-dihydroisoxazol-3-yl)phenyl)-3-fluoroazetidin-1-yl)-2-methylpropane-1-thione;

(1-(3-(4-(5-(3,5-dichloro-4-fluorophenyl)-5-(trifluoromethyl)-4,5-dihydroisoxazol-3-yl)phenyl)-3-fluoroazetidin-1-yl)-2-methylpropylidene)cyanamide;

(1-(3-Fluoro-3-{4-[5-(3,4,5-trichloro-phenyl)-5-trifluoromethyl-4,5-dihydro-isoxazol-3-yl]-phenyl}-azetidin-1-yl)-2-methanesulfonyl-ethanone; and 1-(3-{4-[5-(3,4-Dichloro-5-trifluoromethyl-phenyl)-5-trifluoromethyl-4,5-dihydro-isoxazol-3-yl]-phenyl}-3-fluoro-azetidin-1-yl)-2-methanesulfonyl-ethanone, stereoisomers thereof, pharmaceutical and veterinarily acceptable salts thereof.

In another aspect of the invention, are Formula (1) compounds that were shown to have biological data within at least one of the bio-assays with an $ED^{100}$, $LD^{100}$, $LD^{90}$, and/or $ED^{80}$ value of $\leq 1$ μg/mL or 1 μg/fly and are selected from Examples 1-60, 65-70, 72-77, 82, 84-85, 87, 89, 91, 95-101, 103-104, 106-107, 109-110, 113, 116-117, 119-121, 123-126, 128-133, 135-143, 145-146, 148, 152-155, 158, 160-165, 167-171, 173-176, 187-188, 197-199, and 200-224, stereoisomers thereof, pharmaceutical and veterinarily acceptable salts thereof.

In another aspect of the invention, are Formula (1) compounds that were shown to have biological data within at least one of the bio-assays with an $ED^{100}$, $LD^{100}$, $LD^{90}$, and/or $ED^{80}$ value of $\leq 0.3$ μg/mL or $\leq 0.3$ μg/fly and are selected from Examples 1-17, 19-30, 32-54, 56-60, 65-70, 72-74, 76-77, 82, 84, 87, 95-99, 103-104, 117, 131, 133, 135-143, 145-146, 148, 152-155, 158, 160-161, 165, 167-171, 173-175, 187-188, 202-204, 206, 209-221, and 223, stereoisomers thereof, pharmaceutical and veterinarily acceptable salts thereof.

In another aspect of the invention, are Formula (1) compounds that were shown to have biological data within at least one of the bio-assays with an $ED^{100}$, $LD^{100}$, $LD^{90}$, and/or $ED^{80}$ value of $\leq 0.1$ μg/mL or $\leq 0.1$ μg/fly and are selected from Examples 1-17, 19-21, 24, 26-30, 32-34, 36-48, 50-54, 56-60, 65-70, 72-74, 76-77, 84, 87, 95-99, 103-104, 117, 131, 133, 135-137, 139-143, 145-146, 148, 152-155, 158, 160, 165, 168-171, 173-175, 188, 202, 206, 209-213, 215-221, and 223, stereoisomers thereof, pharmaceutical and veterinarily acceptable salts thereof.

In another aspect of the invention, are Formula (1) compounds that were shown to have biological data within at least one of the bio-assays with an $ED^{100}$, $LD^{100}$, $LD^{90}$, and/or $ED^{80}$ value of $\leq 0.03$ μg/mL and are selected from Examples 1-17, 19-21, 26-28, 32-34, 36-38, 40-48, 50-54, 56, 59-60, 65-66, 68, 70, 72-74, 76, 84, 95-99, 103, 131, 133, 135, 141-143, 145-146, 155, 158, 165, 168-169, 171, 173-175, 202, 206, 209-210, 212-213, 215-216, 218-219, and 221, stereoisomers thereof, pharmaceutical and veterinarily acceptable salts thereof.

In another aspect of the invention, are Formula (1) compounds that were shown to have biological data within at least one of the bio-assays with an $ED^{100}$, $LD^{100}$, $LD^{90}$, and/or $ED^{80}$ value of $\leq 0.01$ μg/mL or $\leq 0.01$ μg/fly and are selected from Examples 1, 5, 10-12,16,19-21, 26-28, 33-34, 38, 40, 47, 50, 52, 54, 60, 84, 95, 99, 146, 168-169, 173-175, 202, and 221, stereoisomers thereof, pharmaceutical and veterinarily acceptable salts thereof.

In another aspect of the invention, are Formula (1) compounds that were shown to have biological data within at least one of the bio-assays with an $ED^{100}$, $LD^{100}$, $LD^{90}$, and/or $ED^{80}$ value of $\leq 0.003$ μg/mL and are selected from Examples 11, 19, 40, 169, and 175, stereoisomers thereof, pharmaceutical and veterinarily acceptable salts thereof.

In another aspect of the invention, are Formula (1) compounds selected from:

5-(3,5-dichloro-4-fluorophenyl)-3-(4-{3-fluoro-1-[(methylsulfonyl)acetyl]azetidin-3-yl}phenyl)-5-(trifluoromethyl)-4,5-dihydroisoxazole;

1-(3-{4-[5-(3,5-dichloro-4-fluorophenyl)-5-(trifluoromethyl)-4,5-dihydroisoxazol-3-yl]phenyl}-3-fluoroazetidin-1-yl)-2-methyl-1-oxopropan-2-ol;

1-(3-(4-(5-(3,5-dichloro-4-fluorophenyl)-5-(trifluoromethyl)-4,5-dihydroisoxazol-3-yl)phenyl)-3-fluoroazetidin-1-yl)-3,3,3-trifluoropropan-1-one;

5-(3,5-dichloro-4-fluorophenyl)-3-[4-(3-fluoro-1-isobutyrylazetidin-3-yl)phenyl]-5-(trifluoromethyl)-4,5-dihydroisoxazole; and (3-(4-(5-(3,5-dichloro-4-fluorophenyl)-5-(trifluoromethyl)-4,5-dihydroisoxazol-3-yl)phenyl)-3-fluoroazetidin-1-yl)(1,1-dioxidothietan-3-yl)methanone, stereoisomers thereof, pharmaceutical and veterinarily acceptable salts thereof.

In another aspect of the invention, are Formula (1) compounds selected from:

2,2-dichloro-1-(3-(4-(5-(3,5-dichloro-4-fluorophenyl)-5-(trifluoromethyl)-4,5-dihydroisoxazol-3-yl)phenyl)-3-fluoroazetidin-1-yl)ethanone;

1-(3-(4-(5-(3,5-dichloro-4-fluorophenyl)-5-(trifluoromethyl)-4,5-dihydroisoxazol-3-yl)phenyl)-3-fluoroazetidin-1-yl)-2-fluoro-2-methylpropan-1-one;

1-(3-(4-(5-(3,5-dichloro-4-fluorophenyl)-5-(trifluoromethyl)-4,5-dihydroisoxazol-3-yl)phenyl)-3-fluoroazetidin-1-yl)-3-(methylthio)propan-1-one 1-(3-(4-(5-(3,5-dichloro-4-fluorophenyl)-5-(trifluoromethyl)-4,5-dihydroisoxazol-3-yl)phenyl)-3-fluoroazetidin-1-yl)-3-(methylsulfonyl)propan-1-one;

(3-(4-(5-(3,5-dichloro-4-fluorophenyl)-5-(trifluoromethyl)-4,5-dihydroisoxazol-3-yl)phenyl)-3-fluoroazetidin-1-yl)(thietan-3-yl)methanone;
1-(3-(4-(5-(3,5-dichloro-4-fluorophenyl)-5-(trifluoromethyl)-4,5-dihydroisoxazol-3-yl)phenyl)-3-fluoroazetidin-1-yl)-3,3,3-trifluoro-2-methylpropan-1-one;
1-(3-(4-(5-(3,5-dichloro-4-fluorophenyl)-5-(trifluoromethyl)-4,5-dihydroisoxazol-3-yl)phenyl)-3-fluoroazetidin-1-yl)-2-methyl-2-(methylsulfonyl)propan-1-one;
1-(3-(4-(5-(3,5-dichloro-4-fluorophenyl)-5-(trifluoromethyl)-4,5-dihydroisoxazol-3-yl)phenyl)-3-fluoroazetidin-1-yl)-2-(methylsulfonyl)propan-1-one;
(3-(4-(5-(3,5-dichloro-4-fluorophenyl)-5-(trifluoromethyl)-4,5-dihydroisoxazol-3-yl)phenyl)-3-fluoroazetidin-1-yl)(1-(methylsulfonyl)cyclopropyl)methanone;
5-(3,5-dichloro-4-fluorophenyl)-3-(4-(3-fluoro-1-(1,1,1,3,3,3-hexafluoropropan-2-yl)azetidin-3-yl)phenyl)-5-(trifluoromethyl)-4,5-dihydroisoxazole;
1-(3-(4-(5-(3,5-dichloro-4-fluorophenyl)-5-(trifluoromethyl)-4,5-dihydroisoxazol-3-yl)phenyl)-3-fluoroazetidin-1-yl)-3,3-difluoropropan-1-one;
2-(3-(4-(5-(3,5-dichloro-4-fluorophenyl)-5-(trifluoromethyl)-4,5-dihydroisoxazol-3-yl)phenyl)-3-fluoroazetidin-1-yl)-N-methyl-2-oxoethanesulfonamide;
2-(3-(4-(5-(3,5-dichloro-4-fluorophenyl)-5-(trifluoromethyl)-4,5-dihydroisoxazol-3-yl)phenyl)-3-fluoroazetidin-1-yl)-N-isopropyl-2-oxoethanesulfonamide;
1-(3-(4-(5-(3,5-dichloro-4-fluorophenyl)-5-(trifluoromethyl)-4,5-dihydroisoxazol-3-yl)phenyl)-3-fluoroazetidin-1-yl)-2-(3-hydroxyazetidin-1-yl)ethanone;
1-(3-(4-(5-(3,5-dichloro-4-hydroxyphenyl)-5-(trifluoromethyl)-4,5-dihydroisoxazol-3-yl)phenyl)-3-fluoroazetidin-1-yl)-2-methylpropan-1-one;
(3-(4-(5-(3,5-dichloro-4-fluorophenyl)-5-(trifluoromethyl)-4,5-dihydroisoxazol-3-yl)phenyl)-3-fluoroazetidin-1-yl)(thietan-2-yl)methanone;
N-(1-(3-(4-(5-(3,5-dichloro-4-fluorophenyl)-5-(trifluoromethyl)-4,5-dihydroisoxazol-3-yl)phenyl)-3-fluoroazetidin-1-yl)-2-methyl-1-oxopropan-2-yl)acetamide;
1-(3-(4-(5-(3,5-dichloro-4-fluorophenyl)-5-(trifluoromethyl)-4,5-dihydroisoxazol-3-yl)phenyl)-3-fluoroazetidin-1-yl)-2-mercapto-2-methylpropan-1-one;
1-(3-(4-(5-(3,5-dichloro-4-fluorophenyl)-5-(trifluoromethyl)-4,5-dihydroisoxazol-3-yl)phenyl)-3-fluoroazetidin-1-yl)-3,3,3-trifluoro-2-hydroxy-2-methylpropan-1-one;
1-(3-(4-(5-(3,5-dichloro-4-fluorophenyl)-5-(trifluoromethyl)-4,5-dihydroisoxazol-3-yl)phenyl)-3-fluoroazetidin-1-yl)-3-hydroxy-2,2-dimethylpropan-1-one;
3-(3-(4-(5-(3,5-dichloro-4-fluorophenyl)-5-(trifluoromethyl)-4,5-dihydroisoxazol-3-yl)phenyl)-3-fluoroazetidin-1-yl)-2,2-dimethyl-3-oxopropanenitrile;
1-(3-(4-(5-(3,5-dichloro-4-fluorophenyl)-5-(trifluoromethyl)-4,5-dihydroisoxazol-3-yl)phenyl)-3-fluoroazetidin-1-yl)-3,3-difluoropropan-1-one;
S-(1-(3-(4-(5-(3,5-dichloro-4-fluorophenyl)-5-(trifluoromethyl)-4,5-dihydroisoxazol-3-yl)phenyl)-3-fluoroazetidin-1-yl)-2-methyl-1-oxopropan-2-yl)ethanethioate;
1-(3-(4-(5-(3,5-dichloro-4-fluorophenyl)-5-(trifluoromethyl)-4,5-dihydroisoxazol-3-yl)phenyl)-3-fluoroazetidin-1-yl)-2-methyl-2-(methylthio)propan-1-one;
1-(3-(4-(5-(3,5-dichloro-4-fluorophenyl)-5-(trifluoromethyl)-4,5-dihydroisoxazol-3-yl)phenyl)-3-fluoroazetidin-1-yl)-2-methyl-2-(methylsulfonyl)propan-1-one;
1-(3-(4-(5-(3,5-dichloro-4-fluorophenyl)-5-(trifluoromethyl)-4,5-dihydroisoxazol-3-yl)phenyl)-3-fluoroazetidin-1-yl)-2-methyl-1-oxopropane-2-sulfonamide;
1-(1-(3-(4-(5-(3,5-dichloro-4-fluorophenyl)-5-(trifluoromethyl)-4,5-dihydroisoxazol-3-yl)phenyl)-3-fluoroazetidin-1-yl)-2-methyl-1-oxopropan-2-yl)urea;
1-(3-(4-(5-(3,5-dichloro-4-fluorophenyl)-5-(trifluoromethyl)-4,5-dihydroisoxazol-3-yl)phenyl)-3-fluoroazetidin-1-yl)-2-(methylsulfinyl)ethanone;
1-(3-(4-(5-(3,5-dichloro-4-fluorophenyl)-5-(trifluoromethyl)-4,5-dihydroisoxazol-3-yl)phenyl)-3-fluoroazetidin-1-yl)-2-(methylsulfonyl)ethanone;
1-(3-(4-(5-(3,5-dichloro-4-fluorophenyl)-5-(trifluoromethyl)-4,5-dihydroisoxazol-3-yl)phenyl)-3-fluoroazetidin-1-yl)-2-(1H-pyrazol-1-yl)ethanone;
1-(3-(4-(5-(3,5-dichloro-4-fluorophenyl)-5-(trifluoromethyl)-4,5-dihydroisoxazol-3-yl)phenyl)-3-fluoroazetidin-1-yl)-2-hydroxy-2-methylpropan-1-one;
(3-{4-[5-(3,5-Dichloro-4-fluoro-phenyl)-5-trifluoromethyl-4,5-dihydro-isoxazol-3-yl]-phenyl}-3-fluoro-azetidin-1-yl)-thietan-3-yl-methanone
(E)-N-(1-(3-(4-(5-(3,5-dichloro-4-fluorophenyl)-5-(trifluoromethyl)-4,5-dihydroisoxazol-3-yl)phenyl)-3-fluoroazetidin-1-yl)-2-methylpropylidene)-cyanamide;
1-(3-fluoro-3-(4-(5-(3,4,5-trichlorophenyl)-5-(trifluoromethyl)-4,5-dihydroisoxazol-3-yl)phenyl)azetidin-1-yl)-2-methylpropan-1-one;
3,3,3-trifluoro-1-(3-fluoro-3-(4-(5-(3,4,5-trichlorophenyl)-5-(trifluoromethyl)-4,5-dihydroisoxazol-3-yl)phenyl)azetidin-1-yl)propan-1-one;
1-(3-fluoro-3-(4-(5-(3,4,5-trichlorophenyl)-5-(trifluoromethyl)-4,5-dihydroisoxazol-3-yl)phenyl)azetidin-1-yl)-2-(methylthio)ethanone;
1-(3-fluoro-3-(4-(5-(3,4,5-trichlorophenyl)-5-(trifluoromethyl)-4,5-dihydroisoxazol-3-yl)phenyl)azetidin-1-yl)-2-(methylsulfinyl)ethanone;
1-(3-fluoro-3-(4-(5-(3,4,5-trichlorophenyl)-5-(trifluoromethyl)-4,5-dihydroisoxazol-3-yl)phenyl)azetidin-1-yl)-2-(methylsulfonyl)ethanone;
1-(3-fluoro-3-(4-(5-(3,4,5-trichlorophenyl)-5-(trifluoromethyl)-4,5-dihydroisoxazol-3-yl)phenyl)azetidin-1-yl)-2-(1H-pyrazol-1-yl)ethanone;
1-(3-fluoro-3-(4-(5-(3,4,5-trichlorophenyl)-5-(trifluoromethyl)-4,5-dihydroisoxazol-3-yl)phenyl)azetidin-1-yl)-2-hydroxy-2-methylpropan-1-one; (3-Fluoro-3-{4-[5-(3,4,5-trichloro-phenyl)-5-trifluoromethyl-4,5-dihydro-isoxazol-3-yl]-phenyl}-azetidin-1-yl)-thietan-3-yl-methanone;
(3-fluoro-3-(4-(5-(3,4,5-trichlorophenyl)-5-(trifluoromethyl)-4,5-dihydroisoxazol-3-yl)phenyl)azetidin-1-yl)(1-oxidothietan-3-yl)methanone;
(1,1-dioxidothietan-3-yl)(3-fluoro-3-(4-(5-(3,4,5-trichlorophenyl)-5-(trifluoromethyl)-4,5-dihydroisoxazol-3-yl)phenyl)azetidin-1-yl)methanone;
(E)-N-(1-(3-fluoro-3-(4-(5-(3,4,5-trichlorophenyl)-5-(trifluoromethyl)-4,5-dihydroisoxazol-3-yl)phenyl)azetidin-1-yl)-2-methylpropylidene)cyanamide;
1-(3-(4-(5-(3,4-dichloro-5-(trifluoromethyl)phenyl)-5-(trifluoromethyl)-4,5-dihydroisoxazol-3-yl)phenyl)-3-fluoroazetidin-1-yl)-2-methylpropan-1-one;
cyclopropyl(3-(4-(5-(3,4-dichloro-5-(trifluoromethyl)phenyl)-5-(trifluoromethyl)-4,5-dihydroisoxazol-3-yl)phenyl)-3-fluoroazetidin-1-yl)methanone;
1-(3-(4-(5-(3,4-dichloro-5-(trifluoromethyl)phenyl)-5-(trifluoromethyl)-4,5-dihydroisoxazol-3-yl)phenyl)-3-fluoroazetidin-1-yl)-3,3,3-trifluoropropan-1-one;
1-(3-(4-(5-(3,4-dichloro-5-(trifluoromethyl)phenyl)-5-(trifluoromethyl)-4,5-dihydroisoxazol-3-yl)phenyl)-3-fluoroazetidin-1-yl)-2-(methylthio)ethanone;

1-(3-(4-(5-(3,4-dichloro-5-(trifluoromethyl)phenyl)-5-(trifluoromethyl)-4,5-dihydroisoxazol-3-yl)phenyl)-3-fluoroazetidin-1-yl)-2-(methylsulfinyl)ethanone;
1-(3-(4-(5-(3,4-dichloro-5-(trifluoromethyl)phenyl)-5-(trifluoromethyl)-4,5-dihydroisoxazol-3-yl)phenyl)-3-fluoroazetidin-1-yl)-2-(methylsulfonyl)ethanone;
1-(3-(4-(5-(3,4-dichloro-5-(trifluoromethyl)phenyl)-5-(trifluoromethyl)-4,5-dihydroisoxazol-3-yl)phenyl)-3-fluoroazetidin-1-yl)-2-(1H-pyrazol-1-yl)ethanone;
1-(3-(4-(5-(3,4-dichloro-5-(trifluoromethyl)phenyl)-5-(trifluoromethyl)-4,5-dihydroisoxazol-3-yl)phenyl)-3-fluoroazetidin-1-yl)-2-hydroxy-2-methylpropan-1-one;
(3-{4-[5-(3,4-Dichloro-5-trifluoromethyl-phenyl)-5-trifluoromethyl-4,5-dihydro-isoxazol-3-yl]-phenyl}-3-fluoroazetidin-1-yl)-thietan-3-yl-methanone;
(3-(4-(5-(3,4-dichloro-5-(trifluoromethyl)phenyl)-5-(trifluoromethyl)-4,5-dihydroisoxazol-3-yl)phenyl)-3-fluoroazetidin-1-yl)(1-oxidothietan-3-yl)methanone;
(3-(4-(5-(3,4-dichloro-5-(trifluoromethyl)phenyl)-5-(trifluoromethyl)-4,5-dihydroisoxazol-3-yl)phenyl)-3-fluoroazetidin-1-yl)(1,1-dioxidothietan-3-yl)methanone;
(E)-N-(1-(3-(4-(5-(3,4-dichloro-5-(trifluoromethyl)phenyl)-5-(trifluoromethyl)-4,5-dihydroisoxazol-3-yl)phenyl)-3-fluoroazetidin-1-yl)-2-methylpropylidene)cyanamide;
1-(3-(4-(5-(4-chloro-3-(trifluoromethyl)phenyl)-5-(trifluoromethyl)-4,5-dihydroisoxazol-3-yl)phenyl)-3-fluoroazetidin-1-yl)-2-methylpropan-1-one;
(3-(4-(5-(4-chloro-3-(trifluoromethyl)phenyl)-5-(trifluoromethyl)-4,5-dihydroisoxazol-3-yl)phenyl)-3-fluoroazetidin-1-yl)(cyclopropyl)methanone;
1-(3-(4-(5-(4-chloro-3-(trifluoromethyl)phenyl)-5-(trifluoromethyl)-4,5-dihydroisoxazol-3-yl)phenyl)-3-fluoroazetidin-1-yl)-3,3,3-trifluoropropan-1-one;
1-(3-(4-(5-(4-chloro-3-(trifluoromethyl)phenyl)-5-(trifluoromethyl)-4,5-dihydroisoxazol-3-yl)phenyl)-3-fluoroazetidin-1-yl)-2-(methylthio)ethanone;
1-(3-(4-(5-(4-chloro-3-(trifluoromethyl)phenyl)-5-(trifluoromethyl)-4,5-dihydroisoxazol-3-yl)phenyl)-3-fluoroazetidin-1-yl)-2-(methylsulfinyl)ethanone;
1-(3-(4-(5-(4-chloro-3-(trifluoromethyl)phenyl)-5-(trifluoromethyl)-4,5-dihydroisoxazol-3-yl)phenyl)-3-fluoroazetidin-1-yl)-2-(methylsulfonyl)ethanone;
1-(3-(4-(5-(4-chloro-3-(trifluoromethyl)phenyl)-5-(trifluoromethyl)-4,5-dihydroisoxazol-3-yl)phenyl)-3-fluoroazetidin-1-yl)-2-(1H-pyrazol-1-yl)ethanone;
1-(3-(4-(5-(4-chloro-3-(trifluoromethyl)phenyl)-5-(trifluoromethyl)-4,5-dihydroisoxazol-3-yl)phenyl)-3-fluoroazetidin-1-yl)-2-hydroxy-2-methylpropan-1-one;
(3-{4-[5-(3-Chloro-4-trifluoromethyl-phenyl)-5-trifluoromethyl-4,5-dihydro-isoxazol-3-yl]-phenyl}-3-fluoro-azetidin-1-yl)-thietan-3-yl-methanone;
(3-(4-(5-(4-chloro-3-(trifluoromethyl)phenyl)-5-(trifluoromethyl)-4,5-dihydroisoxazol-3-yl)phenyl)-3-fluoroazetidin-1-yl)(1-oxidothietan-3-yl)methanone;
(3-(4-(5-(4-chloro-3-(trifluoromethyl)phenyl)-5-(trifluoromethyl)-4,5-dihydroisoxazol-3-yl)phenyl)-3-fluoroazetidin-1-yl)(1,1-dioxidothietan-3-yl)methanone;
(E)-N-(1-(3-(4-(5-(4-chloro-3-(trifluoromethyl)phenyl)-5-(trifluoromethyl)-4,5-dihydroisoxazol-3-yl)phenyl)-3-fluoroazetidin-1-yl)-2-methylpropylidene)cyanamide;
1-(3-fluoro-3-(4-(5-(trifluoromethyl)-5-(3-(trifluoromethyl)phenyl)-4,5-dihydroisoxazol-3-yl)phenyl)azetidin-1-yl)-2-methylpropan-1-one;
cyclopropyl(3-fluoro-3-(4-(5-(trifluoromethyl)-5-(3-(trifluoromethyl)phenyl)-4,5-dihydroisoxazol-3-yl)phenyl)azetidin-1-yl)methanone;
3,3,3-trifluoro-1-(3-fluoro-3-(4-(5-(trifluoromethyl)-5-(3-(trifluoromethyl)phenyl)-4,5-dihydroisoxazol-3-yl)phenyl)azetidin-1-yl)propan-1-one;
1-(3-fluoro-3-(4-(5-(trifluoromethyl)-5-(3-(trifluoromethyl)phenyl)-4,5-dihydroisoxazol-3-yl)phenyl)azetidin-1-yl)-2-(methylthio)ethanone;
1-(3-fluoro-3-(4-(5-(trifluoromethyl)-5-(3-(trifluoromethyl)phenyl)-4,5-dihydroisoxazol-3-yl)phenyl)azetidin-1-yl)-2-(methylsulfinyl)ethanone;
1-(3-fluoro-3-(4-(5-(trifluoromethyl)-5-(3-(trifluoromethyl)phenyl)-4,5-dihydroisoxazol-3-yl)phenyl)azetidin-1-yl)-2-(methylsulfonyl)ethanone;
1-(3-fluoro-3-(4-(5-(trifluoromethyl)-5-(3-(trifluoromethyl)phenyl)-4,5-dihydroisoxazol-3-yl)phenyl)azetidin-1-yl)-2-(1H-pyrazol-1-yl)ethanone;
1-(3-fluoro-3-(4-(5-(trifluoromethyl)-5-(3-(trifluoromethyl)phenyl)-4,5-dihydroisoxazol-3-yl)phenyl)azetidin-1-yl)-2-hydroxy-2-methylpropan-1-one;
(3-Fluoro-3-{-4-[5-trifluoromethyl-5-(4-trifluoromethyl-phenyl)-4,5-dihydro-isoxazol-3-yl]-phenyl}-azetidin-1-yl)-thietan-3-yl-methanone;
(3-fluoro-3-(4-(5-(trifluoromethyl)-5-(3-(trifluoromethyl)phenyl)-4,5-dihydroisoxazol-3-yl)phenyl)azetidin-1-yl)(1-oxidothietan-3-yl)methanone;
(1,1-dioxidothietan-3-yl)(3-fluoro-3-(4-(5-(trifluoromethyl)-5-(3-(trifluoromethyl)phenyl)-4,5-dihydroisoxazol-3-yl)phenyl)azetidin-1-yl)methanone;
(E)-N-(1-(3-fluoro-3-(4-(5-(trifluoromethyl)-5-(3-(trifluoromethyl)phenyl)-4,5-dihydroisoxazol-3-yl)phenyl)azetidin-1-yl)-2-methylpropylidene)cyanamide;
1-(3-(4-(5-(3,4-difluoro-5-(trifluoromethyl)phenyl)-5-(trifluoromethyl)-4,5-dihydroisoxazol-3-yl)phenyl)-3-fluoroazetidin-1-yl)-2-methylpropan-1-one;
cyclopropyl(3-(4-(5-(3,4-difluoro-5-(trifluoromethyl)phenyl)-5-(trifluoromethyl)-4,5-dihydroisoxazol-3-yl)phenyl)-3-fluoroazetidin-1-yl)methanone;
1-(3-(4-(5-(3,4-difluoro-5-(trifluoromethyl)phenyl)-5-(trifluoromethyl)-4,5-dihydroisoxazol-3-yl)phenyl)-3-fluoroazetidin-1-yl)-3,3,3-trifluoropropan-1-one;
1-(3-(4-(5-(3,4-difluoro-5-(trifluoromethyl)phenyl)-5-(trifluoromethyl)-4,5-dihydroisoxazol-3-yl)phenyl)-3-fluoroazetidin-1-yl)-2-(methylthio)ethanone;
1-(3-(4-(5-(3,4-difluoro-5-(trifluoromethyl)phenyl)-5-(trifluoromethyl)-4,5-dihydroisoxazol-3-yl)phenyl)-3-fluoroazetidin-1-yl)-2-(methylsulfinyl)ethanone;
1-(3-(4-(5-(3,4-difluoro-5-(trifluoromethyl)phenyl)-5-(trifluoromethyl)-4,5-dihydroisoxazol-3-yl)phenyl)-3-fluoroazetidin-1-yl)-2-(methylsulfonyl)ethanone;
1-(3-(4-(5-(3,4-difluoro-5-(trifluoromethyl)phenyl)-5-(trifluoromethyl)-4,5-dihydroisoxazol-3-yl)phenyl)-3-fluoroazetidin-1-yl)-2-(1H-pyrazol-1-yl)ethanone;
1-(3-(4-(5-(3,4-difluoro-5-(trifluoromethyl)phenyl)-5-(trifluoromethyl)-4,5-dihydroisoxazol-3-yl)phenyl)-3-fluoroazetidin-1-yl)-2-hydroxy-2-methylpropan-1-one;
(3-{4-[5-(3,4-Difluoro-5-trifluoromethyl-phenyl)-5-trifluoromethyl-4,5-dihydro-isoxazol-3-yl]-phenyl}-3-fluoroazetidin-1-yl)-thietan-3-yl-methanone;
(3-(4-(5-(3,4-difluoro-5-(trifluoromethyl)phenyl)-5-(trifluoromethyl)-4,5-dihydroisoxazol-3-yl)phenyl)-3-fluoroazetidin-1-yl)(1-oxidothietan-3-yl)methanone;
(3-(4-(5-(3,4-difluoro-5-(trifluoromethyl)phenyl)-5-(trifluoromethyl)-4,5-dihydroisoxazol-3-yl)phenyl)-3-fluoroazetidin-1-yl)(1,1-dioxidothietan-3-yl)methanone;
(E)-N-(1-(3-(4-(5-(3,4-difluoro-5-(trifluoromethyl)phenyl)-5-(trifluoromethyl)-4,5-dihydroisoxazol-3-yl)phenyl)-3-fluoroazetidin-1-yl)-2-methylpropylidene)cyanamide;

1-(3-(4-(5-(3-chloro-4-fluorophenyl)-5-(trifluoromethyl)-4,5-dihydroisoxazol-3-yl)phenyl)-3-fluoroazetidin-1-yl)-2-methylpropan-1-one;

(3-(4-(5-(3-chloro-4-fluorophenyl)-5-(trifluoromethyl)-4,5-dihydroisoxazol-3-yl)phenyl)-3-fluoroazetidin-1-yl)(cyclopropyl)methanone;

1-(3-(4-(5-(3-chloro-4-fluorophenyl)-5-(trifluoromethyl)-4,5-dihydroisoxazol-3-yl)phenyl)-3-fluoroazetidin-1-yl)-3,3,3-trifluoropropan-1-one;

1-(3-(4-(5-(3-chloro-4-fluorophenyl)-5-(trifluoromethyl)-4,5-dihydroisoxazol-3-yl)phenyl)-3-fluoroazetidin-1-yl)-2-(methylthio)ethanone;

1-(3-(4-(5-(3-chloro-4-fluorophenyl)-5-(trifluoromethyl)-4,5-dihydroisoxazol-3-yl)phenyl)-3-fluoroazetidin-1-yl)-2-(methylsulfinyl)ethanone;

1-(3-(4-(5-(3-chloro-4-fluorophenyl)-5-(trifluoromethyl)-4,5-dihydroisoxazol-3-yl)phenyl)-3-fluoroazetidin-1-yl)-2-(methylsulfonyl)ethanone;

1-(3-(4-(5-(3-chloro-4-fluorophenyl)-5-(trifluoromethyl)-4,5-dihydroisoxazol-3-yl)phenyl)-3-fluoroazetidin-1-yl)-2-(1H-pyrazol-1-yl)ethanone;

1-(3-(4-(5-(3-chloro-4-fluorophenyl)-5-(trifluoromethyl)-4,5-dihydroisoxazol-3-yl)phenyl)-3-fluoroazetidin-1-yl)-2-hydroxy-2-methylpropan-1-one;

(3-{4-[5-(3-Chloro-4-fluoro-phenyl)-5-trifluoromethyl-4,5-dihydro-isoxazol-3-yl]-phenyl}-3-fluoro-azetidin-1-yl)-thietan-3-yl-methanone;

(3-(4-(5-(3-chloro-4-fluorophenyl)-5-(trifluoromethyl)-4,5-dihydroisoxazol-3-yl)phenyl)-3-fluoroazetidin-1-yl)(1-oxidothietan-3-yl)methanone;

(3-(4-(5-(3-chloro-4-fluorophenyl)-5-(trifluoromethyl)-4,5-dihydroisoxazol-3-yl)phenyl)-3-fluoroazetidin-1-yl)(1,1-dioxidothietan-3-yl)methanone;

(E)-N-(1-(3-(4-(5-(3-chloro-4-fluorophenyl)-5-(trifluoromethyl)-4,5-dihydroisoxazol-3-yl)phenyl)-3-fluoroazetidin-1-yl)-2-methylpropylidene)cyanamide;

1-(3-(4-(5-(3-chloro-5-fluorophenyl)-5-(trifluoromethyl)-4,5-dihydroisoxazol-3-yl)phenyl)-3-fluoroazetidin-1-yl)-2-methylpropan-1-one;

(3-(4-(5-(3-chloro-5-fluorophenyl)-5-(trifluoromethyl)-4,5-dihydroisoxazol-3-yl)phenyl)-3-fluoroazetidin-1-yl)(cyclopropyl)methanone;

1-(3-(4-(5-(3-chloro-5-fluorophenyl)-5-(trifluoromethyl)-4,5-dihydroisoxazol-3-yl)phenyl)-3-fluoroazetidin-1-yl)-3,3,3-trifluoropropan-1-one;

1-(3-(4-(5-(3-chloro-5-fluorophenyl)-5-(trifluoromethyl)-4,5-dihydroisoxazol-3-yl)phenyl)-3-fluoroazetidin-1-yl)-2-(methylthio)ethanone;

1-(3-(4-(5-(3-chloro-5-fluorophenyl)-5-(trifluoromethyl)-4,5-dihydroisoxazol-3-yl)phenyl)-3-fluoroazetidin-1-yl)-2-(methylsulfinyl)ethanone;

1-(3-(4-(5-(3-chloro-5-fluorophenyl)-5-(trifluoromethyl)-4,5-dihydroisoxazol-3-yl)phenyl)-3-fluoroazetidin-1-yl)-2-(methylsulfonyl)ethanone;

1-(3-(4-(5-(3-chloro-5-fluorophenyl)-5-(trifluoromethyl)-4,5-dihydroisoxazol-3-yl)phenyl)-3-fluoroazetidin-1-yl)-2-(1H-pyrazol-1-yl)ethanone;

1-(3-(4-(5-(3-chloro-5-fluorophenyl)-5-(trifluoromethyl)-4,5-dihydroisoxazol-3-yl)phenyl)-3-fluoroazetidin-1-yl)-2-hydroxy-2-methylpropan-1-one;

(3-{4-[5-(3-chloro-5-fluorophenyl)-5-trifluoromethyl-4,5-dihydro-isoxazol-3-yl]-phenyl}-3-fluoro-azetidin-1-yl)-thietan-3-yl-methanone;

(3-(4-(5-(3-chloro-5-fluorophenyl)-5-(trifluoromethyl)-4,5-dihydroisoxazol-3-yl)phenyl)-3-fluoroazetidin-1-yl)(1-oxidothietan-3-yl)methanone;

(3-(4-(5-(3-chloro-5-fluorophenyl)-5-(trifluoromethyl)-4,5-dihydroisoxazol-3-yl)phenyl)-3-fluoroazetidin-1-yl)(1,1-dioxidothietan-3-yl)methanone;

(E)-N-(1-(3-(4-(5-(3-chloro-5-fluorophenyl)-5-(trifluoromethyl)-4,5-dihydroisoxazol-3-yl)phenyl)-3-fluoroazetidin-1-yl)-2-methylpropylidene)cyanamide;

1-(3-fluoro-3-(4-(5-(trifluoromethyl)-5-(3,4,5-trifluorophenyl)-4,5-dihydroisoxazol-3-yl)phenyl)azetidin-1-yl)-2-methylpropan-1-one;

cyclopropyl(3-fluoro-3-(4-(5-(trifluoromethyl)-5-(3,4,5-trifluorophenyl)-4,5-dihydroisoxazol-3-yl)phenyl)azetidin-1-yl)methanone;

3,3,3-trifluoro-1-(3-fluoro-3-(4-(5-(trifluoromethyl)-5-(3,4,5-trifluorophenyl)-4,5-dihydroisoxazol-3-yl)phenyl)azetidin-1-yl)propan-1-one;

1-(3-fluoro-3-(4-(5-(trifluoromethyl)-5-(3,4,5-trifluorophenyl)-4,5-dihydroisoxazol-3-yl)phenyl)azetidin-1-yl)-2-(methylthio)ethanone;

1-(3-fluoro-3-(4-(5-(trifluoromethyl)-5-(3,4,5-trifluorophenyl)-4,5-dihydroisoxazol-3-yl)phenyl)azetidin-1-yl)-2-(methylsulfinyl)ethanone;

1-(3-fluoro-3-(4-(5-(trifluoromethyl)-5-(3,4,5-trifluorophenyl)-4,5-dihydroisoxazol-3-yl)phenyl)azetidin-1-yl)-2-(methylsulfonyl)ethanone;

1-(3-fluoro-3-(4-(5-(trifluoromethyl)-5-(3,4,5-trifluorophenyl)-4,5-dihydroisoxazol-3-yl)phenyl)azetidin-1-yl)-2-(1H-pyrazol-1-yl)ethanone;

1-(3-fluoro-3-(4-(5-(trifluoromethyl)-5-(3,4,5-trifluorophenyl)-4,5-dihydroisoxazol-3-yl)phenyl)azetidin-1-yl)-2-hydroxy-2-methylpropan-1-one;

(3-Fluoro-3-{-4-[5-trifluoromethyl-5-(3,4,5-trifluorophenyl)-4,5-dihydro-isoxazol-3-yl]-phenyl}-azetidin-1-yl)-thietan-3-yl-methanone;

(3-fluoro-3-(4-(5-(trifluoromethyl)-5-(3,4,5-trifluorophenyl)-4,5-dihydroisoxazol-3-yl)phenyl)azetidin-1-yl)(1-oxidothietan-3-yl)methanone;

(1,1-dioxidothietan-3-yl)(3-fluoro-3-(4-(5-(trifluoromethyl)-5-(3,4,5-trifluorophenyl)-4,5-dihydroisoxazol-3-yl)phenyl)azetidin-1-yl)methanone;

(E)-N-(1-(3-fluoro-3-(4-(5-(trifluoromethyl)-5-(3,4,5-trifluorophenyl)-4,5-dihydroisoxazol-3-yl)phenyl)azetidin-1-yl)-2-methylpropylidene)cyanamide;

2-(1-(cyclopropanecarbonyl)-3-fluoroazetidin-3-yl)-5-(5-(3,4,5-trichlorophenyl)-5-(trifluoromethyl)-4,5-dihydroisoxazol-3-yl)benzonitrile; and cyclopropyl(3-(4-(5-(3,4-dichloro-5-(trifluoromethyl)phenyl)-5-(trifluoromethyl)-4,5-dihydroisoxazol-3-yl)phenyl)-3-hydroxyazetidin-1-yl)methanone, stereoisomers thereof, pharmaceutical and veterinarily acceptable salts thereof.

In another aspect of the invention are Formula (1) compounds selected from:

1-(3-(5-(5-(3,5-dichloro-4-fluorophenyl)-5-(trifluoromethyl)-4,5-dihydroisoxazol-3-yl)pyridin-2-yl)-3-fluoroazetidin-1-yl)-2-methylpropan-1-one;

cyclopropyl(3-(5-(5-(3,5-dichloro-4-fluorophenyl)-5-(trifluoromethyl)-4,5-dihydroisoxazol-3-yl)pyridin-2-yl)-3-fluoroazetidin-1-yl)methanone;

1-(3-(5-(5-(3,5-dichloro-4-fluorophenyl)-5-(trifluoromethyl)-4,5-dihydroisoxazol-3-yl)pyridin-2-yl)-3-fluoroazetidin-1-yl)-3,3,3-trifluoropropan-1-one;

1-(3-(5-(5-(3,5-dichloro-4-fluorophenyl)-5-(trifluoromethyl)-4,5-dihydroisoxazol-3-yl)pyridin-2-yl)-3-fluoroazetidin-1-yl)-2-(methylthio)ethanone;

1-(3-(5-(5-(3,5-dichloro-4-fluorophenyl)-5-(trifluoromethyl)-4,5-dihydroisoxazol-3-yl)pyridin-2-yl)-3-fluoroazetidin-1-yl)-2-(methylsulfinyl)ethanone;

1-(3-(5-(5-(3,5-dichloro-4-fluorophenyl)-5-(trifluoromethyl)-4,5-dihydroisoxazol-3-yl)pyridin-2-yl)-3-fluoroazetidin-1-yl)-2-(methylsulfonyl)ethanone;
1-(3-(5-(5-(3,5-dichloro-4-fluorophenyl)-5-(trifluoromethyl)-4,5-dihydroisoxazol-3-yl)pyridin-2-yl)-3-fluoroazetidin-1-yl)-2-(1H-pyrazol-1-yl)ethanone;
1-(3-(5-(5-(3,5-dichloro-4-fluorophenyl)-5-(trifluoromethyl)-4,5-dihydroisoxazol-3-yl)pyridin-2-yl)-3-fluoroazetidin-1-yl)-2-hydroxy-2-methylpropan-1-one;
(3-{5-[5-(3,5-Dichloro-4-fluoro-phenyl)-5-trifluoromethyl-4,5-dihydro-isoxazol-3-yl]-pyridin-2-yl}-3-fluoro-azetidin-1-yl)-thietan-3-yl-methanone;
(3-(5-(5-(3,5-dichloro-4-fluorophenyl)-5-(trifluoromethyl)-4,5-dihydroisoxazol-3-yl)pyridin-2-yl)-3-fluoroazetidin-1-yl)(1-oxidothietan-3-yl)methanone;
(3-(5-(5-(3,5-dichloro-4-fluorophenyl)-5-(trifluoromethyl)-4,5-dihydroisoxazol-3-yl)pyridin-2-yl)-3-fluoroazetidin-1-yl)(1,1-dioxidothietan-3-yl)methanone;
(E)-N-(1-(3-(5-(5-(3,5-dichloro-4-fluorophenyl)-5-(trifluoromethyl)-4,5-dihydroisoxazol-3-yl)pyridin-2-yl)-3-fluoroazetidin-1-yl)-2-methylpropylidene)cyanamide;
1-(3-fluoro-3-(5-(5-(3,4,5-trichlorophenyl)-5-(trifluoromethyl)-4,5-dihydroisoxazol-3-yl)pyridin-2-yl)azetidin-1-yl)-2-methylpropan-1-one;
cyclopropyl(3-fluoro-3-(5-(5-(3,4,5-trichlorophenyl)-5-(trifluoromethyl)-4,5-dihydroisoxazol-3-yl)pyridin-2-yl)azetidin-1-yl)methanone;
3,3,3-trifluoro-1-(3-fluoro-3-(5-(5-(3,4,5-trichlorophenyl)-5-(trifluoromethyl)-4,5-dihydroisoxazol-3-yl)pyridin-2-yl)azetidin-1-yl)propan-1-one;
1-(3-fluoro-3-(5-(5-(3,4,5-trichlorophenyl)-5-(trifluoromethyl)-4,5-dihydroisoxazol-3-yl)pyridin-2-yl)azetidin-1-yl)-2-(methylthio)ethanone;
1-(3-fluoro-3-(5-(5-(3,4,5-trichlorophenyl)-5-(trifluoromethyl)-4,5-dihydroisoxazol-3-yl)pyridin-2-yl)azetidin-1-yl)-2-(methylsulfinyl)ethanone;
1-(3-fluoro-3-(5-(5-(3,4,5-trichlorophenyl)-5-(trifluoromethyl)-4,5-dihydroisoxazol-3-yl)pyridin-2-yl)azetidin-1-yl)-2-(methylsulfonyl)ethanone;
1-(3-fluoro-3-(5-(5-(3,4,5-trichlorophenyl)-5-(trifluoromethyl)-4,5-dihydroisoxazol-3-yl)pyridin-2-yl)azetidin-1-yl)-2-(1H-pyrazol-1-yl)ethanone;
1-(3-fluoro-3-(5-(5-(3,4,5-trichlorophenyl)-5-(trifluoromethyl)-4,5-dihydroisoxazol-3-yl)pyridin-2-yl)azetidin-1-yl)-2-hydroxy-2-methylpropan-1-one;
(3-Fluoro-3-{5-[5-(3,4,5-trichloro-phenyl)-5-trifluoromethyl-4,5-dihydro-isoxazol-3-yl]-pyridin-2-yl}-azetidin-1-yl)-thietan-3-yl-methanone;
(3-fluoro-3-(5-(5-(3,4,5-trichlorophenyl)-5-(trifluoromethyl)-4,5-dihydroisoxazol-3-yl)pyridin-2-yl)azetidin-1-yl)(1-oxidothietan-3-yl)methanone;
(1,1-dioxidothietan-3-yl)(3-fluoro-3-(5-(5-(3,4,5-trichlorophenyl)-5-(trifluoromethyl)-4,5-dihydroisoxazol-3-yl)pyridin-2-yl)azetidin-1-yl)methanone;
(E)-N-(1-(3-fluoro-3-(5-(5-(3,4,5-trichlorophenyl)-5-(trifluoromethyl)-4,5-dihydroisoxazol-3-yl)pyridin-2-yl)azetidin-1-yl)-2-methylpropylidene)cyanamide;
1-(3-(5-(5-(3,4-dichloro-5-(trifluoromethyl)phenyl)-5-(trifluoromethyl)-4,5-dihydroisoxazol-3-yl)pyridin-2-yl)-3-fluoroazetidin-1-yl)-2-methylpropan-1-one;
cyclopropyl(3-(5-(5-(3,4-dichloro-5-(trifluoromethyl)phenyl)-5-(trifluoromethyl)-4,5-dihydroisoxazol-3-yl)pyridin-2-yl)-3-fluoroazetidin-1-yl)methanone;
1-(3-(5-(5-(3,4-dichloro-5-(trifluoromethyl)phenyl)-5-(trifluoromethyl)-4,5-dihydroisoxazol-3-yl)pyridin-2-yl)-3-fluoroazetidin-1-yl)-3,3,3-trifluoropropan-1-one;
1-(3-(5-(5-(3,4-dichloro-5-(trifluoromethyl)phenyl)-5-(trifluoromethyl)-4,5-dihydroisoxazol-3-yl)pyridin-2-yl)-3-fluoroazetidin-1-yl)-2-(methylthio)ethanone;
1-(3-(5-(5-(3,4-dichloro-5-(trifluoromethyl)phenyl)-5-(trifluoromethyl)-4,5-dihydroisoxazol-3-yl)pyridin-2-yl)-3-fluoroazetidin-1-yl)-2-(methylsulfinyl)ethanone;
1-(3-(5-(5-(3,4-dichloro-5-(trifluoromethyl)phenyl)-5-(trifluoromethyl)-4,5-dihydroisoxazol-3-yl)pyridin-2-yl)-3-fluoroazetidin-1-yl)-2-(methylsulfonyl)ethanone;
1-(3-(5-(5-(3,4-dichloro-5-(trifluoromethyl)phenyl)-5-(trifluoromethyl)-4,5-dihydroisoxazol-3-yl)pyridin-2-yl)-3-fluoroazetidin-1-yl)-2-(1H-pyrazol-1-yl)ethanone;
1-(3-(5-(5-(3,4-dichloro-5-(trifluoromethyl)phenyl)-5-(trifluoromethyl)-4,5-dihydroisoxazol-3-yl)pyridin-2-yl)-3-fluoroazetidin-1-yl)-2-hydroxy-2-methylpropan-1-one;
(3-{5-[5-(3,4-Dichloro-5-trifluoromethyl-phenyl)-5-trifluoromethyl-4,5-dihydro-isoxazol-3-yl]-pyridin-2-yl}-3-fluoro-azetidin-1-yl)-thietan-3-yl-methanone;
(3-(5-(5-(3,4-dichloro-5-(trifluoromethyl)phenyl)-5-(trifluoromethyl)-4,5-dihydroisoxazol-3-yl)pyridin-2-yl)-3-fluoroazetidin-1-yl)(1-oxidothietan-3-yl)methanone;
(3-(5-(5-(3,4-dichloro-5-(trifluoromethyl)phenyl)-5-(trifluoromethyl)-4,5-dihydroisoxazol-3-yl)pyridin-2-yl)-3-fluoroazetidin-1-yl)(1,1-dioxidothietan-3-yl)methanone;
(E)-N-(1-(3-(5-(5-(3,4-dichloro-5-(trifluoromethyl)phenyl)-5-(trifluoromethyl)-4,5-dihydroisoxazol-3-yl)pyridin-2-yl)-3-fluoroazetidin-1-yl)-2-methylpropylidene)cyanamide;
1-(3-(5-(5-(4-chloro-3-(trifluoromethyl)phenyl)-5-(trifluoromethyl)-4,5-dihydroisoxazol-3-yl)pyridin-2-yl)-3-fluoroazetidin-1-yl)-2-methylpropan-1-one;
(3-(5-(5-(4-chloro-3-(trifluoromethyl)phenyl)-5-(trifluoromethyl)-4,5-dihydroisoxazol-3-yl)pyridin-2-yl)-3-fluoroazetidin-1-yl)(cyclopropyl)methanone;
1-(3-(5-(5-(4-chloro-3-(trifluoromethyl)phenyl)-5-(trifluoromethyl)-4,5-dihydroisoxazol-3-yl)pyridin-2-yl)-3-fluoroazetidin-1-yl)-3,3,3-trifluoropropan-1-one;
1-(3-(5-(5-(4-chloro-3-(trifluoromethyl)phenyl)-5-(trifluoromethyl)-4,5-dihydroisoxazol-3-yl)pyridin-2-yl)-3-fluoroazetidin-1-yl)-2-(methylthio)ethanone;
1-(3-(5-(5-(4-chloro-3-(trifluoromethyl)phenyl)-5-(trifluoromethyl)-4,5-dihydroisoxazol-3-yl)pyridin-2-yl)-3-fluoroazetidin-1-yl)-2-(methylsulfinyl)ethanone;
1-(3-(5-(5-(4-chloro-3-(trifluoromethyl)phenyl)-5-(trifluoromethyl)-4,5-dihydroisoxazol-3-yl)pyridin-2-yl)-3-fluoroazetidin-1-yl)-2-(methylsulfonyl)ethanone;
1-(3-(5-(5-(4-chloro-3-(trifluoromethyl)phenyl)-5-(trifluoromethyl)-4,5-dihydroisoxazol-3-yl)pyridin-2-yl)-3-fluoroazetidin-1-yl)-2-(1H-pyrazol-1-yl)ethanone;
1-(3-(5-(5-(4-chloro-3-(trifluoromethyl)phenyl)-5-(trifluoromethyl)-4,5-dihydroisoxazol-3-yl)pyridin-2-yl)-3-fluoroazetidin-1-yl)-2-hydroxy-2-methylpropan-1-one;
(3-{5-[5-(4-Chloro-3-trifluoromethyl-phenyl)-5-trifluoromethyl-4,5-dihydro-isoxazol-3-yl]-pyridin-2-yl}-3-fluoro-azetidin-1-yl)-thietan-3-yl-methanone;
(3-(5-(5-(4-chloro-3-(trifluoromethyl)phenyl)-5-(trifluoromethyl)-4,5-dihydroisoxazol-3-yl)pyridin-2-yl)-3-fluoroazetidin-1-yl)(1-oxidothietan-3-yl)methanone;
(3-(5-(5-(4-chloro-3-(trifluoromethyl)phenyl)-5-(trifluoromethyl)-4,5-dihydroisoxazol-3-yl)pyridin-2-yl)-3-fluoroazetidin-1-yl)(1,1-dioxidothietan-3-yl)methanone;
(E)-N-(1-(3-(5-(5-(4-chloro-3-(trifluoromethyl)phenyl)-5-(trifluoromethyl)-4,5-dihydroisoxazol-3-yl)pyridin-2-yl)-3-fluoroazetidin-1-yl)-2-methylpropylidene)cyanamide;
1-(3-fluoro-3-(5-(5-(trifluoromethyl)-5-(3-(trifluoromethyl)phenyl)-4,5-dihydroisoxazol-3-yl)pyridin-2-yl)azetidin-1-yl)-2-methylpropan-1-one;

cyclopropyl(3-fluoro-3-(5-(5-(trifluoromethyl)-5-(3-(trifluoromethyl)phenyl)-4,5-dihydroisoxazol-3-yl)pyridin-2-yl)azetidin-1-yl)methanone;
3,3,3-trifluoro-1-(3-fluoro-3-(5-(5-(trifluoromethyl)-5-(3-(trifluoromethyl)phenyl)-4,5-dihydroisoxazol-3-yl)pyridin-2-yl)azetidin-1-yl)propan-1-one;
1-(3-fluoro-3-(5-(5-(trifluoromethyl)-5-(3-(trifluoromethyl)phenyl)-4,5-dihydroisoxazol-3-yl)pyridin-2-yl)azetidin-1-yl)-2-(methylthio)ethanone;
1-(3-fluoro-3-(5-(5-(trifluoromethyl)-5-(3-(trifluoromethyl)phenyl)-4,5-dihydroisoxazol-3-yl)pyridin-2-yl)azetidin-1-yl)-2-(methylsulfinyl)ethanone;
1-(3-fluoro-3-(5-(5-(trifluoromethyl)-5-(3-(trifluoromethyl)phenyl)-4,5-dihydroisoxazol-3-yl)pyridin-2-yl)azetidin-1-yl)-2-(methylsulfonyl)ethanone;
1-(3-fluoro-3-(5-(5-(trifluoromethyl)-5-(3-(trifluoromethyl)phenyl)-4,5-dihydroisoxazol-3-yl)pyridin-2-yl)azetidin-1-yl)-2-(1H-pyrazol-1-yl)ethanone;
1-(3-fluoro-3-(5-(5-(trifluoromethyl)-5-(3-(trifluoromethyl)phenyl)-4,5-dihydroisoxazol-3-yl)pyridin-2-yl)azetidin-1-yl)-2-hydroxy-2-methylpropan-1-one;
(3-Fluoro-3-{5-[5-trifluoromethyl-5-(3-trifluoromethyl-phenyl)-4,5-dihydro-isoxazol-3-yl]-pyridin-2-yl}-azetidin-1-yl)-thietan-3-yl-methanone;
(3-fluoro-3-(5-(5-(trifluoromethyl)-5-(3-(trifluoromethyl)phenyl)-4,5-dihydroisoxazol-3-yl)pyridin-2-yl)azetidin-1-yl)(1-oxidothietan-3-yl)methanone;
(1,1-dioxidothietan-3-yl)(3-fluoro-3-(5-(5-(trifluoromethyl)-5-(3-(trifluoromethyl)phenyl)-4,5-dihydroisoxazol-3-yl)pyridin-2-yl)azetidin-1-yl)methanone;
(E)-N-(1-(3-fluoro-3-(5-(5-(trifluoromethyl)-5-(3-(trifluoromethyl)phenyl)-4,5-dihydroisoxazol-3-yl)pyridin-2-yl)azetidin-1-yl)-2-methylpropylidene)cyanamide;
1-(3-(5-(5-(3,4-difluoro-5-(trifluoromethyl)phenyl)-5-(trifluoromethyl)-4,5-dihydroisoxazol-3-yl)pyridin-2-yl)-3-fluoroazetidin-1-yl)-2-methylpropan-1-one;
cyclopropyl(3-(5-(5-(3,4-difluoro-5-(trifluoromethyl)phenyl)-5-(trifluoromethyl)-4,5-dihydroisoxazol-3-yl)pyridin-2-yl)-3-fluoroazetidin-1-yl)methanone;
1-(3-(5-(5-(3,4-difluoro-5-(trifluoromethyl)phenyl)-5-(trifluoromethyl)-4,5-dihydroisoxazol-3-yl)pyridin-2-yl)-3-fluoroazetidin-1-yl)-3,3,3-trifluoropropan-1-one;
1-(3-(5-(5-(3,4-difluoro-5-(trifluoromethyl)phenyl)-5-(trifluoromethyl)-4,5-dihydroisoxazol-3-yl)pyridin-2-yl)-3-fluoroazetidin-1-yl)-2-(methylthio)ethanone;
1-(3-(5-(5-(3,4-difluoro-5-(trifluoromethyl)phenyl)-5-(trifluoromethyl)-4,5-dihydroisoxazol-3-yl)pyridin-2-yl)-3-fluoroazetidin-1-yl)-2-(methylsulfinyl)ethanone;
1-(3-(5-(5-(3,4-difluoro-5-(trifluoromethyl)phenyl)-5-(trifluoromethyl)-4,5-dihydroisoxazol-3-yl)pyridin-2-yl)-3-fluoroazetidin-1-yl)-2-(methylsulfonyl)ethanone;
1-(3-(5-(5-(3,4-difluoro-5-(trifluoromethyl)phenyl)-5-(trifluoromethyl)-4,5-dihydroisoxazol-3-yl)pyridin-2-yl)-3-fluoroazetidin-1-yl)-2-(1H-pyrazol-1-yl)ethanone;
1-(3-(5-(5-(3,4-difluoro-5-(trifluoromethyl)phenyl)-5-(trifluoromethyl)-4,5-dihydroisoxazol-3-yl)pyridin-2-yl)-3-fluoroazetidin-1-yl)-2-hydroxy-2-methylpropan-1-one;
(3-{5-[5-(3,4-Difluoro-5-trifluoromethyl-phenyl)-5-trifluoromethyl-4,5-dihydro-isoxazol-3-yl]-pyridin-2-yl}-3-fluoro-azetidin-1-yl)-thietan-3-yl-methanone;
(3-(5-(5-(3,4-difluoro-5-(trifluoromethyl)phenyl)-5-(trifluoromethyl)-4,5-dihydroisoxazol-3-yl)pyridin-2-yl)-3-fluoroazetidin-1-yl)(1-oxidothietan-3-yl)methanone;
(3-(5-(5-(3,4-difluoro-5-(trifluoromethyl)phenyl)-5-(trifluoromethyl)-4,5-dihydroisoxazol-3-yl)pyridin-2-yl)-3-fluoroazetidin-1-yl)(1,1-dioxidothietan-3-yl)methanone;
(E)-N-(1-(3-(5-(5-(3,4-difluoro-5-(trifluoromethyl)phenyl)-5-(trifluoromethyl)-4,5-dihydroisoxazol-3-yl)pyridin-2-yl)-3-fluoroazetidin-1-yl)-2-methylpropylidene)cyanamide;
1-(3-(5-(5-(3-chloro-4-fluorophenyl)-5-(trifluoromethyl)-4,5-dihydroisoxazol-3-yl)pyridin-2-yl)-3-fluoroazetidin-1-yl)-2-methylpropan-1-one;
(3-(5-(5-(3-chloro-4-fluorophenyl)-5-(trifluoromethyl)-4,5-dihydroisoxazol-3-yl)pyridin-2-yl)-3-fluoroazetidin-1-yl)(cyclopropyl)methanone;
1-(3-(5-(5-(3-chloro-4-fluorophenyl)-5-(trifluoromethyl)-4,5-dihydroisoxazol-3-yl)pyridin-2-yl)-3-fluoroazetidin-1-yl)-3,3,3-trifluoropropan-1-one;
1-(3-(5-(5-(3-chloro-4-fluorophenyl)-5-(trifluoromethyl)-4,5-dihydroisoxazol-3-yl)pyridin-2-yl)-3-fluoroazetidin-1-yl)-2-(methylthio)ethanone;
1-(3-(5-(5-(3-chloro-4-fluorophenyl)-5-(trifluoromethyl)-4,5-dihydroisoxazol-3-yl)pyridin-2-yl)-3-fluoroazetidin-1-yl)-2-(methylsulfinyl)ethanone;
1-(3-(5-(5-(3-chloro-4-fluorophenyl)-5-(trifluoromethyl)-4,5-dihydroisoxazol-3-yl)pyridin-2-yl)-3-fluoroazetidin-1-yl)-2-(methylsulfonyl)ethanone;
1-(3-(5-(5-(3-chloro-4-fluorophenyl)-5-(trifluoromethyl)-4,5-dihydroisoxazol-3-yl)pyridin-2-yl)-3-fluoroazetidin-1-yl)-2-(1H-pyrazol-1-yl)ethanone;
1-(3-(5-(5-(3-chloro-4-fluorophenyl)-5-(trifluoromethyl)-4,5-dihydroisoxazol-3-yl)pyridin-2-yl)-3-fluoroazetidin-1-yl)-2-hydroxy-2-methylpropan-1-one;
(3-{5-[5-(3-Chloro-4-fluoro-phenyl)-5-trifluoromethyl-4,5-dihydro-isoxazol-3-yl]-pyridin-2-yl}-3-fluoro-azetidin-1-yl)-thietan-3-yl-methanone;
(3-(5-(5-(3-chloro-4-fluorophenyl)-5-(trifluoromethyl)-4,5-dihydroisoxazol-3-yl)pyridin-2-yl)-3-fluoroazetidin-1-yl)(1-oxidothietan-3-yl)methanone;
(3-(5-(5-(3-chloro-4-fluorophenyl)-5-(trifluoromethyl)-4,5-dihydroisoxazol-3-yl)pyridin-2-yl)-3-fluoroazetidin-1-yl)(1,1-dioxidothietan-3-yl)methanone;
(E)-N-(1-(3-(5-(5-(3-chloro-4-fluorophenyl)-5-(trifluoromethyl)-4,5-dihydroisoxazol-3-yl)pyridin-2-yl)-3-fluoroazetidin-1-yl)-2-methylpropylidene)cyanamide;
1-(3-(5-(5-(3-chloro-5-fluorophenyl)-5-(trifluoromethyl)-4,5-dihydroisoxazol-3-yl)pyridin-2-yl)-3-fluoroazetidin-1-yl)-2-methylpropan-1-one;
(3-(5-(5-(3-chloro-5-fluorophenyl)-5-(trifluoromethyl)-4,5-dihydroisoxazol-3-yl)pyridin-2-yl)-3-fluoroazetidin-1-yl)(cyclopropyl)methanone;
1-(3-(5-(5-(3-chloro-5-fluorophenyl)-5-(trifluoromethyl)-4,5-dihydroisoxazol-3-yl)pyridin-2-yl)-3-fluoroazetidin-1-yl)-3,3,3-trifluoropropan-1-one;
1-(3-(5-(5-(3-chloro-5-fluorophenyl)-5-(trifluoromethyl)-4,5-dihydroisoxazol-3-yl)pyridin-2-yl)-3-fluoroazetidin-1-yl)-2-(methylthio)ethanone;
1-(3-(5-(5-(3-chloro-5-fluorophenyl)-5-(trifluoromethyl)-4,5-dihydroisoxazol-3-yl)pyridin-2-yl)-3-fluoroazetidin-1-yl)-2-(methylsulfinyl)ethanone;
1-(3-(5-(5-(3-chloro-5-fluorophenyl)-5-(trifluoromethyl)-4,5-dihydroisoxazol-3-yl)pyridin-2-yl)-3-fluoroazetidin-1-yl)-2-(methylsulfonyl)ethanone;
1-(3-(5-(5-(3-chloro-5-fluorophenyl)-5-(trifluoromethyl)-4,5-dihydroisoxazol-3-yl)pyridin-2-yl)-3-fluoroazetidin-1-yl)-2-(1H-pyrazol-1-yl)ethanone;
1-(3-(5-(5-(3-chloro-5-fluorophenyl)-5-(trifluoromethyl)-4,5-dihydroisoxazol-3-yl)pyridin-2-yl)-3-fluoroazetidin-1-yl)-2-hydroxy-2-methylpropan-1-one;
(3-{5-[5-(3-Chloro-5-fluoro-phenyl)-5-trifluoromethyl-4,5-dihydro-isoxazol-3-yl]-pyridin-2-yl}-3-fluoro-azetidin-1-yl)-thietan-3-yl-methanone;

(3-(5-(5-(3-chloro-5-fluorophenyl)-5-(trifluoromethyl)-4,5-dihydroisoxazol-3-yl)pyridin-2-yl)-3-fluoroazetidin-1-yl)(1-oxidothietan-3-yl)methanone;
(3-(5-(5-(3-chloro-5-fluorophenyl)-5-(trifluoromethyl)-4,5-dihydroisoxazol-3-yl)pyridin-2-yl)-3-fluoroazetidin-1-yl)(1,1-dioxidothietan-3-yl)methanone;
(E)-N-(1-(3-(5-(5-(3-chloro-5-fluorophenyl)-5-(trifluoromethyl)-4,5-dihydroisoxazol-3-yl)pyridin-2-yl)-3-fluoroazetidin-1-yl)-2-methylpropylidene)cyanamide;
1-(3-fluoro-3-(5-(5-(trifluoromethyl)-5-(3,4,5-trifluorophenyl)-4,5-dihydroisoxazol-3-yl)pyridin-2-yl)azetidin-1-yl)-2-methylpropan-1-one;
cyclopropyl(3-fluoro-3-(5-(5-(trifluoromethyl)-5-(3,4,5-trifluorophenyl)-4,5-dihydroisoxazol-3-yl)pyridin-2-yl)azetidin-1-yl)methanone;
3,3,3-trifluoro-1-(3-fluoro-3-(5-(5-(trifluoromethyl)-5-(3,4,5-trifluorophenyl)-4,5-dihydroisoxazol-3-yl)pyridin-2-yl)azetidin-1-yl)propan-1-one;
1-(3-fluoro-3-(4-(5-(trifluoromethyl)-5-(3,4,5-trifluorophenyl)-4,5-dihydroisoxazol-3-yl)phenyl)-1,2-diazetidin-1-yl)-2-(methylthio)ethanone;
1-(3-fluoro-3-(5-(5-(trifluoromethyl)-5-(3,4,5-trifluorophenyl)-4,5-dihydroisoxazol-3-yl)pyridin-2-yl)azetidin-1-yl)-2-(methylsulfinyl)ethanone;
1-(3-fluoro-3-(5-(5-(trifluoromethyl)-5-(3,4,5-trifluorophenyl)-4,5-dihydroisoxazol-3-yl)pyridin-2-yl)azetidin-1-yl)-2-(methylsulfonyl)ethanone;
1-(3-fluoro-3-(5-(5-(trifluoromethyl)-5-(3,4,5-trifluorophenyl)-4,5-dihydroisoxazol-3-yl)pyridin-2-yl)azetidin-1-yl)-2-(1H-pyrazol-1-yl)ethanone;
1-(3-fluoro-3-(5-(5-(trifluoromethyl)-5-(3,4,5-trifluorophenyl)-4,5-dihydroisoxazol-3-yl)pyridin-2-yl)azetidin-1-yl)-2-hydroxy-2-methylpropan-1-one;
(3-fluoro-3-{5-[5-trifluoromethyl-5-(3,4,5-trifluorophenyl)-4,5-dihydro-isoxazol-3-yl]-pyridin-2-yl}-azetidin-1-yl)-thietan-3-yl-methanone;
(3-fluoro-3-(5-(5-(trifluoromethyl)-5-(3,4,5-trifluorophenyl)-4,5-dihydroisoxazol-3-yl)pyridin-2-yl)azetidin-1-yl)(1-oxidothietan-3-yl)methanone;
(1,1-dioxidothietan-3-yl)(3-fluoro-3-(5-(5-(trifluoromethyl)-5-(3,4,5-trifluorophenyl)-4,5-dihydroisoxazol-3-yl)pyridin-2-yl)azetidin-1-yl)methanone; and
(E)-N-(1-(3-fluoro-3-(5-(5-(trifluoromethyl)-5-(3,4,5-trifluorophenyl)-4,5-dihydroisoxazol-3-yl)pyridin-2-yl)azetidin-1-yl)-2-methyl propylidene)cyanamide, stereoisomers thereof, pharmaceutical and veterinarily acceptable salts thereof.

In another aspect of the invention, is a compound of Formula (XX)

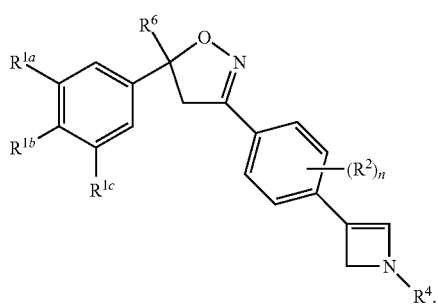

XX

In yet another aspect of the invention is a composition that comprises a) a Formula (XX) compound, stereoisomers thereof, or a veterinarily or pharmaceutically acceptable salt thereof, and (b) a veterinarily or pharmaceutically acceptable excipient, diluent, or carrier. The variables $R^{1a}$, $R^{1b}$, $R^{1c}$, $R^2$, $R^4$, $R^6$, and n are as defined herein. Preferably, the composition comprises a therapeutically effective amount of a Formula (XX) compound, stereoisomer thereof, or veterinarily or pharmaceutically acceptable salt thereof, and a veterinarily or pharmaceutically acceptable excipient, diluent, or carrier.

In another aspect of the invention, is a veterinary or pharmaceutical composition that comprises a) a Formula (1) or Formula (XX) compound, stereoisomers thereof, or a veterinarily or pharmaceutically acceptable salt thereof, and (b) a veterinarily or pharmaceutically acceptable excipient, diluent, or carrier. Preferably, the composition comprises a therapeutically effective amount of a Formula (1) or Formula (XX) compound, stereoisomer thereof, or veterinarily or pharmaceutically acceptable salt thereof, and a veterinarily or pharmaceutically acceptable excipient, diluent, or carrier.

The composition may comprise at least one additional veterinary agent. Preferred additional veterinary agents include endoparasiticides, endectocides, ectoparasiticides, insecticides, and anthelmintics.

In yet another aspect of the invention is the use of a Formula (1) or Formula (XX) compound for the manufacture of a medicament.

In yet another aspect of the invention is a method for treating a parasitic infection or infestation in an animal that includes the step of administering to said animal, in need of such treatment, a therapeutically effective amount of a compound of the present invention, stereoisomer thereof, or veterinarily or pharmaceutically acceptable salt thereof. Formula (1) and Formula (XX) compounds, stereoisomers thereof, veterinarily or pharmaceutically acceptable salts thereof, or compositions thereof, may be administered orally, topically, intramuscularly, subcutaneously, and by intraperitoneal injection. Preferably, the animal is a mammal. More preferably, the mammal is a companion animal or livestock. Preferably, the companion animal is a dog, cat, or horse. Preferably, livestock is bovine, swine, or ovine. Preferably, the animal is a bird. More preferably, the bird is fowl. Preferably the animal is a fish. The compounds of the present invention, and compositions thereof, can be administered to the animal by oral, topical, and intramuscular-, intraperitoneal-, and subcutaneous-injection. Preferably, the compounds of the present invention, and compositions thereof, can be administered to the animal orally or topically.

In yet another aspect of the invention is a method for treating a parasitic infection or infestation in an animal that includes the step of administering to said animal in need of such treatment, a therapeutically effective amount of a Formula (1) or Formula (XX) compound, stereoisomer thereof, or veterinarily or pharmaceutically acceptable salt thereof, in combination with at least one additional veterinary agent. Formula (1) or Formula (XX) compounds, stereoisomers thereof, veterinarily or pharmaceutically acceptable salts thereof, alone, with an additional veterinary agent, or composition thereof, may be administered to the animal orally, topically, or by injection (intramuscular, intraperitoneal, or subcutaneous). Preferred additional veterinary agents include endoparasiticides, endectocides, ectoparasiticides, insecticides, and anthelmintics.

Compounds of the present invention alone, or in combination with an additional veterinary agent may be administered as (a) a single veterinary composition which comprises a compound of the present invention, stereoisomer thereof, veterinarily or pharmaceutically acceptable salt thereof, and optionally, at least one additional veterinary agent as described herein and a veterinarily or pharmaceutically acceptable excipient, diluent, or carrier; or (b) two separate veterinary compositions comprising (i) a first composition comprising a compound of the present invention, stereoisomer thereof, veterinarily or pharmaceutically acceptable salt thereof, and a veterinarily or pharmaceutically acceptable excipient, diluent, or carrier, and (ii) a second composition comprising at least one additional veterinary agent, as described herein and a veterinarily or pharmaceutically acceptable excipient, diluent, or carrier. The veterinary or pharmaceutical compositions may be administered simultaneously or sequentially and in any order.

In another aspect of the invention are compositions comprising a Formula (1) compound, stereoisomer thereof, pharmaceutical or veterinary salt thereof, optionally, at least one additional veterinary agent, which are useful for the control and treatment of parasites in animals.

All of the recited patent publications, patents, and priority documents herein are incorporated by reference, in their entirety.

DEFINITIONS

For purposes of the present invention, as described and claimed herein, the following terms and phrases are defined as follows:

"Additional veterinary agent(s)" as used herein, unless otherwise indicated, refers to other veterinary or pharmaceutical compounds or products that provide a therapeutically effective amount of said agents that are useful for the treatment of a parasitic infection in an animal, as described herein.

"Alkoxy", as used herein, unless otherwise indicated, refers to an oxygen moiety having a further alkyl substituent. The alkyl portion (i.e., alkyl moiety) of an alkoxy group has the same definition as below. Non-limiting examples include: —OCH$_3$, —OCH$_2$CH$_3$, and the like.

"Alkyl", as used herein, unless otherwise indicated, refers to saturated monovalent hydrocarbon alkane radicals of the general formula $C_nH_{2n+1}$. The alkane radical may be straight or branched and may be unsubstituted or substituted. For example, the term "(C$_1$-C$_6$) alkyl" refers to a monovalent, straight or branched aliphatic group containing 1 to 6 carbon atoms. Non-exclusive examples of (C$_1$-C$_6$) alkyl groups include, but are not limited to methyl, ethyl, propyl, isopropyl, sec-butyl, t-butyl, n-propyl, n-butyl, i-butyl, s-butyl, n-pentyl, 1-methylbutyl, 2-methylbutyl, 3-methylbutyl, neopentyl, 3,3-dimethylpropyl, 2-methylpentyl, hexyl, and the like. The alkyl moiety may be attached to the chemical moiety by any one of the carbon atoms of the aliphatic chain. Alkyl groups are optionally substituted as described herein.

"Alkenyl" as used herein, unless otherwise indicated, refers to a straight or branched aliphatic hydrocarbon chain having 2- to 6-carbon atoms and containing at least one carbon-carbon double bond (for example —C═C—, or —C═CH$_2$). Non-exclusive examples of alkenyl include: ethenyl, 1-propenyl, 2-propenyl, isopropenyl, 1-butenyl, 2-butenyl, 3-butenyl, 2-pentenyl, and the like.

"Alkynyl" as used herein, unless otherwise indicated, refers to straight or branched aliphatic hydrocarbon chain having 2- to 6-carbon atoms and containing at least one carbon-carbon triple bond (for example, —C≡C— or —C≡CH). Non-exclusive examples of alkynyl include: ethynyl, 2-propynyl, 1-methyl-2-propynyl, 2-butynyl, 3-butynyl, 2-methyl-3-butynyl, and the like.

"Animal", as used herein, unless otherwise indicated, refers to an individual animal that is a mammal, bird, or fish. Specifically, mammal refers to a vertebrate animal that is human and non-human, which are members of the taxonomic class Mammalia. Non-exclusive examples of non-human mammals include companion animals and livestock. Non-exclusive examples of a companion animal include: dog, cat, llama, goat, and horse. Preferred companion animals are dog, cat, and horse. More preferred is dog. Equally preferred is cat or horse. Non-exclusive examples of livestock include: swine, camel, rabbits, goat, sheep, deer, elk, bovine (cattle), and bison. Preferred livestock is cattle. Equally preferred is swine. Specifically, bird refers to a vertebrate animal of the taxonomic class Aves. Birds are feathered, winged, bipedal, endothermic, and egg-laying. Non-exclusive examples of bird include, poultry (e.g., chicken, turkey, duck, and geese), all of which are also referred to herein as fowl. Specifically, fish refers to the taxonomic class Chondrichthyes (cartilaginous fishes, e.g., sharks and rays) and Osteichthyes (bony fishes) which live in water, have gills or mucus-covered skin for respiration, fins, and may have scales. Non-exclusive examples of fish include shark, salmon, trout, whitefish, catfish, tilapia, sea bass, tuna, halibut, turbot, flounder, sole, striped bass, eel, yellowtail, grouper, and the like.

"Compounds of the present invention", as used herein, unless otherwise indicated, refers to compounds of Formula (1) or Formula (XX), stereoisomers thereof, and veterinarily or pharmaceutically acceptable salts thereof.

"Cycloalkyl", as used herein, unless otherwise indicated, includes fully saturated or partially saturated carbocyclic alkyl moieties. Non-limiting examples of partially saturated cycloalkyls include: cyclopropene, cyclobutene, cycloheptene, cyclooctene, cyclohepta-1,3-diene, and the like. Preferred cycloalkyls are 3- to 6-membered saturated monocyclic rings including cyclopropyl, cyclobutyl, cyclopentyl, and cyclohexyl. The cycloalkyl group may be attached to the chemical moiety by any one of the carbon atoms within the carbocyclic ring. Cycloalkyl groups are optionally substituted with at least one substituent. Further when used in compound words such as alkylcycloalkyl, said alkyl and cycloalkyl moiety has the same meaning as herein defined and may be attached to the chemical moiety by any one of the carbon atoms of the aliphatic chain. Examples of "alkylcycloalkyl" include, methylcyclopropane (—CH$_2$-cyclopropane), ethylcyclopropane (—CH$_2$CH$_2$-cyclopropane), methylcyclobutane (—CH$_2$-cyclobutane), ethylcyclobutane (—CH$_2$CH$_2$-cyclobutane), methylcyclohexane (—CH$_2$-cyclohexane), and the like. Cycloalkyls are optionally substituted as described herein.

"Halogen" or "halo", as used herein, unless otherwise indicated, refers to fluorine, chlorine, bromine and iodine. Further, when used in compound words such as "haloalkyl", "haloalkoxy", "haloalkenyl", or "haloalkynyl", said alkyl, alkoxy, alkenyl, and alkynyl may be partially or fully substituted with halogen atoms which may be the same or different and said alkyl, alkoxy, alkenyl, and alkynyl moiety has the same meaning as above and may be attached to the chemical moiety by any one of the carbon atoms of the aliphatic chain. Examples of "haloalkyl" include F$_3$C—, ClCH$_2$—, CF$_3$CH$_2$— and CF$_3$CCl$_2$—, and the like. The term "haloalkoxy" is defined analogously to the term "haloalkyl". Examples of "haloalkoxy" include CF$_3$O—, CCl$_3$CH$_2$O—, HCF$_2$CH$_2$CH$_2$O— and CF$_3$CH$_2$O—, and the like. The term "haloalkenyl" is defined analogously to the term "haloalkyl" except that the aliphatic chain contains at least one carbon-carbon double bond. Examples of "haloalkenyl" include CF$_3$C═C—, CCl$_3$C═C—, HCF$_2$C═C— and CF$_3$C═CC—, and the like. The term "haloalkynyl" is defined analogously to the term "haloalkyl" except that the aliphatic chain contains at least one carbon-carbon triple bond. Examples of "haloalkynyl" include CF₃C≡C—, CCl₃C≡C—, HCF₂C≡C— and CF₃C≡CC—, and the like.

"Heterocycle", as used herein, unless otherwise indicated, refers to a partially saturated or saturated 3- to 6-membered monocyclic ring containing one or more heteroatoms each independently selected from N, O, or S, preferably from one to four heteroatoms. Non-exclusive examples of heterocycle include oxiranyl, thiaranyl, aziridinyl, oxetanyl, thiatanyl, azetidinyl, tetrahydrofuran, tetrahydrothiophene, pyrrolidinyl, tetrahydropyranyl, piperidinyl, piperazinyl, tetrahydropyridinyl, 2H-azirine, 2,3-dihydro-azete, 3,4-dihydro-2H-pyrrole, and the like. The heterocycle group may be attached to the chemical moiety by any one of the carbon atoms or heteroatoms (e.g., N, O, and S) within the monocyclic ring. Heterocycles are optionally substituted as described herein.

"Heteroaryl" or "Het", as used herein, unless otherwise indicated, refers to a 5- to 6-membered aromatic monocyclic ring or an 8- to 10-membered fused aromatic ring where said monocyclic- and fused-ring moiety contains one or more heteroatoms each independently selected from N, O, or S, preferably from one to four heteroatoms. Non-exclusive examples of monocyclic heteroaryls include pyrrolyl, furanyl, thiophenyl, pyrazolyl, imidazolyl, triazolyl, tetrazolyl, thiazolyl, isoxazolyl, oxazolyl, oxadiazolyl, thiadiazolyl, pyridinyl, pyridazinyl, pyrimidinyl, pyrazinyl, and the like. Non-exclusive examples of fused heteroaryls include: benzofuranyl, benzothiophenyl, indolyl, benzimidazolyl, indazolyl, benzotriazolyl, thieno[2,3-c]pyridine, thieno[3,2-b]pyridine, benzo[1,2,5]thiadiazole, and the like. The heteroaryl group may be attached to the chemical moiety by any one of the carbon atoms or heteroatoms (e.g., N, O, and S) within the monocyclic or fused ring. Heteroaryls are optionally substituted as described herein.

"Optionally substituted", is used herein interchangeably with the phrase substituted or unsubstituted. Unless otherwise indicated, an optionally substituted group may have a substituent at each substitutable position of the group, and each substitution is independent of the other. An optionally substituted group also may have no substituents. Therefore, the phrase "optionally substituted with at least one substituent" means that the number of substituents may vary from zero up to a number of available positions for substitution.

"Parasite(s)", as used herein, unless otherwise indicated, refers to endoparasites and ectoparasites. Endoparasites are parasites that live within the body of its host and include helminths (e.g., trematodes, cestodes, and nematodes) and protozoa. Ectoparasites are organisms of the *Arthropoda phylum* (e.g., arachnids, insects, and crustaceans (e.g., copepods-sea lice) which feed through or upon the skin of its host. Preferred arachnids are of the order Acarina, e.g., ticks and mites. Preferred insects are midges, fleas, mosquitos, biting flies (stable fly, horn fly, blow fly, horse fly, and the like) and lice. Preferred compounds of the present invention can be used for the treatment of parasites, i.e., treatment of a parasitic infection or infestation.

"Therapeutically effective amount", as used herein, unless otherwise indicated, refers to an amount of the compounds of the present invention that (i) treat the particular parasitic infection or infestation, (ii) attenuates, ameliorates, or eliminates one or more symptoms of the particular parasitic infection or infestation, or (iii) prevents or delays the onset of one or more symptoms of the particular parasitic infection or infestation described herein.

"Treatment", "treating", and the like, as used herein, unless otherwise indicated, refers to reversing, alleviating, or inhibiting the parasitic infection, infestation, or condition. As used herein, these terms also encompass, depending on the condition of the mammal, preventing the onset of a disorder or condition, or of symptoms associated with a disorder or condition, including reducing the severity of a disorder or condition or symptoms associated therewith prior to affliction with said infection or infestation. Thus, treatment can refer to administration of the compounds of the present invention to a mammal that is not at the time of administration afflicted with the infection or infestation. Treating also encompasses preventing the recurrence of an infection or infestation or of symptoms associated therewith as well as references to "control" (e.g., kill, repel, expel, incapacitate, deter, eliminate, alleviate, minimize, and eradicate).

"Veterinary acceptable" as used herein, unless otherwise indicated, indicates that the substance or composition must be compatible chemically and/or toxicologically, with the other ingredients comprising a formulation, composition, and/or the mammal being treated therewith. The term "pharmaceutically" acceptable has the same meaning as that recited for "veterinarily" acceptable.

The "⁓" as used herein, unless otherwise indicated, refers to a point of attachment.

DETAILED DESCRIPTION

The present invention provides Formula (1) compounds, stereoisomers thereof, as well as veterinary compositions that are useful as antiparasitic agents for animals and birds, in particular, compounds that act as ectoparasiticides. Further, the present invention provides Formula (XX) compounds, stereoisomers thereof, as well as veterinary compositions that are useful as antiparasitic agents for animals and birds, in particular, compounds that act as ectoparasiticides.

Compounds of the present invention may be synthesized by synthetic routes that include processes analogous to those well known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, "Reagents for Organic Synthesis", 1; 19, Wiley, New York (1967, 1999 ed.), or *Beilsteins Handbuch der organischen Chemie*, 4, Aufl. ed. Springer-Verlag, Berlin, including supplements (also available via the Beilstein online database)).

Compounds of this invention can exist as one or more stereoisomers. The various stereo isomers include enantiomers, diastereomers and atropisomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereo isomers or as an optically active form. For example, two possible enantiomers of Formula 1 are depicted as Formula 1a and Formula 1b involving the isoxazoline chiral center identified with an asterisk (*). Molecular depictions drawn herein follow standard conventions for depicting stereochemistry.

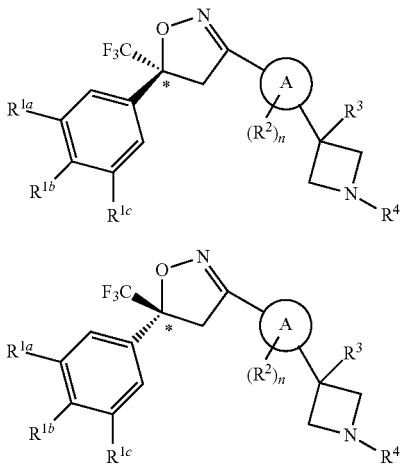

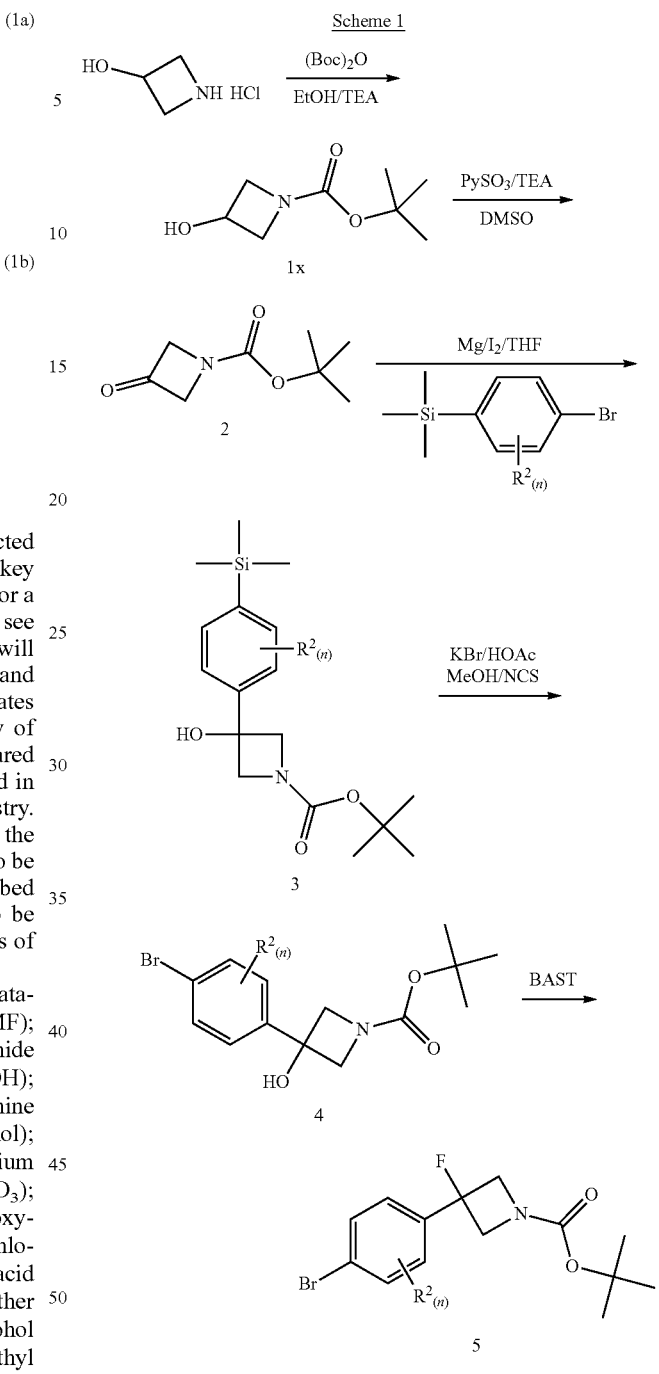

For illustrative purposes, the reaction schemes depicted below demonstrate potential routes for synthesizing key intermediates and compounds of the present invention. For a more detailed description of the individual reaction steps, see the Examples section below. Those skilled in the art will appreciate that other suitable starting materials, reagents, and synthetic routes may be used to synthesize the intermediates and compounds of the present invention and a variety of derivatives thereof. Further, many of the compounds prepared by the methods described below can be further modified in light of this disclosure using conventional chemistry. Schemes 1-17 outline the general procedures useful for the preparation of compounds of the present invention. It is to be understood, however, that the invention, as fully described herein and as recited in the claims, is not intended to be limited by the details of the following schemes or modes of preparation.

In the Schemes and Examples below, the following catalysts/reactants include: N,N-dimethyl formamide (DMF); N—N-dimethylsulfoxide (DMSO); N-chloro-succinimide (NCS); N-bromo-succinimide (NBS); ethanol (EtOH); methanol (MeOH); tetrahydrofuran (THF); triethylamine (TEA); acetonitrile ($CH_3CN$, ACN); n-BuOH (n-butanol); lithium hydroxide (LiOH); hydrazine ($H_2NNH_2$); potassium bicarbonate ($KHCO_3$); potassium carbonate ($K_2CO_3$); diethyl ether ($Et_2O$); sodium carbonate ($Na_2CO_3$); hydroxylamine ($NH_2OH$); sulfuric acid ($H_2SO_4$); ammonium chloride ($NH_4Cl$); dichloromethane ($CH_2Cl_2$); hydrochloric acid (HCl); trifluoroacetic acid (TFA); methyl tert-butyl ether (MTBE); potassium acetate (KOAc); isopropyl alcohol (IPA); n-butyllithium (n-BuLi); triethylamine ($Et_3N$); ethyl acetate (EtOAc); sodium acetate (NaOAc); bis(triphenylphosphine) palladium II chloride ($PdCl_2$ ($PPh_3$)$_2$) from Strem; N,N,N',N'-Tetramethyl-O-(7-azabenzotriazol-1-yl) uronium hexafluorophosphate (HATU); 1-hydroxybenzotriazole hydrate (HOBt); di-tert-butyl dicarbonate ($Boc_2O$); carbonyldiimidazole (CDI); diethylaminosulfur trioxide (DAST); 2,2'-azobis(2-methylpropionitrile) (AIBN); tetrabutylammonium fluoride (TBAF); Bis(2-methoxyethyl) aminosulfur trifluoride (BAST); tert-butyl carbonate (Boc); pyridine sulphurtrioxide ($PySO_3$); triphenylphosphine palladium ($Pd(PPh_3)_4$); 4-dimethylaminopyridine (DMAP); hexamethyldisilazide (KHMDS); (2,2,6,6-tetramethylpiperidin-1-yl)oxyl (TEMPO); and diisobutylaluminium hydride (DIBAL-H).

$R^2$ and n are as defined herein.

The phenyl azetidines can be prepared as shown in Scheme 1. Boc protection of hydroxyazetidine hydrochloride followed by oxidation of the hydroxyl group gave the ketoazetidine 2. This could be condensed with bromoaryl silanes by formation of the aryl Grignard reagent and subsequent condensation with the ketone to provide the silyl phenyl azetadine 3. Replacement of the silane with bromine was accomplished by treatment with potassium bromide in acetic acid to give the desired bromophenyl azetidine 4. Fluorination of the hydroxyazetidine 4 can be accomplished by treatment with BAST to provide 5.

Scheme 1.5

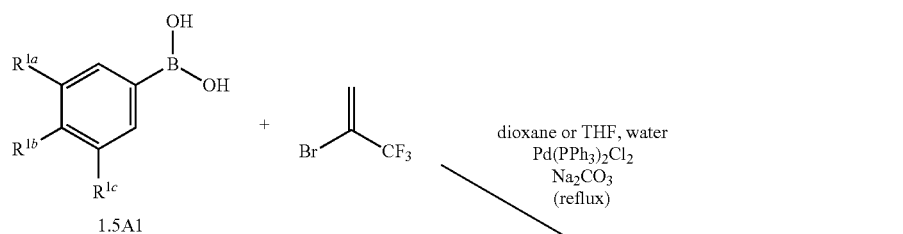

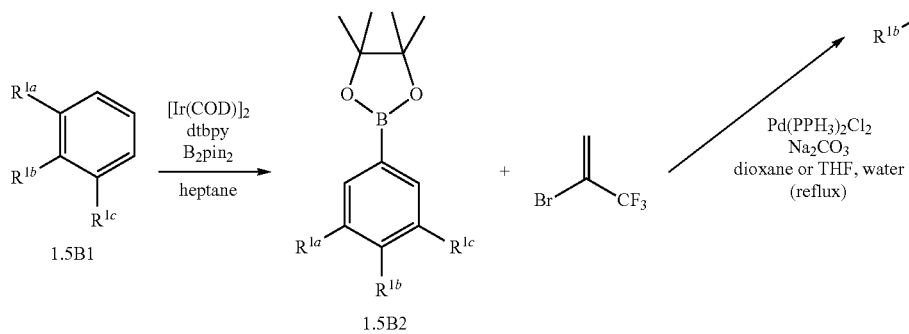

$R^{1a}$, $R^{1b}$, and $R^{1c}$ are as defined herein.

The aryl olefins (8) can be prepared according to Scheme 1.5. The requisite organoborates can be prepared as boronate ester intermediates (1.5B2) from literature methods (*Org. Lett.* 2007, 9, 761-764) or purchased as boronic acids (1.5A1) such as 3,5-dichloroboronic acid from Aldrich. Intermediate 1.5A1 or 1.5B2 compounds can be added to dioxane or THF and water, followed by 2-bromo-3,3,3-trifluoropropene, potassium carbonate, and bis(triphenylphosphine) palladium II chloride to afford the intermediate (8) compounds.

Scheme 2

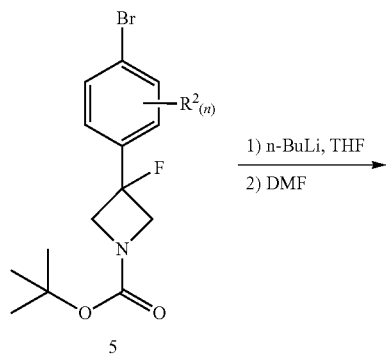

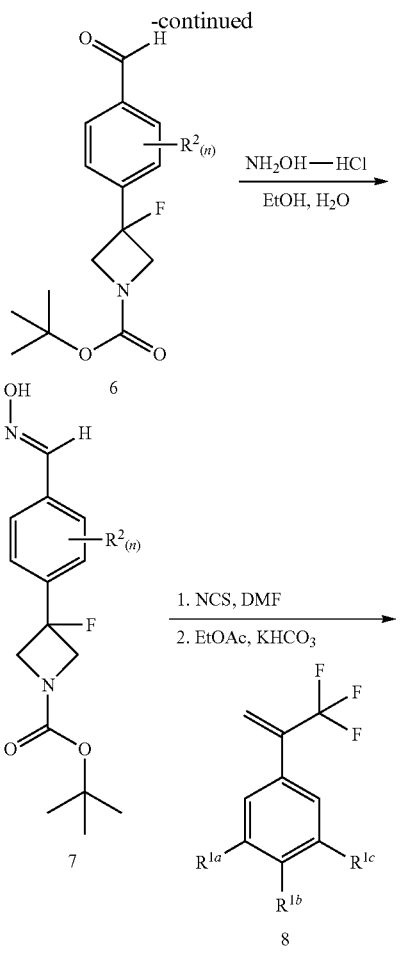

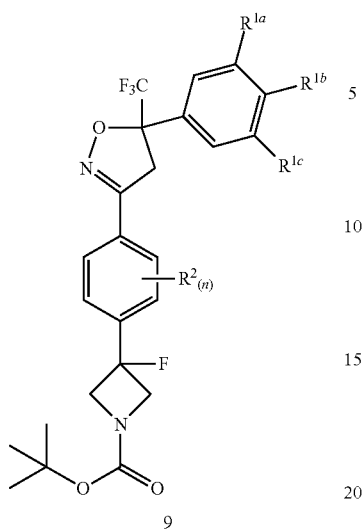

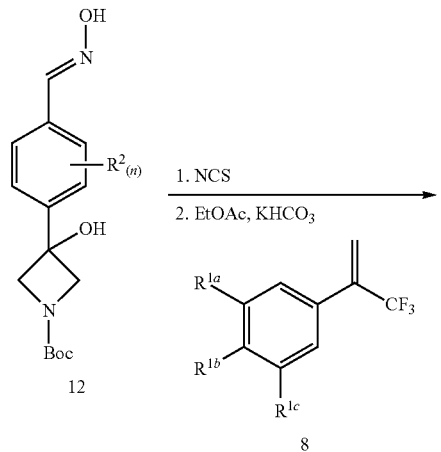

$R^{1a}$, $R^{1b}$, $R^{1c}$, $R^2$, and n are as defined herein.

Scheme 2 describes the preparation of isoxazolines from the aryl bromides or aryl aldehydes. From the bromophenyl azetidine 5, halogen-metal exchange followed by quenching with DMF provides the aryl aldehyde 6 which can also be prepared by other methods (Schemes 3 and 4). The aldehyde is condensed with hydroxylamine to provide the oxime 7. From the oxime, the isoxazoline ring can be prepared in a one-pot, two step process. Treatment of the oxime with N-chlorosuccinimide provides the chlorooxime which undergoes [3+2] cyclization with aryl olefins 8 to provide the isoxazoline 9. These steps can also be done as separate reactions. Removal of the Boc protecting group on the azetidine can be accomplished by treatment with trifluoroacetic acid.

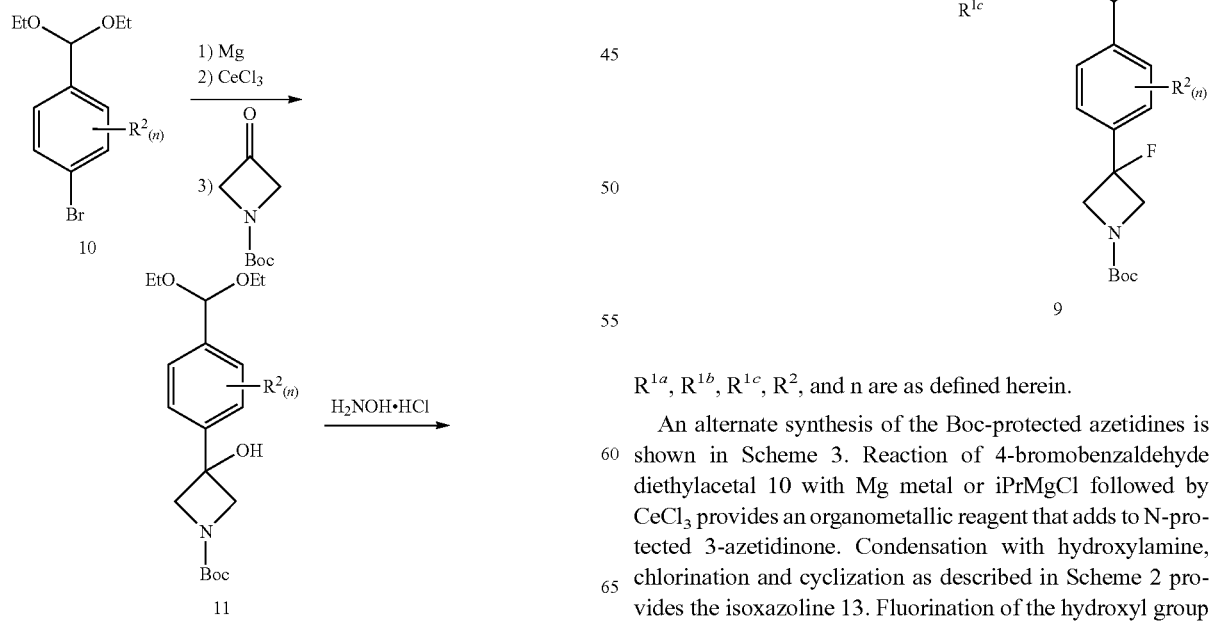

$R^{1a}$, $R^{1b}$, $R^{1c}$, $R^2$, and n are as defined herein.

An alternate synthesis of the Boc-protected azetidines is shown in Scheme 3. Reaction of 4-bromobenzaldehyde diethylacetal 10 with Mg metal or iPrMgCl followed by CeCl₃ provides an organometallic reagent that adds to N-protected 3-azetidinone. Condensation with hydroxylamine, chlorination and cyclization as described in Scheme 2 provides the isoxazoline 13. Fluorination of the hydroxyl group can be achieved by reaction with Xtaflor-E.

Scheme 4

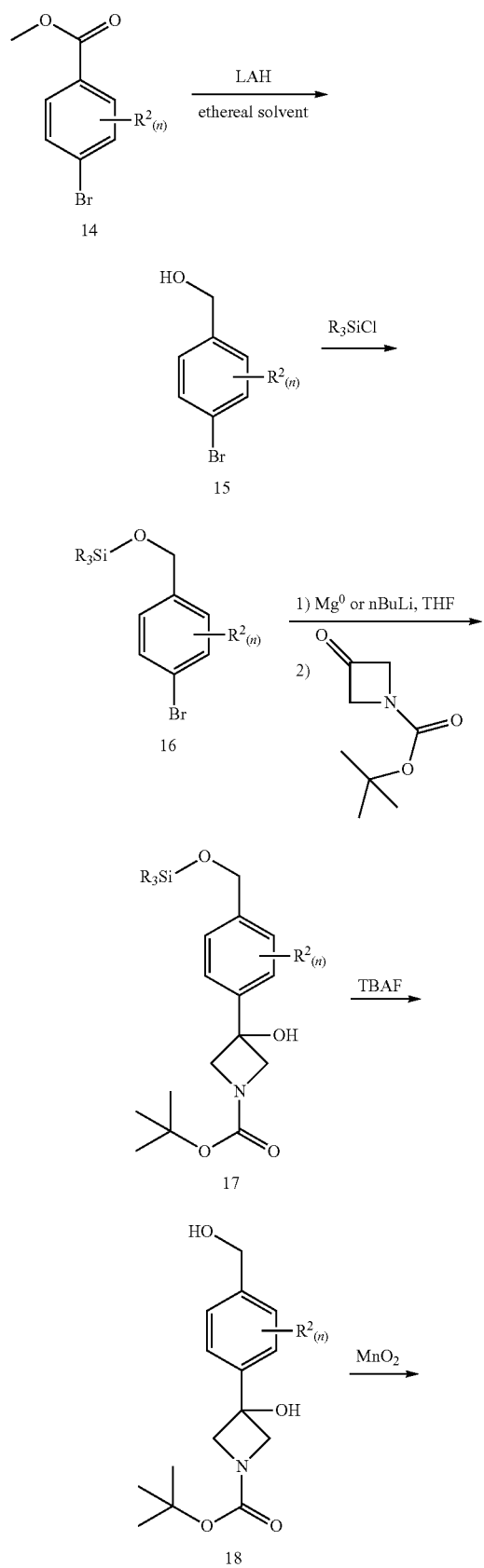

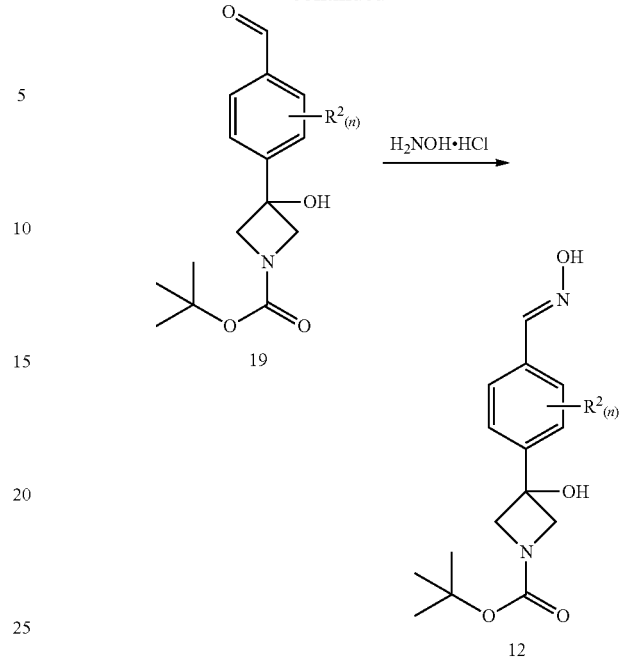

$R^2$ and n are as defined herein.

Alternatively, the phenyl azetidines can be prepared from bromo aryl esters or bromoaryl methanols as shown in Scheme 4. Reduction of the aryl ester with lithium aluminum hydride provides the aryl methanol 15 which can be protected as a silane. Formation of the aryl Grignard with magnesium or halogen metal exchange provides the aryl anion which can condense with the N-protected azetidinone 2 to give the aryl azetidine 17. Deprotection of the alcohol and oxidation provides the formyl phenylazetidine 19 which can undergo condensation with hydroxylamine to provide the oxime 12.

Scheme 5

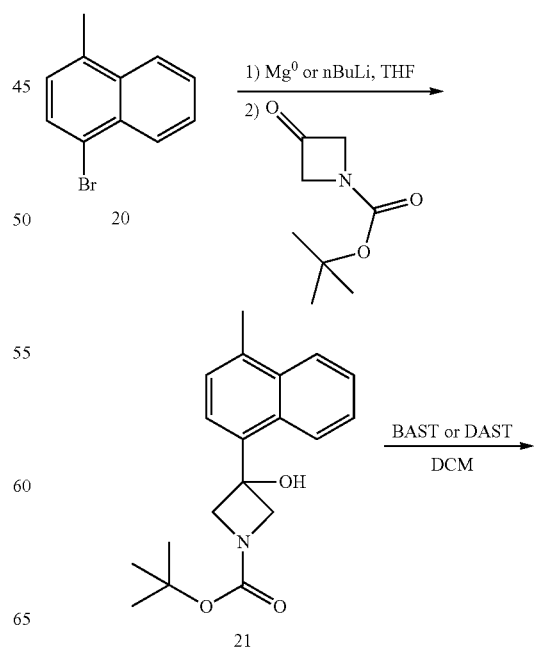

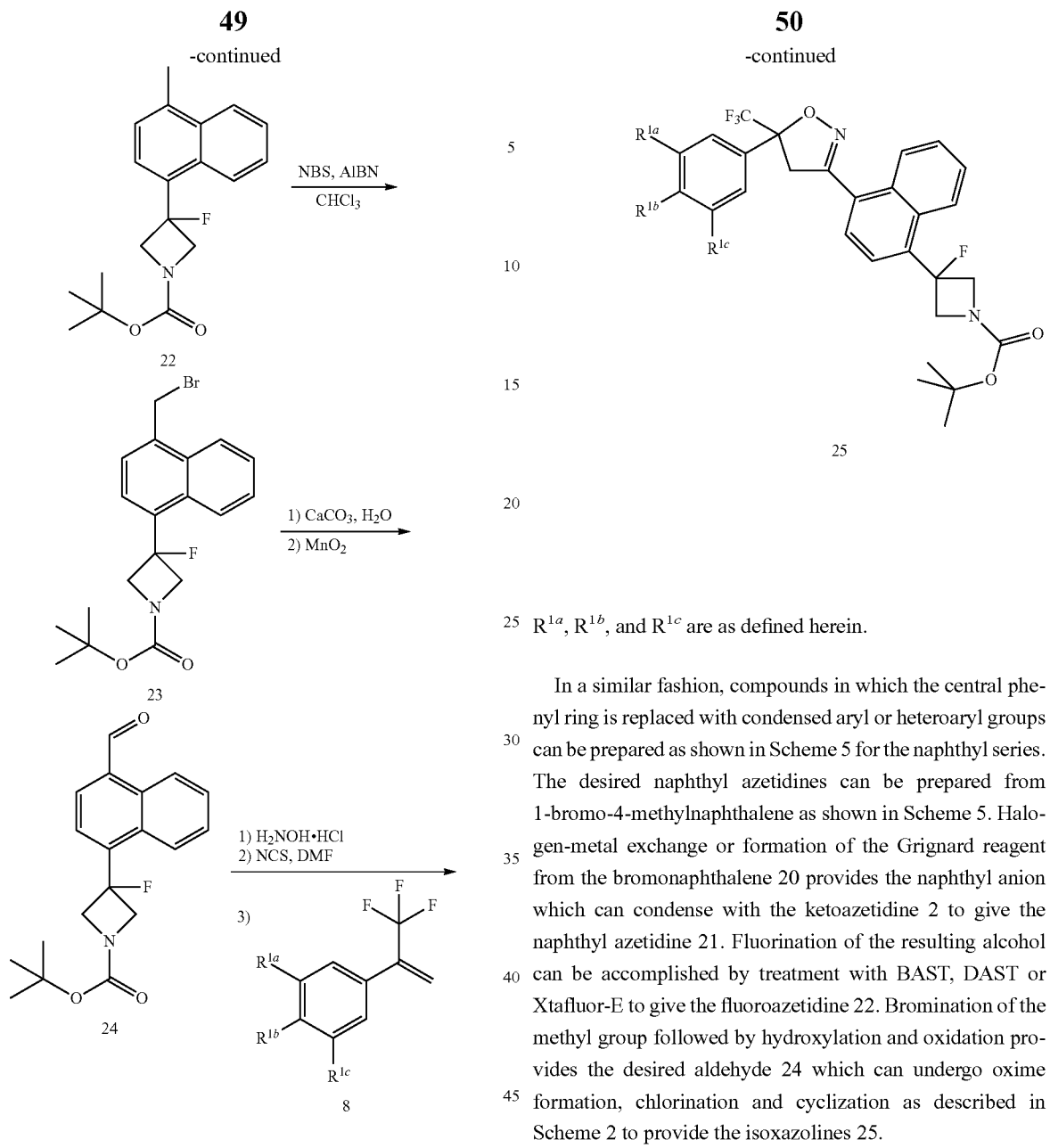

$R^{1a}$, $R^{1b}$, and $R^{1c}$ are as defined herein.

In a similar fashion, compounds in which the central phenyl ring is replaced with condensed aryl or heteroaryl groups can be prepared as shown in Scheme 5 for the naphthyl series. The desired naphthyl azetidines can be prepared from 1-bromo-4-methylnaphthalene as shown in Scheme 5. Halogen-metal exchange or formation of the Grignard reagent from the bromonaphthalene 20 provides the naphthyl anion which can condense with the ketoazetidine 2 to give the naphthyl azetidine 21. Fluorination of the resulting alcohol can be accomplished by treatment with BAST, DAST or Xtafluor-E to give the fluoroazetidine 22. Bromination of the methyl group followed by hydroxylation and oxidation provides the desired aldehyde 24 which can undergo oxime formation, chlorination and cyclization as described in Scheme 2 to provide the isoxazolines 25.

Scheme 6

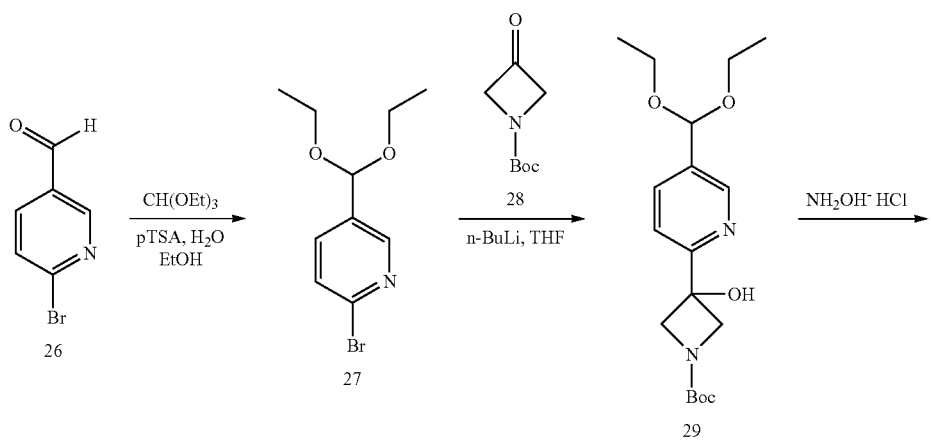

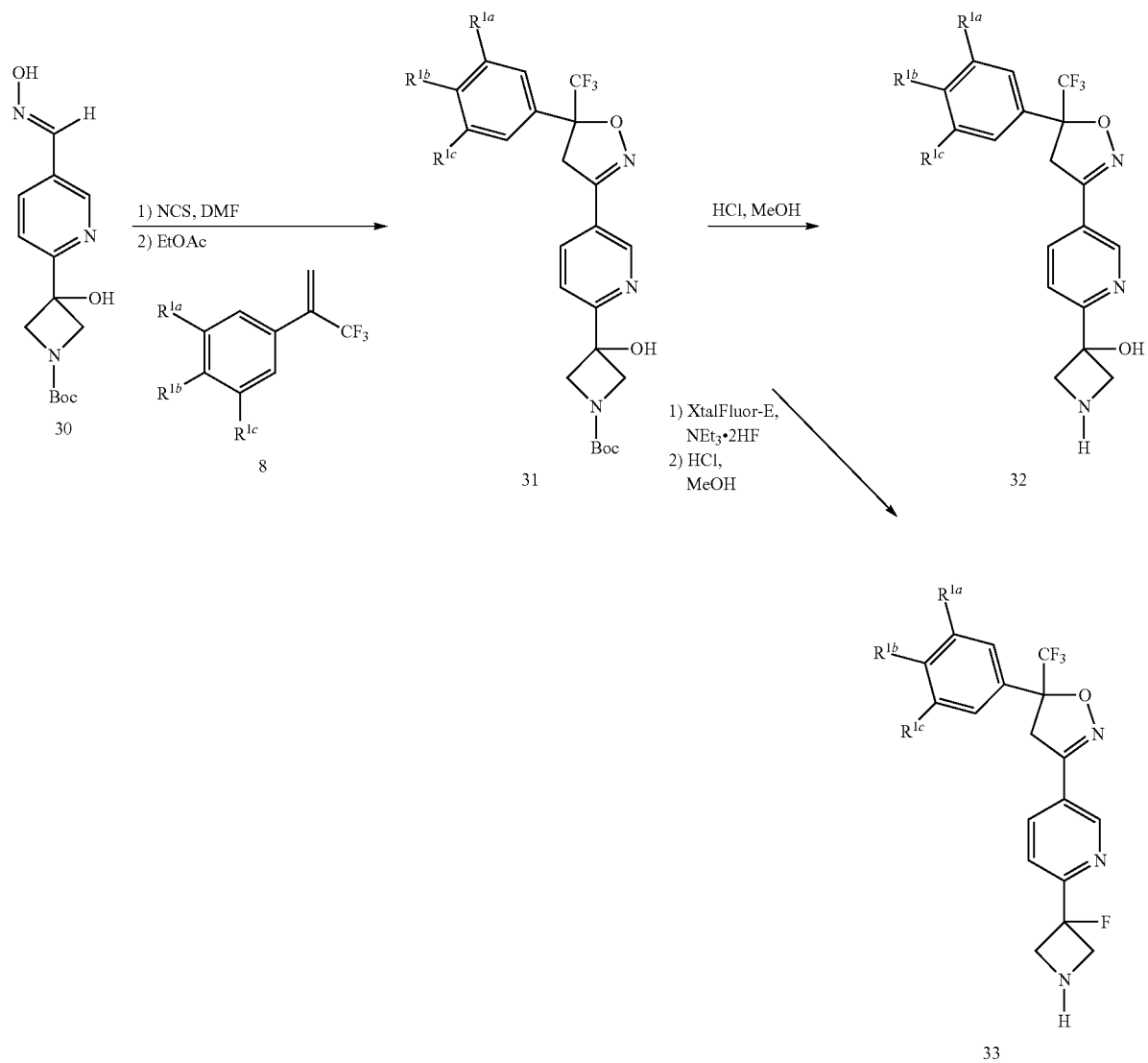

$R^{1a}$, $R^{1b}$, and $R^{1c}$ are as defined herein.

Compounds in which the central phenyl ring is replaced with heteroaryl groups can be prepared as shown in Scheme 6 for the pyridyl series. Formation of the diethylacetal can be accomplished with ethyl formate. Treatment of the iodopyridine 27 with n-BuLi provides the organometallic reagent which adds to the N-protected 3-azetidinone 28. Condensation of the resulting masked aldehyde with hydroxylamine followed by chlorination and cyclization provides the isoxazoline 31. The benzhydryl protecting group can be removed by hydrogenation or treatment with chloroethyl chloroformate to provide the hydroxyazetidine 32 or alternatively, the hydroxyazetidine 31 can be fluorinated by treatment with XtaFluor-E followed by a similar deprotection to provide the fluoroazetidine 33.

Scheme 7

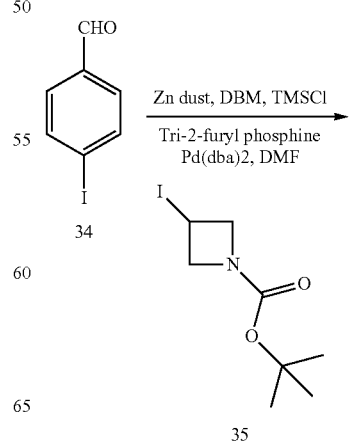

Scheme 8

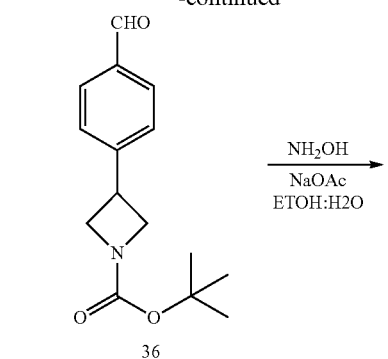

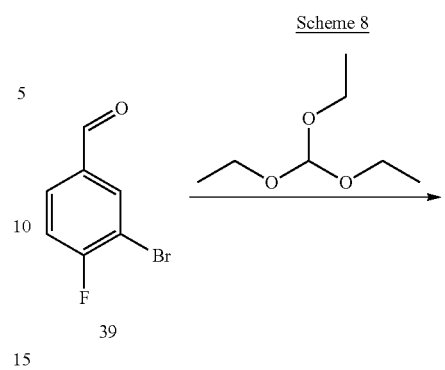

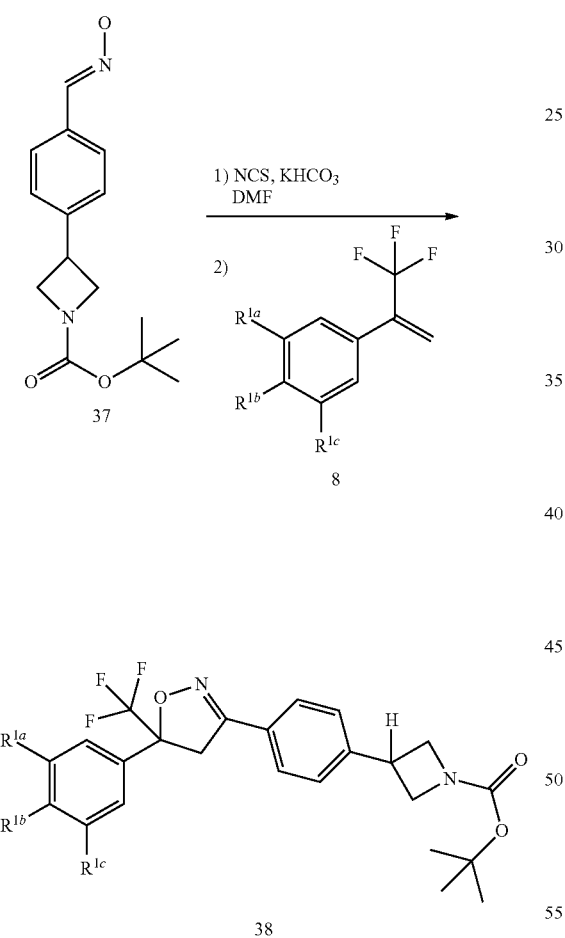

$R^{1a}$, $R^{1b}$, and $R^{1c}$ are as defined herein.

The substituent on the azetidine ring can be eliminated as shown in Scheme 7. A palladium/zinc catalyzed cross coupling reaction of the iodoaldehyde 34 with the N-protected iodoazetidine 35 provides the phenyl azetidine 36. This aldehyde can undergo condensation with hydroxylamine, chlorination and cyclization as described in Scheme 2 to give the hydrido compound 38.

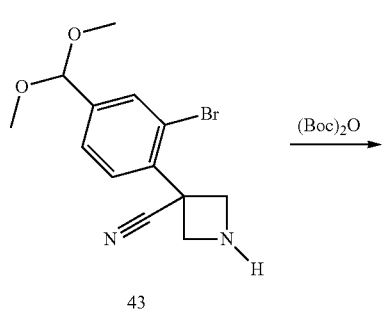

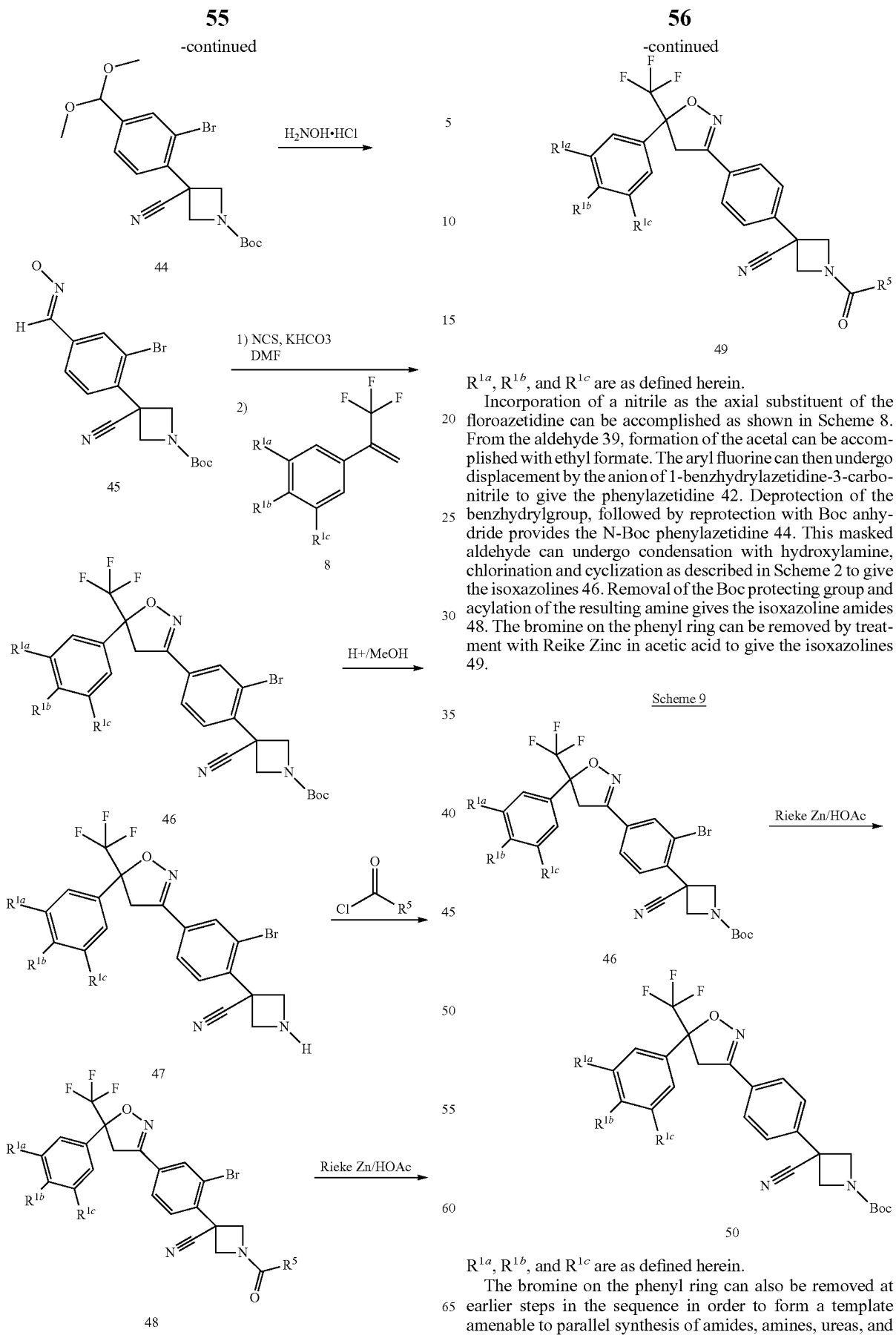

$R^{1a}$, $R^{1b}$, and $R^{1c}$ are as defined herein.

Incorporation of a nitrile as the axial substituent of the floroazetidine can be accomplished as shown in Scheme 8. From the aldehyde 39, formation of the acetal can be accomplished with ethyl formate. The aryl fluorine can then undergo displacement by the anion of 1-benzhydrylazetidine-3-carbonitrile to give the phenylazetidine 42. Deprotection of the benzhydrylgroup, followed by reprotection with Boc anhydride provides the N-Boc phenylazetidine 44. This masked aldehyde can undergo condensation with hydroxylamine, chlorination and cyclization as described in Scheme 2 to give the isoxazolines 46. Removal of the Boc protecting group and acylation of the resulting amine gives the isoxazoline amides 48. The bromine on the phenyl ring can be removed by treatment with Reike Zinc in acetic acid to give the isoxazolines 49.

Scheme 9

$R^{1a}$, $R^{1b}$, and $R^{1c}$ are as defined herein.

The bromine on the phenyl ring can also be removed at earlier steps in the sequence in order to form a template amenable to parallel synthesis of amides, amines, ureas, and the like.

Scheme 10
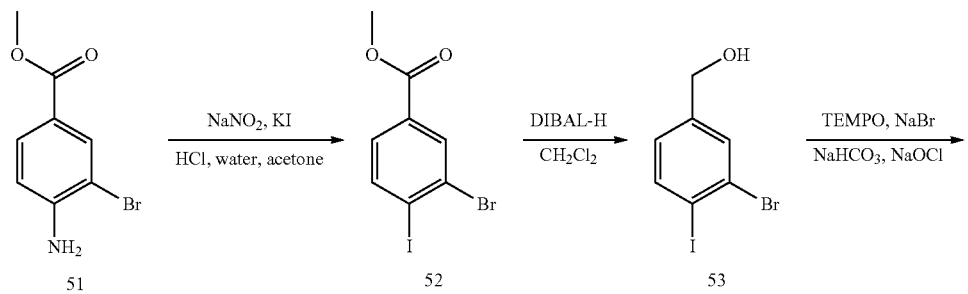
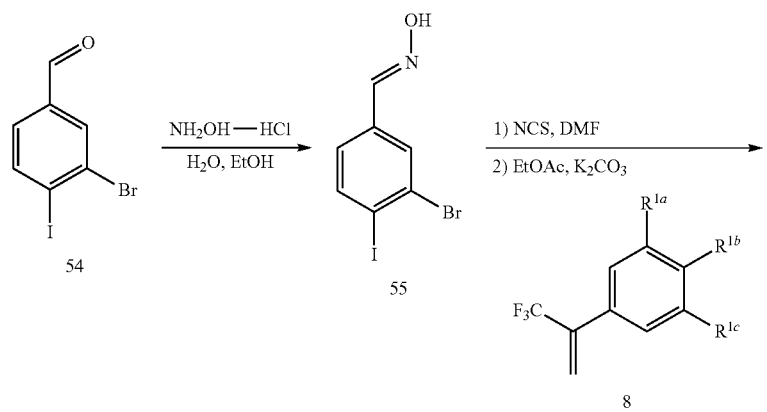
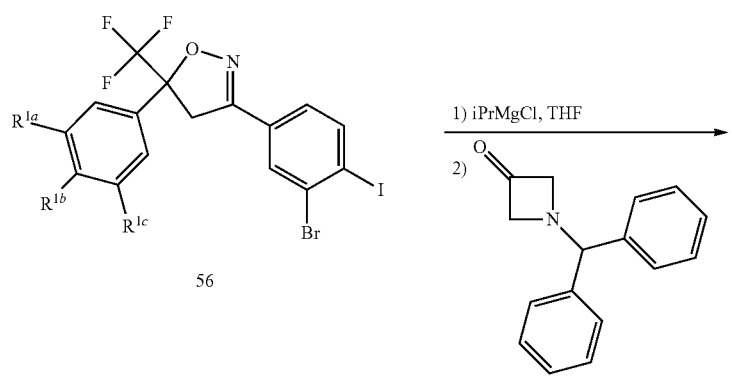
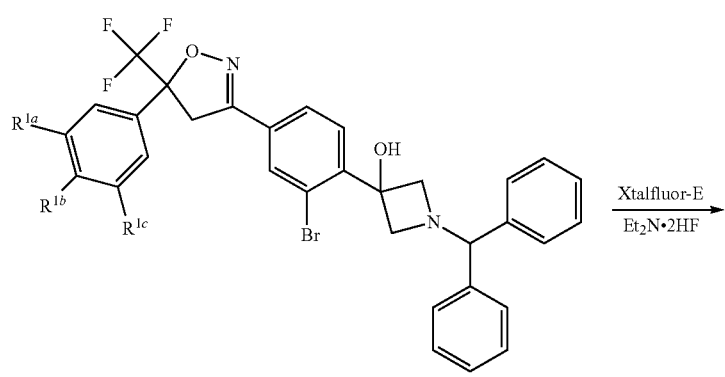

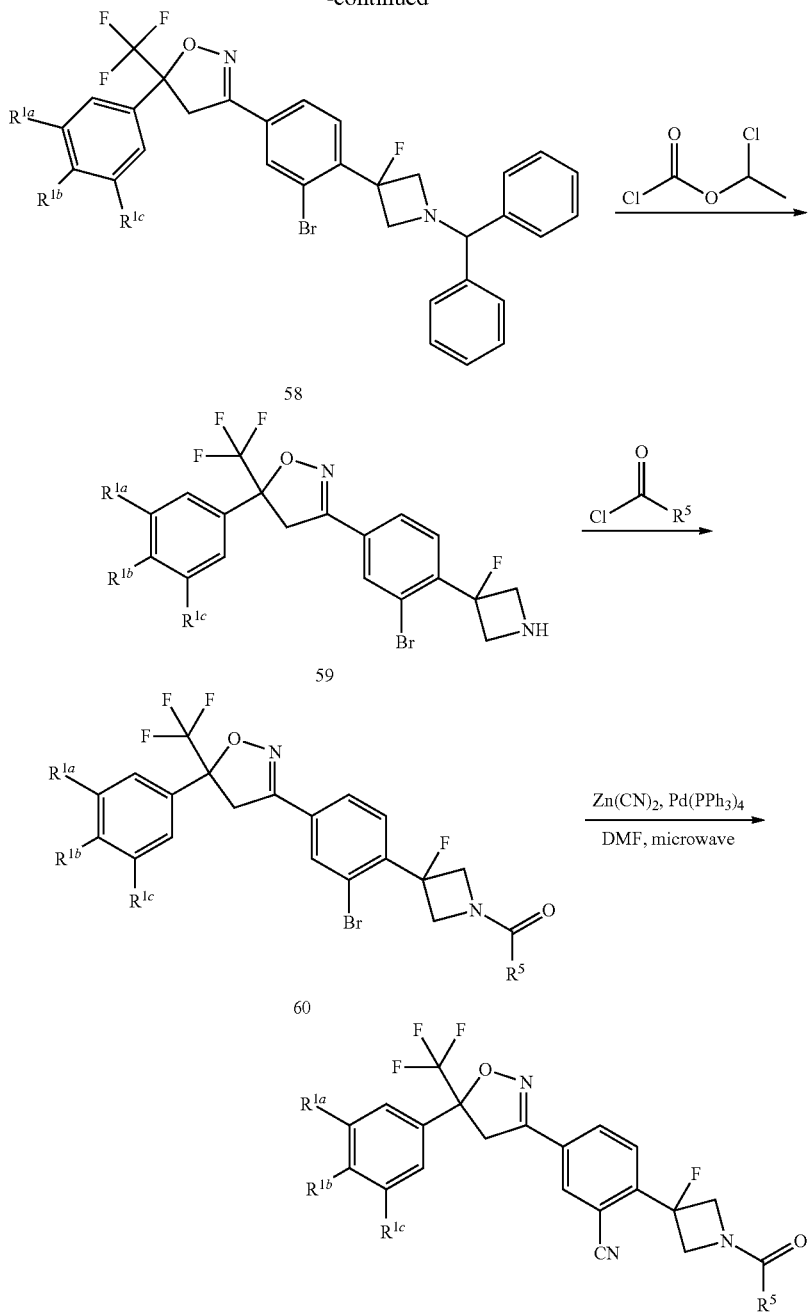

$R^{1a}$, $R^{1b}$, $R^{1c}$, and $R^5$ are as defined herein.

The identity of the $R^2$ substituent can be altered either by choice of starting material or by interconversion of substituents on the aryl ring as shown in Scheme 10. The iodoester 52 can be prepared by treatment of the aminoester 51 with sodium nitrite and potassium iodide. Reduction of the ester to the alcohol with diisobutylaluminum hydride followed by oxidation with TEMPO affords the iodoaldehyde 54. This aldehyde can undergo condensation with hydroxylamine, chlorination and cyclization as described in Scheme 2 to give the isoxazoline 56. Grignard formation using iPrMgCl occurs selectively with the iodine and the resulting organometallic adds to the N-protected azetidinone to afford the phenylazetidine 57. Fluoroination of the azetidine can be accomplished with Xtafluoro-E. Removal of the benzhydryl protecting group with chloroethylchloroformate and acylation of the resulting amine with acid chlorides or anhydrides (or coupling with desired organic acids) provides the phenylazetidine amides 60. At this point, the bromine of the phenyl ring can undergo interconversion to other functional groups (i.e. nitrile as shown) by metal catalyzed cross-couplings. Alternatively, 58 can be converted to a nitrile through palladium a cross-coupling reaction, followed by benzhydral protection and acylation to form final products 61.

Scheme 11
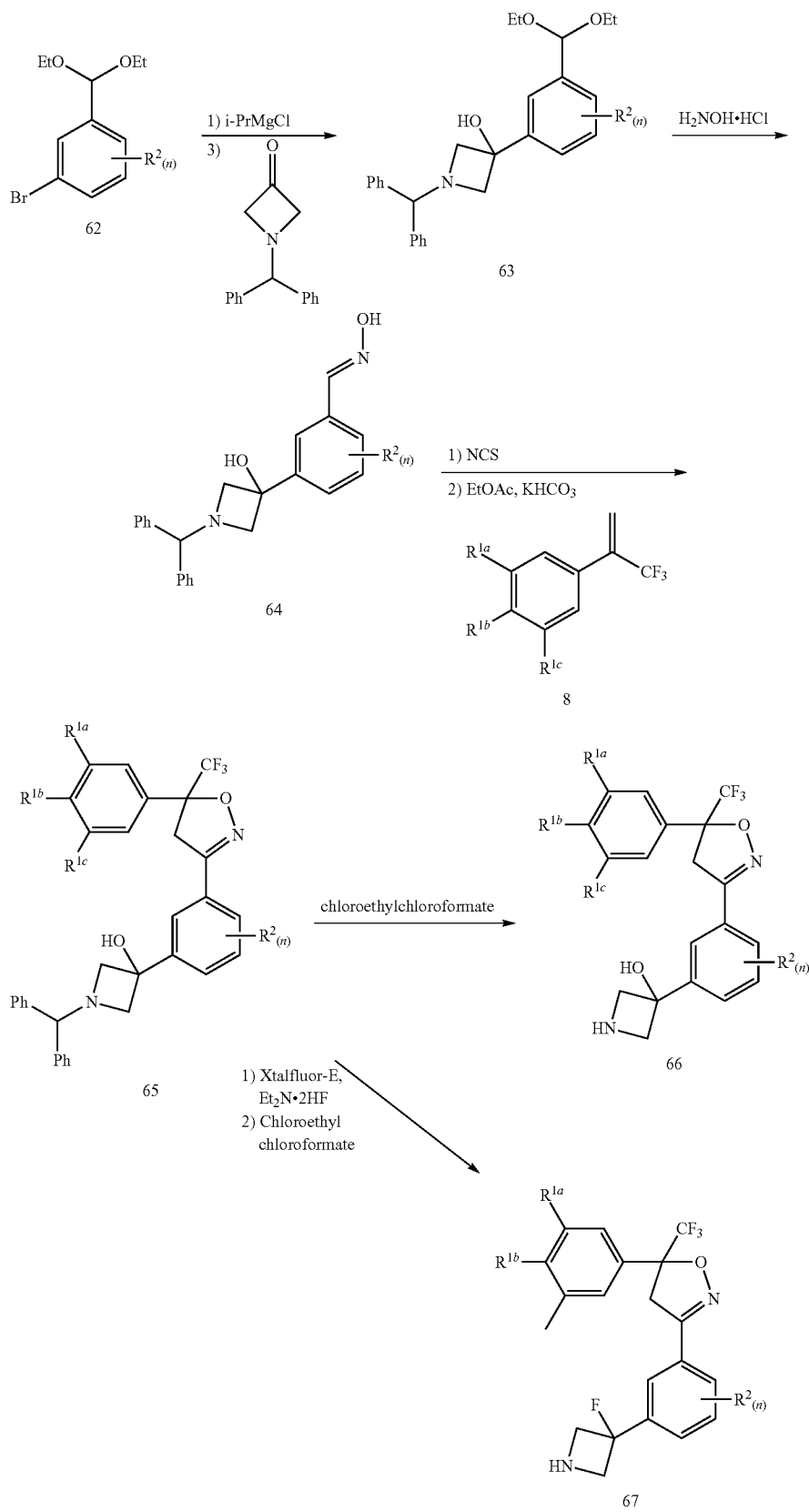

$R^{1a}$, $R^{1b}$, $R^{1c}$, $R^2$, and n are as defined herein.

Analogs in which the azetidine ring is meta to the isoxazoline can be prepared from 3-bromobenzaldehyde derivatives as shown in Scheme 11. Treatment of the bromoaldehyde 62 with i-PrMgCl provides the organometallic reagent that adds to the N-protected azetinone to provide the hydroxyazetidine 63. This masked aldehyde can undergo condensation with hydroxylamine, chlorination and cyclization as described in Scheme 2 to provide the isoxazoline 65. Deprotection with chloroethyl chloroformate or fluorination followed by deprotection provides the requisite amines (66 and 67) which can be further functionalized to the desired amides, ureas, amines and sulfonamides described below.

Scheme 12

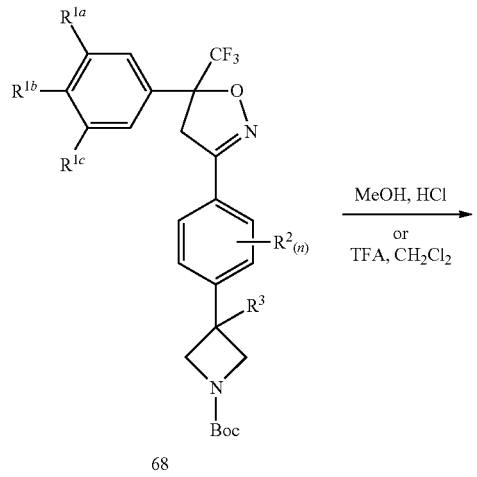

68

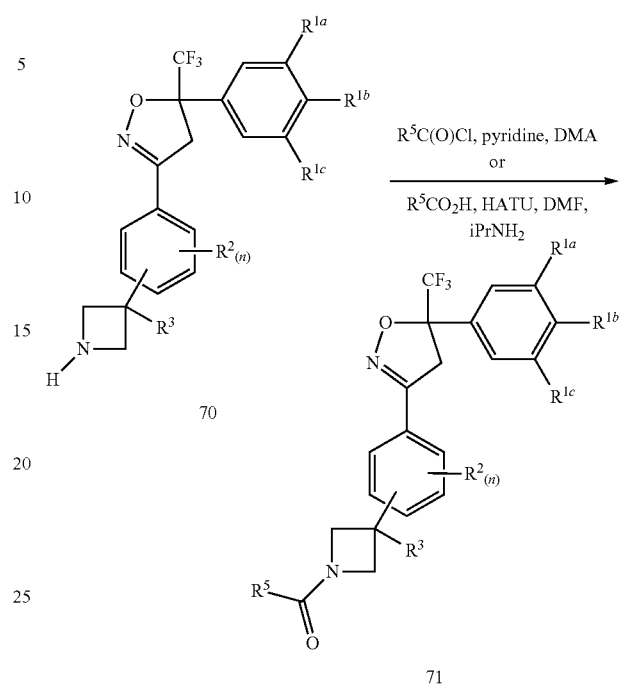

71

$R^{1a}$, $R^{1b}$, $R^{1c}$, $R^2$, $R^3$, $R^5$, and n are as defined herein.

Amide analogs of the azetidine ring can be prepared as shown in Scheme 13. Acylation of the azetidine ring can be accomplished by reaction of the azetidine 70 with an acid chloride in pyridine/DMA or by a condensation with a carboxylic acid utilizing a condensing agent such as HATU or HOBt.

Scheme 14

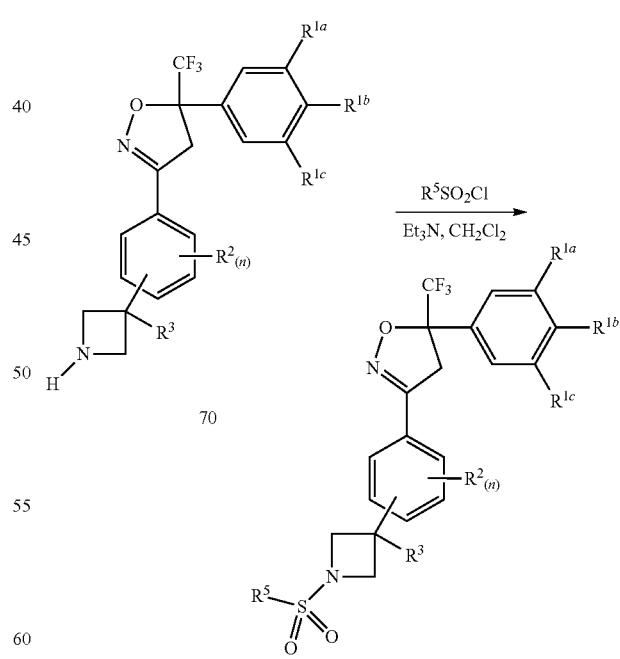

72

$R^{1a}$, $R^{1b}$, $R^{1c}$, $R^2$, $R^3$, and n are as defined herein.

Removal of the Boc protecting group on the azetidines in the schemes above (e.g. structures 9, 25, 38, 50) can be accomplished by treatment with HCl in methanol or with trifluoroacetic acid in dichloromethane.

$R^{1a}$, $R^{1b}$, $R^{1c}$, $R^2$, $R^3$, $R^5$, and n are as defined herein.

Sulfonamide anlogos of the azetidine ring can be prepared as shown in Scheme 14. Reaction of azetidine 70 with sulfonyl chlorides in the presence of triethylamine can give the desired sulfonamides.

Scheme 15

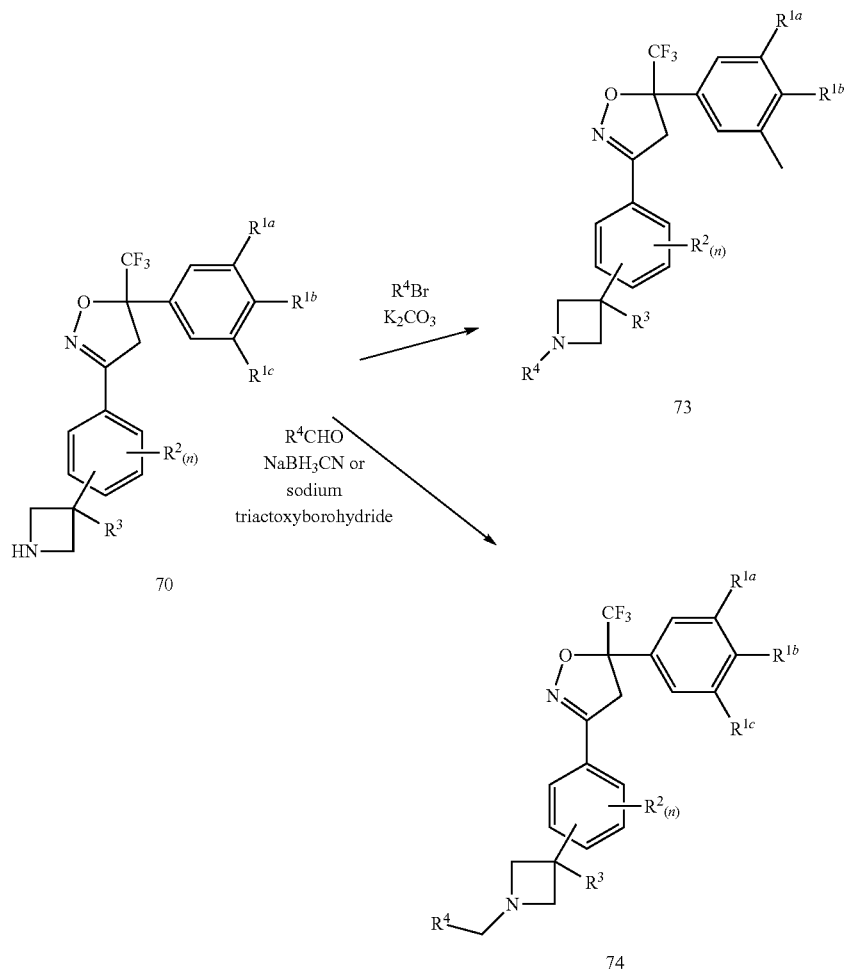

$R^{1a}$, $R^{1b}$, $R^{1c}$, $R^2$, $R^3$, $R^4$, and n are as defined herein.

Compounds in which $R^4$ is alkyl or substituted alkyl can be prepared from the azetidine 70 by standard alkylation chemistry or by reductive amination with the corresponding aldehydes as shown in Scheme 15.

Scheme 16

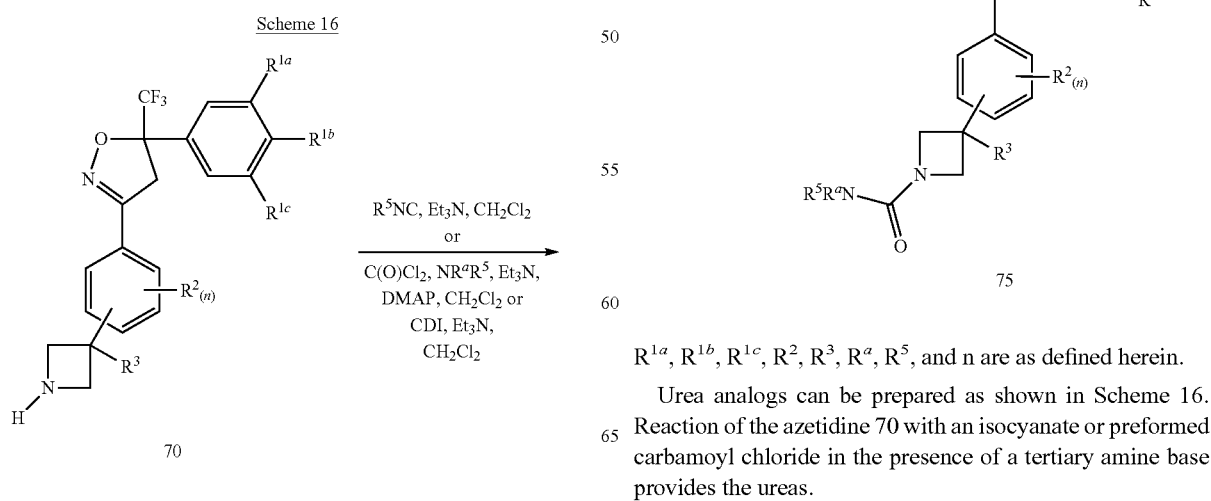

-continued

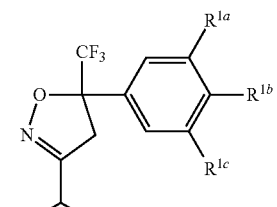

$R^{1a}$, $R^{1b}$, $R^{1c}$, $R^2$, $R^3$, $R^a$, $R^5$, and n are as defined herein.

Urea analogs can be prepared as shown in Scheme 16. Reaction of the azetidine 70 with an isocyanate or preformed carbamoyl chloride in the presence of a tertiary amine base provides the ureas.

Scheme 17

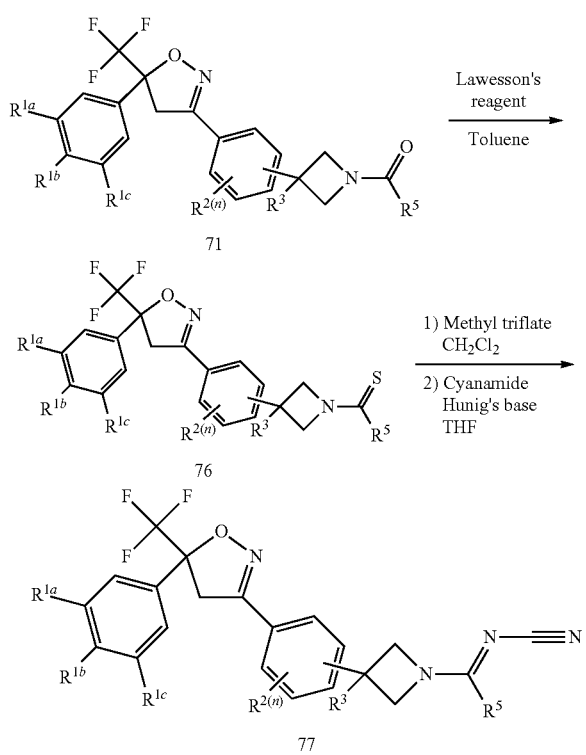

Thioamide 76 can be prepared by treatment of amide 71 with Lawesson's reagent in refluxing toluene. Methyl triflate can be added to thioamide 76 in a solvent such as $CH_2Cl_2$ to form a thioimidate intermediate as a solution. Cyanamide and Hunig's base in THF can be subsequently added directly to the thioimidate solution to afford cyanamide 77.

One, skilled in the art will recognize that, in some cases, after the introduction of a given reagent as it is depicted in the schemes, it may be necessary to perform additional routine synthetic steps not described in detail to complete the synthesis of Formula (1) or Formula (XX) compounds.

The present invention includes all veterinarily acceptable isotopically-labelled Formula (1) and Formula (XX) compounds wherein one or more atoms are replaced by atoms having the same atomic number, but an atomic mass or mass number different from the atomic mass or mass number usually found in nature.

Examples of isotopes suitable for inclusion in the compounds of the present invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, and sulphur, such as $^{36}S$.

The skilled person will appreciate that the compounds of the present invention could be made by methods other than those herein described as incorporated herein by reference, by adaptation of the methods herein described and/or adaptation of methods known in the art, for example the art described herein, or using standard textbooks such as "Comprehensive Organic Transformations—A Guide to Functional Group Transformations", R C Larock, Wiley-VCH (1999 or later editions).

The Formula (1) and Formula (XX) compounds are useful as ectoparasitic and endoparasitic agents, therefore, another embodiment of the present invention is a veterinary or pharmaceutical composition comprising a therapeutically effective amount of a Formula (1) or Formula (XX) compound, stereoisomer thereof, and a veterinarily or pharmaceutically acceptable excipient, diluent or carrier. The compounds of the present invention (including the compositions and processes used therein) may also be used in the manufacture of a medicament for the therapeutic applications described herein.

A typical formulation is prepared by mixing a Formula (1) or Formula (XX) compound with a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe to be administered to an animal. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or veterinary composition thereof) or aid in the manufacturing of the veterinary or pharmaceutical product (i.e., medicament).

The formulations can be prepared using conventional dissolution and mixing procedures. Such compositions and methods for their preparation may be found, for example, in 'Remington's Veterinary Sciences', 19th Edition (Mack Publishing Company, 1995; and "Veterinary Dosage Forms: Tablets, Vol. 1", by H. Lieberman and L. Lachman, Marcel Dekker, N.Y., 1980 (ISBN 0-8247-6918-X). For example, the bulk drug substance (i.e., compound of the present invention or stabilized form of the compound (e.g., complex with a cyclodextrin derivative or other known complexation agent)) is dissolved in a suitable solvent in the presence of one or more other excipients. The compounds of the present invention are typically formulated into veterinary or pharmaceutical dosage forms to provide an easily controllable dosage form for administration. Compounds of the present invention can also be admixed with animal feed.

The compounds may be administered alone or in a formulation appropriate to the specific use envisaged, the particular species of host animal being treated and the parasite involved. Generally, they will be administered as a formulation in association with one or more veterinarily or pharmaceutically acceptable salts, excipients, diluents, or carriers. The term "excipient", "diluent" or "carrier" is used herein to describe any ingredient other than the Formula (1) or Formula (XX) compounds or any additional antiparasitic agent. The choice of excipient, diluent, or carrier will to a large extent depend on factors such as the particular mode of administration, the effect of the excipient, carrier, or diluent on solubility and stability, nature of the dosage form, and animal specie.

The methods by which the compounds of the present invention may be administered include oral, topical, and injectable (subcutaneous, intraperitoneal, and intramuscular) administration. The preferred method of administration of the Formula (1) or Formula (XX) compounds is in an oral solid dosage form or oral liquid dosage form. Equally preferred is topical administration.

The Formula (1) or Formula (XX) compounds can be administered orally by capsule, bolus, tablet, powders, lozenges, chews, multi and nanoparticulates, gels, solid solution, films, sprays, liquid form, or admixed with food. Oral administration is the preferred method of administration and as such it is desirable to develop active Formula (1) or Formula (XX) compounds that are particularly suited to such formulations. Such formulations may be employed as fillers in soft or hard capsules, tablets, or chews, and typically comprise a carrier, for example, water, ethanol, polyethylene glycol, N-methylpyrrolidone, propylene glycol, methylcellulose, or a suitable oil, and one or more emulsifying agents and/or suspending agents. Liquid forms include suspensions, solutions, syrups, drenches and elixirs. Liquid formulations may also be prepared by the reconstitution of a solid, for example, from a sachet. Oral drenches are commonly prepared by dissolving or suspending the active ingredient in a suitable medium. Feed admixtures can be prepared for livestock and fish. Oral formulations can comprise from about 0.5 mg/kg to 50 mg/kg of a Formula (1) or Formula (XX) compound, and preferably about 1 mg/kg to 30 mg/kg of a Formula (1) or Formula (XX) compound. Depending upon the host specie treated and the parasite being treated, dose adjustments can be made.

The compounds may be administered topically to the skin or mucosa, that is dermally or transdermally. This is a preferred method of administration and as such it is desirable to develop active Formula (1) or Formula (XX) compounds that are particularly suited to such formulations, for example liquid forms. Typical formulations for this purpose include pour-on, spot-on, multi-spot-on, stripe-on, comb-on, roll-on, dip, spray, mousse, shampoo, powder formulation, gels, hydrogels, lotions, solutions, creams, ointments, dusting powders, dressings, foams, films, skin patches, wafers, implants, sponges, fibers, bandages and micro emulsions. Liposomes may also be used. Typical carriers include alcohol, water, mineral oil, liquid petrolatum, white petrolatum, glycerin, N-methyl formamide, glycol monomethyl ethers, polyethylene glycol, propylene glycol, and the like. Penetration enhancers may be incorporated—see, for example, J Pharm Sci, 88 (10), 955-958 by Finnin and Morgan (October 1999). Pour-on or spot-on formulations may be prepared by dissolving the active ingredients in an acceptable liquid carrier vehicle such as butyl digol, liquid paraffin or a non-volatile ester, optionally with the addition of a volatile component such as propan-2-ol or a glycol ether. Alternatively, pour-on, spot-on or spray formulations can be prepared by encapsulation, to leave a residue of active agent on the surface of the animal, this effect may ensure that the Formula (1) or Formula (XX) compounds have increased persistence of action and are more durable, for example they may be more water fast. Topical formulations of the combination contemplated herein can comprise from about 0.5 mg/kg to 50 mg/kg of a Formula (1) compound, and preferably about 1 mg/kg to 10 mg/kg of a Formula (1) or Formula (XX) compound. The compositions suitable for spot-on application according to the invention can be prepared by conventional mixing means. The volume of the applied composition can be from about 0.5 mL/kg to 5 mL/kg and preferably from about 1 mL/kg to 3 mL/kg. Similarly, dose can be adjusted.

The compounds of the present invention can also be administered topically via a support matrix for example, a synthetic or natural resin, plastic, cloth, leather, or other such polymeric system in the shape of a collar or ear tag. Said collar or ear tag may be coated, impregnated, layered, by any means so as to provide a veterinarily or pharmaceutically acceptable amount of a compound of the present invention alone, or with a veterinarily or pharmaceutically acceptable excipient, diluent, or carrier, and optionally an additional veterinary agent, or veterinarily or pharmaceutically acceptable salt thereof.

Agents may be added to the formulations of the present invention to improve the persistence of such formulations on the surface of the animal to which they are applied, for example to improve their persistence on the coat of the animal. It is particularly preferred to include such agents in a formulation which is to be applied as a pour-on or spot-on formulation. Examples of such agents include acrylic copolymers and in particular fluorinated acrylic copolymers. A particular suitable reagent is the trademark reagent "Foraperle" (Redline Products Inc, Texas, USA). Certain topical formulations may include unpalatable additives to minimize oral exposure.

Injectable formulations may be prepared in the form of a sterile solution, which may contain other substances, for example enough salts or glucose to make the solution isotonic with blood. Acceptable liquid carriers include vegetable oils such as sesame oil, glycerides such as triacetin, esters such as benzyl benzoate, isopropyl myristate and fatty acid derivatives of propylene glycol, as well as organic solvents such as pyrrolidin-2-one and glycerol formal. The formulations are prepared by dissolving or suspending compounds of the present invention alone or with an additional veterinary agent in the liquid carrier such that the final formulation contains from about 0.01 to 50% by weight of the active ingredients, preferably from about 0.01% to about 10% by weight of the active ingredients.

Suitable devices for injection include needle (including micro needle) injectors, needle-free injectors and infusion techniques. Subcutaneous formulations are typically aqueous solutions which may contain excipients such as salts, carbohydrates and buffering agents (preferably to a pH of from 3 to 9), but, for some applications, they may be more suitably formulated as a sterile non-aqueous solution or as a dry powder form to be used in conjunction with a suitable vehicle such as sterile, pyrogen-free water. The preparation of subcutaneous formulations under sterile conditions, for example, by lyophilisation, may readily be accomplished using standard veterinary techniques well known to those skilled in the art. The solubility of compounds of Formula (1) or Formula (XX) used in the preparation of subcutaneous solutions may be increased by the use of appropriate formulation techniques, such as the incorporation of solubility-enhancing agents.

Such formulations are prepared in a conventional manner in accordance with standard medicinal or veterinary practice. Further, these formulations will vary with regard to the weight of active compound contained therein, depending on the species of host animal to be treated, the severity and type of infection or infestation, and the body weight of the animal.

For fish, compounds of the present invention can be formulated for oral administration by way of feed admixture. For example, the compounds of the present invention can be formulated in a food product (e.g., pellets) that can be easily dispersed to fish as a feeding agent. Further, a compound of the present invention can be administered topically by immersing the fish into an aqueous environment containing at least one of the compounds of the present invention. For example, fish may be transferred into a tank for treatment or caused to pass from one holding zone into another. The compounds of the present invention may also be administered directly to the water containing the fish. The compound of the present invention can be in any dispersible formulation such that upon introduction to water the compound dissolves into the solution. Alternatively, the compounds of the present invention can be administered by injection. Preferable injection routes for treatment of fish are intraparitoneal or intramuscular. The injectable formulations include any liquid suspension, such as oils, aqueous solutions, or oil and water emersions. The compounds of the present invention can also be co-administered with additional agents, antigens, adjuvants, carriers, diluents or nutrients.

The Formula (1) and Formula (XX) compounds are also active against all or individual developmental stages of animal pests showing normal sensitivity, as well as those showing resistance to widely used parasiticides.

As described herein, compounds of the present invention may be administered alone or in combination with at least one additional veterinary agent including insecticides, acaricides, anthelmintics, fungicides, nematocides, antiprotozoals, bactericides, and growth regulators to form a multi-component agent giving an even broader spectrum of veterinary utility. Thus, the present invention also pertains to a composition comprising an effective amount of a Formula (1) compound, a stereoisomer thereof, and an effective amount of at least one additional veterinary agent and can further comprise one or more of a veterinarily or pharmaceutically acceptable excipient, diluent, or carrier.

The following list of additional veterinary agents together with which the compounds of the present invention can be used is intended to illustrate the possible combinations, but not to impose any limitation. Non-limiting examples of additional veterinary agents include: amitraz, arylpyrazoles as recited in publications WO1998/24767 and WO2005/060749, amino acetonitriles, anthelmintics (e.g., albendazole, cambendazole, fenbendazole, flubendazole, mebendazole, octadepsipeptides, oxfendazole, oxibendazole, paraherquamide (2-desoxoparaherquamide, derquantel), parbendazole, piperazines, praziquantel, thiabendazole, tetramisole, triclabendazole, levamisole, pyrantel pamoate, oxantel, morantel, and the like), indoxacarb and derivatives thereof, avermectins (e.g., abamectin, doramectin, emamectin, eprinomectin, ivermectin, moxidectin, selamectin, and the like), milbemycin, milbemycin oxime, DEET, demiditraz, diethylcarbamazine, fipronil, insect growth regulators (e.g., hydroprene, kinoprene, methoprene, pyriproxyfen, and the like), metaflumizone, niclosamide, permethrin, pyrethrins, spinosad, and formamidines (e.g., demiditraz, amitraz, and the like). In certain instances, combinations of a Formula (1) or Formula (XX) compound with an additional veterinary agent(s) can result in a greater-than-additive effect. Reducing the quantity of active ingredients released in the environment while ensuring effective pest control is always desirable.

It may be desirable to administer a compound of the present invention, stereoisomers thereof, alone or in a composition comprising a veterinarily acceptable excipient, diluent, or carrier, for example, for the purpose of treating a particular parasitic infection or infestation or condition associated therewith. It is within the scope of the present invention that two or more veterinary compositions, at least one of which contains a Formula (1) or Formula (XX) compound in accordance with the invention, and the other, an additional veterinary agent, may conveniently be combined in the form of a kit suitable for coadministration of the compositions.

The compounds of the present invention (including the compositions and processes used therein) may also be used in the manufacture of a medicament for the therapeutic applications described herein.

The compounds of the present invention, stereoisomers thereof, and compositions comprising a therapeutically effective amount of a Formula (1) or Formula (XX) compound and a veterinarily acceptable excipient, diluent, or carrier are useful as parasiticides (endo- and ecto-parasites) for the control and treatment of infections or infestations manifested by said parasite in an animal. The compounds of the present invention have utility as an ectoparasiticide, in particular, as an acaricide and insecticide. They may, in particular, be used in the fields of veterinary medicine, livestock husbandry, fish farming, and the maintenance of public health: against acarids and insects which are parasitic upon vertebrates, particularly warm-blooded vertebrates, including companion animals, livestock, and birds. The compounds of the present invention are also parasiticides for cold-blooded fish. Some non-limiting examples of acaride and insect parasites include: ticks (e.g., *Ixodes* spp., *Rhipicephalus* spp., *Boophilus* spp., *Amblyomma* spp., *Hyalomma* spp., *Haemaphysalis* spp., *Dermacentor* spp., *Ornithodorus* spp., and the like); mites (e.g., *Dermanyssus* spp., *Sarcoptes* spp., *Psoroptes* spp., *Chorioptes* spp., *Demodex* spp., and the like); chewing and sucking lice (e.g., *Damalinia* spp., *Linognathus* spp., and the like); fleas (e.g., *Siphonaptera* spp., *Ctenocephalides* spp., and the like); and biting flies and midges (e.g., *Tabanidae* spp., *Haematobia* spp., *Stomoxys* spp., *Dermatobia* spp., *Simuliidae* spp., *Ceratopogonidae* spp., *Psychodidae* spp., and the like). In another example, ectoparasites of the crustacean order copepod, more particularly of the genera *Lepeophtheirus* (especially the salmon louse, *Lepeoptheirus salmonis*) and/or *Caligus* (e.g., *C. elongates, C. rogercreysii, C. teres, C. flexispina*, and the like), particularly sea lice, can be treated with a compound of the present invention. The compounds of the invention can also be used for the treatment of endoparasites, for example, heartworms, roundworms, hookworms, whipworms, and tapeworms.

The compounds of the present invention and compositions comprising compounds of the present invention in conjunction with at least one other veterinary agent are of particular value in the control of ectoparasites, endoparasites, and insects which are injurious to, or spread or act as vectors of diseases in animals. The ectoparasites, insects, and endoparasites which can be treated with a combination of a Formula (1) or Formula (XX) compound and an additional veterinary agent include those as herein before described and including helminthes of the phylum platyhelminthes (e.g., trematodes, eucestoda, and cestoda), and nemathelminthes (e.g., nematodes).

Any of the compounds of the present invention, or a suitable combination of a compound of the present invention and optionally, with at least one additional veterinary agent may be administered directly to the animal and/or indirectly by applying it to the local environment in which the animal dwells. Direct administration includes contacting the skin, fur, or feathers of a subject animal or bird with the compound(s), or by feeding or injecting the compounds into the animal or bird.

The Formula (1) or Formula (XX) compounds, stereoisomers thereof, and combinations with at least one additional veterinary agent, as described herein, are of value for the treatment and control of the various lifecycle stages of insects and parasites including egg, nymph, larvae, juvenile and adult stages.

The present invention also relates to a method of administering a compound of the present invention alone or in combination with at least one additional veterinary agent, and optionally a veterinarily or pharmaceutically acceptable excipient, diluent, or carrier, to animals in good health comprising the application to said animal to reduce or eliminate the potential for human parasitic infection or infestation from parasites carried by the animal and to improve the environment in which the animal and human inhabit.

The reactions set forth below were done generally under a positive pressure of argon or nitrogen or with a drying tube, at ambient temperature (unless otherwise stated), in anhydrous solvents, and the reaction flasks were fitted with rubber septa for the introduction of substrates and reagents via syringe. Glassware was oven dried and/or heat dried. Analytical thin layer chromatography (TLC) was performed using glass-backed silica gel 60 F 254 precoated plates and eluted with appropriate solvent ratios (v/v). Reactions were assayed by TLC or LCMS and terminated as judged by the consumption of starting material. Visualization of the TLC plates was done with UV light (254 nM wavelength) or with an appropriate TLC visualizing solvent and activated with heat. Flash column chromatography (Still et al., *J. Org. Chem.* 43, 2923, (1978) was performed using silica gel (RediSep Rf) or various MPLC systems, such as Biotage or ISCO purification system.

Conventional methods and/or techniques of separation and purification known to one of ordinary skill in the art can be used to isolate the compounds of the present invention, as well as the various intermediates related thereto. Such techniques will be well-known to one of ordinary skill in the art and may include, for example, all types of chromatography (high pressure liquid chromatography (HPLC), column chromatography using common adsorbents such as silica gel, and thin-layer chromatography (TLC), recrystallization, and differential (i.e., liquid-liquid) extraction techniques.

The compound structures in the examples below were confirmed by one or more of the following methods: proton magnetic resonance spectroscopy, and mass spectroscopy. Proton magnetic resonance ($^1$H NMR) spectra were determined using a Bruker spectrometer operating at a field strength of 400 megahertz (MHz). Chemical shifts are reported in parts per million (PPM, δ) downfield from an internal tetramethylsilane standard. Mass spectra (MS) data were obtained using Agilent mass spectrometer with atmospheric pressure chemical ionization. Method: Acquity HPLC with chromatography performed on a Waters BEH C18 column (2.1×50 mm, 1.7 μm) at 50° C. The mobile phase was a binary gradient of acetonitrile (containing 0.1% trifluoroacetic acid) and water (5-100%).

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

One skilled in the art will also recognize that Formula (1) or Formula (XX) compounds and the intermediates described herein can be subjected to various electrophilic, nucleophilic, radical, organometallic, oxidation, and reduction reactions to add substituents or modify existing substituents.

The following examples provide a more detailed description of the process conditions. It is to be understood, however, that the invention, as fully described herein and as recited in the claims, is not intended to be limited by the details of the following schemes or modes of preparation.

Preparation 1: tert-butyl-3-hydroxyazetidine-1-carboxylate

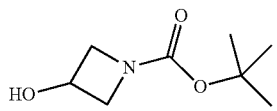

To a stirred cold (0° C.) solution of 3-hydroxyazetidine hydrochloride (75 g, 0.68 mol) in ethanol (1300 mL) was added triethylamine (208 g/280 mL, 2.05 mol) followed by Boc$_2$O (164 g, 0.75 mol). The resultant solution was stirred at ambient temperature for 16 hours. GC/MS analysis of the reaction mixture revealed complete reaction. Volatiles were removed in vacuo and the residue was diluted with EtOAc (1300 mL) and washed with 10% citric acid (700 mL), water (700 mL) and brine (700 mL). The organics were dried over sodium sulfate filtered, and concentrated to give the desired product (100.8 g, 85% yield). $^1$H NMR (CDCl$_3$) δ 4.6 (m, 1H), 4.2 (m, 2H), 3.8 (m, 2H), 1.4 (s, 9H).

Preparation 2: tert-butyl 3-oxoazetidine-1-carboxylate

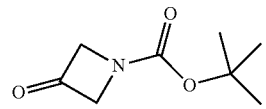

A 5 L-3-neck flask equipped with mechanical stirrer, thermocouple, addition funnel and nitrogen inlet was charged with Py-SO$_3$ (277 g, 1.74 mol) and DMSO (900 mL) and cooled to 10° C. in ice-bath. TEA (177 g/244 mL, 1.74 mol) was added. A solution of tert-butyl-3 hydroxyazetidine-1-carboxylate (Preparation 1, 100.8 g, 0.58 mol) in DMSO (500 mL) was added slowly via addition funnel at 10° C. The reaction was stirred at ambient temperature overnight. GC/MS analysis of the reaction mixture reveals that the reaction was completed. The reaction was quenched with brine (1 L). Solids were filtered and the aqueous was extracted with ethyl acetate (3×1 L). The combined organics were washed with saturated aqueous NaHCO3 (1.5 L), brine (1.5 L), dried over sodium sulfate, filtered, and concentrated to give the desired product (94 g, 95% yield). $^1$H NMR (CDCl$_3$) δ 4.6 (s, 4H), 1.4 (s, 9H).

Preparation 3: tert-butyl 3-hydroxy-3-(4-(trimethylsilyl)phenyl)azetidine-1-carboxylate

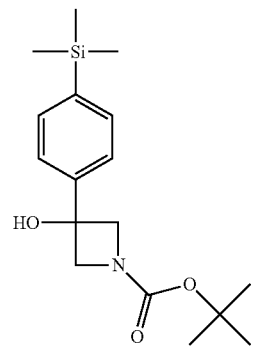 [SMILES: CC(C)(C)OC(=O)N1CC(O)(c2ccc([Si](C)(C)C)cc2)C1]

A 2 L-3neck flask equipped with mechanical stirrer, thermocouple, addition funnel and nitrogen inlet was charged with (4-bromophenyl)trimethylsilane (80.4 g, 0.35 mol), THF (600 mL), Mg (8.5 g), and I$_2$ (catalytic amount). The suspension was refluxed at 68° C. for 1.5 hours until all magnesium disappeared. The solution was cooled to 0° C. in ice-bath. Then, a solution of tert-butyl 3-oxoazetidine-1-carboxylate (Preparation 2, 30 g, 0.17 mol) in THF (200 mL) was added slowly via addition funnel. The solution was stirred at 0° C. for 3 hours. LC/MS indicated the formation of desired product. The reaction was quenched with brine at 0° C. The aqueous layer was extracted with EtOAc (2×800 mL). The combined organics were dried over sodium sulfate, filtered and concentrated to give the desired product (47.4 g, 84% yield). ¹H NMR (CDCl₃) δ 7.3 (d, 2H), 7.2 (d, 2H), 4.0 (d, 2H), 3.9 (d, 2H), 2.9 (s, 1H), 1.2 (s, 9H), 0.0 (s, 9H).

Preparation 4: tert-butyl 3-(4-bromophenyl)-3-hydroxyazetidine-1-carboxylate

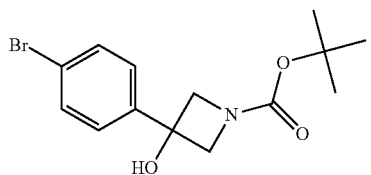 [SMILES: CC(C)(C)OC(=O)N1CC(O)(c2ccc(Br)cc2)C1]

A mixture of tert-butyl 3-hydroxy-3-(4-(trimethylsilyl)phenyl)azetidine-1-carboxylate (Preparation 3, 45 g, 0.14 mol) and KBr (25 g, 0.21 mol) in acetic acid (10 and MeOH (100 mL) was heated at 60° C. for 20 minutes. Then N-chlorosuccinimide (22.4 g, 0.17 mol) was added to the reaction mixture and stirred at 60° C. for 2 hours. LC/MS indicated the reaction was complete (only product peak). After cooling to ambient temperature, the mixture was poured into ice-water (1 L). The mixture was extracted with CHCl₃ (2×800 mL). The combined organics were washed with 3M NaOH (2×600 mL), water (600 mL), dried over sodium sulfate, filtered and concentrated. The crude product was washed with ether to afford the desired product (35 g, 76% yield). ¹H NMR (CDCl₃) δ 7.5 (d, 2H), 7.4 (d, 2H), 4.2 (s, 4H), 3.4 (s, 1H), 1.4 (s, 9H).

Preparation 5: tert-butyl-3-(4-bromophenyl)-3-fluoroazetidine-1-carboxylate

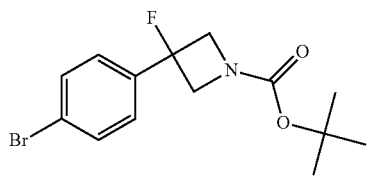 [SMILES: CC(C)(C)OC(=O)N1CC(F)(c2ccc(Br)cc2)C1]

Tert-butyl-3-(4-bromophenyl)-3-hydroxyazetidine-1-carboxylate (Preparation 4, 25 g, 0.076 mol) in CH₂Cl₂ (500 mL) was cooled to −78° C. To this slurry was slowly added BAST (20.2 g, 0.09 mol) via addition funnel. The temperature of the reaction was increased slowly from −78° C. to ambient temperature. The mixture was stirred at ambient temperature overnight. LC/MS indicated that the reaction was complete. The reaction was quenched with saturated aqueous NaHCO₃ solution (500 mL) and 1M NaOH (500 mL). The aqueous layer was extracted with CH₂Cl₂ (2×800 mL). The combined organics were washed with aqueous citric acid (2×700 mL), dried over Na₂SO₄, filtered, and concentrated to afford the desired product as tan solid (24.4 g, 97% yield). ¹H NMR (CDCl₃) δ 7.5 (d, 2H), 7.3 (d, 2H), 4.4 (m, 2H), 4.2 (m, 2H), 1.4 (s, 9H).

Preparation 6: tert-butyl 3-fluoro-3-(4-formylphenyl)azetidine-1-carboxylate

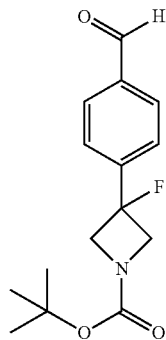 [SMILES: CC(C)(C)OC(=O)N1CC(F)(c2ccc(C=O)cc2)C1]

To a solution of tert-butyl-3-(4-bromophenyl)-3-fluoro-azetidine-1-carboxylate (Preparation 5, 1.0 g, 3 mmol) in THF (10 mL) at −78° C. was slowly added n-BuLi (2.1 mL of 1.6M solution in hexanes). The reaction was stirred at −78° C. for 15 minutes at which time DMF (0.5 mL, 6 mmol) was added. Reaction mixture was allowed to warm to room temperature and stir for additional 1 hour. Saturated aqueous NH₄Cl (10 mL) was added and the aqueous phase was extracted with ether (2×10 mL). The combined organic phases were dried (Na₂SO₄) and concentrated under vacuum. Crude product was chromatographed on silica (12 g column) using a gradient of 0-30% EtOAc/hexanes in a 12 minute run. Yield 460 mg. LC/MS retention time=3.004 minutes; MS calculated for (C₁₅H₁₈FNO₃), 279.127; found 180.2 M-BOC. ¹H NMR (CDCl₃) δ 10.0 (s, 1H), 8.0 (d, 2H), 7.7 (d, 2H), 4.5 (m, 2H), 4.2 (m, 2H), 1.6 (s, 9H).

Preparation 7: tert-butyl 3-fluoro-3-(4-((hydroxyimino)methyl)phenyl)azetidine-1-carboxylate

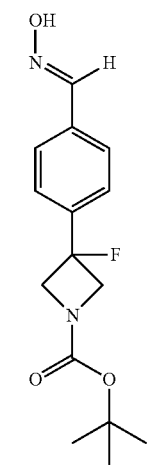 [SMILES: CC(C)(C)OC(=O)N1CC(F)(c2ccc(/C=N/O)cc2)C1]

To a solution of tert-butyl 3-fluoro-3-(4-formylphenyl)azetidine-1-carboxylate (Preparation 6, 460 mg, 1.65 mmol) in ethanol (30 mL) was added NH₂OH.HCl (127 mg, 1.8 mmol) and water (2.5 mL). The solution was heated to 50° C. for 1 hour and then allowed to stir at room temperature for 2 hours. The reactants were concentrated under vacuum to remove the ethanol. Water (5 mL) was added to the remaining residue and extracted with EtOAc (2×10 mL). Combined organic phases were dried (Na₂SO₄) and concentrated under vacuum to afford the intermediate as a solid. Yield 485 mg. ¹H NMR (CDCl₃) δ 8.17 (s, 1H), 7.65 (d, 2H), 7.50 (d, 2H), 5.32 (s, 1H), 4.37-4.50 (m, 2H), 4.28 (m, 2H), 1.45-1.55 (m, 9H). LC/MS retention time=2.926 minutes; MS calculated for (C₁₅H₁₉FN₂O₃), 294.13; found 195.0 M-Boc.

Preparation 8: tert-butyl 3-fluoro-3-(4-(5-(3,4,5-trichlorophenyl)-5-(trifluoromethyl)-4,5-dihydroisoxazol-3-yl)phenyl)azetidine-1-carboxylate

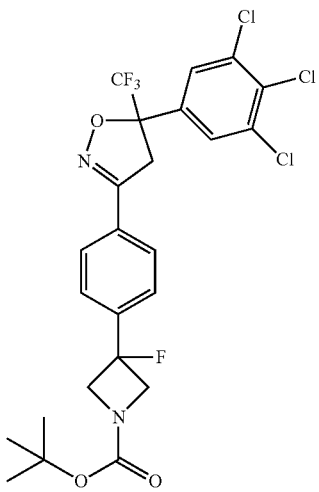 [SMILES: CC(C)(C)OC(=O)N1CC(F)(c2ccc(C3=NOC(c4cc(Cl)c(Cl)c(Cl)c4)(C(F)(F)F)C3)cc2)C1]

To a DMF (8 mL) solution of tert-butyl 3-fluoro-3-(4-((hydroxyimino)methyl)-phenyl)azetidine-1-carboxylate (Preparation 7, 486 mg, 1.65 mmol) was added NCS (232 mg, 1.65 mmol) in two portions over 10 minutes. The reaction was stirred at room temperature overnight. The reaction was diluted with EtOAc (8 mL) and 1,2,3-trichloro-5-(1,1,1-trifluoroprop-2-en-2-yl)benzene (546 mg, 1.98 mmol) was added, followed by potassium bicarbonate (248 mg, 2.48 mmol). The reaction was stirred at room temperature for 3 days. The reaction was concentrated under vacuum. The residue was partitioned between EtOAc (50 mL) and water (50 mL). The aqueous layer was extracted with EtOAc (3×50 mL). The combined organic layers were dried and condensed. The crude material was adsorbed on silica and chromatographed on a 40 g silica column eluting with a gradient of 0%-40% EtOAc/hexanes over 20 minutes. Fractions containing the desired material were combined and concentrated to yield 526 mg of a white solid. $^1$H NMR (CDCl$_3$) δ 7.74 (d, 2H), 7.67 (s, 2H), 7.56 (d, 2H), 4.39-4.51 (m, 2H), 4.24 (m 2H), 4.12 (d, 1H), 3.72 (d, 1H), 1.5 (s, 9H).

Preparation 9: 3-(4-(3-fluoroazetidin-3-yl)phenyl)-5-(3,4,5-trichlorophenyl)-5-(trifluoromethyl)-4,5-dihydroisoxazole

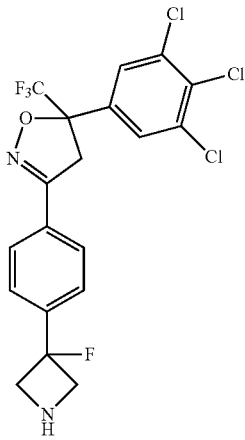 [SMILES: FC1(c2ccc(C3=NOC(c4cc(Cl)c(Cl)c(Cl)c4)(C(F)(F)F)C3)cc2)CNC1]

To a solution of 250 mg of tert-butyl 3-fluoro-3-(4-(5-(3,4,5-trichlorophenyl)-5-(trifluoromethyl)-4,5-dihydroisoxazol-3-yl)phenyl)azetidine-1-carboxylate (Preparation 8) in 2 mL CH$_2$Cl$_2$ was added 1 mL of trifluoroacetic acid. The reaction was stirred overnight under a positive pressure of nitrogen. The reaction was concentrated. The residue was partitioned between EtOAc and saturated aqueous NaHCO$_3$. The aqueous layer was extracted 2× with EtOAc (20 mL). The combined organics were dried over Na$_2$SO$_4$ and condensed to yield 188 mg of a film. TLC shows much more polar spot. The crude product was carried on to the next reactions. MS calculated for (C$_{19}$H$_{13}$Cl$_3$F$_4$N$_2$O), 466.00; found 467.9 M+H Example 1

1-(3-fluoro-3-(4-(5-(3,4,5-trichlorophenyl)-5-(trifluoromethyl)-4,5-dihydroisoxazol-3-yl)phenyl)azetidin-1-yl)ethanone

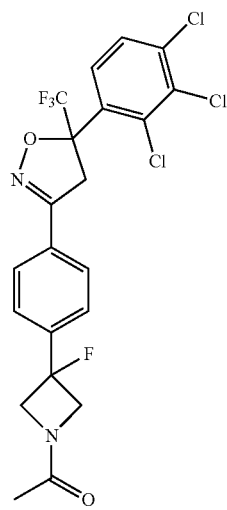 [SMILES: CC(=O)N1CC(F)(c2ccc(C3=NOC(c4ccc(Cl)c(Cl)c4Cl)(C(F)(F)F)C3)cc2)C1]

To a solution of 3-(4-(3-fluoroazetidin-3-yl)phenyl)-5-(3,4,5-trichlorophenyl)-5-(trifluoromethyl)-4,5-dihydroisoxazole (Preparation 9, 94 mg) in 2 mL CH$_2$Cl$_2$ was added pyridine (0.05 mL) followed by acetyl chloride (31 mg). The reaction was allowed to stir at room temperature for 1 hour. Water (3 mL) was added. The reaction was diluted with 3 mL of CH$_2$Cl$_2$, stirred for 30 minutes and poured through a phase extractor. The CH$_2$Cl$_2$ layer was collected and concentrated. The crude product from the reaction was adsorbed onto silica and chromatographed on a 12 g silica column eluting with a gradient of 50% EtOAc/hexanes to 100% EtOAc/hexanes to yield 90 mg of the desired compound as a white foam. $^1$H NMR (CDCl$_3$) δ 7.76 (d, 2H). 7.67 (s, 2H), 7.56 (d, 2H), 4.71-4.31 (m, 4H), 4.12 (d, 1H), 3.72 (d, 1H), 2.01 (s, 3H). LC/MS retention time=3.591 minutes; MS calculated for (C$_{21}$H$_{15}$Cl$_3$F$_4$N$_2$O$_2$), 509.714; found 511 M+H.

Example 2

Cyclopropyl(3-fluoro-3-(4-(5-(3,4,5-trichlorophenyl)-5-(trifluoromethyl)-4,5-dihydroisoxazol-3-yl)phenyl)azetidin-1-yl)methanone

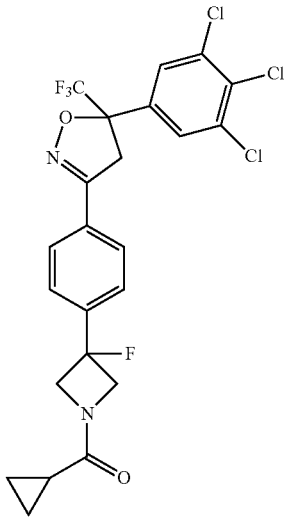 [SMILES: O=C(C1CC1)N1CC(F)(c2ccc(C3=NOC(c4cc(Cl)c(Cl)c(Cl)c4)(C(F)(F)F)C3)cc2)C1]

To a solution of the 3-(4-(3-fluoroazetidin-3-yl)phenyl)-5-(3,4,5-trichlorophenyl)-5-(trifluoromethyl)-4,5-dihydroisoxazole (Preparation 9, 94 mg) in 2 mL $CH_2Cl_2$ was added pyridine (0.05 mL) followed by cyclopropane carbonyl chloride (31 mg). The reaction was allowed to stir at room temperature for 1 hour. Water (10 mL) was added. The reaction was diluted with an additional 10 mL of $CH_2Cl_2$, stirred for 30 minutes at room temperature then passed through a phase separation tube. The $CH_2Cl_2$ layer was collected and condensed. The crude material was adsorbed on silica and chromatographed on a 12 g silica column, eluting with a gradient of 20% EtOAc/hexane to 80% EtOAc/hexane. Fractions containing the desired material were combined and concentrated. $Et_2O$ (~½ mL) was added to the resulting film. Placing the flask on high vac overnight resulted in formation of the product as a white foam (87 mg). $^1$H NMR ($CDCl_3$) δ ppm 7.76 (d, 2H), 7.67 (s, 2H), 7.58 (d, 2H), 4.8-4.7 (m, 1H), 4.6-4.2 (m, 3H), 4.12 (d, 1H), 3.72 (d, 1H), 1.5-1.4 (m, 1H), 1.08 (m, 2H), 0.86 (m, 2H). LC/MS retention time=3.710 minutes, MS calculated for ($C_{23}H_{17}Cl_3F_4N_2O_2$), 534.03; found 535.0 M+H.

Example 3

3-fluoro-N-methyl-3-(4-(5-(3,4,5-trichlorophenyl)-5-(trifluoromethyl)-4,5-dihydroisoxazol-3-yl)phenyl)azetidine-1-carboxamide

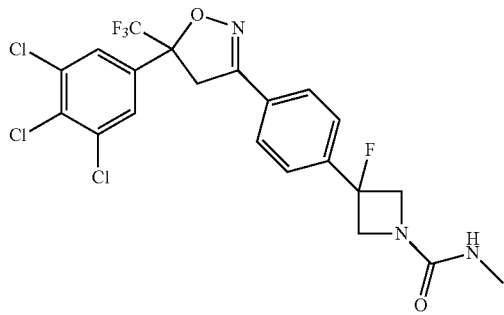 [SMILES: CNC(=O)N1CC(F)(c2ccc(C3=NOC(c4cc(Cl)c(Cl)c(Cl)c4)(C(F)(F)F)C3)cc2)C1]

The compound was prepared using a procedure similar to that of Example 2 using methyl isocyanate in place of cyclopropane carbonyl chloride. Yield 124 mg (94%). $^1$H NMR ($CDCl_3$) δ 7.73 (d, 2H), 7.66 (s, 2H), 7.56 (d, 2H), 4.49-4.40 (m, 2H), 4.28-4.17 (m, 3H), 4.10 (d, 1H), 3.70 (d, 1H), 2.86 (d, 3H). LC/MS retention time=3.559 minutes, MS calculated for ($C_{21}H_{16}Cl_3F_4N_3O_2$), 523.02; found 524.0 M+H.

Example 4

N-ethyl-3-fluoro-3-(4-(5-(3,4,5-trichlorophenyl)-5-(trifluoromethyl)-4,5-dihydroisoxazol-3-yl)phenyl)azetidine-1-carboxamide

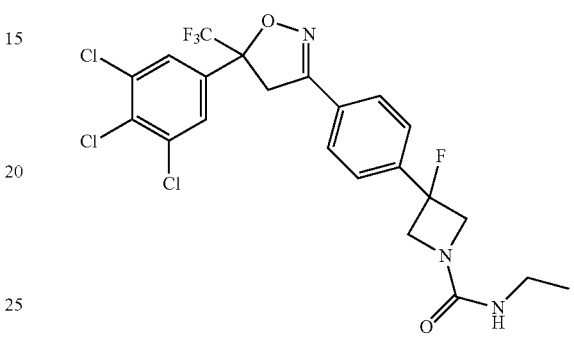

The compound was prepared using a procedure similar to that of Example 2 using ethyl isocyanate in place of cyclopropane carbonyl chloride. Yield 130 mg (96%). $^1$H NMR ($CDCl_3$) δ 7.73 (d, 2H), 7.66 (s, 2H), 7.56 (d, 2H), 4.49-4.38 (m, 2H), 4.27-4.15 (m, 3H), 4.10 (d, 1H), 3.70 (d, 1H), 3.31 (m, 2H), 1.18 (t, 3H). LC/MS retention time=3.638 minutes, MS calculated for ($C_{22}H_{18}Cl_3F_4N_3O_2$), 537.04; found 538.0 M+H.

Example 5

N-cyclopropyl-3-fluoro-3-(4-(5-(3,4,5-trichlorophenyl)-5-(trifluoromethyl)-4,5-dihydroisoxazol-3-yl)phenyl)azetidine-1-carboxamide

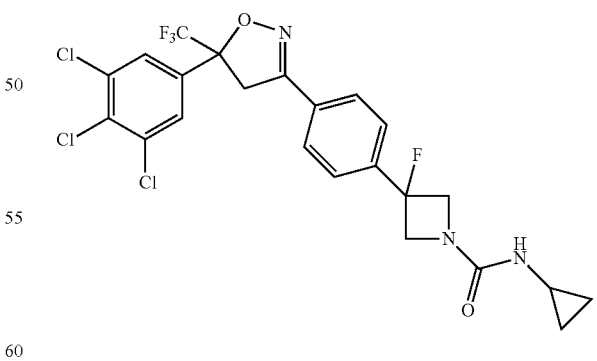

The compound was prepared using a procedure similar to that of Example 2 using cyclopropyl isocyanate in place of cyclopropane carbonyl chloride. Yield 130 mg (94%). $^1$H NMR ($CDCl_3$) δ 7.73 (d, 2H), 7.66 (s, 2H), 7.56 (d, 2H), 4.55-4.40 (m, 3H), 4.28-4.19 (m, 2H), 4.10 (d, 1H), 3.70 (d, 1H), 2.65 (m, 1H), 0.78 (m, 2H), 0.55 (m, 2H). LC/MS Preparation 10: tert-butyl 3-(4-(diethoxymethyl)phenyl)-3-hydroxyazetidine-1-carboxylate

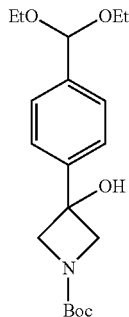

Cerium chloride (71.4 g, 290 mmoles) was slurried in tetrahydrofuran (600 mL) and heated to 65° C. for 2.5 hours, then cooled to room temperature In a separate flask, 4-bromobenzaldehyde diethylacetal (100 g, 386 mmoles) was dissolved in tetrahydrofuran (750 mL). Magnesium turnings (5.9 g, 241 mmoles) and dibromoethane (0.5 mL) were added and the mixture heated to reflux for 2.5 hours, until all the magnesium had reacted. Heating was removed and the Grignard solution cooled in an ice bath. The cerium chloride/tetrahydrofuran slurry was cooled in an ice bath to 0° C. The Grignard solution was added, portionwise, and the mixture stirred at 0° C. for 45 minutes. N-(t-butoxycarbonyl)azetidinone (41.3 g, 241 mmoles) dissolved in tetrahydrofuran (200 mL) was added portionwise and the reaction allowed to stir at 0° C. for 30 minutes. The reaction was quenched with saturated sodium carbonate solution (500 mL) and then diluted with ethyl acetate (2000 mL). The organic phase was washed with water (3×500 mL), separated, dried over anhydrous magnesium sulphate, filtered and evaporated to dryness to give a yellow oil weighing 120 g which was purified using normal phase chromatography (600 g SiO$_2$ column, loaded as a solution in 25 mL of dichloromethane, linear gradient of 10% tert-butylmethylether in n-heptane to 100% tert-butylmethylether over 60 minutes, 150 mL/minutes, 55 mL fractions using the 'Threshold OR Slope' method) to give a light yellow oil weighing 65 g, which NMR suggests is the desired acetal product. $^1$HNMR (CDCl$_3$) δ ppm: 7.50 (4H), 5.50 (1H), 4.15 (2H), 4.30 (2H), 3.55 (4H), 1.50 (9H), 1.25 (6H); m/z (ESI) 252 [M+H-Boc]$^+$.

Preparation 11: (E)-tert-butyl 3-hydroxy-3-(4-((hydroxyimino)methyl)phenyl)-azetidine-1-carboxylate

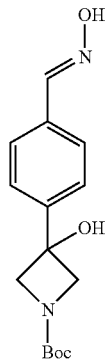 [SMILES: CC(C)(C)OC(=O)N1CC(O)(c2ccc(/C=N/O)cc2)C1]

The product of Preparation 10 (54 g, 195 mmoles) was dissolved in methanol (800 mL) and water (400 mL). Hydroxylamine hydrochloride (14 g, 200 mmoles) was added portionwise and the mixture stirred at room temperature for 60 minutes. The reaction mixture was evaporated to remove excess methanol. The aqueous residue was extracted with ethyl acetate (3000 mL), separated, dried over anhydrous magnesium sulphate, filtered and evaporated to dryness to give a thick yellow syrup weighing 49 g $^1$HNMR (CDCl$_3$) δ ppm: 8.15 (1H), 7.60 (2H), 7.50 (2H), 4.20 (4H), 1.52 (9H); m/z (ESI) 193 [M+H-Boc]$^+$.

Preparation 12: tert-butyl 3-(4-(5-(3,5-dichlorophenyl)-5-(trifluoromethyl)-4,5-dihydroisoxazol-3-yl)phenyl)-3-hydroxyazetidine-1-carboxylate

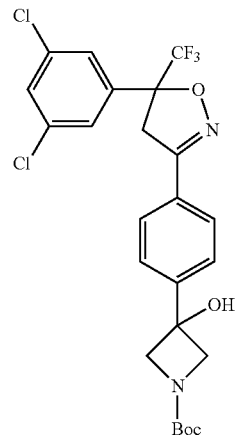 [SMILES: CC(C)(C)OC(=O)N1CC(O)(c2ccc(C3=NOC(c4cc(Cl)cc(Cl)c4)(C(F)(F)F)C3)cc2)C1]

The product of Preparation 11 (56 g, 192 mmoles) was dissolved in ethyl acetate (1000 mL) and stirred at room temperature. N-chlorosuccinimide (29.9 g, 224 mmoles) was added portionwise. After 60 minutes, to the reaction mixture was added potassium bicarbonate (57.5 g, 575 mmoles), water (5 mL) and 1,3-dichloro-2-fluoro-5-(3,3,3-trifluoroprop-1-en-2-yl)benzene (49.7 g, 192 mmoles). The mixture was stirred overnight at room temperature. The reaction was quenched with water (750 mL), diluted with ethyl acetate (1500 mL), layers shaken to dissolve all the solids, separated, organic phase dried over anhydrous magnesium sulphate, filtered and evaporated to a slurry (approx 1 liter in volume). Hexanes (1 liter) were added and the mixture shaken and filtered to give a white filter cake which was washed through with a further 300 mL of hexanes and dried at the pump to give a white solid weighing 52 g $^1$HNMR (DMSO-D6) δ ppm: 7.80 (2H), 7.75 (2H), 7.62 (2H), 4.32 (2H), 4.05 (4H), 1.40 (9H); m/z (ESI) 449 [M+H-Boc]$^+$, 547 [M−H]$^+$ Preparation 13: 3-(4-(5-(3,5-dichlorophenyl)-5-(trifluoromethyl)-4,5-dihydroisoxazol-3-yl)phenyl)azetidin-3-ol

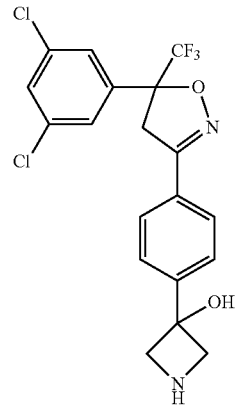 [SMILES: OC1(c2ccc(C3=NOC(c4cc(Cl)cc(Cl)c4)(C(F)(F)F)C3)cc2)CNC1]

To a slurry of the product of Preparation 12 (52 g, 95 mmoles) in methanol (650 mL) was added concentrated aqueous hydrochloric acid (38 mL). The mixture was heated with stirring. At around 50° C., the slurry started to dissolve—forming a solution at reflux. After refluxing for 2 hours, the reaction was cooled to room temperature and evaporated under reduced pressure, chasing with toluene to give a white solid which was slurried with toluene (1000 mL) and filtered under reduced pressure. The filter cake was washed with hexanes (500 mL) and then dried in the vacuum oven at 50° C. to give a white solid weighing 42 g. $^1$HNMR (DMSO-D6) δ ppm: 7.80 (6H), 4.30 (4H), 4.12 (2H); m/z (ESI) 449 [M+H]$^+$, 447 [M–H]$^+$ Preparation 14: tert-butyl 3-(4-(5-(3,5-dichlorophenyl)-5-(trifluoromethyl)-4,5-dihydroisoxazol-3-yl)phenyl)-3-fluoroazetidine-1-carboxylate

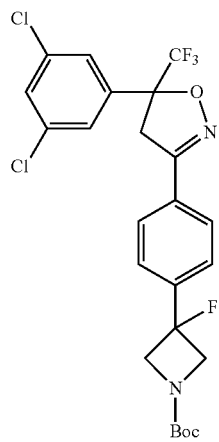 [SMILES: CC(C)(C)OC(=O)N1CC(F)(c2ccc(C3=NOC(c4cc(Cl)cc(Cl)c4)(C(F)(F)F)C3)cc2)C1]

Reference: J. Org. Chem. 2010, 75, 3401-3411. Triethylamine trihydrofluoride (5.3 g, 32.8 mmoles) was dissolved in dichloromethane (97 mL). Triethylamine (2.3 mL, 16.4 mmoles) was added and the solution cooled to −78° C. To the cooled mixture was added XtalFluor-E (5.6 g, 24.6 mmoles) and then the product of Preparation 12 (9 g, 16.4 mmoles). This resulted in a thick slurry. Cooling was removed and the mixture allowed to warm to room temperature, with stirring. The slurry dissolved to give a light brown solution. After stirring at room temperature, overnight, the reaction was quenched by addition of saturated aqueous sodium carbonate solution (100 mL) and dichloromethane (100 mL). The layers were then separated. The organic phase was dried over anhydrous magnesium sulphate, filtered and evaporated to dryness to give a brown oil weighing 9 g $^1$HNMR (CDCl$_3$) δ ppm: 7.75 (2H), 7.60 (2H), 7.55 (2H), 4.45 (2H), 4.25 (2H), 4.15 (1H), 3.70 (1H), 1.50 (9H); m/z (ESI) 451 [M+H-Boc]$^+$, 549 [M–H]$^+$ Preparation 15: 5-(3,5-dichlorophenyl)-3-(4-(3-fluoroazetidin-3-yl)phenyl)-5-(trifluoromethyl)-4,5-dihydroisoxazole

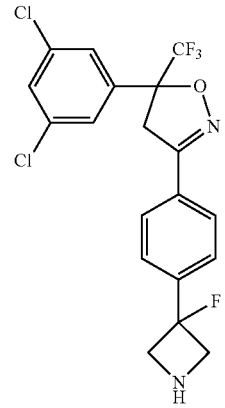 [SMILES: FC1(c2ccc(C3=NOC(c4cc(Cl)cc(Cl)c4)(C(F)(F)F)C3)cc2)CNC1]

To a solution of tert-butyl 3-(4-(5-(3,5-dichlorophenyl)-5-(trifluoromethyl)-4,5-dihydroisoxazol-3-yl)phenyl)-3-fluoroazetidine-1-carboxylate (Preparation 14) in methanol (10 mL) was added a methanolic solution of HCl (10 mL of 1.25 M). Reaction mixture warmed to 65° C. for 1.5 hours. Reaction concentrated via rotavap to yield a viscous oil. CH$_2$Cl$_2$ was added and a precipitate formed. Volatiles removed under reduced pressure to yield 573 mg of the title compound as a white solid. $^1$H NMR (DMSO-d$_6$) δ 9.8-9.6 (br s, 2H) 7.9-7.8 (m, 3H), 7.75 (d, 2H), 7.63 (d, 2H), 4.64-4.29 (m, 6H)). LC/MS retention time=3.039 minutes, MS calculated for (C$_{19}$H$_{14}$Cl$_2$F$_4$N$_2$O), 432.04; found 433.0 M+H.

Example 6

Cyclopropyl(3-(4-(5-(3,5-dichlorophenyl)-5-(trifluoromethyl)-4,5-dihydroisoxazol-3-yl)phenyl)-3-fluoroazetidin-1-yl)methanone

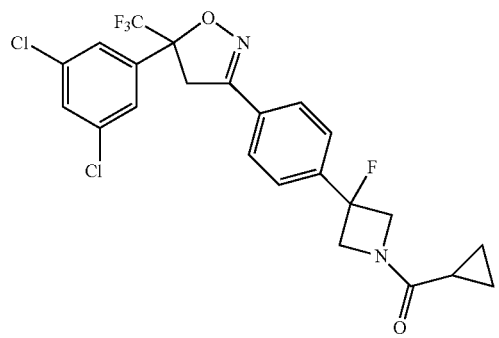 [SMILES: O=C(C1CC1)N1CC(F)(c2ccc(C3=NOC(c4cc(Cl)cc(Cl)c4)(C(F)(F)F)C3)cc2)C1]

To a solution of the 5-(3,5-dichlorophenyl)-3-(4-(3-fluoroazetidin-3-yl)phenyl)-5-(trifluoromethyl)-4,5-dihydroisoxazole (Preparation 15, 65 mg) in 2 mL CH$_2$Cl$_2$ was added triethyl amine (50 μL) followed by cyclopropane carbonyl chloride (19 mg). The reaction was allowed to stir at room temperature for 30 minutes. Water (5 mL) was added. The reaction was diluted with an additional 5 mL of CH$_2$Cl$_2$, stirred for 5 minutes at room temp then passed through a phase separation tube. The CH$_2$Cl$_2$ layer was collected and condensed. The crude material was adsorbed on silica and chromatographed on a 12 g silica column, eluting with a gradient of 0% to 100% ethyl acetate in heptane. Fractions containing the desired material were combined and concentrated. Et$_2$O (~½ mL) was added to the resulting film. Placing the flask on high vacuum overnight resulted in formation of a white foam. Yield 67 mg (98%) of the desired product. $^1$H NMR (CDCl$_3$) δ ppm 7.76 (d, 2H), 7.63-7.51 (s, 4H), 7.45 (s, 1H), 4.8-4.7 (m, 1H), 4.6-4.3 (m, 3H), 4.12 (d, 1H), 3.74 (d, 1H), 1.6-1.4 (m, 1H), 1.07 (m, 2H), 0.86 (m, 2H). LC/MS retention time=3.654 minutes, MS calculated for (C$_{23}$H$_{18}$Cl$_2$F$_4$N$_2$O$_2$), 500.07; found 501.0 M+H.

Example 7

1-(3-(4-(5-(3,5-dichlorophenyl)-5-(trifluoromethyl)-4,5-dihydroisoxazol-3-yl)phenyl)-3-fluoroazetidin-1-yl)-2-methylpropan-1-one

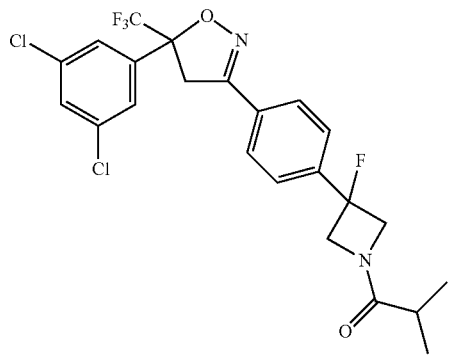 [SMILES: CC(C)C(=O)N1CC(F)(c2ccc(C3=NOC(c4cc(Cl)cc(Cl)c4)(C(F)(F)F)C3)cc2)C1]

The compound was prepared using a procedure similar to that of Example 6 using of isobutyroyl chloride in place of cyclopropane carbonyl chloride. Yield 146 mg (95%). $^1$H NMR (CDCl$_3$) δ 7.76 (d, 2H), 7.58-7.51 (m, 4H), 7.45 (m, 1H), 4.71-4.58 (m, 1H), 4.56-4.32 (m 3H), 4.12 (d, 1H), 3.73 (d, 1H), 2.53 (m, 1H), 1.22-1.14 (m, 6H). LC/MS retention time=3.660 minutes, MS calculated for (C$_{23}$H$_{20}$Cl$_2$F$_4$N$_2$O$_2$), 502.08; found 503.0 M+H.

Example 8

3-(4-(5-(3,5-dichlorophenyl)-5-(trifluoromethyl)-4,5-dihydroisoxazol-3-yl)phenyl)-3-fluoro-N-methylazetidine-1-carboxamide

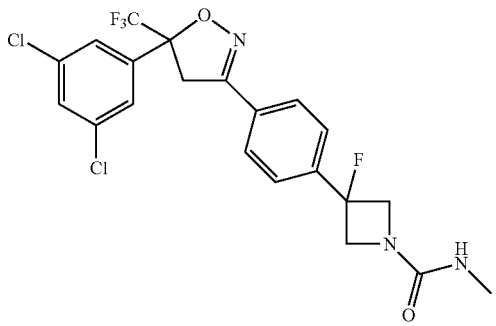 [SMILES: CNC(=O)N1CC(F)(c2ccc(C3=NOC(c4cc(Cl)cc(Cl)c4)(C(F)(F)F)C3)cc2)C1]

The compound was prepared using a procedure similar to that of Example 6 using methyl isocyanate in place of cyclopropane carbonyl chloride. Yield 118 mg (96%). $^1$H NMR (CDCl$_3$) δ 7.73 (d, 2H), 7.61-7.51 (m, 4H), 7.44 (m, 1H), 4.50-4.39 (m, 2H), 4.28-4.16 (m, 3H), 4.10 (d, 1H), 3.71 (d, 1H), 2.87 (d, 3H). LC/MS retention time=2.965 minutes, MS calculated for (C$_{21}$H$_{17}$Cl$_2$F$_4$N$_3$O$_2$), 489.06; found 490.0 M+H.

Example 9

3-(4-(5-(3,5-dichlorophenyl)-5-(trifluoromethyl)-4,5-dihydroisoxazol-3-yl)phenyl)-N-ethyl-3-fluoroazetidine-1-carboxamide

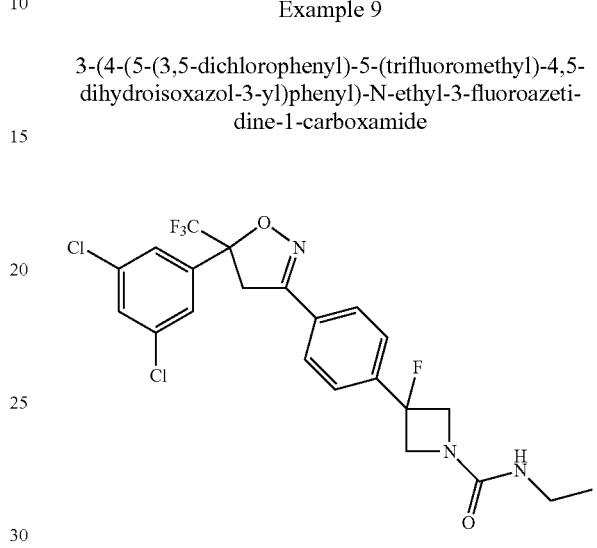

The compound was prepared using a procedure similar to that of Example 6 using ethyl isocyanate in place of cyclopropane carbonyl chloride. Yield 123 mg (97%). $^1$H NMR (CDCl$_3$) δ 7.73 (d, 2H), 7.59-7.50 (m, 4H), 7.44 (m, 1H), 4.50-4.38 (m, 2H), 4.27-4.14 (m, 3H), 4.10 (d, 1H), 3.71 (d, 1H), 3.31 (m, 2H), 1.18 (t, 3H). LC/MS retention time=3.018 minutes, MS calculated for (C$_{22}$H$_{19}$Cl$_2$F$_4$N$_3$O$_2$), 503.08; found 504.0 M+H.

Example 10

N-cyclopropyl-3-(4-(5-(3,5-dichlorophenyl)-5-(trifluoromethyl)-4,5-dihydroisoxazol-3-yl)phenyl)-3-fluoroazetidine-1-carboxamide

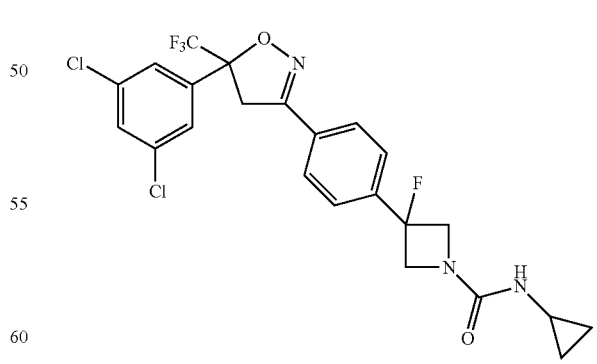

The compound was prepared using a procedure similar to that of Example 6 using cyclopropyl isocyanate in place of cyclopropane carbonyl chloride. Yield 124 mg (96%). $^1$H NMR (CDCl$_3$) δ 7.73 (d, 2H), 7.58-7.51 (m, 4H), 7.44 (m, 1H), 4.55-4.39 (m, 3H), 4.29-4.19 (m, 2H), 4.10 (d, 1H), 3.71

(d, 1H), 2.65 (m, 1H), 0.77 (m, 2H), 0.55 (m, 2H). LC/MS retention time=3.026 minutes, MS calculated for ($C_{23}H_{19}O_2F_4N_3O_2$), 515.08; found 516.0 M+H.

Preparation 16: 5-(3,5-dichloro-4-fluorophenyl)-3-(4-(3-fluoroazetidin-3-yl)phenyl)-5-(trifluoromethyl)-4,5-dihydroisoxazole

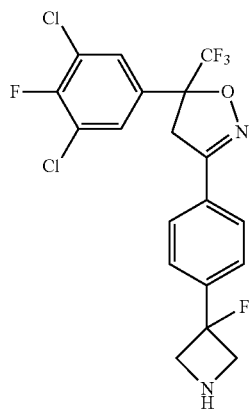 [SMILES: Fc1c(Cl)cc(C2(C(F)(F)F)CC(c3ccc(C4(F)CNC4)cc3)=NO2)cc1Cl]

The product was prepared according to the methods of Preparation 12, 14, and 15 using 1,3-dichloro-2-fluoro-5-(3,3,3-trifluoroprop-1-en-2-yl)benzene. $^1$H NMR (DMSO-d$_6$) δ 10.0-9.6 (br s, 2H) 7.9-7.7 (m, 6H), 4.68-4.24 (m, 6H). LC/MS retention time=3.020 minutes, MS calculated for ($C_{19}H_{13}Cl_2F_6N_2O$), 450.03; found 450.9 M+H.

Example 11

1-(3-(4-(5-(3,5-dichloro-4-fluorophenyl)-5-(trifluoromethyl)-4,5-dihydroisoxazol-3-yl)phenyl)-3-fluoroazetidin-1-yl)propan-1-one

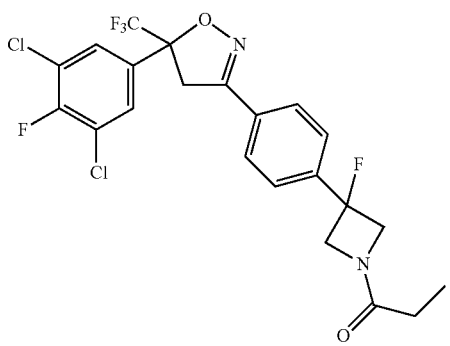 [SMILES: CCC(=O)N1CC(F)(c2ccc(C3=NOC(c4cc(Cl)c(F)c(Cl)c4)(C(F)(F)F)C3)cc2)C1]

The compound was prepared from the compound of preparation 16 according to the method of Example 6 using propionyl chloride in place of cyclopropane carbonyl chloride. $^1$H NMR (CDCl$_3$) δ 7.74 (d, 2H), 7.60 (d, 2H), 7.54 (d, 2H), 4.66-4.30 (m, 4H), 2.22 (m, 1H), 1.19 (m, 3H). LC/MS retention time=3.611 minutes, MS calculated for ($C_{22}H_{17}Cl_2F_5N_2O_2$), 506.6; found 507.0 M+H.

Example 12

1-(3-(4-(5-(3,5-dichloro-4-fluorophenyl)-5-(trifluoromethyl)-4,5-dihydroisoxazol-3-yl)phenyl)-3-fluoroazetidin-1-yl)butan-1-one

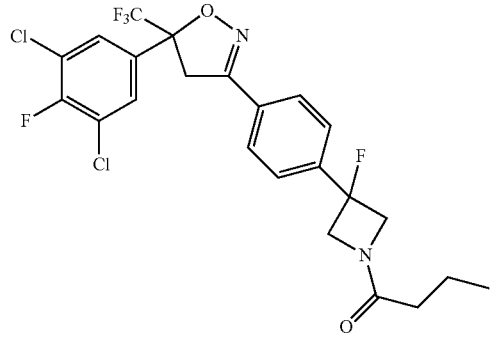

To a solution of butyric acid (50 mg) in DMF (5 mL) was added HATU (200 mg) then triethyl amine (150 μL). The resulting solution was stirred at ambient temperature for 15 minutes then 5-(3,5-dichloro-4-fluorophenyl)-3-(4-(3-fluoroazetidin-3-yl)phenyl)-5-(trifluoromethyl)-4,5-dihydroisoxazole hydrochloride (Preparation 16 100 mg) was added in one portion. Reaction stirred at ambient temperature for 16 hours. Solvent was removed in vacuo and the residue partitioned between water (10 mL) and CH$_2$Cl$_2$ (10 mL). Organic phase collected and condensed. The crude material was adsorbed on silica and chromatographed on a 12 g silica column, eluting with a gradient of 0% to 100% ethyl acetate in heptane. Fractions containing the desired material were combined and concentrated. Et$_2$O (~½ mL) was added to the resulting film. Placing the flask on high vacuum overnight resulted in formation of a white foam. Yield 86 mg (80%). $^1$H NMR (CDCl$_3$) δ 7.75 (d, 2H), 7.61 (d, 2H), 7.55 (d, 2H), 4.68-4.33 (m, 4H), 4.12 (d, 1H), 3.72 (d, 1H), 2.19 (m, 2H), 1.73 (m, 2H), 1.01 (m, 3H). LC/MS retention time=3.688 minutes, MS calculated for ($C_{23}H_{19}Cl_2F_5N_2O_2$), 520.07; found 521.0 M+H.

Example 13

2-cyclopropyl-1-(3-(4-(5-(3,5-dichloro-4-fluorophenyl)-5-(trifluoromethyl)-4,5-dihydroisoxazol-3-yl)phenyl)-3-fluoroazetidin-1-yl)ethanone

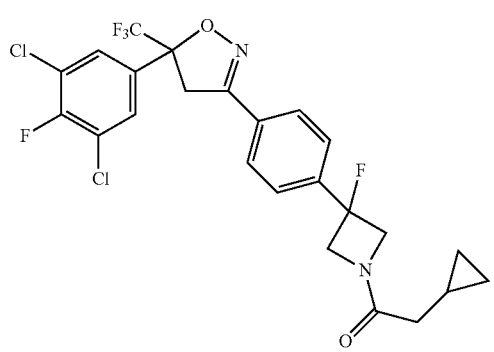 [SMILES: O=C(CC1CC1)N1CC(F)(c2ccc(C3=NOC(c4cc(Cl)c(F)c(Cl)c4)(C(F)(F)F)C3)cc2)C1]

The compound was prepared from the compound of Preparation 16 according to the method of Example 12 using cyclopropyl acetic acid in place of butyric acid. Yield 73 mg (67%).

¹H NMR (CDCl₃) δ 7.74 (d, 2H), 7.60 (d, 2H), 7.54 (d, 2H), 4.67-4.33 (m, 4H), 4.10 (d, 1H), 3.70 (d, 1H), 2.03 (m, 2H), 1.09 (m, 1H), 0.61 (m, 2H), 0.20 (m, 2H). LC/MS retention time=3.694 minutes, MS calculated for (C₂₄H₁₉Cl₂F₅N₂O₂), 532.07; found 533.0 M+H.

Example 14

3-(3-(4-(5-(3,5-dichloro-4-fluorophenyl)-5-(trifluoromethyl)-4,5-dihydroisoxazol-3-yl)phenyl)-3-fluoroazetidin-1-yl)-3-oxopropanenitrile

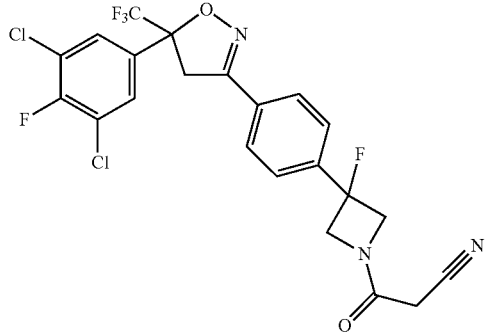 [SMILES: N#CCC(=O)N1CC(F)(c2ccc(C3=NOC(c4cc(Cl)c(F)c(Cl)c4)(C(F)(F)F)C3)cc2)C1]

The compound was prepared from the compound of Preparation 16 according to the method of Example 12 using cyanoacetic acid in place of butyric acid. Yield 88 mg (55%). ¹H NMR (CDCl₃) δ 7.77 (d, 2H), 7.60 (d, 2H), 7.55 (d, 2H), 4.79 (m, 1H), 4.71-4.40 (m, 3H), 4.11 (d, 1H), 3.71 (d, 1H), 3.40 (s, 2H). LC/MS retention time=3.533 minutes, MS calculated for (C₂₂H₁₄Cl₂F₅N₃O₂), 517.04; found 539.9 M+H+Na⁺.

Example 15

1-(3-(4-(5-(3,5-dichloro-4-fluorophenyl)-5-(trifluoromethyl)-4,5-dihydroisoxazol-3-yl)phenyl)-3-fluoroazetidin-1-yl)-2-(methylthio)ethanone

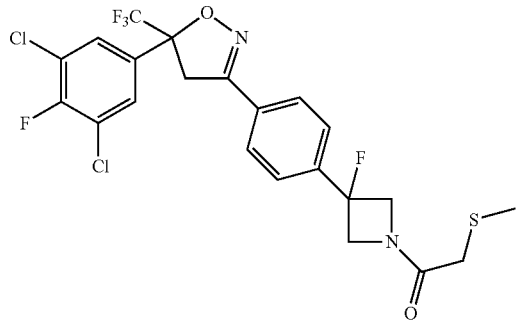 [SMILES: CSCC(=O)N1CC(F)(c2ccc(C3=NOC(c4cc(Cl)c(F)c(Cl)c4)(C(F)(F)F)C3)cc2)C1]

The compound was prepared from the compound of Preparation 16 according to the method of Example 12 using 2-(methylthio)acetic acid in place of butyric acid. Yield 208 mg (94%). ¹H NMR (CDCl₃) δ 7.75 (d, 2H), 7.60 (d, 2H), 7.55 (d, 2H), 4.72 (m, 1H), 4.61-4.34 (m, 3H), 4.11 (d, 1H), 3.71 (d, 1H), 3.15 (s, 2H), 2.26 (s, 3H). LC/MS retention time=3.637 minutes, MS calculated for (C₂₂H₁₇Cl₂F₅N₂O₂S), 538.03; found 538.9 M+H+.

Example 16

1-(3-(4-(5-(3,5-dichloro-4-fluorophenyl)-5-(trifluoromethyl)-4,5-dihydroisoxazol-3-yl)phenyl)-3-fluoroazetidin-1-yl)-2-methoxyethanone

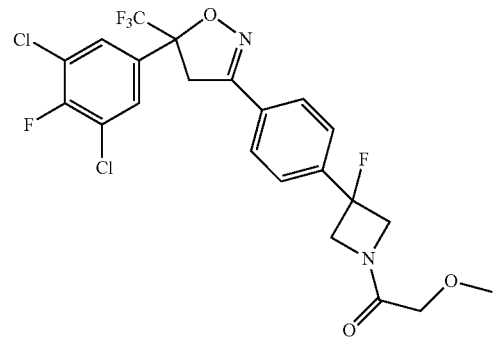 [SMILES: COCC(=O)N1CC(F)(c2ccc(C3=NOC(c4cc(Cl)c(F)c(Cl)c4)(C(F)(F)F)C3)cc2)C1]

The compound was prepared from the compound of preparation 16 according to the method of Example 6 using methoxy acetyl chloride in place of cyclopropane carbonyl chloride. Yield 114 mg (88%). ¹H NMR (CDCl₃) δ 7.74 (d, 2H), 7.60 (d, 2H), 7.54 (d, 2H), 4.82-4.68 (m, 1H), 4.66-4.34 (m, 3H), 4.15-4.04 (m, 3H), 3.71 (d, 1H), 3.42 (s, 3H). LC/MS retention time=3.543 minutes, MS calculated for (C₂₂H₁₇Cl₂F₅N₂O₃), 522.05; found 523.0 M+H.

Example 17

Cyclobutyl(3-(4-(5-(3,5-dichloro-4-fluorophenyl)-5-(trifluoromethyl)-4,5-dihydroisoxazol-3-yl)phenyl)-3-fluoroazetidin-1-yl)methanone

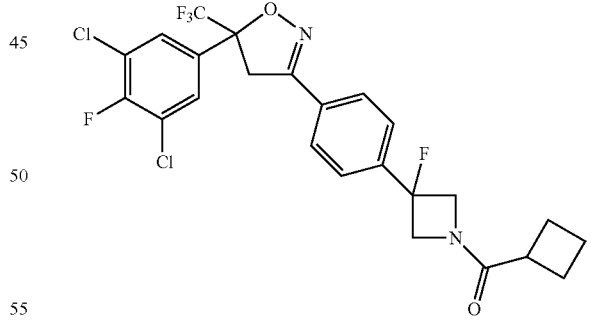

The compound was prepared from the compound of preparation 16 according to the method of Example 6 using cyclobutanecarbonyl chloride in place of cyclopropane carbonyl chloride. Yield 115 mg (88%). ¹H NMR (CDCl₃) δ 7.73 (d, 2H), 7.59 (d, 2H), 7.51 (d, 2H), 4.59-4.26 (m, 4H), 4.10 (d, 1H), 3.71 (d, 1H), 3.12 (m, 1H), 2.38 (m, 2H), 2.16 (m, 2H), 2.07-1.87 (m, 2H). LC/MS retention time=3.743 minutes, MS calculated for (C₂₄H₁₉Cl₂F₅N₂O₂), 532.07; found 533.0 M+H.

Example 18

1-(3-(4-(5-(3,5-dichloro-4-fluorophenyl)-5-(trifluoromethyl)-4,5-dihydroisoxazol-3-yl)phenyl)-3-fluoroazetidin-1-yl)-2-methylpropan-1-one

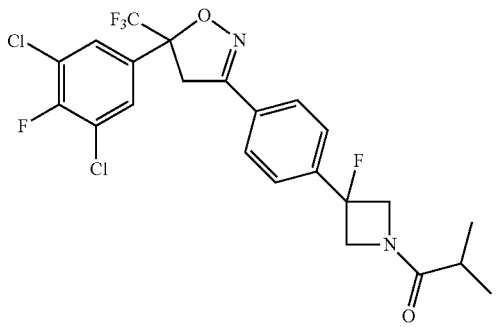 [SMILES: CC(C)C(=O)N1CC(F)(c2ccc(C3=NOC(c4cc(Cl)c(F)c(Cl)c4)(C(F)(F)F)C3)cc2)C1]

The compound was prepared from the compound of preparation 16 according to the method of Example 6 using isobutyroyl chloride in place of cyclopropane carbonyl chloride. Yield 166 mg (90%). $^1$H NMR (CDCl$_3$) δ 7.74 (d, 2H), 7.60 (d, 2H), 7.53 (d, 2H), 4.70-4.29 (m, 4H), 4.10 (d, 1H), 3.71 (d, 1H), 2.51 (m, 1H), 1.17 (m, 6H). LC/MS retention time=3.685 minutes, MS calculated for (C$_{23}$H$_{19}$Cl$_2$F$_5$N$_2$O$_2$), 520.07; found 521.0 M+H.

Example 19

1-(3-(4-(5-(3,5-dichloro-4-fluorophenyl)-5-(trifluoromethyl)-4,5-dihydroisoxazol-3-yl)phenyl)-3-fluoroazetidin-1-yl)-3,3,3-trifluoropropan-1-one

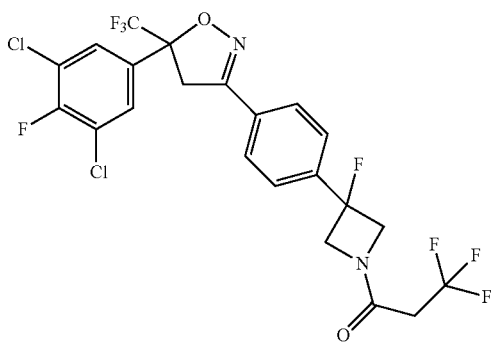 [SMILES: O=C(CC(F)(F)F)N1CC(F)(c2ccc(C3=NOC(c4cc(Cl)c(F)c(Cl)c4)(C(F)(F)F)C3)cc2)C1]

The compound was prepared from the compound of preparation 16 according to the method of Example 6 using 3,3,3-trifluoropropanoyl chloride in place of cyclopropane carbonyl chloride. Yield 96 mg (70%). $^1$H NMR (CDCl$_3$) δ 7.76 (d, 2H), 7.60 (d, 2H), 7.53 (d, 2H), 4.76-4.65 (m, 1H), 4.61-4.38 (m, 3H), 4.10 (d, 1H), 3.71 (d, 1H), 3.09 (m, 2H). LC/MS retention time=3.712 minutes, MS calculated for (C$_{22}$H$_{14}$Cl$_2$F$_8$N$_2$O$_2$), 560.03; found 561.0 M+H.

Example 20

N-cyclopropyl-3-(4-(5-(3,5-dichloro-4-fluorophenyl)-5-(trifluoromethyl)-4,5-dihydroisoxazol-3-yl)phenyl)-3-fluoroazetidine-1-carboxamide

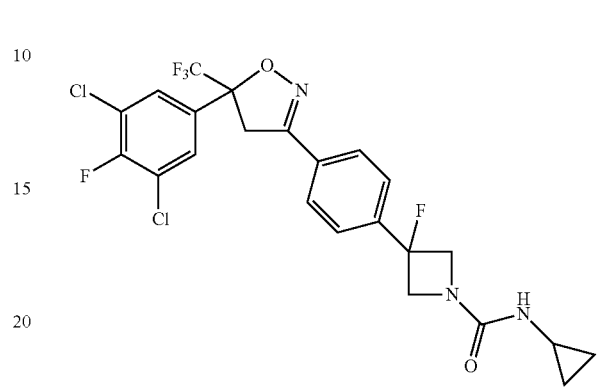

The compound was prepared from the compound of preparation 16 according to the method of Example 6 using cyclopropyl isocyanate in place of cyclopropane carbonyl chloride. Yield 126 mg (94%). $^1$H NMR (CDCl$_3$) δ 7.73 (d, 2H), 7.60 (d, 2H), 7.56 (d, 2H), 4.56-4.39 (m, 3H), 4.29-4.18 (m, 2H), 4.10 (d, 1H), 3.70 (d, 1H), 2.65 (m, 1H), 0.78 (m, 2H), 0.55 (m, 2H). LC/MS retention time=3.233 minutes, MS calculated for (C$_{23}$H$_{18}$Cl$_2$F$_5$N$_3$O$_2$), 533.07; found 534.0 M+H.

Example 21

3-(4-(5-(3,5-dichloro-4-fluorophenyl)-5-(trifluoromethyl)-4,5-dihydroisoxazol-3-yl)phenyl)-3-fluoro-N-methylazetidine-1-carboxamide

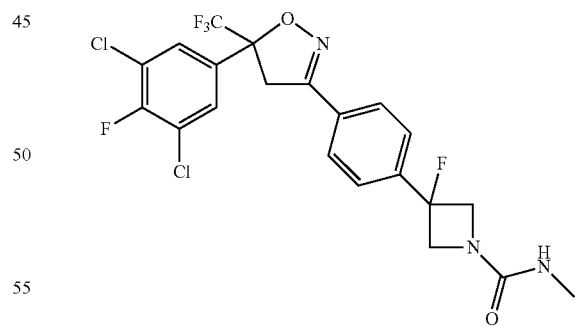

The compound was prepared from the compound of preparation 16 according to the method of Example 6 using methyl isocyanate in place of cyclopropane carbonyl chloride. Yield 44 mg (94%). $^1$H NMR (CDCl$_3$) δ 7.71 (d, 2H), 7.59-7.53 (m, 4H), 4.45 (d, 1H), 4.39 (d, 1H), 4.23 (d, 1H), 4.21 (d, 1H), 4.24-4.17 (m, 3H), 4.08 (d, 1H), 3.68 (d, 1H), 2.83 (d, 3H). LC/MS retention time=3.001 minutes, MS calculated for (C$_{21}$H$_{16}$Cl$_2$F$_5$N$_3$O$_2$), 507; found 508 M+H.

Example 22

3-(4-(5-(3,5-dichloro-4-fluorophenyl)-5-(trifluoromethyl)-4,5-dihydroisoxazol-3-yl)phenyl)-N-ethyl-3-fluoroazetidine-1-carboxamide

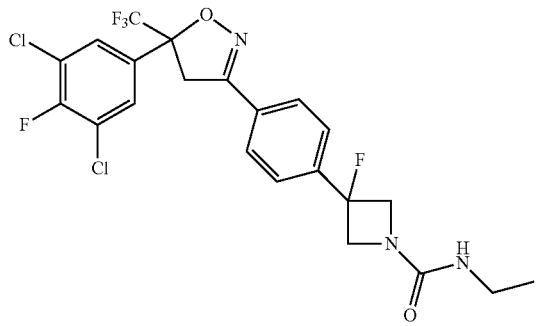 [SMILES: CCNC(=O)N1CC(F)(c2ccc(C3=NOC(c4cc(Cl)c(F)c(Cl)c4)(C(F)(F)F)C3)cc2)C1]

The compound was prepared from the compound of preparation 16 according to the method of Example 6 using ethyl isocyanate in place of cyclopropane carbonyl chloride. Yield 44 mg (91%). $^1$H NMR (CDCl$_3$) δ 7.71 (d, 2H), 7.59-7.53 (m, 4H), 4.44 (d, 1H), 4.39 (d, 1H), 4.24-4.17 (m, 3H), 4.08 (d, 1H), 3.68 (d, 1H), 3.33-3.26 (m, 2H), 1.16 (t, 3H). LC/MS retention time=3.531 minutes, MS calculated for (C$_{22}$H$_{18}$Cl$_2$F$_5$N$_3$O$_2$), 521; found 522 M+H.

Example 23

3-(4-(5-(3,5-dichloro-4-fluorophenyl)-5-(trifluoromethyl)-4,5-dihydroisoxazol-3-yl)phenyl)-3-fluoroazetidine-1-carboxamide

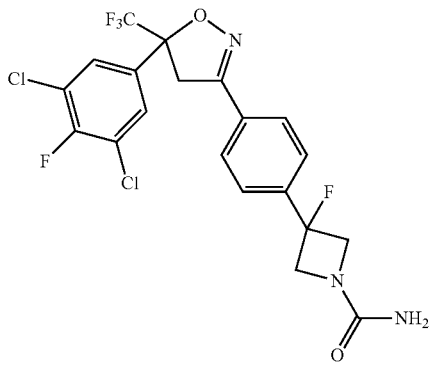 [SMILES: NC(=O)N1CC(F)(c2ccc(C3=NOC(c4cc(Cl)c(F)c(Cl)c4)(C(F)(F)F)C3)cc2)C1]

Triethylamine (0.070 mL, 0.492 mmol) was added to a suspension of azetidine hydrochloride salt (Preparation 16, 0.200 g, 0.410 mmol) in CH$_2$Cl$_2$ (5 mL). Subsequently, trimethylsilyl isocyanate (0.308 mL, 2.05 mmol) was added and the reaction mixture was stirred at room temperature overnight. A saturated aqueous solution of Na$_2$CO$_3$ (5 mL) was added and the reaction mixture was stirred for 5 minutes. The organic phase was separated, washed with brine and dried (anhydrous Na$_2$SO$_4$). Solvent was evaporated under reduced pressure to yield an off-white solid. The residue was purified by chromatography [Teledyne Isco CombiFlash Rf system, 24 g silica gel RediSep Rf cartridge, CH$_2$Cl$_2$ to CH$_2$Cl$_2$-MeOH (95:5) over 10 CV gradient elution] to afford the purified desired compound as a white solid (0.089 g, 44%). LC/MS R$_t$=3.378 minutes, m/z 494 [M+H]$^+$ Preparation 17: 3-(4-(5-(3,4-dichloro-5-(trifluoromethyl)phenyl)-5-(trifluoromethyl)-4,5-dihydroisoxazol-3-yl)phenyl)azetidin-3-ol

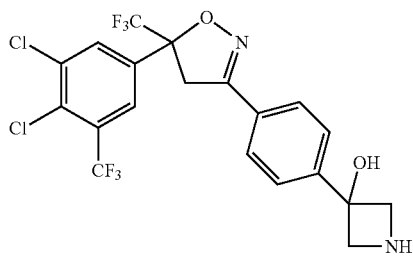 [SMILES: OC1(c2ccc(C3=NOC(c4cc(Cl)c(Cl)c(C(F)(F)F)c4)(C(F)(F)F)C3)cc2)CNC1]

Prepared according to the methods of Preparation 12 and Preparation 13 using 1,2-dichloro-3-(trifluoromethyl)-5-(3,3,3-trifluoroprop-1-en-2-yl)benzene.

Preparation 18: 5-(3,4-dichloro-5-(trifluoromethyl)phenyl)-3-(4-(3-fluoroazetidin-3-yl)phenyl)-5-(trifluoromethyl)-4,5-dihydroisoxazole

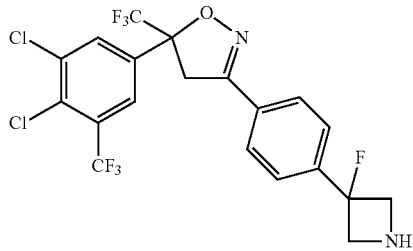 [SMILES: FC(F)(F)c1cc(C2(C(F)(F)F)CC(c3ccc(C4(F)CNC4)cc3)=NO2)cc(Cl)c1Cl]

Prepared according to the methods of Preparations 12, 14 and 15 using 1,2-dichloro-3-(trifluoromethyl)-5-(3,3,3-trifluoroprop-1-en-2-yl)benzene. $^1$H NMR (DMSO-d$_6$) δ ppm: 8.20 (1H), 7.93 (1H), 7.86 (2H), 7.75 (2H), 4.62-4.36 (6H); m/z (Cl) 501 ([M+H]$^+$.

Example 24

Cyclopropyl(3-(4-(5-(3,4-dichloro-5-(trifluoromethyl)phenyl)-5-(trifluoromethyl)-4,5-dihydroisoxazol-3-yl)phenyl)-3-hydroxyazetidin-1-yl)methanone

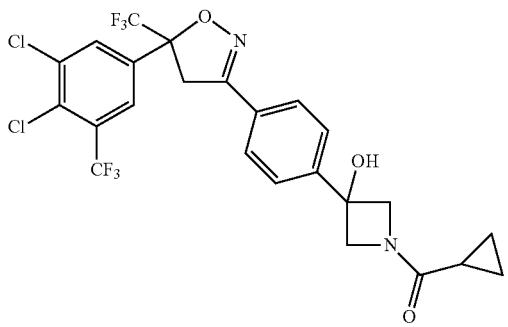 [SMILES: O=C(C1CC1)N1CC(O)(c2ccc(C3=NOC(c4cc(Cl)c(Cl)c(C(F)(F)F)c4)(C(F)(F)F)C3)cc2)C1]

The compound was prepared from the compound of preparation 17 according to the method of Example 6 using cyclopropylylcarboxyl chloride in place of cyclopropane carbonyl chloride. Yield 112 mg (88%). $^1$H NMR (CDCl$_3$) δ 7.96 (d, 1H), 7.85 (d, 1H), 7.71 (m, 2H), 7.62 (m, 2H), 4.51 (m, 2H), 4.29 (m, 2H), 4.16 (d, 1H), 3.95 (s, 1H), 3.73 (d, 1H), 1.47 (m, 1H), 1.01 (m, 2H), 0.82 (m, 2H). LC/MS retention time=3.564 minutes, MS calculated for (C$_{24}$H$_{18}$Cl$_2$F$_6$N$_2$O$_3$), 566.06; found 567.0 M+H.

Example 25

Cyclobutyl(3-(4-(5-(3,4-dichloro-5-(trifluoromethyl)phenyl)-5-(trifluoromethyl)-4,5-dihydroisoxazol-3-yl)phenyl)-3-hydroxyazetidin-1-yl)methanone

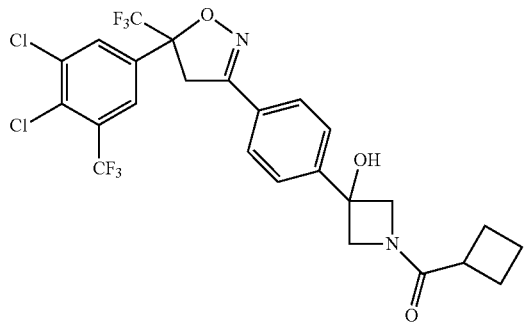

The compound was prepared from the compound of preparation 17 according to the method of Example 6 using cyclobutanecarbonyl chloride in place of cyclopropane carbonyl chloride. Yield 111 mg (85%). $^1$H NMR (CDCl$_3$) δ 7.96 (d, 1H), 7.85 (d, 1H), 7.70 (m, 2H), 7.58 (m, 2H), 4.37-4.21 (m, 4H), 4.15 (m, 1H), 4.04 (d, 1H), 3.72 (m, 1H), 3.10 (m, 1H), 2.33 (m, 2H), 2.12 (m, 2H), 2.06-1.83 (m, 2H). LC/MS retention time=3.650 minutes, MS calculated for (C$_{25}$H$_{20}$Cl$_2$F$_6$N$_2$O$_3$), 580.08; found 581.0 M+H.

Example 26

3-(4-(5-(3,4-dichloro-5-(trifluoromethyl)phenyl)-5-(trifluoromethyl)-4,5-dihydroisoxazol-3-yl)phenyl)-3-fluoro-N-methylazetidine-1-carboxamide

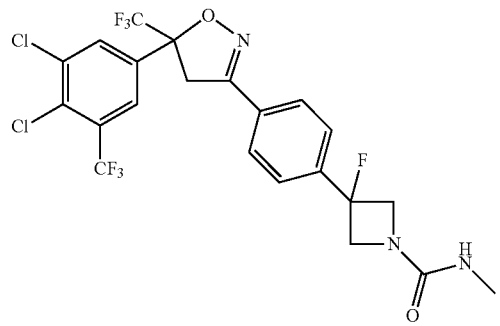

The compound was prepared from the compound of preparation 18 according to the method of Example 6 using methyl isocyanate in place of cyclopropane carbonyl chloride. Yield 132 mg (94%). $^1$H NMR (CDCl$_3$) δ 7.96 (m, 1H), 7.85 (m, 1H), 7.73 (d, 2H), 7.57 (d, 2H), 4.50-4.39 (m, 2H), 4.28-4.11 (m, 4H), 3.72 (d, 1H), 2.86 (d, 3H). LC/MS retention time=3.090 minutes, MS calculated for (C$_{22}$H$_{16}$Cl$_2$F$_7$N$_3$O$_2$), 557.05; found 558.0 M+H.

Example 27

3-(4-(5-(3,4-dichloro-5-(trifluoromethyl)phenyl)-5-(trifluoromethyl)-4,5-dihydroisoxazol-3-yl)phenyl)-N-ethyl-3-fluoroazetidine-1-carboxamide

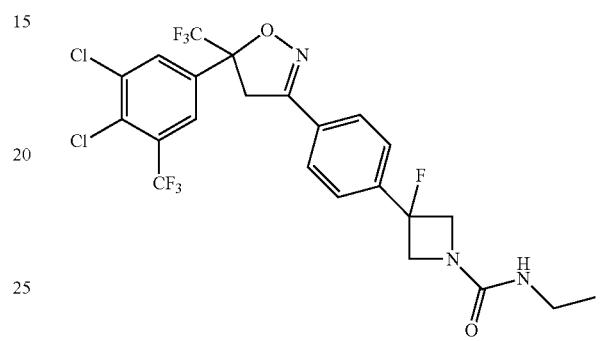

The compound was prepared from the compound of preparation 18 according to the method of Example 6 using ethyl isocyanate in place of cyclopropane carbonyl chloride. Yield 141 mg (98%). $^1$H NMR (CDCl$_3$) δ 7.96 (m, 1H), 7.85 (m, 1H), 7.74 (d, 2H), 7.57 (d, 2H), 4.49-4.38 (m, 2H), 4.27-4.11 (m, 4H), 3.72 (d, 1H), 3.31 (m, 2H), 1.18 (t, 3H). LC/MS retention time=3.133 minutes, MS calculated for (C$_{23}$H$_{18}$Cl$_2$F$_7$N$_3$O$_2$), 571.01; found 572.0 M+H.

Example 28

N-cyclopropyl-3-(4-(5-(3,4-dichloro-5-(trifluoromethyl)phenyl)-5-(trifluoromethyl)-4,5-dihydroisoxazol-3-yl)phenyl)-3-fluoroazetidine-1-carboxamide

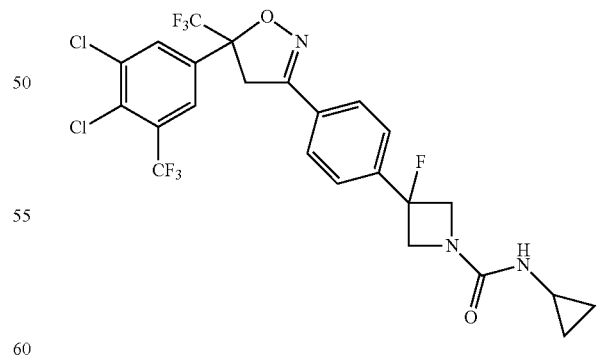

The compound was prepared from the compound of preparation 18 according to the method of Example 6 using cyclopropyl isocyanate in place of cyclopropane carbonyl chloride. Yield 142 mg (97%). $^1$H NMR (CDCl$_3$) δ 7.96 (m, 1H), 7.85 (m, 1H), 7.74 (d, 2H), 7.56 (d, 2H), 4.55-4.38 (m, 3H), 4.29-4.19 (m, 2H), 4.16 (d, 1H), 3.72 (d, 1H), 2.64 (m, 1H), 0.78

(m, 2H), 0.55 (m, 2H). LC/MS retention time=3.152 minutes, MS calculated for ($C_{24}H_{18}Cl_2F_7N_3O_2$), 583.07; found 584.0 M+H.

Example 29

3-(4-(5-(3,4-dichloro-5-(trifluoromethyl)phenyl)-5-(trifluoromethyl)-4,5-dihydroisoxazol-3-yl)phenyl)-N-ethyl-3-hydroxyazetidine-1-carboxamide

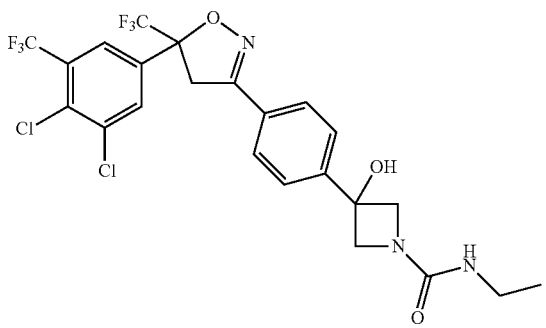 [SMILES: CCNC(=O)N1CC(O)(c2ccc(C3=NOC(c4cc(Cl)c(Cl)c(C(F)(F)F)c4)(C(F)(F)F)C3)cc2)C1]

The compound was prepared from the compound of preparation 17 according to the method of Example 6 using ethyl isocyanate in place of cyclopropane carbonyl chloride. Yield 50 mg (94%). $^1$H NMR (CDCl$_3$) δ 7.94 (s, 1H), 7.83 (s, 1H), 7.68 (d. 2H), 7.62 (d, 2H) 4.21-4.11 (m, 6H), 3.90 (s, 1H), 3.70 (d, 1H), 3.26 (q, 2H), 1.13 (t, 3H). LC/MS retention time=3.179 minutes, MS calculated for ($C_{23}H_{19}Cl_2F_6N_3O_3$), 569; found 570 M+H.

Example 30

N-cyclopropyl-3-(4-(5-(3,4-dichloro-5-(trifluoromethyl)phenyl)-5-(trifluoromethyl)-4,5-dihydroisoxazol-3-yl)phenyl)-3-hydroxyazetidine-1-carboxamide

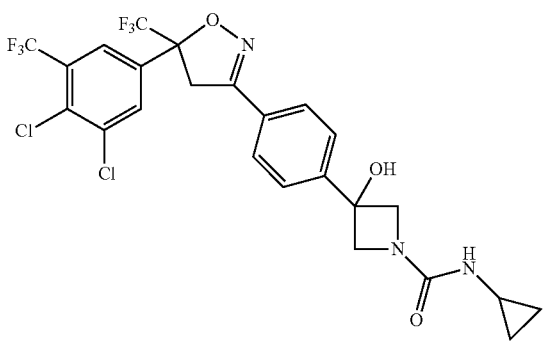 [SMILES: O=C(NC1CC1)N1CC(O)(c2ccc(C3=NOC(c4cc(Cl)c(Cl)c(C(F)(F)F)c4)(C(F)(F)F)C3)cc2)C1]

The compound was prepared from the compound of preparation 17 according to the method of Example 6 using cyclopropane carbonyl chloride. Yield 51 mg (94%). $^1$H NMR (CDCl$_3$) δ 7.94 (s, 1H), 7.83 (s, 1H), 7.68 (d, 2H), 7.62 (d, 2H), 4.49 (s, 1H) 4.23-4.18 (m, 4H), 4.13 (d, 1H), 3.70 (d, 1H), 3.3.8 (s, 1H), 2.63-2.59 (m, 1H), 0.76-0.72 (m, 2H), 0.53-0.49 (m, 2H). LC/MS retention time=3.481 minutes, MS calculated for ($C_{24}H_{19}Cl_2F_6N_3O_3$), 581; found 582 M+H.

Preparation 19: 3-(4-(5-(3,5-bis(trifluoromethyl)phenyl)-5-(trifluoromethyl)-4,5-dihydroisoxazol-3-yl)phenyl)azetidin-3-ol

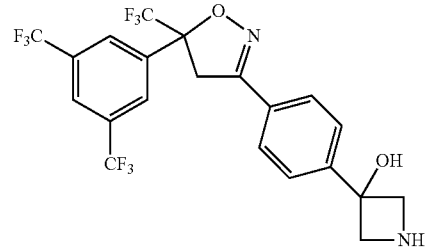 [SMILES: OC1(c2ccc(C3=NOC(c4cc(C(F)(F)F)cc(C(F)(F)F)c4)(C(F)(F)F)C3)cc2)CNC1]

Prepared according to the methods of Preparation 12 and Preparation 13 using 1,3-bis(trifluoromethyl)-5-(3,3,3-trifluoroprop-1-en-2-yl)benzene.

Preparation 20: 5-(3,5-bis(trifluoromethyl)phenyl)-3-(4-(3-fluoroazetidin-3-yl)phenyl)-5-(trifluoromethyl)-4,5-dihydroisoxazole

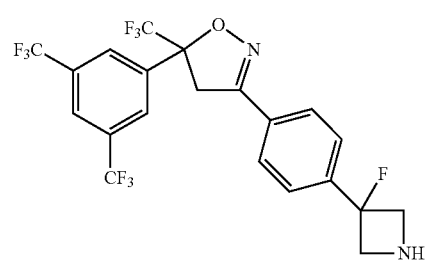 [SMILES: FC(F)(F)c1cc(C(F)(F)F)cc(C2(C(F)(F)F)CC(c3ccc(C4(F)CNC4)cc3)=NO2)c1]

Prepared according to the methods of Preparations 12, 14 and 15 using 1,3-bis(trifluoromethyl)-5-(3,3,3-trifluoroprop-1-en-2-yl)benzene. $^1$H NMR (DMSO-d$_6$) δ ppm: 8.36 (1H), 8.22 (2H), 7.87 (2H), 7.76 (2H), 4.62-4.42 (6H); m/z (Cl) 501 ([M+H]$^+$.

Example 31

3-(4-(5-(3,5-bis(trifluoromethyl)phenyl)-5-(trifluoromethyl)-4,5-dihydroisoxazol-3-yl)phenyl)-3-fluoro-N-methylazetidine-1-carboxamide

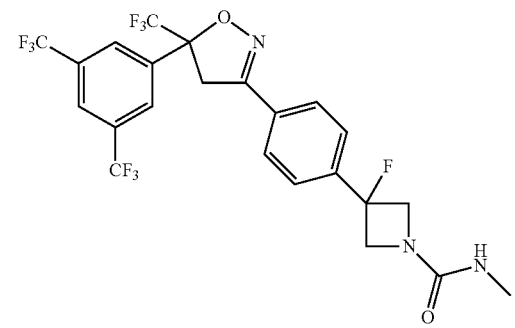 [SMILES: CNC(=O)N1CC(F)(c2ccc(C3=NOC(c4cc(C(F)(F)F)cc(C(F)(F)F)c4)(C(F)(F)F)C3)cc2)C1]

The compound was prepared from the compound of Preparation 20 according to the method of Example 6 using methyl isocyanate in place of cyclopropane carbonyl chloride. Yield 131 mg (94%). $^1$H NMR (CDCl$_3$) δ 8.10 (s, 2H), 7.98 (s, 1H), 7.75 (d, 2H), 7.57 (d, 2H), 4.50-4.39 (m, 2H), 4.28-4.17 (m, 4H), 3.76 (d, 1H), 2.86 (d, 3H). LC/MS retention time=3.015 minutes, MS calculated for (C$_{23}$H$_{17}$F$_{10}$N$_3$O$_2$), 557.12; found 558.0 M+H.

Example 32

3-(4-(5-(3,5-bis(trifluoromethyl)phenyl)-5-(trifluoromethyl)-4,5-dihydroisoxazol-3-yl)phenyl)-N-ethyl-3-fluoroazetidine-1-carboxamide

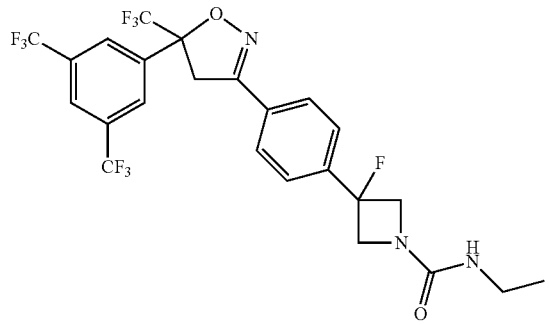 [SMILES: CCNC(=O)N1CC(F)(c2ccc(C3=NOC(c4cc(C(F)(F)F)cc(C(F)(F)F)c4)(C(F)(F)F)C3)cc2)C1]

The compound was prepared from the compound of Preparation 20 according to the method of Example 6 using ethyl isocyanate in place of cyclopropane carbonyl chloride. Yield 131 mg (92%). $^1$H NMR (CDCl$_3$) δ 8.10 (s, 2H), 7.98 (s, 1H), 7.75 (d, 2H), 7.57 (d, 2H), 4.50-4.39 (m, 2H), 4.27-4.16 (m, 4H), 3.76 (d, 1H), 3.31 (m, 2H), 1.18 (t, 3H). LC/MS retention time=3.089 minutes, MS calculated for (C$_{24}$H$_{19}$F$_{10}$N$_3$O$_2$), 571.13; found 572.0 M+H.

Example 33

3-(4-(5-(3,5-bis(trifluoromethyl)phenyl)-5-(trifluoromethyl)-4,5-dihydroisoxazol-3-yl)phenyl)-N-cyclopropyl-3-fluoroazetidine-1-carboxamide

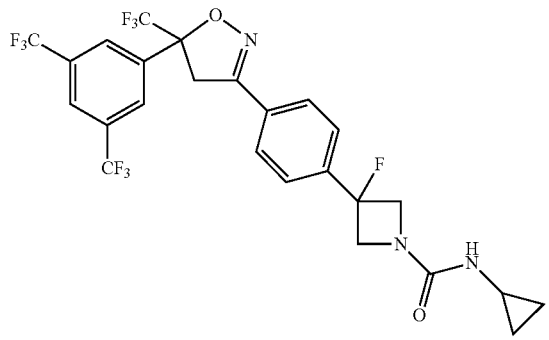 [SMILES: O=C(NC1CC1)N1CC(F)(c2ccc(C3=NOC(c4cc(C(F)(F)F)cc(C(F)(F)F)c4)(C(F)(F)F)C3)cc2)C1]

The compound was prepared from the compound of Preparation 20 according to the method of Example 6 using cyclopropyl isocyanate in place of cyclopropane carbonyl chloride. Yield 141 mg (96%). $^1$H NMR (CDCl$_3$) δ 8.10 (s, 2H), 7.98 (s, 1H), 7.75 (d, 2H), 7.57 (d, 2H), 4.55-4.39 (m, 3H), 4.28-4.18 (m, 3H), 3.77 (d, 1H), 2.65 (m, 1H), 0.78 (m, 2H), 0.55 (m, 2H). LC/MS retention time=3.086 minutes, MS calculated for (C$_{25}$H$_{19}$F$_{10}$N$_3$O$_2$), 583.13; found 584.0 M+H.

Example 34

3-(4-(5-(3,5-bis(trifluoromethyl)phenyl)-5-(trifluoromethyl)-4,5-dihydroisoxazol-3-yl)phenyl)-N-cyclopropyl-3-hydroxyazetidine-1-carboxamide

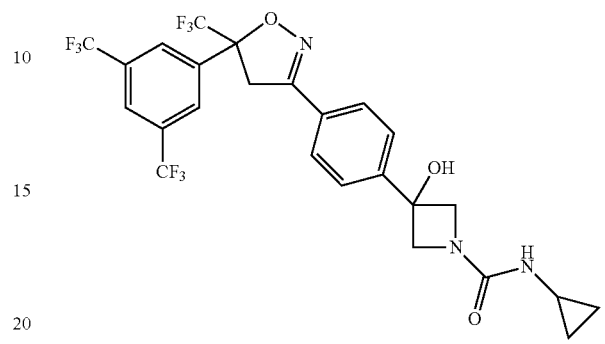

The compound was prepared from the compound of Preparation 19 according to the method of Example 6 using cyclopropyl isocyanate in place of cyclopropane carbonyl chloride. Yield 119 mg (89%). $^1$H NMR (CDCl$_3$) δ 8.10 (s, 2H), 7.97 (s, 1H), 7.71 (m, 2H), 7.64 (m, 2H), 4.57 (d, 1H), 4.28-4.16 (m, 6H), 3.77 (d, 1H), 2.61 (m, 1H), 0.74 (m, 2H), 0.52 (m, 2H). LC/MS retention time=2.989 minutes, MS calculated for (C$_{25}$H$_{20}$F$_9$N$_3$O$_3$), 581.14; found 582.0 M+H.

Preparation 21: 3-(4-(5-(3-chloro-5-(trifluoromethyl)phenyl)-5-(trifluoromethyl)-4,5-dihydroisoxazol-3-yl)phenyl)azetidin-3-ol

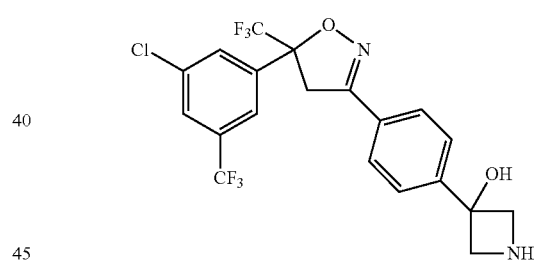

Prepared according to the methods of Preparation 12 and Preparation 13 using 1-chloro-3-(trifluoromethyl)-5-(3,3,3-trifluoroprop-1-en-2-yl)benzene.

Preparation 22: 5-(3-chloro-5-(trifluoromethyl)phenyl)-3-(4-(3-fluoroazetidin-3-yl)phenyl)-5-(trifluoromethyl)-4,5-dihydroisoxazole

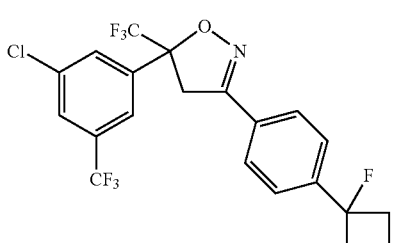

Prepared according to the methods of Preparations 12, 14 and 15 using 1-chloro-3-(trifluoromethyl)-5-(3,3,3-trifluoroprop-1-en-2-yl)benzene. $^1$H NMR (DMSO-d$_6$) δ ppm: 8.10 (1H), 7.99 (1H), 7.87-7.85 (3H), 7.75 (2H), 4.62-4.37 (6H); m/z (CI) 467 ([M+H]$^+$.

Example 35

3-(4-(5-(3-chloro-5-(trifluoromethyl)phenyl)-5-(trifluoromethyl)-4,5-dihydroisoxazol-3-yl)phenyl)-N-ethyl-3-hydroxyazetidine-1-carboxamide

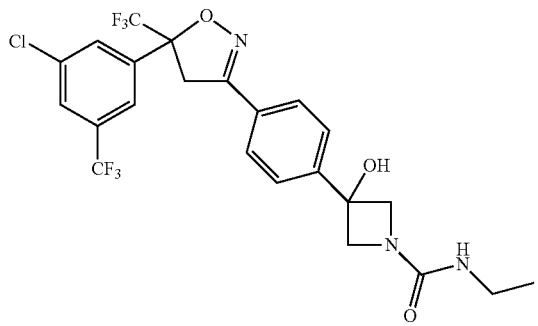 [SMILES: CCNC(=O)N1CC(O)(c2ccc(C3=NOC(c4cc(Cl)cc(C(F)(F)F)c4)(C(F)(F)F)C3)cc2)C1]

The compound was prepared from the compound of Preparation 21 according to the method of Example 6 using ethyl isocyanate in place of cyclopropane carbonyl chloride. Yield 121 mg (90%). $^1$H NMR (CDCl$_3$) δ 7.84 (s, 1H), 7.77 (m, 1H), 7.74-7.68 (m, 3H), 7.66-7.62 (m, 2H), 4.22-4.13 (m, 6H), 3.74 (d, 1H), 3.30 (m, 2H), 1.16 (t, 3H). LC/MS retention time=3.312 minutes, MS calculated for (C$_{23}$H$_{20}$ClF$_6$N$_3$O$_3$), 535.11; found 536.0 M+H.

Example 36

3-(4-(5-(3-chloro-5-(trifluoromethyl)phenyl)-5-(trifluoromethyl)-4,5-dihydroisoxazol-3-yl)phenyl)-N-ethyl-3-fluoroazetidine-1-carboxamide

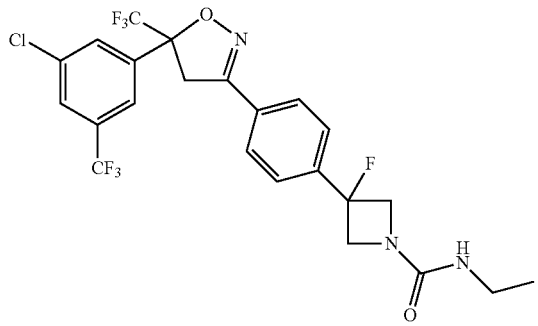 [SMILES: CCNC(=O)N1CC(F)(c2ccc(C3=NOC(c4cc(Cl)cc(C(F)(F)F)c4)(C(F)(F)F)C3)cc2)C1]

The compound was prepared from the compound of Preparation 22 according to the method of Example 6 using ethyl isocyanate in place of cyclopropane carbonyl chloride. Yield 133 mg (99%). $^1$H NMR (CDCl$_3$) δ 7.84 (s, 1H), 7.79-7.68 (m, 4H), 7.57 (d, 2H), 4.49-4.38 (m, 2H), 4.27-4.12 (m, 4H), 3.74 (d, 1H), 3.32 (m, 2H), 1.18 (t, 3H). LC/MS retention time=3.571 minutes, MS calculated for (C$_{23}$H$_{19}$ClF$_7$N$_3$O$_2$), 537.11; found 538.0 M+H.

Example 37

3-(4-(5-(3-chloro-5-(trifluoromethyl)phenyl)-5-(trifluoromethyl)-4,5-dihydroisoxazol-3-yl)phenyl)-N-cyclopropyl-3-fluoroazetidine-1-carboxamide

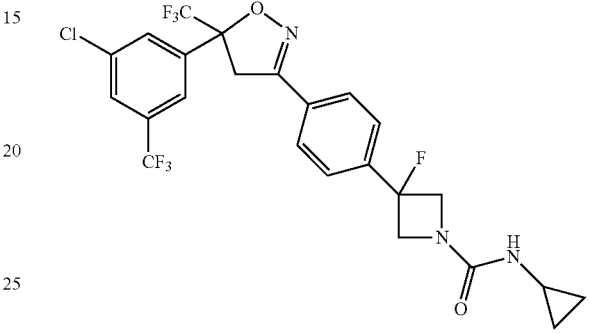

The compound was prepared from the compound of Preparation 22 according to the method of Example 6 using cyclopropyl isocyanate in place of cyclopropane carbonyl chloride. Yield 131 mg (95%). $^1$H NMR (CDCl$_3$) δ 7.83 (s, 1H), 7.79-7.68 (m, 4H), 7.56 (d, 2H), 4.55-4.39 (m, 3H), 4.29-4.20 (m, 2H), 4.16 (d, 1H), 3.74 (d, 1H), 2.65 (m, 1H), 0.78 (m, 2H), 0.55 (m, 2H). LC/MS retention time=3.574 minutes, MS calculated for (C$_{22}$H$_{17}$ClF$_7$N$_3$O$_2$), 549.11; found 550.0 M+H.

Example 38

3-(4-(5-(3-chloro-5-(trifluoromethyl)phenyl)-5-(trifluoromethyl)-4,5-dihydroisoxazol-3-yl)phenyl)-3-fluoro-N-methylazetidine-1-carboxamide

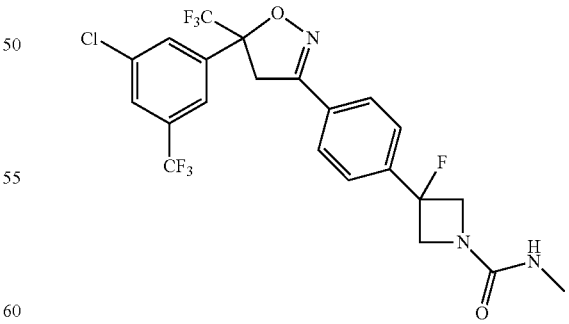

The compound was prepared from the compound of Preparation 22 according to the method of Example 6 using methyl isocyanate in place of cyclopropane carbonyl chloride. Yield 126 mg (96%). $^1$H NMR (CDCl$_3$) δ 7.83 (s, 1H), 7.79-7.68 (m, 4H), 7.57 (d, 2H), 4.50-4.39 (m, 2H), 4.28-4.12 (m, 4H), 3.74 (d, 1H), 2.86 (d, 3H). LC/MS retention time=3.487 minutes, MS calculated for ($C_{22}H_{17}ClF_7N_3O_2$), 523.09; found 524.0 M+H.

Example 39

1-(3-(4-(5-(3,5-Dichlorophenyl)-5-(trifluoromethyl)-4,5-dihydroisoxazol-3-yl)phenyl)-3-fluoroazetidin-1-yl)ethanone

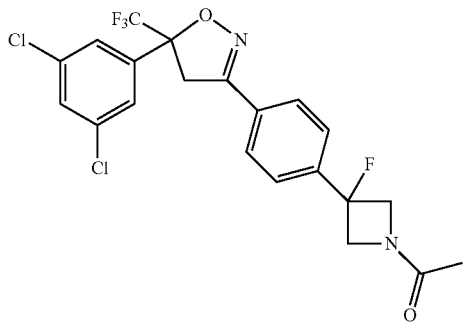 [SMILES: CC(=O)N1CC(F)(c2ccc(C3=NOC(c4cc(Cl)cc(Cl)c4)(C(F)(F)F)C3)cc2)C1]

To a solution of 5-(3,5-dichlorophenyl)-3-(4-(3-fluoroazetidin-3-yl)phenyl)-5-(trifluoromethyl)-4,5-dihydroisoxazole (Preparation 15, 200 mg, 0.462 mMol) in dichloromethane (3 mL) was added triethylamine (0.192 mL) followed by acetic anhydride (50.2 μL). The reaction was allowed to stir at room temperature overnight. The solution was diluted with water and allowed to stir for 10 minutes. The mixture was passed through an ISCO Phase Separator. A stream of nitrogen was blown onto the organics then placed under high vacuum to form a white foam 200 mg (91% yield) $^1$H NMR (400 MHz, CDCl$_3$-d) δ ppm 2.01 (s, 3H) 3.73 (d, 1H) 3.92 (qd, 1H) 4.12 (d, 1H) 4.32-4.56 (m, 3H) 4.59-4.70 (m, 1H) 7.46 (t, 1H) 7.52-7.59 (m, 4H) 7.76 (d, 2H), LC/MS retention time=3.510 min; MS calculated for ($C_{21}H_{16}Cl_2F_4N_2O_2$), 474.052; found 475.0 M+H.

Example 40

Cyclopropyl(3-(4-(5-(3,5-dichloro-4-fluorophenyl)-5-(trifluoromethyl)-4,5-dihydroisoxazol-3-yl)phenyl)-3-fluoroazetidin-1-yl)methanone

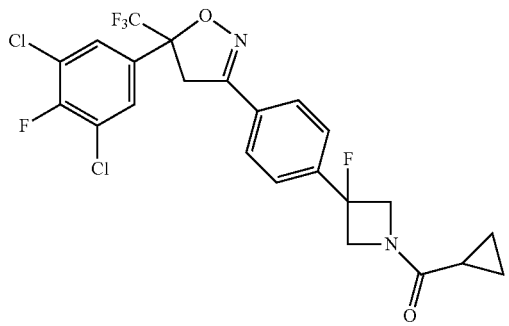 [SMILES: O=C(C1CC1)N1CC(F)(c2ccc(C3=NOC(c4cc(Cl)c(F)c(Cl)c4)(C(F)(F)F)C3)cc2)C1]

The compound was prepared from the compound of Preparation 16 according to the method of Example 6 using cyclo-propyl isocyanate in place of cyclopropane carbonyl chloride. Yield: 87% of a glassy solid. $^1$H NMR (400 MHz, CDCl$_3$-d) δ ppm 0.85 (t, Hz, 2H) 1.06 (dd, 2H) 1.42-1.51 (m, 1H) 3.71 (d, 1H) 4.11 (d, 1H) 4.28-4.82 (m, 4H) 7.53-7.64 (m, 4H) 7.75 (d, 2H) LC/MS retention time=3.675 minutes; MS calculated for ($C_{23}H_{17}Cl_2F_5N_2O_2$), 518.059; found 519 M+H.

Example 41

2-Cyclopropyl-1-(3-(4-(5-(3,5-dichlorophenyl)-5-(trifluoromethyl)-4,5-dihydroisoxazol-3-yl)phenyl)-3-fluoroazetidin-1-yl)ethanone

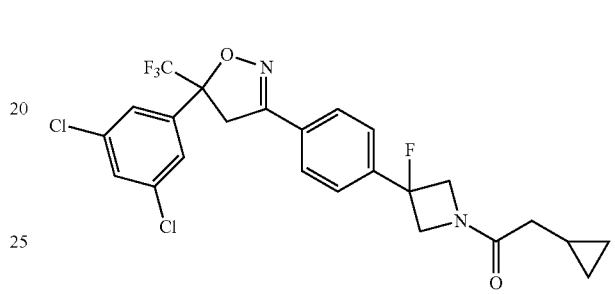

The compound was prepared from the compound of preparation 15 according to the method of Example 12 using 2-cyclopropylacetic acid in place of butyric acid. $^1$H NMR (400 MHz, CDCl$_3$-d) δ ppm −0.04-0.04 (m, 2H) 0.41 (d, 2H) 0.86-0.92 (m, 1H) 1.95 (d, 2H) 3.51 (d, 1H) 3.90 (d, 1H) 4.12-4.46 (m, 4H) 7.24 (t, 1H) 7.30-7.37 (m, 4H) 7.54 (d, 2H), LC/MS retention time=3.682 minutes; MS calculated for ($C_{24}H_{20}Cl_2F_4N_2O_2$), 514.084; found 515.0 [M+H]$^+$.

Example 42

3-(3-(4-(5-(3,5-Dichlorophenyl)-5-(trifluoromethyl)-4,5-dihydroisoxazol-3-yl)phenyl)-3-fluoroazetidin-1-yl)-3-oxopropanenitrile

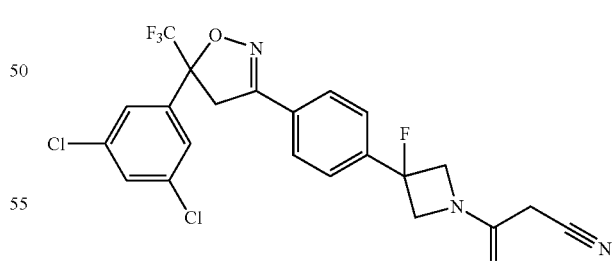

The compound was prepared from the compound of preparation 15 according to the method of Example 12 using 2-cyanoacetic acid in place of butyric acid to provide a glassy solid. $^1$H NMR (400 MHz, CDCl$_3$-d) δ ppm 3.41 (s, 1H) 3.73 (d, 1H) 4.12 (d, 1H) 4.41-4.72 (m, 4H) 4.76-4.86 (m, 1H) 7.46 (t, 1H) 7.54-7.58 (m, 4H) 7.78 (d, 2H); MS calculated for ($C_{22}H_{15}Cl_2F_4N_3O_2$), 499.048; found 500.0 [M+H]$^+$.

Example 43

1-(3-(4-(5-(3,5-Dichlorophenyl)-5-(trifluoromethyl)-4,5-dihydroisoxazol-3-yl)phenyl)-3-fluoroazetidin-1-yl)-3,3,3-trifluoropropan-1-one

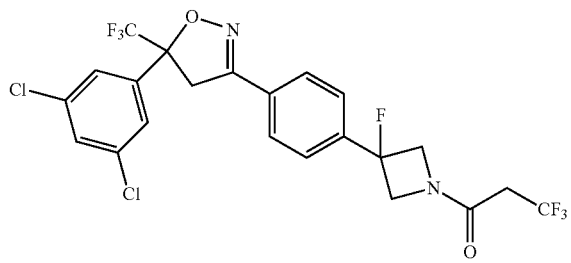 [SMILES: O=C(CC(F)(F)F)N1CC(F)(c2ccc(C3=NOC(c4cc(Cl)cc(Cl)c4)(C(F)(F)F)C3)cc2)C1]

The compound was prepared from the compound of Preparation 15 according to the method of Example 6 using 3,3,3-trifluoropropanoyl chloride in place of cyclopropane carbonyl chloride. $^1$H NMR (400 MHz, CDCl$_3$-d) δ ppm 3.09 (q, 2H) 3.64 (d, 1H) 4.10 (d, 1H) 4.39-4.63 (m, 4H) 7.37 (t, 1H) 7.44-7.46 (m, 4H) 7.76 (d, 2H); MS calculated for (C$_{22}$H$_{15}$Cl$_2$F$_7$N$_2$O$_2$), 543.266; found 544.0 [M+H]$^+$.

Example 44

1-(3-(4-(5-(3,5-Dichlorophenyl)-5-(trifluoromethyl)-4,5-dihydroisoxazol-3-yl)phenyl)-3-fluoroazetidin-1-yl)-2-methoxyethanone

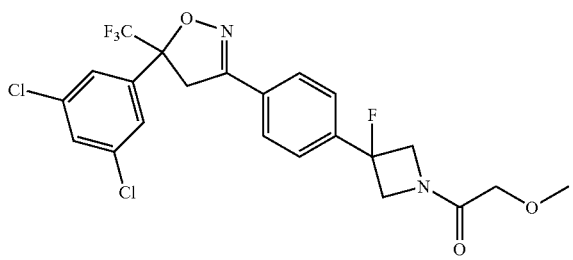 [SMILES: COCC(=O)N1CC(F)(c2ccc(C3=NOC(c4cc(Cl)cc(Cl)c4)(C(F)(F)F)C3)cc2)C1]

The compound was prepared from the compound of Preparation 15 according to the method of Example 6 using 2-methoxyacetyl chloride in place of cyclopropane carbonyl chloride to provide a white solid. $^1$H NMR (400 MHz, CDCl$_3$-d) δ ppm 3.44 (s, 3H) 3.73 (d, 1H) 4.09-4.14 (m, 3H) 4.37-4.63 (m, 3H) 4.65-4.85 (m, 1H) 7.43-7.49 (m, 1H) 7.51-7.60 (m, 4H) 7.76 (d, 2H); MS calculated for (C$_{22}$H$_{18}$Cl$_2$F$_4$N$_3$O$_3$), 505.295; found m/z (ESI) 506.0 [M+H]$^+$.

Example 45

1-(3-(4-(5-(3,5-Dichlorophenyl)-5-(trifluoromethyl)-4,5-dihydroisoxazol-3-yl)phenyl)-3-fluoroazetidin-1-yl)propan-1-one

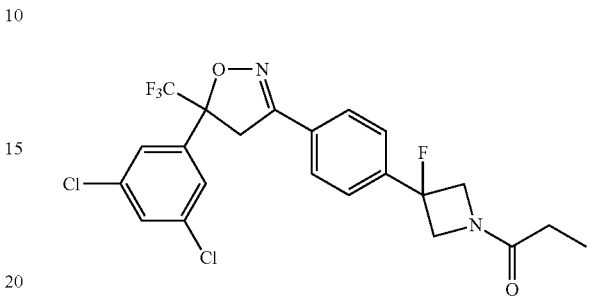

The compound was prepared from the compound of Preparation 15 according to the method of Example 6 using propionyl chloride in place of cyclopropane carbonyl chloride to provide a white solid $^1$H NMR (400 MHz, CDCl$_3$-d) δ ppm 1.14-1.25 (m, 3H) 2.24 (m, 2H) 3.73 (d, 1H) 4.11 (d, 1H) 4.32-4.67 (m, 4H) 7.46 (t, 1H) 7.52-7.60 (m, 4H) 7.76 (d, 2H); MS calculated for (C$_{22}$H$_{18}$Cl$_2$F$_4$N$_2$O$_2$), 489.296; found m/z (ESI) 490.0 [M+H]$^+$.

Example 46

1-(3-(4-(5-(3,5-Dichlorophenyl)-5-(trifluoromethyl)-4,5-dihydroisoxazol-3-yl)phenyl)-3-fluoroazetidin-1-yl)butan-1-one

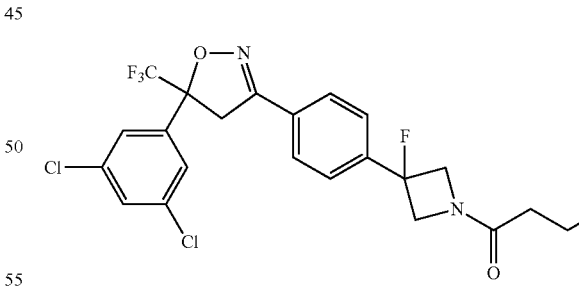

The compound was prepared from the compound of Preparation 15 according to the method of Example 6 using butyryl chloride in place of cyclopropane carbonyl chloride to provide a white solid. $^1$H NMR (400 MHz, CDCl$_3$-d) δ ppm 1.01 (t, 3H) 1.73 (m, 2H) 2.19 (m, 2H) 3.73 (d, 1H) 4.11 (d, 1H) 4.33-4.66 (m, 4H) 7.46 (t, 1H) 7.53-7.58 (m, 4H) 7.76 (d, 2H); MS calculated for (C$_{23}$H$_{20}$Cl$_2$F$_4$N$_2$O$_2$), 503.323; found m/z (ESI) 503.0 [M+H]$^+$.

Examples 47-82

The Examples in Table 1 below were prepared under the following conditions

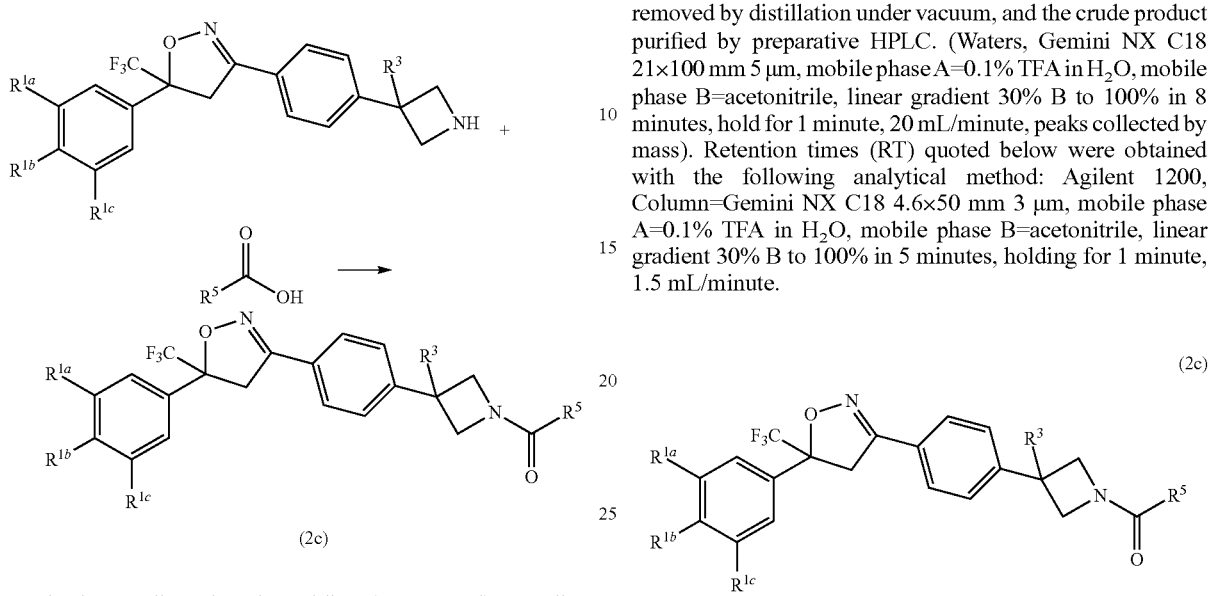

The isoxazoline phenyl azetidine (0.05 mmol) was dissolved in dimethyl formamide (0.5 mL). This was added to the respective acid (0.2 mmol), followed by a solution of O-(7-azabenzotriazol-1-yl)-N,N,N',N'-tetramethyluronium-hexafluorophosphate (0.10 mmol) in dimethyl formamide (0.5 mL) and $Et_3N$ (0.5 mmol). The resulting mixture was shaken at ambient temperature for 16 hours. The solvent was removed by distillation under vacuum, and the crude product purified by preparative HPLC. (Waters, Gemini NX C18 21×100 mm 5 μm, mobile phase A=0.1% TFA in $H_2O$, mobile phase B=acetonitrile, linear gradient 30% B to 100% in 8 minutes, hold for 1 minute, 20 mL/minute, peaks collected by mass). Retention times (RT) quoted below were obtained with the following analytical method: Agilent 1200, Column=Gemini NX C18 4.6×50 mm 3 μm, mobile phase A=0.1% TFA in $H_2O$, mobile phase B=acetonitrile, linear gradient 30% B to 100% in 5 minutes, holding for 1 minute, 1.5 mL/minute.

TABLE 1

| Example No. | $R^{1a}$ | $R^{1b}$ | $R^{1c}$ | $R^3$ | $R^5$ | m/z (ESI) $[M + H]^+$ | RT (minutes) |
|---|---|---|---|---|---|---|---|
| 47 | $CF_3$ | H | $CF_3$ | F | cyclobutyl | 583 | 4.66 |
| 48 | $CF_3$ | H | $CF_3$ | F | cyclopropyl | 569 | 4.45 |
| 49 | $CF_3$ | H | $CF_3$ | F | isopropyl | 571 | 4.55 |
| 50 | $CF_3$ | H | Cl | F | propyl | 538 | 4.55 |
| 51 | $CF_3$ | H | Cl | F | ethyl | 524 | 4.34 |
| 52 | $CF_3$ | H | Cl | F | methyl | 510 | 4.07 |
| 53 | $CF_3$ | H | Cl | F | —$CH_2CN$ | 535 | 4.21 |
| 54 | Cl | H | Cl | F | ⌇⟨⟩—OH (cyclopropyl-OH) | 517 | 3.98 |
| 55 | Cl | F | Cl | F | ⌇⟨⟩—OH (cyclopropyl-OH) | 535 | 4.04 |
| 56 | Cl | Cl | Cl | F | —$CH_2OCH_3$ | 539 | 4.43 |
| 57 | Cl | Cl | $CF_3$ | OH | isopropyl | 569 | 8.75 |
| 58 | Cl | Cl | $CF_3$ | OH | propyl | 569 | 8.77 |
| 59 | $CF_3$ | H | $CF_3$ | F | ⌇—CH₂—cyclopropyl | 583 | 4.55 |
| 60 | $CF_3$ | H | $CF_3$ | F | —$CH_2OH$ | 559 | 3.83 |
| 61 | $CF_3$ | H | Cl | F | —$CH_2SCH_3$ | 556 | 4.44 |
| 62 | $CF_3$ | H | Cl | F | cyclobutyl | 550 | 4.66 |
| 63 | $CF_3$ | Cl | Cl | F | —$CH_2C(O)NH_2$ | 586 | 5.15 |
| 64 | Cl | F | Cl | F | 1-(NHC(O)H)cyclopropyl | 562 | 3.71 |

TABLE 1-continued

| Example No. | R¹ᵃ | R¹ᵇ | R¹ᶜ | R³ | R⁵ | m/z (ESI) [M + H]⁺ | RT (minutes) |
|---|---|---|---|---|---|---|---|
| 65 | Cl | Cl | Cl | F | 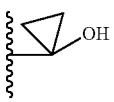 [SMILES: *C1(O)CC1] | 551 | 4.29 |
| 66 | Cl | H | Cl | F | isobutyl | 517 | 9.61 |
| 67 | Cl | Cl | Cl | F | —CH₂SCH₃ | 555 | 9.59 |
| 68 | Cl | F | Cl | OH | ethyl | 505 | 7.76 |
| 69 | CF₃ | H | Cl | F | cyclopropyl | 536 | 4.44 |
| 70 | Cl | F | Cl | F | 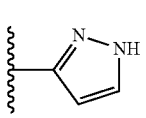 | 545 | 4.03 |
| 71 | CF₃ | H | CF₃ | F | 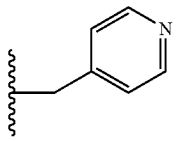 [SMILES: *Cc1ccncc1] | 620 | 2.75 |
| 72 | CF₃ | H | Cl | F | 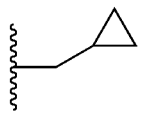 [SMILES: *CC1CC1] | 550 | 4.53 |
| 73 | CF₃ | Cl | Cl | F | ethyl | 557 | 7.31 |
| 74 | CF₃ | Cl | Cl | F | cyclopropyl | 569 | 7.58 |
| 75 | CF₃ | Cl | Cl | F | methyl | 543 | 6.67 |
| 76 | CF₃ | Cl | Cl | F | isopropyl | 571 | 7.84 |
| 77 | CF₃ | Cl | Cl | F | —CH₂CN | 568 | 6.72 |
| 78 | Cl | Cl | Cl | F | 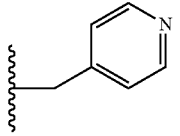 | 572 | 7.40 |
| 79 | CF₃ | H | CF₃ | F | ethyl | 557 | 4.36 |
| 80 | CF₃ | Cl | Cl | F | cyclopentyl | 597 | 8.66 |
| 81 | CF₃ | Cl | Cl | F | —CH₂SCH₃ | 589 | 7.56 |
| 82 | Cl | F | Cl | OH | cyclopropyl | 517 | 8 |

 is the point of attachment,
RT = retention time

The following IUPAC names for Examples (47-82) of Table 1 include: 5-[3,5-bis(trifluoromethyl)phenyl]-3-{4-[1-(cyclobutylcarbonyl)-3-fluoroazetidin-3-yl]phenyl}-5-(trifluoromethyl)-4,5-dihydroisoxazole (47); 5-[3,5-bis(trifluoromethyl)phenyl]-3-{4-[1-(cyclopropylcarbonyl)-3-fluoroazetidin-3-yl]phenyl}-5-(trifluoromethyl)-4,5-dihydroisoxazole (48); 5-[3,5-bis(trifluoromethyl)phenyl]-3-[4-(3-fluoro-1-isobutyrylazetidin-3-yl)phenyl]-5-(trifluoromethyl)-4,5-dihydroisoxazole (49); 3-[4-(1-butyryl-3-fluoroazetidin-3-yl)phenyl]-5-[3-chloro-5-(trifluoromethyl)phenyl]-5-(trifluoromethyl)-4,5-dihydroisoxazole (50); 5-[3-chloro-5-(trifluoromethyl)phenyl]-3-[4-(3-fluoro-1-propionylazetidin-3-yl)phenyl]-5-(trifluoromethyl)-4,5-dihydroisoxazole (51); 3-[4-(1-acetyl-3-fluoroazetidin-3-yl)phenyl]-5-[3-chloro-5-(trifluoromethyl)phenyl]-5-(trifluoromethyl)-4,5-dihydroisoxazole (52); 3-[3-(4-{5-[3-chloro-5-(trifluoromethyl)phenyl]-5-(trifluoromethyl)-4,5-dihydroisoxazol-3-yl}phenyl)-3-fluoroazetidin-1-yl]-3-oxopropanenitrile (53); 1-[(3-{4-[5-(3,5-dichlorophenyl)-5-(trifluoromethyl)-4,5-dihydroisoxazol-3-yl]phenyl}-3-fluoroazetidin-1-yl)carbonyl]cyclopropanol (54); 1-[(3-{4-[5-(3,5-dichloro-4-fluorophenyl)-5-(trifluoromethyl)-4,5-dihydroisoxazol-3-yl]phenyl}-3-fluoroazetidin-1-yl)carbonyl]cyclopropanol (55); 3-{4-[3-fluoro-1-(methoxyacetyl)azetidin-3-yl]phenyl}-5-(3,4,5- trichlorophenyl)-5-(trifluoromethyl)-4,5-dihydroisoxazole (56); 3-(4-{5-[3,4-dichloro-5-(trifluoromethyl)phenyl]-5-(trifluoromethyl)-4,5-dihydroisoxazol-3-yl}phenyl)-1-isobutyrylazetidin-3-ol (57); 1-butyryl-3-(4-{5-[3,4-dichloro-5-(trifluoromethyl)phenyl]-5-(trifluoromethyl)-4,5-dihydroisoxazol-3-yl}phenyl)azetidin-3-ol (58); 5-[3,5-bis(trifluoromethyl)phenyl]-3-{4-[1-(cyclopropylacetyl)-3-fluoroazetidin-3-yl]phenyl}-5-(trifluoromethyl)-4,5-dihydroisoxazole (59); 2-[3-(4-{5-[3,5-bis(trifluoromethyl)phenyl]-5-(trifluoromethyl)-4,5-dihydroisoxazol-3-yl}phenyl)-3-fluoroazetidin-1-yl]-2-oxoethanol (60); 5-[3-chloro-5-(trifluoromethyl)phenyl]-3-(4-{3-fluoro-1-[(methylthio)acetyl]azetidin-3-yl}phenyl)-5-(trifluoromethyl)-4,5-dihydroisoxazole (61); 5-[3-chloro-5-(trifluoromethyl)phenyl]-3-{4-[1-(cyclobutylcarbonyl)-3-fluoroazetidin-3-yl]phenyl}-5-(trifluoromethyl)-4,5-dihydroisoxazole (62); 3-[3-(4-{5-[3,4-dichloro-5-(trifluoromethyl)phenyl]-5-(trifluoromethyl)-4,5-dihydroisoxazol-3-yl}phenyl)-3-fluoroazetidin-1-yl]-3-oxopropanamide (63); 3-[3-(4-{5-[3,4-dichloro-5-(trifluoromethyl)phenyl]-5-(trifluoromethyl)-4,5-dihydroisoxazol-3-yl}phenyl)-3-fluoroazetidin-1-yl]-3-oxopropanamide (64); 1-[(3-fluoro-3-{4-[5-(3,4,5-trichlorophenyl)-5-(trifluoromethyl)-4,5-dihydroisoxazol-3-yl]phenyl}azetidin-1-yl)carbonyl]cyclopropanol (65); 5-(3,5-dichlorophenyl)-3-{-4-[3-fluoro-1-(3-methylbutanoyl)azetidin-3-yl]phenyl}-5-(trifluoromethyl)-4,5-dihydroisoxazole (66); 3-(4-{3-fluoro-1-[(methylthio)acetyl]azetidin-3-yl}phenyl)-5-(3,4,5-trichlorophenyl)-5-(trifluoromethyl)-4,5-dihydroisoxazole (67); 3-{4-[5-(3,5-dichloro-4-fluorophenyl)-5-(trifluoromethyl)-4,5-dihydroisoxazol-3-yl]phenyl}-1-propionylazetidin-3-ol (68); 5-[3-chloro-5-(trifluoromethyl)phenyl]-3-{4-[1-(cyclopropylcarbonyl)-3-fluoroazetidin-3-yl]phenyl}-5-(trifluoromethyl)-4,5-dihydroisoxazole (69); 5-(3,5-dichloro-4-fluorophenyl)-3-{-4-[3-fluoro-1-(1H-pyrazol-3-ylcarbonyl)azetidin-3-yl]phenyl}-5-(trifluoromethyl)-4,5-dihydroisoxazole (70); 4-{2-[3-(4-{5-[3,5-bis(trifluoromethyl)phenyl]-5-(trifluoromethyl)-4,5-dihydroisoxazol-3-yl}phenyl)-3-fluoroazetidin-1-yl]-2-oxoethyl}pyridine (71); 5-[3-chloro-5-(trifluoromethyl)phenyl]-3-{4-[1-(cyclopropylacetyl)-3-fluoroazetidin-3-yl]phenyl}-5-(trifluoromethyl)-4,5-dihydroisoxazole (72); 5-[3,4-dichloro-5-(trifluoromethyl)phenyl]-3-[4-(3-fluoro-1-propionylazetidin-3-yl)phenyl]-5-(trifluoromethyl)-4,5-dihydroisoxazole (73); 3-{4-[1-(cyclopropylcarbonyl)-3-fluoroazetidin-3-yl]phenyl}-5-[3,4-dichloro-5-(trifluoromethyl)phenyl]-5-(trifluoromethyl)-4,5-dihydroisoxazole (74); 3-[4-(1-acetyl-3-fluoroazetidin-3-yl)phenyl]-5-[3,4-dichloro-5-(trifluoromethyl)phenyl]-5-(trifluoromethyl)-4,5-dihydroisoxazole (75); 5-[3,4-dichloro-5-(trifluoromethyl)phenyl]-3-[4-(3-fluoro-1-isobutyrylazetidin-3-yl)phenyl]-5-(trifluoromethyl)-4,5-dihydroisoxazole (76); 3-[3-(4-{5-[3,4-dichloro-5-(trifluoromethyl)phenyl]-5-(trifluoromethyl)-4,5-dihydroisoxazol-3-yl}phenyl)-3-fluoroazetidin-1-yl]-3-oxopropanenitrile (77); 4-[(3-fluoro-3-{4-[5-(3,4,5-trichlorophenyl)-5-(trifluoromethyl)-4,5-dihydroisoxazol-3-yl]phenyl}azetidin-1-yl)carbonyl]pyridine (78); 5-[3,5-bis(trifluoromethyl)phenyl]-3-[4-(3-fluoro-1-propionylazetidin-3-yl)phenyl]-5-(trifluoromethyl)-4,5-dihydroisoxazole (79); 3-{4-[1-(cyclopentylcarbonyl)-3-fluoroazetidin-3-yl]phenyl}-5-[3,4-dichloro-5-(trifluoromethyl)phenyl]-5-(trifluoromethyl)-4,5-dihydroisoxazole (80); 5-[3,4-dichloro-5-(trifluoromethyl)phenyl]-3-(4-{3-fluoro-1-[(methylthio)acetyl]azetidin-3-yl}phenyl)-5-(trifluoromethyl)-4,5-dihydroisoxazole (81); and 1-(cyclopropylcarbonyl)-3-{4-[5-(3,5-dichloro-4-fluorophenyl)-5-(trifluoromethyl)-4,5-dihydroisoxazol-3-yl]phenyl}azetidin-3-ol (82).

Preparation 23: Methyl 3-bromo-4-iodobenzoate

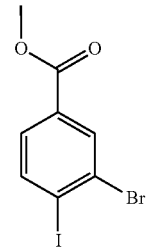

A solution of 4-amino-3-bromo-benzoic acid methyl ester (5.0 g, 22.0 mmol from Aldrich) in acetone (35 mL) was treated with 6M HCl (35 mL). The solution was cooled to 0° C. and treated dropwise with $NaNO_2$ (1.84 g, 26.1 mmol) dissolved in 10 mL water. After stirring for 2 hours at 0° C., the reaction was slowly treated with potassium iodide (5.47 g, 32.6 mmol) dissolved in 20 mL water. The reaction mixture was allowed to warm to room temperature and stir for 1 hour. Reaction mixture was diluted with water and extracted with EtOAc (2×150 mL). The combined organic phase was dried ($Na_2SO_4$) and concentrated under vacuum The residue was chromatographed (80 g Redi-Sep column) eluting from 100% heptane to 20:80 EtOAc:heptane to afford the intermediate (4.1 g, 55%) as a solid. $^1$HNMR ($CDCl_3$): 8.27 (1H), 7.98 (1H), 7.64 (1H), 3.94 (3H).

Preparation 24: (3-bromo-4-iodophenyl)methanol

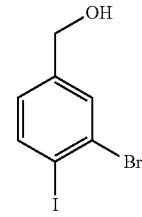

A solution of methyl 3-bromo-4-iodobenzoate (Preparation 23, 4.3 g, 12.6 mmol) in $CH_2Cl_2$ was cooled, under $N_2$, to −78° C. DIBAL-H was added slowly to the solution, which was stirred at −78° C. for 45 minutes and then allowed to come to room temperature. Next, the reaction mixture was diluted with 1M HCL (40 mL) and stirred for 30 minutes. The reaction was further diluted with water and extracted with $CH_2Cl_2$. The organic phase was dried ($Na_2SO_4$) and concentrated under vacuum to afford the intermediate (3.2 g, 82%) as a solid. $^1$HNMR ($CDCl_3$): 7.85 (1H), 7.67 (1H), 7.02 (1H), 4.65 (2H), 1.76 (1H, OH).

Preparation 25: 3-bromo-4-iodobenzaldehyde

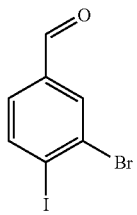

A solution of (3-bromo-4-iodophenyl)methanol (Preparation 24, 3.1 g, 9.9 mmol) in CH$_2$Cl$_2$/water (2:1, 225 mL) was treated with NaHCO$_3$ (915 mg, 10.9 mmol), NaBr (1060 mg, 10.2 mmol) and TEMPO free radical (40 mg, 0.2 mmol). The resulting mixture was cooled to 0° C. and NaOCl solution (0.8 mL, 10% aqueous) was added dropwise. The reaction mixture was left to come to room temperature while stirring. TLC after 30 minutes showed approximately 50% conversion to less polar spot. Sequence repeated using same equivalent of reagents. TLC 25:75 EtOAc:heptane still showed unreacted starting material. The reaction mixture was separated and the organic phase was treated with 1.0× Dess-Martin periodinane (2.1 g, 4.9 mmol) while stirring. TLC after 10 minutes showed complete conversion to less polar spot. The organic phase was washed with sat NaHCO$_3$, dried over Na$_2$SO$_4$, filtered and evaporated to give an orange solid. The crude material was chromatographed (80 g Redi-Sep column) eluting from 100% heptane to 50:50 EtOAc/heptane to give the intermediate (2.7 g, 87%) as a white solid. $^1$HNMR (CDCl$_3$): 9.94 (1H), 8.10 (2H), 7.50 (1H).

Preparation 26: (E/Z)-3-bromo-4-iodobenzaldehyde oxime

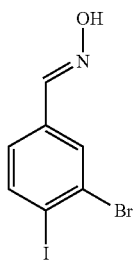 [SMILES: O/N=C/c1ccc(I)c(Br)c1]

To a solution of 3-bromo-4-iodobenzaldehyde (Preparation 25, 1000 mg, 3.2 mmol) in EtOH (50 mL) was added NH$_2$OH.HCl (345 mg, 4.8 mmol) and water (10 mL). The reaction was heated to 50° C. for 1 hour and then allowed to stir for 18 hours at room temperature. The reaction mixture was concentrated under vacuum to remove EtOH. Water was added to residue and extracted with EtOAc (2×75 mL). The combined organic phase was dried (Na$_2$SO$_4$) and concentrated under vacuum to afford the intermediate (1035 mg, 98%) as a glass. M/z (Cl)=326 [M+H]$^+$.

Preparation 27: 3-(3-bromo-4-iodophenyl)-5-(3,4,5-trichlorophenyl)-5-(trifluoromethyl)-4,5-dihydroisoxazole

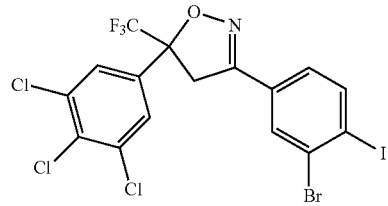 [SMILES: FC(F)(F)C1(c2cc(Cl)c(Cl)c(Cl)c2)CC(c2ccc(I)c(Br)c2)=NO1]

To a DMF (25 mL) solution of (E/Z)-3-bromo-4-iodobenzaldehyde oxime (1000 mg, 3.1 mmol) was added NCS (Preparation 26, 500 mg, 3.7 mmol) portionwise. The reaction was stirred at room temperature for 18 hours. TLC 50:50 EtOAc:heptane shows slightly less polar spot, no starting material. The reaction mixture was diluted with EtOAc (100 mL) and washed with water (2×50 mL). The organic phase was dried over sodium sulfate and concentrated to give the chlorooxime intermediate (1056 mg, 96%) as a solid. Next, to an ethyl acetate (70 mL) solution of the chlorooxime (1000 mg, 2.8 mmol) and 1,2,3-trichloro-5-(1,1,1-trifluoroprop-2-en-2-yl)benzene (765 mg, 2.8 mmol) was added potassium bicarbonate (310 mg, 3.1 mmol). The mixture was allowed to stir at room temperature for at least 48 hours. Reaction mixture filtered and concentrated under vacuum. The residue was chromatographed (80 g Redi-Sep column) eluting from 100% heptane to 20:80 EtOAc:heptane to afford the intermediate (1.53 g, 92%) as a solid. $^1$HNMR (CDCl$_3$): 7.95 (1H), 7.88 (1H), 7.65 (2H), 7.33 (1H), 4.07 (1H), 3.67 (1H).

Preparation 28: 1-benzhydryl-3-(2-bromo-4-(5-(3,4,5-trichlorophenyl)-5-(trifluoromethyl)-4,5-dihydroisoxazol-3-yl)phenyl)azetidin-3-ol

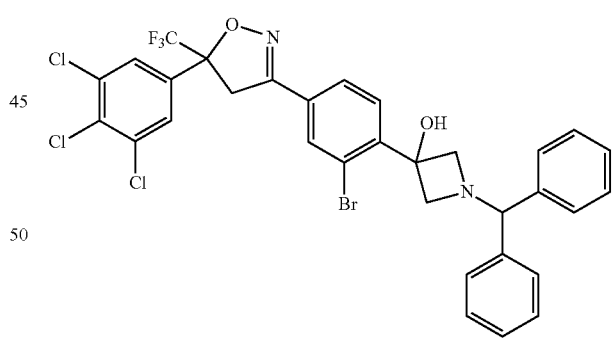

In an oven-dried flask containing 3-(3-bromo-4-iodophenyl)-5-(3,4,5-trichlorophenyl)-5-(trifluoromethyl)-4,5-dihydroisoxazole (Preparation 27, 1000 mg, 1.67 mmol) in THF (25 mL) at −40° C. was slowly added isopropyl magnesium chloride (1.7 mL of 2.0M solution). The reaction was stirred at approx. −40° C. for 1.5 under nitrogen. 1-benzhydrylazetidin-3-one (520 mg in 4 mL THF) was slowly added. The reaction was stirred at −40° C. for an additional 30 minutes and allowed to warm to room temperature. Stirring was continued for 2 hours at room temperature. The reaction was quenched with saturated NH$_4$Cl and extracted with EtOAc (2×75 mL). The combined organic phase was dried (Na$_2$SO$_4$)

and concentrated under vacuum. The crude material was chromatographed (40 g Redi-Sep column) eluting from 100% heptane to 60:40 EtOAc:heptane, collecting the intermediate (615 mg, 52%) as a glass. $^1$HNMR (CDCl$_3$): 7.87 (1H), 7.66-7.63 (3H), 7.45 (4H), 7.36-7.21 (7H), 4.39 (1H), 4.07 (1H), 3.73-3.58 (5H), 3.06 (1H); m/z (Cl) 711 ([M+H]$^+$.

Preparation 29: 3-(4-(1-benzhydryl-3-fluoroazetidin-3-yl)-3-bromophenyl)-5-(3,4,5-trichlorophenyl)-5-(trifluoromethyl)-4,5-dihydroisoxazole

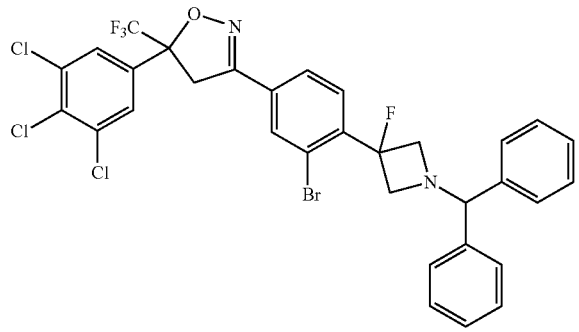 [SMILES: FC1(c2ccc(C3=NOC(c4cc(Cl)c(Cl)c(Cl)c4)(C(F)(F)F)C3)cc2Br)CN(C(c2ccccc2)c2ccccc2)C1]

Triethylamine trihydrofluoride (0.3 mL, 1.7 mmol) and triethylamine (0.11 mL, 0.8 mL) were dissolved in dichloromethane (30 mL) and cooled to −78° C. To the cooled mixture was added XtalFluor-E (310 mg, 1.4 mmol) and then 1-benzhydryl-3-(2-bromo-4-(5-(3,4,5-trichlorophenyl)-5-(trifluoromethyl)-4,5-dihydroisoxazol-3-yl)phenyl)azetidin-3-ol (Preparation 28, 600 mg, 0.8 mmol). Cooling was removed and the mixture was allowed to warm to room temperature with stirring for 2 hours. The reaction was poured into saturated aqueous sodium carbonate solution (100 mL) and the organic phase was separated, dried over anhydrous sodium sulfate, filtered and evaporated to dryness. Crude material was chromatographed (40 G Redi-Sep Column) eluting from 100% heptane to 20:80 EtOAc:heptane to afford the intermediate (523 mg, 87%) as a glass. $^1$HNMR (CDCl$_3$) δ ppm: 7.90 (1H), 7.69-7.66 (3H), 7.47-7.21 (11H), 4.46 (1H), 4.08 (1H), 3.90-3.66 (5H); m/z (Cl) 713 ([M+H]$^+$.

Preparation 30: 3-(3-bromo-4-(3-fluoroazetidin-3-yl)phenyl)-5-(3,4,5-trichlorophenyl)-5-(trifluoromethyl)-4,5-dihydroisoxazole

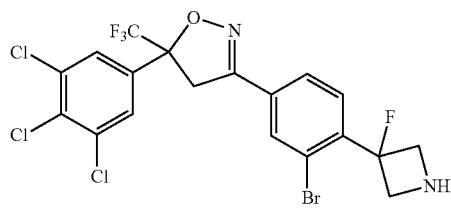 [SMILES: FC1(c2ccc(C3=NOC(c4cc(Cl)c(Cl)c(Cl)c4)(C(F)(F)F)C3)cc2Br)CNC1]

To a solution of 3-(4-(1-benzhydryl-3-fluoroazetidin-3-yl)-3-bromophenyl)-5-(3,4,5-trichlorophenyl)-5-(trifluoromethyl)-4,5-dihydroisoxazole (Preparation 29, 515 mg, 0.76 mmol) in MeCN/DCM (5:1, 60 mL) at 0° C. was added 1-chloroethyl chloroformate (275 uL, 2.5 mmol). The reaction was heated to reflux for 3 hours then allowed to cool to room temperature while stirring for 18 hours. Next, the reaction mixture was concentrated under vacuum, re-dissolved in anhydrous MeOH (50 mL), and refluxed for 1 hour. The reaction was cooled, concentrated under reduced pressure, and diethyl ether was added to residue. The resulting precipitate was filtered, rinsed with diethyl ether, and air dried to afford the intermediate (365 mg, 87%) as a solid. M/z (Cl) 713 ([M+H]$^+$.

Example 83

(3-(2-bromo-4-(5-(3,4,5-trichlorophenyl)-5-(trifluoromethyl)-4,5-dihydroisoxazol-3-yl)phenyl)-3-fluoroazetidin-1-yl)(cyclopropyl)methanone

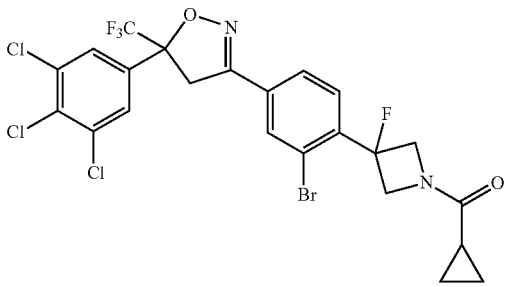 [SMILES: O=C(C1CC1)N1CC(F)(c2ccc(C3=NOC(c4cc(Cl)c(Cl)c(Cl)c4)(C(F)(F)F)C3)cc2Br)C1]

Prepared from the compound of Preparation 30, according to the method of Example 6. $^1$H NMR (CDCl$_3$) δ ppm: 7.98 (1H), 7.71 (1H), 7.66 (2H), 7.53 (1H), 4.96-4.46 (4H), 4.09 (1H), 3.70 (1H), 1.49 (1H), 1.11-0.77 (4H); m/z (Cl) 615 ([M+H]$^+$.

Example 84

2-(1-(cyclopropanecarbonyl)-3-fluoroazetidin-3-yl)-5-(5-(3,4,5-trichlorophenyl)-5-(trifluoromethyl)-4,5-dihydroisoxazol-3-yl)benzonitrile

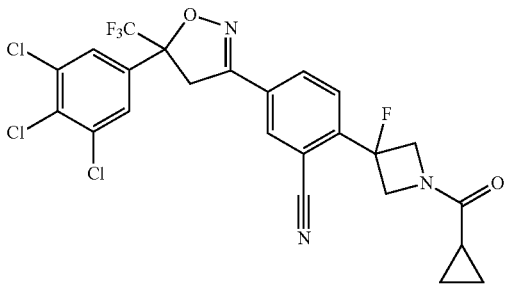 [SMILES: N#Cc1cc(C2=NOC(c3cc(Cl)c(Cl)c(Cl)c3)(C(F)(F)F)C2)ccc1C1(F)CN(C(=O)C2CC2)C1]

To a solution of (3-(2-bromo-4-(5-(3,4,5-trichlorophenyl)-5-(trifluoromethyl)-4,5-dihydroisoxazol-3-yl)phenyl)-3-fluoroazetidin-1-yl)(cyclopropyl)methanone (Example 83, 35 mg, 0.06 mmol) in DMF was added ZnCN (15 mg, 0.12 mmol) and the reaction was degassed with N$_2$ purge. Pd(PPh$_3$)$_4$ (4 mg, 0.003 mmol) was added and the reaction mixture was heated under microwave irradiation at 150° C. for 15 minutes. Next, the reaction mixture was diluted with water and extracted with EtOAc (75 mL). The organic phase was dried (Na$_2$SO$_4$) and concentrated under vacuum. Crude product was chromatographed (12 g Redi-Sep column) eluting from 100% heptane to 60:40 EtOAc:heptane to afford the final product (18 mg, 56%) as a solid. $^1$H NMR (CDCl$_3$) δ ppm: 8.08 (1H), 8.00 (1H), 7.70 (1H), 7.66 (2H), 4.98-4.52 (4H), 4.12 (1H), 3.73 (1H), 1.49 (1H), 1.10-0.81 (4H); m/z (CI) 560 ([M+H]$^+$.

Example 85

5-(3-chloro-5-(trifluoromethyl)phenyl)-3-(4-(3-fluoro-1-(methylsulfonyl)azetidin-3-yl)phenyl)-5-(trifluoromethyl)-4,5-dihydroisoxazole

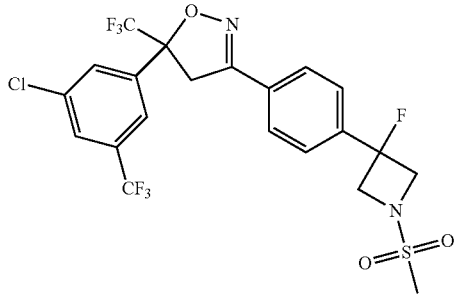 [SMILES: CS(=O)(=O)N1CC(F)(c2ccc(C3=NOC(c4cc(Cl)cc(C(F)(F)F)c4)(C(F)(F)F)C3)cc2)C1]

To a solution of 5-(3-chloro-5-(trifluoromethyl)phenyl)-3-(4-(3-fluoroazetidin-3-yl)phenyl)-5-(trifluoromethyl)-4,5-dihydroisoxazole (Preparation 22, 95 mg, 0.2 mmol) in CH$_2$Cl$_2$ (5 mL) was added triethylamine (0.15 mL, 1.1 mmol) and DMAP (5 mg, 0.04 mmol). Contents were stirred for 30 minutes at which time mesyl chloride (25 mg, 0.2 mmol) was added and the reaction was stirred for 18 hours at room temperature. Next, the reaction was concentrated to ~3 mL under nitrogen purge and injected directly onto a 24 g Redi-Sep column. The crude material was chromatographed eluting from 100% heptane to 30:70 EtOAc:heptane to afford the final product (95 mg, 94%) as a solid. $^1$HNMR (CDCl$_3$) δ ppm: 7.85 (1H), 7.79-7.77 (3H), 7.72 (1H), 7.64 (2H), 4.50-4.42, (2H), 4.34-4.27 (2H), 4.18 (1H), 3.76 (1H), 3.03 (3H); m/z (CI) 545 ([M+H]$^+$.

Preparation 31:
2-bromo-4-(diethoxymethyl)-1-fluorobenzene

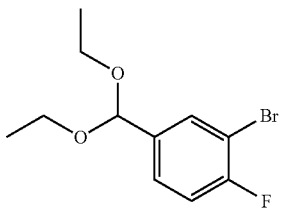

A 10 mL vial equipped with stir bar was charged with 1 g of 3-bromo-4-fluoro-benzaldehyde, 2 mL of triethyl orthoformate, and 5 mL of anhydrous ethanol. 50 mgs of tetrabutylammonium tribromide was then added, and the reaction mixture was stirred at ambient temperature overnight. TLC shows complete conversion to slightly less polar product. The crude reaction is poured into NaHCO$_3$, and extracted with ethyl acetate (2×25 mL). Combined organics are dried over MgSO4, and filtered over a pad of silica. The solvents are reduced under vacuum and a colorless oil (1 g) is isolated. The diethyl acetal intermediate is used as such in the next step. 74% yield.

Preparation 32: 1-benzhydryl-3-(2-bromo-4-(diethoxymethyl)phenyl)azetidine-3-carbonitrile

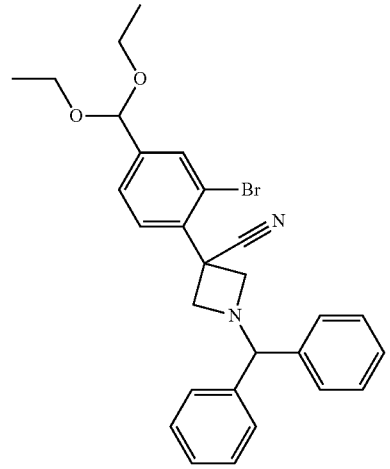 [SMILES: CCOC(OCC)c1ccc(C2(C#N)CN(C(c3ccccc3)c3ccccc3)C2)c(Br)c1]

2-bromo-4-(diethoxymethyl)-1-fluorobenzene (Preparation 31, 1 g) and 1-benzhydrylazetidine-3-carbonitrile (2.7 g) were dissolved in anhydrous THF (4 mL). KHMDS (2.2 g) was then added all at once. The solution became dark brown instantaneously. The reaction was stirred at room temperature overnight. An LC-Ms confirms complete conversion into the desired product: [433]~3.31 minutes and [505]~3.62 min. Both peaks correspond to desired product: one is the aldehyde, and the other is the acetal. The crude reaction mixture was concentrated to an oil, and loaded on a 80 g SiO$_2$ cartridge, then eluted with a gradient 0-100% ethylacetate in heptane. The desired fractions were collected and concentrated in vacuum. The resulting oil was suspended in methanol and sonicated for 30 sec, and the resulting white powder is filtered and used as such in the next step. 55% yield. LC-MS [505].

Preparation 33: 3-(2-bromo-4-(dimethoxymethyl)phenyl)azetidine-3-carbonitrile

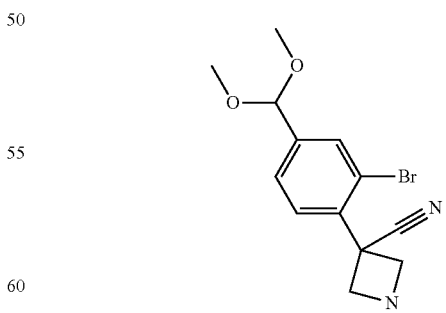

The product from Preparation 32 (500 mg) was dissolved in acetonitrile and the reaction mixture was cooled to 0° C., then chloroethylchloroformate (0.2 mL) was added all at once. The reaction mixture was heated to reflux for 2 hours. LC-MS shows desired peak forming ~2.329 minutes [339], but some starting material left. Another equivalent of chloroethylchloroformate was added, and the reaction mixture is left stirring for another hour at reflux. TLC shows completion. The crude reaction was concentrated in vacuum, and the resulting yellow oil was dissolved in MeOH, and re-heated to reflux for 30 minutes. TLC shows complete conversion to a baseline spot. The reaction was concentrated to an oil, and 20 mL diethylether was added. The gum was then sonicated for 15 minutes, and the solid is filtered and analysed. LC-MS ([311]~2.036 min) confirms desired product, although the ethylacetal is now a methylacetal due to reflux in methanol. Used as such in the next step. Assumed quantitative yield.

Preparation 34: tert-butyl 3-(2-bromo-4-(dimethoxymethyl)phenyl)-3-cyanoazetidine-1-carboxylate

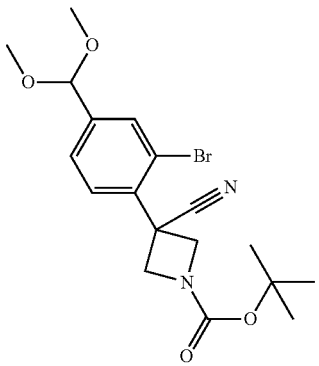 [SMILES: COC(OC)c1ccc(C2(C#N)CN(C(=O)OC(C)(C)C)C2)c(Br)c1]

The product of Preparation 33 (300 mg) and boc anhydride (252 mg) were mixed in $CH_2Cl_2$ (4 mL), and Hunig's base was added (500 µL). The reaction mixture was left stirring at room temperature for 1 hour, then a TLC was taken (50/50 ethylacetate/heptane) and shows completion. The crude mixture was concentrated to an oil and was chromatographed on a 25 g $SiO_2$ column, eluting with a gradient 0-100% ethylacetate in heptane. The desired fractions were collected, and concentrated in vacuum. LC-MS and NMR confirms desired product [m/z 411], used as such in the next step. Mixture of the aldehyde and dimethoxyacetal.

Preparation 35: tert-butyl 3-(2-bromo-4-((hydroxyimino)methyl)phenyl)-3-cyanoazetidine-1-carboxylate

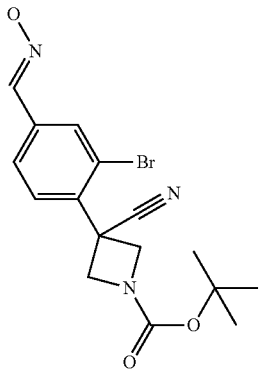 [SMILES: CC(C)(C)OC(=O)N1CC(C#N)(c2ccc(/C=N/O)cc2Br)C1]

The product of Preparation 34 (320 mg) was added to 4 mL MeOH and 1 mL water was added, followed by hydroxylamine hydrochloride (85 mg). The reaction mixture was stirred at room temp, and after 30 minutes, LC-MS shows new peak forming 2.976 minutes, no ionisation. After 60 minutes, LC-MS shows little progress so the mixture was heated to 65° C. for 10 minutes. LC-MS now shows clean conversion to desired mass [446]~3.165 min. The crude reaction was concentrated to a minimum (white suspension), then extracted with ethylacetate/$NaHCO_3$. The ethylacetate layer is dried over $MgSO_4$, filtered and concentrated in vacuum, and the resulting gum is analysed by NMR. Shows desired product. 300 mg, used as such in the next step.

Preparation 36: tert-butyl 3-(2-bromo-4-(5-(3,4,5-trichlorophenyl)-5-(trifluoromethyl)-4,5-dihydroisoxazol-3-yl)phenyl)-3-cyanoazetidine-1-carboxylate

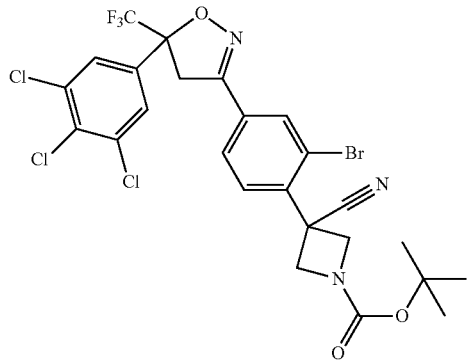 [SMILES: CC(C)(C)OC(=O)N1CC(C#N)(c2ccc(C3=NOC(c4cc(Cl)c(Cl)c(Cl)c4)(C(F)(F)F)C3)cc2Br)C1]

The oxime from Preparation 35 (130 mg) was mixed with N-chlorosuccinimide (50 mg) in ethyl acetate, and the reaction mixture was stirred at 55° C. for 15 minutes. LC-MS confirms desired product formed (starting material was all gone). To the reaction trichlorostyrene (95 mg) was added, followed by $KHCO_3$ (63 mg). The reaction mixture was left stirring at room temperature overnight. LC-MS shows completion. The mixture was filtered over a pad of $MgSO_4$, and the yellow solution was concentrated to yield a solid. LC-MS confirms desired mass [553]~4.059 minutes. The solid was loaded on a 25 g silica column and eluted with 0-100% gradient ethylacetate/heptane. The desired fractions were concentrated, and a white powder collected. 95 mg. 46% yield.

Preparation 37: 3-(2-bromo-4-(5-(3,4,5-trichlorophenyl)-5-(trifluoromethyl)-4,5-dihydroisoxazol-3-yl)phenyl)azetidine-3-carbonitrile

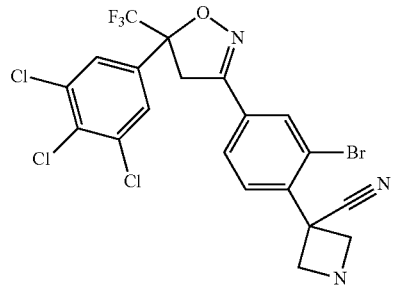 [SMILES: N#CC1(c2ccc(C3=NOC(c4cc(Cl)c(Cl)c(Cl)c4)(C(F)(F)F)C3)cc2Br)CNC1]

The product from Preparation 36 (90 mgs) was dissolved in anhydrous methanol. A methanolic solution of HCl was added (300 µL), and warmed to 65° C. After 3 hours, LC-MS shows desired product [m/z 553]~3.195 min. The mixture was then concentrated to dryness and diethyl ether (6 mL) was added to the solid. The resulting suspension was sonicated for 10 minutes, and a fine white powder was then filtered. It was used as such in the next step. LC-MS confirms desired product [553]. 75 mgs. 98% yield.

Example 86

3-(2-bromo-4-(5-(3,4,5-trichlorophenyl)-5-(trifluoromethyl)-4,5-dihydroisoxazol-3-yl)phenyl)-1-(cyclopropanecarbonyl)azetidine-3-carbonitrile

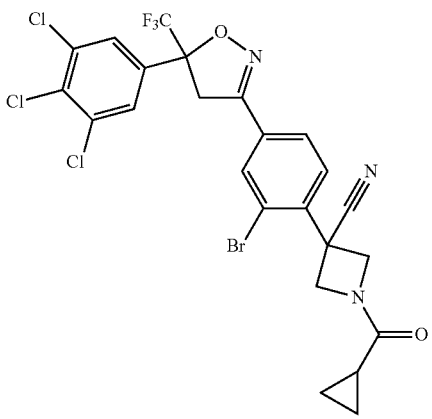 [SMILES: N#CC1(c2ccc(C3=NOC(c4cc(Cl)c(Cl)c(Cl)c4)(C(F)(F)F)C3)cc2Br)CN(C(=O)C2CC2)C1]

The product of Preparation 37 (75 mg) was dissolved in CH$_2$Cl$_2$ (5 mL) and Hunig's base (74 mg, 97 µL) was added. Reaction was stirred at room temperature for 1 minute, then cyclopropanecarbonyl chloride (18.4 mg, 16 µL) was added and the mixture was stirred for 15 minutes. LC-MS shows desired product formed [m/z 621]~3.73 min. The mixture was concentrated and loaded on a 25 g SiO$_2$ column, and eluted with a gradient of ethyl acetate in heptane (0-50% over 8 CV). The desired fractions were isolated and concentrated in vacuum. 60 mg, 62% yield. NMR 400 Mhz δ ppm: 7.99 (s, 1H), 7.74 (d, 1H), 7.64 (s, 2H), 7.49 (d, 1H), 5.05 (m, 1H), 4.73 (m, 2H), 4.65 (m, 1H), 4.08 (d, 1H), 3.68 (d, 1H), 1.41 (m, 1H), 1.10-1.06 (m, 2H), 0.91-0.86 (m, 2H); LC-MS: [m/z 621] @ 3.73 minutes.

Example 87

1-(cyclopropanecarbonyl)-3-(4-(5-(3,4,5-trichlorophenyl)-5-(trifluoromethyl)-4,5-dihydroisoxazol-3-yl)phenyl)azetidine-3-carbonitrile

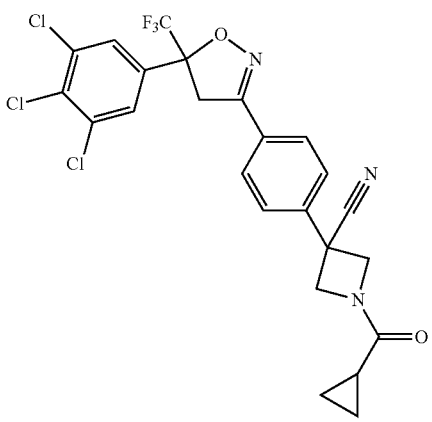 [SMILES: N#CC1(c2ccc(C3=NOC(c4cc(Cl)c(Cl)c(Cl)c4)(C(F)(F)F)C3)cc2)CN(C(=O)C2CC2)C1]

The compound of Example 86 (60 mg) was dissolved in THF (2 mL) and Rieke Zn in THF was then added dropwise (2 mL of a 0.7N solution). The mixture was then sonicated for 5 minutes. LC-MS (THF+a few drops of acetic acid) shows about 50% conversion. Another 4 equivalents of Zn was added, and again 15 minutes sonication. LC-MS shows the reaction mixture is gone to about 90% conversion. About 200 µL of acetic acid was then added, the reaction mixture was stirred for 2 minutes, then filtered over celite. The solution was concentrated under vacuum and the remaining oil dissolved in ethyl acetate and washed with NaHCO$_3$, then dried over MgSO$_4$, filtered and concentrated in vacuum. The remaining oil is purified via reverse phase chromatography. Yield 55 mg. LC-MS confirms desired product [m/z 542]. NMR 400 MHz δ ppm: 7.78 (d, 2H), 7.67 (d, 2H), 7.66 (s, 2H), 4.99 (m, 1H), 4.71 (m, 1H), 4.53 (m, 1H), 4.39 (m, 1H), 4.10 (d, 1H), 3.71 (d, 1H), 1.45-1.39 (m, 1H), 1.10-1.06 (m, 2H), 0.91-0.86 (m, 2H).

Preparation 38:

3-(4-Formyl-phenyl)-azetidine-1-carboxylic acid tert-butyl ester

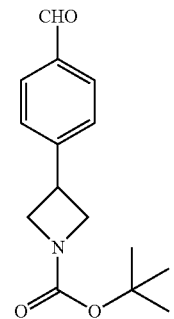 [SMILES: CC(C)(C)OC(=O)N1CC(c2ccc(C=O)cc2)C1]

To a stirred suspension of activated zinc (5.636 g, 86.19 mmol, 2 equivalents) in dry DMF (20 mL) was added pre-dissolved dibromomethane (1.89 g, 10.77 mmol, 0.25 equivalents) in dry DMF (5 mL) and reaction mixture was heated at 70° C. for 30 minutes under nitrogen atmosphere. After 30 minutes reaction was cooled to room temperature. To the resulting reaction mixture was added pre-dissolved chlorotrimethylsilane (1.12 g, 10.77 mmol, and 0.25 equivalents) in dry DMF (5 mL) and stirred for 15 minutes followed by addition of pre-dissolved 3-Iodo-N-Boc-Azetidine (15.24 g, 53.86 mmol, 1.25 eq) in dry DMF (30 mL) and the reaction mixture was heated at 40° C. for 30 minutes under nitrogen atmosphere. Reaction mixture was sonicated for 30 minutes, during sonication zinc dust was uniformly suspended to leave the hazy reaction mixture. To the sonicated reaction mixture (Zincate) was added pre-dissolved 4-Iodo benzaldehyde (10 g, 43.099 mmol, 1 eq) in dry DMF (42 mL) followed by addition of Tri-2-furyl phosphine (1.1 g, 4.73 mmol, 0.1 eq), and Tris (dibenzylidene-acetone) dipalladium(0) (1.18 g, 1.292 mmol, 0.03 equivalents). The resulting reaction mixture was heated at 70° C. for 18 hours under nitrogen atmosphere. Progress of the reaction was monitored by TLC using 10% ethyl acetate in hexane and visualized in UV light (254 nm). Reference of new spot and starting material was 0.3 and 0.7 respectively. After maximum consumption of starting material (18 hours), reaction mixture was quenched with saturated ammonium chloride (100 mL) and extracted by ethyl acetate (3×100 mL). Combined organic layer was dried over sodium sulphate and concentrated in vacuo to afford brown colored liquid (15 g, crude). Crude compound was purified by column chromatography using 100-200 mesh size silica gels. Desired compound was eluted in 10% ethyl acetate in hexanes to afford 6.5 g (57.79%) brown colored liquid. ¹H NMR and LC-MS was consistent. ¹H NMR (400 MHz, DMSO-d₆) δ: 1.40 (s, 9H), 3.86-3.89 (m, 3H), 4.26-4.29 (m, 2H), 7.57 (d, J=8.04 Hz, 2H), 7.90 (d, J=8.16 Hz, 2H), 9.99 (s, 1H). LC-MS (m/z):=262.30 (M+H).

***Activation of zinc: Zinc powder (5 g) was stirred with 10% HCl solution (20 mL) for 5 minutes at room temperature and decanted. This procedure was repeated twice and filtered through Buchner funnel, washed with water (3×25 mL), acetone (2×20 mL), well dried in vacuo to afford activated zinc (2 g).

Preparation 39: 3-[4-(Hydroxyimino-methyl)-phenyl]-azetidine-1-carboxylic acid tert-butyl ester

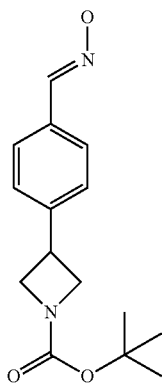 [SMILES: CC(C)(C)OC(=O)N1CC(c2ccc(/C=N/O)cc2)C1]

To a stirred suspension of 3-(4-Formyl-phenyl)-azetidine-1-carboxylic acid tert-butyl ester (Preparation 38, 6.5 g, 24.904 mmol, 1 equivalents) in ethanol:water (1:1, 120 mL) was added hydroxylamine hydrochloride (2.5 g, 37.356 mmol, 1.5 equivalents) followed by sodium acetate (3.67 g, 44.82 mol, 1.8 eq). Resulting reaction mixture was stirred at room temperature for 0.5 hours. Progress of the reaction was monitored by TLC using 20% ethyl acetate in hexane and visualized in UV light (254 nm). Reference of new spot and starting material was 0.32 and 0.67 respectively. After consumption of starting material, solvents was evaporated under reduced pressure and extracted with DCM (3×25 mL). Evaporation of volatiles provided light yellow solid (6.5 g, 94.51%). LC-MS and ¹H NMR was consistent. ¹H NMR (400 MHz, DMSO-d₆) δ 1.39 (s, 9H), 3.81 (broad s, 3H), 4.42 (broad s, 2H), 7.36 (d, J=8 Hz, 2H), 7.57 (d, J=8 Hz, 2H), 8.12 (s, 1H), 11.19 (s, 1H). LC-MS (m/z):=277.30 (M+H).

Preparation 40: 3-{4-[5-(3,5-Dichloro-phenyl)-5-trifluoromethyl-4,5-dihydro-isoxazol-3-yl]-phenyl}-azetidine-1-carboxylic acid tert-butyl ester

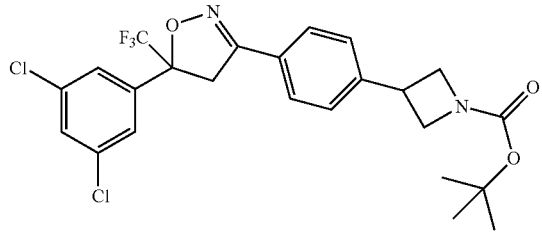 [SMILES: CC(C)(C)OC(=O)N1CC(c2ccc(C3=NOC(c4cc(Cl)cc(Cl)c4)(C(F)(F)F)C3)cc2)C1]

To a stirred solution of 3-[4-(Hydroxyimino-methyl)-phenyl]-azetidine-1-carboxylic acid tert-butyl ester (Preparation 39, 1 g, 3.62 mmol, 1.0 equivalents) in DMF (6.0 mL) was added NCS (725.26 mg, 5.43 mmol, 1.5 equivalents) and heated to 50° C. for 1 hour. Progress of the reaction was monitored by TLC using 5% methanol in dichloromethane. After complete consumption of starting material, reaction was cooled to 0° C. followed by the addition of potassium hydrogen carbonate (543.18 mg, 5.43 mmol, 1.5 equivalents) and pre-dissolved solution of 1,3-Dichloro-5-(1-trifluoromethyl-vinyl)-benzene (1.04 g, 4.345 mmol, 1.2 equivalents) in DMF (4.0 mL). Resulting reaction was stirred at room temperature for 16 hours under nitrogen atmosphere. Progress of the reaction was monitored by TLC using 20% ethyl acetate in hexane and visualized in UV light (254 nm). Reference of required product was 0.6 and 0.5 for starting material. After consumption of starting material, reaction mixture was quenched with water (40 mL) extracted with diethyl ether (3×50 mL). Combined organic layer was washed with brine (20 mL) and dried over anhydrous sodium sulphate and concentrated in vacuo to afford (1.50 g, crude). Further purification by column chromatography (on neutral alumina) using 10% ethyl acetate in hexane as eluent afforded off white solid 1.3 g (69.84%). ¹H NMR and LC-MS were consistent. ¹H NMR (400 MHz, DMSO-d₆) δ 1.39 (s, 9H), 3.84 (m, 3H), 4.25-4.38 (m, 4H), 7.47 (d, J=8 Hz, 2H), 7.62 (d, J=1 Hz, 2H), 7.71 (d, J=8 Hz, 2H), 7.81 (t, J=2 Hz, 1H). LC-MS (m/z):=513 (M-H).

Preparation 41: 3-(4-Azetidin-3-yl-phenyl)-5-(3,5-dichloro-phenyl)-5-trifluoromethyl-4,5-dihydro-isoxazole hydrochloride salt

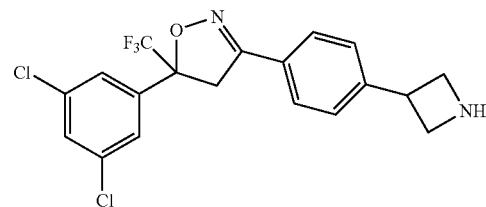 [SMILES: FC(F)(F)C1(c2cc(Cl)cc(Cl)c2)CC(c2ccc(C3CNC3)cc2)=NO1]

To a stirred solution of 3-{4-[5-(3,5-Dichloro-phenyl)-5-trifluoromethyl-4,5-dihydro-isoxazol-3-yl]-phenyl}azetidine-1-carboxylic acid tert-butyl ester (Preparation 40, 1 g, 1.94 mmol, 1 eq) in MeOH (10 mL) was purged HCl (g) at 0° C. for 0.5 hours and then reaction mixture was refluxed at 70° C. for 0.5 hours. Progress of reaction was monitored by TLC, after complete consumption of starting material reaction mixture was evaporated under reduced pressure to dryness to give 1.15 g (crude) Which was washed with methyl t-butyl ether (10 mL×2) to afforded 1.1 g (95.21%). ¹H-NMR and LC-MS were consistent. ¹H NMR (400 MHz, DMSO-d₆) δ 4.05 (t, J=8 Hz, 2H), 4.15-4.21 (m, 1H), 4.24-4.39 (m, 4H), 7.55 (d, J=8 Hz, 2H), 7.62 (d, J=1 Hz, 2H), 7.74 (d, J=8 Hz, 2H), 7.81 (t, J=2 Hz, 1H), 8.99 (bs, 2H). LC-MS (m/z):=415 (M+H).

Preparation 42: 3-(4-(azetidin-3-yl)phenyl)-5-(3,4,5-trichlorophenyl)-5-(trifluoromethyl)-4,5-dihydroisoxazole hydrochloride salt

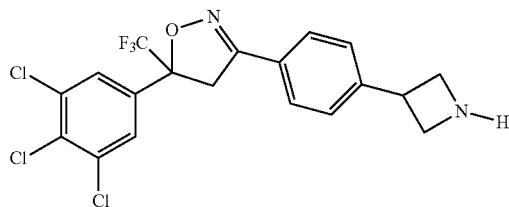 [SMILES: FC(F)(F)C1(c2cc(Cl)c(Cl)c(Cl)c2)CC(c2ccc(C3CNC3)cc2)=NO1]

Prepared from the compound of Preparation 39 using procedures similar to Preparations 40 and 41 using 1,2,3-trichloro-5-(3,3,3-trifluoroprop-1-en-2-yl)benzene instead of 1,3-dichloro-5-(3,3,3-trifluoroprop-1-en-2-yl)benzene. $^1$H NMR (400 MHz, DMSO-$d_6$) δ 4.06 (t, J=17 Hz, 2H), 4.15-4.19 (m, 1H), 4.24-4.29 (m, 2H), 4.35 (t, J=18 Hz, 2H), 7.55 (d, J=8 Hz, 2H), 7.74 (d, J=8 Hz, 2H), 7.84 (s, 2H), 9.004 (bs, 2H). LC-MS (m/z):=488.90 (M+H).

Example 88

1-(3-(4-(5-(3,5-dichlorophenyl)-5-(trifluoromethyl)-4,5-dihydroisoxazol-3-yl)phenyl)azetidin-1-yl)-2-methylpropan-1-one

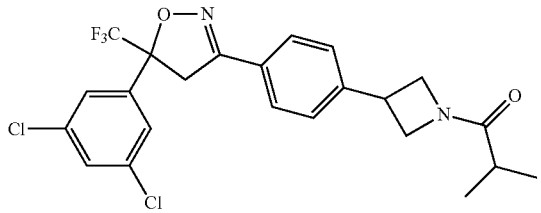 [SMILES: CC(C)C(=O)N1CC(c2ccc(C3=NOC(c4cc(Cl)cc(Cl)c4)(C(F)(F)F)C3)cc2)C1]

The compound was prepared from the compound of preparation 41 using a procedure similar to that of Example 6 using isobutyryl chloride in place of cyclopropane carbonyl chloride. $^1$HNMR (DMSO-$d_6$) δ ppm: 7.81 (1H), 7.72 (2H), 7.63 (2H), 7.49 (2H), 4.59-3.81 (8H), 1.0 (6H); m/z (ES+APCI Positive) 485 [M+H]$^+$.

Example 89

2-methyl-1-(3-(4-(5-(3,4,5-trichlorophenyl)-5-(trifluoromethyl)-4,5-dihydroisoxazol-3-yl)phenyl)azetidin-1-yl)propan-1-one

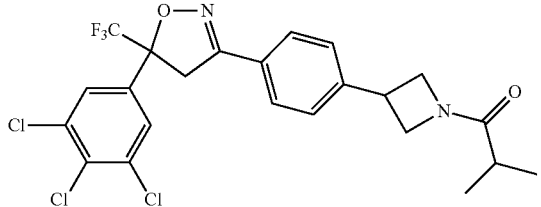 [SMILES: CC(C)C(=O)N1CC(c2ccc(C3=NOC(c4cc(Cl)c(Cl)c(Cl)c4)(C(F)(F)F)C3)cc2)C1]

The compound was prepared from the compound of Preparation 42 using a procedure similar to that of Example 6 using isobutyryl chloride in place of cyclopropane carbonyl chloride. $^1$HNMR (DMSO-d6) δ ppm: 7.84 (2H), 7.72 (2H), 7.50 (2H), 4.59-3.84 (8H), 1.0 (6H); m/z (ES+APCI Positive) 519 [M+H]$^+$.

Example 90

Cyclopropyl(3-(4-(5-(3,5-dichlorophenyl)-5-(trifluoromethyl)-4,5-dihydroisoxazol-3-yl)phenyl)azetidin-1-yl)methanone

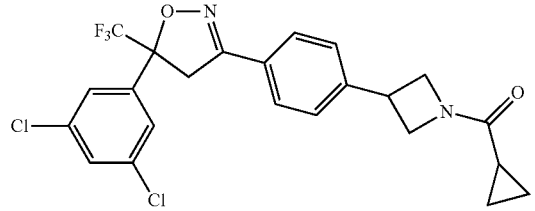 [SMILES: O=C(C1CC1)N1CC(c2ccc(C3=NOC(c4cc(Cl)cc(Cl)c4)(C(F)(F)F)C3)cc2)C1]

The compound was prepared from the compound of Preparation 41 using a procedure similar to that of Example 6 using isobutyryl chloride in place of cyclopropane carbonyl chloride. $^1$HNMR (DMSO-d6) δ ppm: 7.81 (1H), 7.72 (2H), 7.63 (2H), 7.51 (2H), 4.66-3.16 (8H), 0.72 (4H); m/z (ES+APCI Positive) 483 [M+H]$^+$.

Example 91

Cyclopropyl(3-(4-(5-(3,4,5-trichlorophenyl)-5-(trifluoromethyl)-4,5-dihydroisoxazol-3-yl)phenyl)azetidin-1-yl)methanone

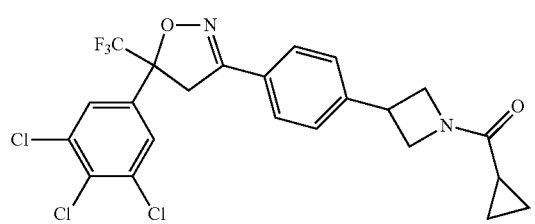 [SMILES: O=C(C1CC1)N1CC(c2ccc(C3=NOC(c4cc(Cl)c(Cl)c(Cl)c4)(C(F)(F)F)C3)cc2)C1]

The compound was prepared from the compound of Preparation 42 using a procedure similar to that of Example 6 using isobutyryl chloride in place of cyclopropane carbonyl chloride. $^1$HNMR (CDCl$_3$) δ ppm: 7.84 (2H), 7.71 (2H), 7.51 (2H), 4.69-3.18 (8H), 0.72 (4H); m/z (ES+APCI Positive) 517 [M+H]$^+$.

Example 92

1-(3-(4-(5-(3,5-dichlorophenyl)-5-(trifluoromethyl)-4,5-dihydroisoxazol-3-yl)phenyl)azetidin-1-yl)ethanone

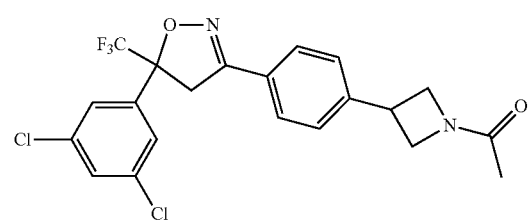 [SMILES: CC(=O)N1CC(c2ccc(C3=NOC(c4cc(Cl)cc(Cl)c4)(C(F)(F)F)C3)cc2)C1]

The compound was prepared from the compound of Preparation 41 using a procedure similar to that of Example 1. $^1$HNMR (CDCl$_3$) δ ppm 7.81 (1H), 7.72 (2H), 7.63 (2H), 7.51 (2H), 4.53-3.80 (7H), 1.80 (3H); m/z (ES+APCI Positive) 457 [M+H]$^+$.

Example 93

1-(3-(4-(5-(3,4,5-trichlorophenyl)-5-(trifluoromethyl)-4,5-dihydroisoxazol-3-yl)phenyl)azetidin-1-yl)ethanone

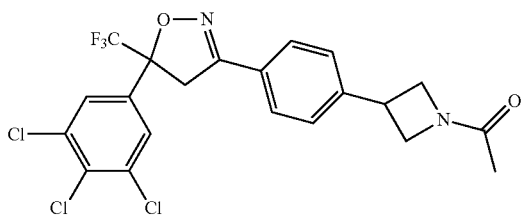 [SMILES: CC(=O)N1CC(c2ccc(C3=NOC(c4cc(Cl)c(Cl)c(Cl)c4)(C(F)(F)F)C3)cc2)C1]

The compound was prepared from the compound of Preparation 42 using a procedure similar to that of Example 1. $^1$HNMR (CDCl$_3$) δ ppm: 7.84 (2H), 7.71 (2H), 7.50 (2H), 4.53-3.83 (7H), 1.80 (3H); m/z (ES+APCI Positive) 491 [M+H]$^+$.

Preparation 43—Oxidation of Sulfide to Sulfoxide 1-(3-(4-(5-(3,5-dichloro-4-fluorophenyl)-5-(trifluoromethyl)-4,5-dihydroisoxazol-3-yl)phenyl)-3-fluoroazetidin-1-yl)-2-(methylsulfinyl)ethanone (Example 162)

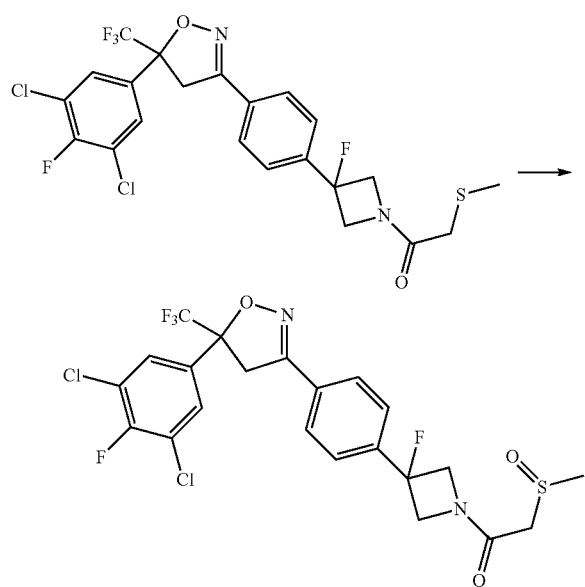

A solution of sodium (meta)periodate (49 mg, 0.23 mmol) in 1:1 methanol/water (6 mL) was cooled with a ice bath and a solution of 1-(3-(4-(5-(3,5-dichloro-4-fluorophenyl)-5-(trifluoromethyl)-4,5-dihydroisoxazol-3-yl)phenyl)-3-fluoroazetidin-1-yl)-2-(methylthio)ethanone (102 mg, 0.19 mmol) in methanol (~2 mL) was added drop wise via pipette. A precipitate forms and the reaction was allowed to stir with the ice bath in place slowly warming to ambient overnight. When complete, the reaction was partitioned between water (5 mL) and CH$_2$Cl$_2$ (5 mL). Aqueous extracted with additional CH$_2$Cl$_2$ (2×5 mL). Organic phase collected and condensed. The crude material was adsorbed on silica and chromatographed on a 12 g silica column, eluting with a gradient of 0% to 100% ethyl acetate in heptane. Fractions containing the desired material were combined and concentrated. CH$_2$Cl$_2$ (~100 μL) was added to the resulting film. Placing the flask on high vacuum overnight resulted in formation of a white foam. Yield 90 mg (86%). LC/MS retention time=3.317 minutes, MS calculated for (C$_{22}$H$_{17}$Cl$_2$F$_5$N$_2$O$_3$S), 554.03; found 555.0 M+H+.

Preparation 44: Amide Coupling by Parallel Chemistry

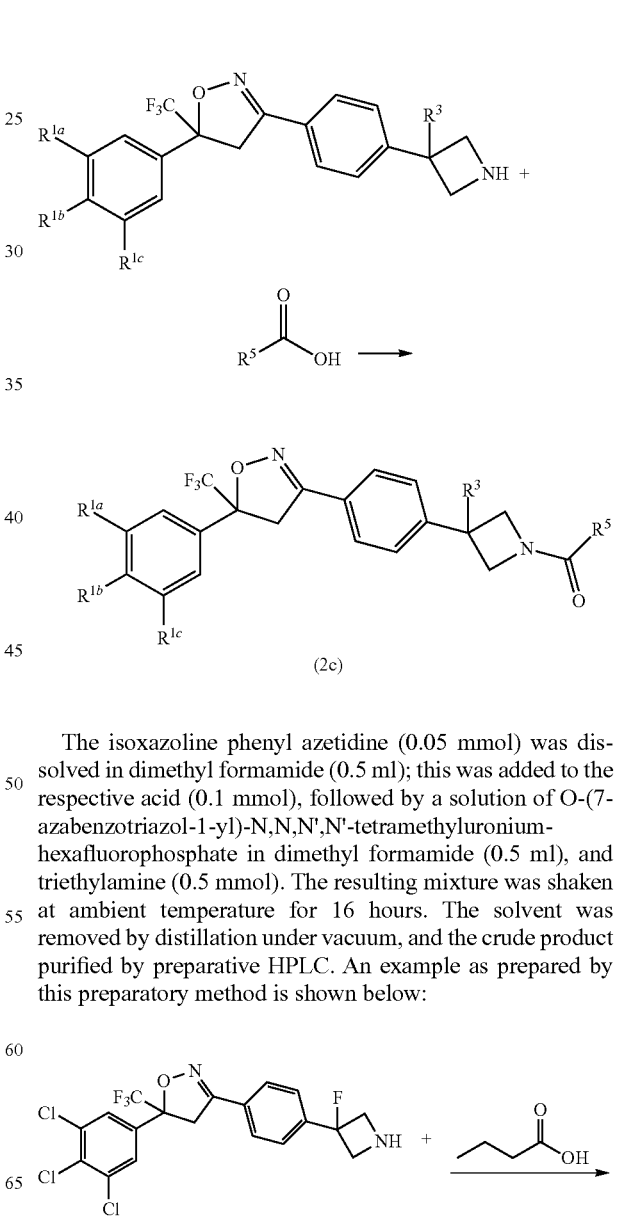

The isoxazoline phenyl azetidine (0.05 mmol) was dissolved in dimethyl formamide (0.5 ml); this was added to the respective acid (0.1 mmol), followed by a solution of O-(7-azabenzotriazol-1-yl)-N,N,N',N'-tetramethyluronium-hexafluorophosphate in dimethyl formamide (0.5 ml), and triethylamine (0.5 mmol). The resulting mixture was shaken at ambient temperature for 16 hours. The solvent was removed by distillation under vacuum, and the crude product purified by preparative HPLC. An example as prepared by this preparatory method is shown below:

-continued

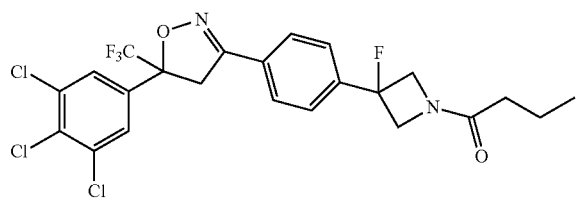

(Example 97)

3-(4-(3-fluoroazetidin-3-yl)phenyl)-5-(3,4,5-trichlorophenyl)-5-(trifluoromethyl)-4,5-dihydroisoxazole (0.05 mmol) was dissolved in dimethyl formamide (0.5 mL); this was added to butyric acid (0.1 mmol), followed by a solution of O-(7-azabenzotriazol-1-yl)-N,N,N',N'-tetramethyluroniumhexafluorophosphate in dimethyl formamide (0.5 mL), and triethylamine (0.5 mmol). The resulting mixture was shaken at ambient temperature for 16 hours. The solvent was removed by distillation under vacuum, and the crude product purified by preparative HPLC to give 3.2 mg of 1-(3-fluoro-3-(4-(5-(3,4,5-trichlorophenyl)-5-(trifluoromethyl)-4,5-dihydroisoxazol-3-yl)phenyl)azetidin-1-yl)butan-1-one. MH+ 537; retention time 9.83 minutes.

Preparation 45: Urea Formation by Parallel Chemistry

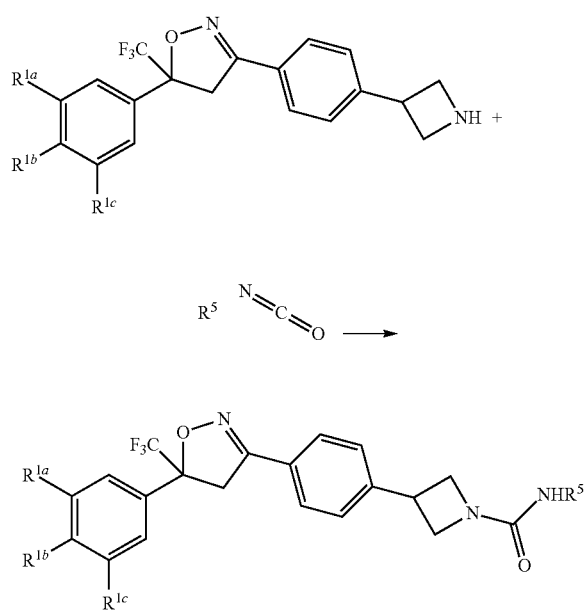

A solution of the isoxazoline phenyl azetidine (0.05 mmol) in DMF (1 mL) was treated with triethylamine (0.20 mmol). A solution of the respective isocyanate (0.055 mmol) in DMF (0.5 mL) was added and the reaction mixture stirred at ambient temperature for 16 hours. The solvent was removed under reduced pressure, and the crude product purified by preparative HPLC. An example prepared by this preparatory method is shown below:

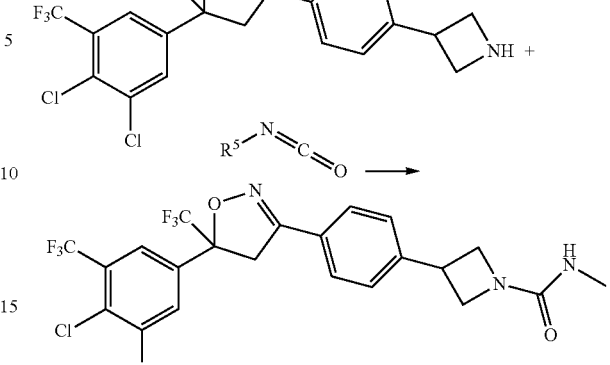

(Example 185)

3-(4-(azetidin-3-yl)phenyl)-5-(3,4-dichloro-5-(trifluoromethyl)phenyl)-5-(trifluoromethyl)-4,5-dihydroisoxazole (0.05 mmol) was dissolved in DMF (1 mL); triethylamine (0.20 mmol) was added, followed by a solution isocyanatomethane. The resulting solution was stirred at ambient temperature for 16 hours. The solvent was removed under reduced pressure and the crude product purified by preparative HPLC to give 3-(4-(5-(3,4-dichloro-5-(trifluoromethyl)phenyl)-5-(trifluoromethyl)-4,5-dihydroisoxazol-3-yl)phenyl)-N-methylazetidine-1-carboxamide (11.2 mg) MH+ 540.1; retention time 6.14 minutes.

Preparation 46: Azido Formation

Azide intermediates can be prepared according to the following procedure for 3-(4-(3-azido-1-benzhydrylazetidin-3-yl)phenyl)-5-(3,4,5-trichlorophenyl)-5-(trifluoromethyl)-4,5-dihydroisoxazole (intermediate for Example 163).

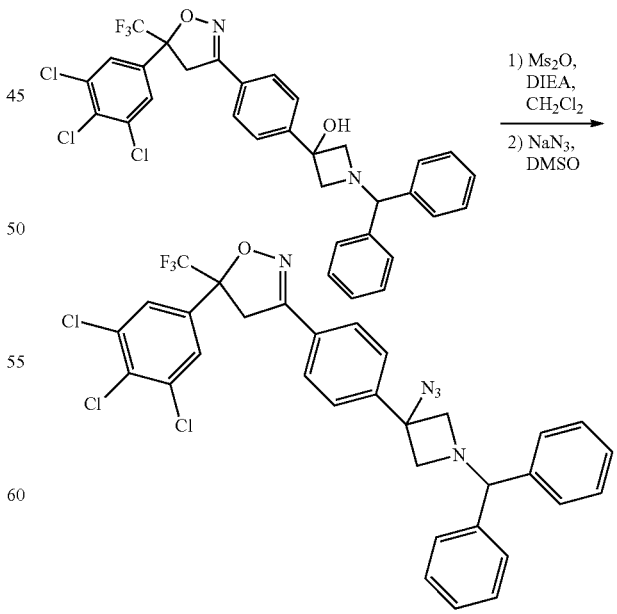

To a solution of 1.19 grams (1.88 mmole, 1.0 eq) of 1-benzhydryl-3-(4-(5-(3,4,5-trichlorophenyl)-5-(trifluoromethyl)-

4,5-dihydroisoxazol-3-yl)phenyl)azetidin-3-ol in 17 mL of $CH_2Cl_2$ was added 500 µL (2.8 mmole, 1.5 eq) of diisopropylethylamine, neat via syringe, followed by 438 mg (2.5 mmole, 1.3 eq) of methylsulfonic anhydride solid. After stirring 3.5 hours at room temperature an aliquot of the reaction mixture was placed in 1.0 mL of methanol and analyzed via LC/MS. The chromatograph indicated the starting material was consumed. The reaction with diluted with 20 mL of $CH_2Cl_2$ and 20 mL of saturated $NaHCO_3$ solution. After stirring for 2 hours the layers were separated via a Biotage Phase Separator cartridge. The organic layer was concentrated under reduced pressure to give 1.29 grams (96% yield) of intermediate 1-benzhydryl-3-(4-(5-(3,4,5-trichlorophenyl)-5-(trifluoromethyl)-4,5-dihydroisoxazol-3-yl)phenyl)azetidin-3-yl methanesulfonate as light yellow solid. A 227 mg sample of 1-benzhydryl-3-(4-(5-(3,4,5-trichlorophenyl)-5-(trifluoromethyl)-4,5-dihydroisoxazol-3-yl)phenyl)azetidin-3-yl methanesulfonate (0.35 mmole, 1.0 eq) and 72.1 mg of sodium azide (1.1 mmole, 3.1 eq) were weighed into a 100 mL flask, to this was added 3 mL of anhydrous DMSO. After stirring for 1.5 hours at room temperature the reaction was diluted with 30 mL of $CH_2Cl_2$ and 15 mL of saturated $NaHCO_3$ solution. After stirring this mixture for 1 hour the layers were separated via a Biotage Phase Separator cartridge. The water layer was rinsed with additional $CH_2Cl_2$ and the combined organic layers were concentrated by evaporation utilizing a stream of $N_2$ gas. The resulting crude oil was purified via silica gel column chromatography eluting with 100% $CH_2Cl_2$. Evaporation of the appropriate fractions gave 144.5 mg of product, 3-(4-(3-azido-1-benzhydrylazetidin-3-yl)phenyl)-5-(3,4,5-trichlorophenyl)-5-(trifluoromethyl)-4,5-dihydroisoxazole, (63% yield) as a glassy yellow solid. ms 656 [M+H], HPLC retention time: 3.600 minutes.

Preparation 47: Chiral Separation of Enantiomers

As an example for separating a single enantiomer from a racemic mixture, racemic Example 18 was separated on a chiral column to provide Example 177 according to the following HPLC chiral resolution: Berger analytical SFC, column-Chiral IC 4.6×250 mm 5µ, mobile phase (A) was $CO_2$ and mobile phase (B) was 0.1% TEA in methanol. Linear gradient 5% B to 65% B in 12 minutes, 3 mL/minute at 100 bar. The preparatory SFC was conducted on a Berger Multigram with a IC 30×250 mm 5µ column, with mobile phase (A) $CO_2$ and mobile phase (B) methanol, isocratic 25% B, at a 100 mL/minute and 120 bar. Example 172 is a single enantiomer from racemate Example 19. Example 176 is a single enantiomer from racemate 24.

The HPLC conditions used to obtain the retention times and mass of the Examples of Tables 2, 3, and 4 were based on the following methods. Each retention time in the corresponding tables is listed with an "a", "b", "c", "d", "e", or "f". Each alphabetic symbol refers to separate HPLC conditions and methods. For Method "a", mass spectra (MS) data were obtained using Agilent mass spectrometer with atmospheric pressure chemical ionization. Method: Acquity HPLC with chromatography performed on a Waters BEH C18 column (2.1×50 mm, 1.7 µm) at 50° C. The mobile phase was a binary gradient of water (containing 0.1% trifluoroacetic acid) and acetonitrile (5-100% acetonitrile in a 5 minute run time), at 254 nm. For Method "b", HPLC with chromatography was performed on a Gemini NX-50×4.60 mm, 5µ column. The mobile phase was a binary gradient of 10 mM ammonium acetate buffer (pH=4.6) and acetonitrile (10-100% acetonitrile gradient in a 12 minute run time with a flow rate of 1 mL/minute) at 254 nm. For Method "c", HPLC with chromatography was performed on a Gemini NX-50×4.60 mm, 5µ column. The mobile phase was a binary gradient of 10 mM ammonium acetate buffer (pH=4.6) and acetonitrile (50-100% acetonitrile gradient in a 4.5 minute run time with a flow rate of 1 mL/minute) at 254 nm. For Method "d", HPLC with chromatography performed on a Waters Alliance 2795 with ZQ MS-ESI+ with a Gemini NX C18 4.6×100, 5µ column. The mobile phase was a binary gradient of water (containing 0.05% trifluoroacetic acid) and acetonitrile (50-95% acetonitrile gradient in a 12 minute run time, flow rate 1 mL/min) at 254 nm. For Method "e", HPLC with chromatography performed on a Waters Alliance 2795 with ZQ MS-ESI+ with a Gemini NX C18 4.6×150, 5µ column. The mobile phase was a binary gradient of water (containing 0.1% trifluoroacetic acid) and acetonitrile (50-95% acetonitrile gradient in a 12 minute run time, flow rate 1 mL/min) at 254 nm. For Method "f", SFC chromatography was performed on a Berger 2-EP 5 µm 4.6×250 mm column. The mobile phase was a binary gradient of $CO_2$ and 0.1% triethylamine in MeOH (5-65% 0.1% TEA in MeOH gradient in a 9 minute run time, flow rate 3 mL/min).

Using procedures similarly described herein, compounds (Examples 94-185) of Formula (2c) were prepared and are presented in Table 2.

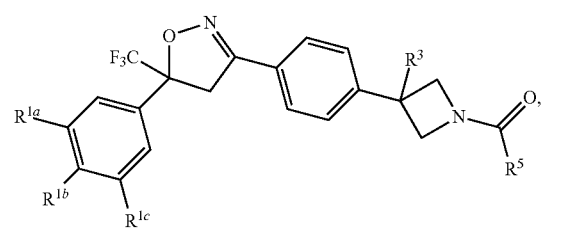

(2c)

TABLE 2

| Example No. | $R^{1a}$ | $R^{1b}$ | $R^{1c}$ | $R^3$ | $R^5$ | m/z (ESI) $[M + H]^+$ | Retention Time (minutes) |
|---|---|---|---|---|---|---|---|
| 94 | Cl | Cl | Cl | OH | isopropyl | 535 | 10.05e |
| 95 | Cl | Cl | Cl | F | $CH_2CF_3$ | 577 | 11.19e |
| 96 | Cl | Cl | Cl | F | $CH_2$-cyclopropyl | 549 | 11.35e |
| 97 | Cl | Cl | Cl | F | propyl | 537 | 9.83d |
| 98 | Cl | Cl | Cl | F | isopropyl | 537 | 9.8d |
| 99 | Cl | Cl | Cl | F | ethyl | 523 | 9.44d |
| 100 | $CF_3$ | H | Cl | F | isopropyl | 537.1 | 4.53d |
| 101 | $CF_3$ | H | Cl | F | $CH_2OH$ | 525.1 | 3.76d |
| 102 | $CF_3$ | H | Cl | F | cyclopentyl | 563.1 | 4.85d |
| 103 | $CF_3$ | Cl | Cl | F | propyl | 571.1 | 7.86d |

TABLE 2-continued

| Example No. | R1a | R1b | R1c | R3 | R5 | m/z (ESI) [M + H]+ | Retention Time (minutes) |
|---|---|---|---|---|---|---|---|
| 104 | Cl | H | Cl | H | ethyl | 471.1 | 6.2d |
| 105 | Cl | H | Cl | H | 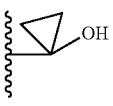 [SMILES: *C1(O)CC1] | 499.1 | 5.27d |
| 106 | Cl | H | Cl | H | CH2OCH3 | 487.1 | 5.62d |
| 107 | CF3 | Cl | Cl | H | CH2-cyclopropyl | 565.1 | 7.69d |
| 108 | CF3 | Cl | Cl | H | CH3 | 525 | 7.11d |
| 109 | CF3 | Cl | Cl | H | ethyl | 539.1 | 7.2d |
| 110 | CF3 | H | Cl | H | propyl | 519.1 | 6.96d |
| 111 | CF3 | Cl | Cl | H | propyl | 553.1 | 7.82d |
| 112 | CF3 | Cl | Cl | H | CH2OH | 541 | 5.53d |
| 113 | CF3 | Cl | Cl | H | 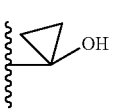 [SMILES: *C1(O)CC1] | 567.1 | 6.24d |
| 114 | CF3 | Cl | Cl | H | CH2SCH3 | 571 | 7.42d |
| 115 | CF3 | H | Cl | H | CH2-cyclopropyl | 531.1 | 6.97d |
| 116 | CF3 | H | Cl | H | CH2OCH3 | 521.1 | 5.72d |
| 117 | CF3 | Cl | Cl | H | CH2CN | 550 | 6.72d |
| 118 | CF3 | H | Cl | H | 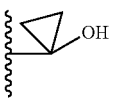 | 533.1 | 5.39d |
| 119 | CF3 | Cl | Cl | H | CH2OCH3 | 555.1 | 6.58d |
| 120 | CF3 | H | Cl | H | ethyl | 505.1 | 6.34d |
| 121 | Cl | Cl | Cl | H | propyl | 519.1 | 7.82d |
| 122 | CF3 | H | Cl | H | isopropyl | 519.1 | 6.94d |
| 123 | Cl | Cl | Cl | H | 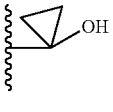 [SMILES: *C1(O)CC1] | 533 | 6.14d |
| 124 | Cl | Cl | Cl | H | ethyl | 505 | 7.17d |
| 125 | Cl | Cl | Cl | H | CH2SCH3 | 537 | 7.41d |
| 126 | Cl | Cl | Cl | H | CH2OCH3 | 521 | 6.42d |
| 127 | Cl | Cl | Cl | H | CH2-cyclopropyl | 531.1 | 7.82d |
| 128 | Cl | F | Cl | H | CH2SCH3 | 521 | 6.55d |
| 129 | Cl | F | Cl | H | CH2OCH3 | 505.1 | 5.74d |
| 130 | Cl | F | Cl | H | 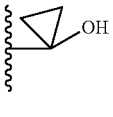 [SMILES: *C1(O)CC1] | 517.1 | 5.41d |
| 131 | Cl | F | Cl | H | ethyl | 489.1 | 6.4d |
| 132 | Cl | F | Cl | H | isopropyl | 503.1 | 7.03d |
| 133 | Cl | F | Cl | F | 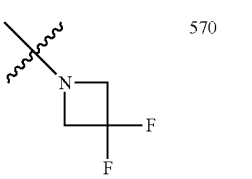 | 570 | 3.674a |
| 134 | Cl | F | Cl | OH | CH2CF3 | 559 | 3.483a |
| 135 | CF3 | Cl | Cl | F | CH2CF3 | 611 | 3.2a |
| 136 | Cl | F | Cl | F | 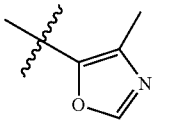 [SMILES: *c1ocnc1C] | 560 | 7.42d |

TABLE 2-continued
| Example No. | R$^{1a}$ | R$^{1b}$ | R$^{1c}$ | R$^3$ | R$^5$ | m/z (ESI) [M + H]$^+$ | Retention Time (minutes) |
|---|---|---|---|---|---|---|---|
| 137 | Cl | F | Cl | F | 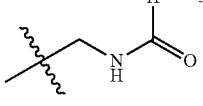 | 536 | 5.28d |
| 138 | Cl | F | Cl | F | 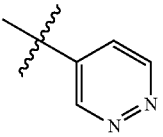 [SMILES: *c1ccnnc1] | 557 | 6.13d |
| 139 | Cl | F | Cl | F | 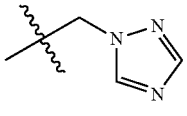 [SMILES: *Cn1cncn1] | 560.1 | 5.7d |
| 140 | Cl | F | Cl | F | CH$_2$S(O)$_2$CH$_3$ | 571 | 6.51d |
| 141 | Cl | F | Cl | F | 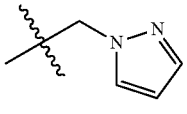 [SMILES: *Cn1cccn1] | 559.1 | 6.7d |
| 142 | Cl | F | Cl | F | 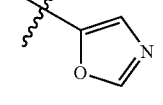 | 546 | 6.71d |
| 143 | Cl | F | Cl | F | CF$_2$CH$_3$ | 543 | 8.54d |
| 144 | CF$_3$ | Cl | Cl | F | 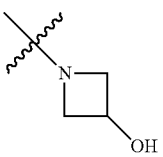 [SMILES: *N1CC(O)C1] | 600 | 3.295a |
| 145 | Cl | F | Cl | F | C(OH)(CH$_3$)$_2$ | 537.1 | 6.74d |
| 146 | Cl | F | Cl | F | CH$_2$CH=CH$_2$ | 519.1 | 7.23d |
| 147 | Cl | F | Cl | F | CH$_2$S(O)$_2$N(CH$_3$)$_2$ | 600 | 6.99d |
| 148 | Cl | F | Cl | F | CH$_2$SCF$_3$ | 592.9 | 3.54a |
| 149 | Cl | F | Cl | F | CH(OCH$_3$)CH$_3$ | 537.1 | 6.93d |
| 150 | Cl | F | Cl | F | 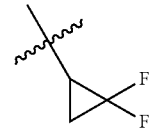 [SMILES: *C1CC1(F)F] | 555 | 7.32d |
| 151 | Cl | F | Cl | F | CH(CH$_3$)CH$_2$OH | 537.1 | 6.39d |
| 152 | Cl | F | Cl | F | 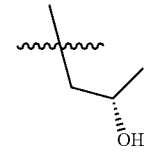 [SMILES: *C[C@H](C)O] | 537.1 | 6.43d |
| 153 | Cl | F | Cl | F | 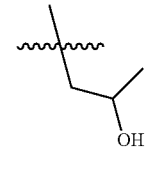 [SMILES: *CC(C)O] | 537.1 | 6.44d |

TABLE 2-continued

| Example No. | $R^{1a}$ | $R^{1b}$ | $R^{1c}$ | $R^3$ | $R^5$ | m/z (ESI) $[M + H]^+$ | Retention Time (minutes) |
|---|---|---|---|---|---|---|---|
| 154 | Cl | F | Cl | Cl | cyclopropyl | nd | Nd-a |
| 155 | $CF_3$ | Cl | Cl | Cl | cyclopropyl | nd | Nd-a |
| 156 | Cl | H | H | F | cyclopropyl | 466.90 | 5.88b |
| 157 | Cl | F | F | OH | cyclopropyl | 498.80 [M − H] | 5.58b |
| 158 | $CF_3$ | F | F | F | cyclopropyl | 534.60 [M − H] | 6.16b |
| 159 | Cl | F | Cl | F | 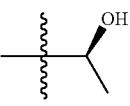 [SMILES: *[C@H](C)O] | 523 | 3.419a |
| 160 | Cl | F | Cl | F | 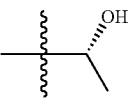 | 523 | 3.406a |
| 161 | Cl | F | Cl | F | 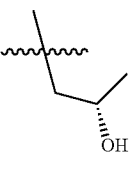 [SMILES: *C[C@H](C)O] | 537 | 3.414a |
| 162 | Cl | F | Cl | F | $CH_2S(O)CH_3$ | 555 | 3.317a |
| 163 | Cl | Cl | Cl | $N_3$ | cyclopropyl | 558 | 3.176a |
| 164 | Cl | Cl | Cl | $N_3$ | ethyl | 546 | 3.271a |
| 165 | Cl | F | Cl | F | $CH_2SC(O)CH_3$ | 567 | 3.604a |
| 166 | F | H | H | F | ethyl | 436.90 [M − H] | 2.38c |
| 167 | Cl | H | H | F | ethyl | 455.20 | 2.60c |
| 168 | Cl | Cl | H | F | ethyl | 486.70 [M − H] | 6.11b |
| 169 | $CF_3$ | H | H | F | cyclopropyl | 498.90 [M − H] | 5.90b |
| 170 | Cl | H | F | F | cyclopropyl | 482.90 [M − H] | 5.45b |
| 171 | F | F | H | F | cyclopropyl | 467.00 [M − H] | 2.55c |
| 172^ | Cl | F | Cl | F | $CH_2CF_3$ | nd | nd-a |
| 173 | Cl | H | Cl | F | 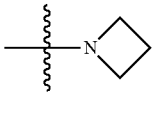 [SMILES: *N1CCC1] | 516 | 3.562a |
| 174 | Cl | Cl | Cl | F | 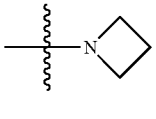 [SMILES: *N1CCC1] | 552 | 3.667a |
| 175 | Cl | F | Cl | F | 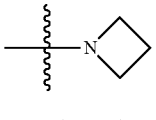 | 534.0 | 3.58a |
| 176^ | $CF_3$ | Cl | Cl | OH | cyclopropyl | nd | nd-a |
| 177^ | Cl | F | Cl | F | isopropyl | nd | nd-a |
| 178 | Cl | F | Cl | F | $CH_2S(O)_2CH_2CN$ | 596 | 3.55d |
| 179 | Cl | F | Cl | F | $CH_2CH_2S(O)_2CH_3$ | 585 | 3.43d |
| 180 | Cl | F | Cl | F | $CH_2S(O)_2CH_2CF_3$ | 639 | 3.66d |
| 181 | Cl | F | Cl | F | $CH_2S(O)_2N(CH_3)_2$ | 600 | 3.55d |
| 182 | Cl | F | Cl | F | $CH_2S(O)_2Phenyl$ | 633 | 3.65d |
| 183 | Cl | F | Cl | F | $CHCH_3S(O)_2CH_3$ | 585 | 3.51d |
| 184 | $CF_3$ | Cl | Cl | NHC(O)-cyclopropyl | cyclopropyl | 634 | 6.315f |
| 185 | $CF_3$ | Cl | Cl | $NH_2$ | cyclopropyl | 567 | 6.23f |

⁀⁀⁀ is the point of attachment.
^ represents single enantiomer resolved on chiral column,
nd = not determined
HPLC methods a, b, c, d, and e are as defined herein.

The following names for Examples (94-185) of Table 2 include: 1-isobutyryl-3-{4-[5-(3,4,5-trichlorophenyl)-5-(trifluoromethyl)-4,5-dihydroisoxazol-3-yl]phenyl}azetidin-3-ol (94); 3-{4-[3-fluoro-1-(3,3,3-trifluoropropanoyl)azetidin-3-yl]phenyl}-5-(3,4,5-trichlorophenyl)-5-(trifluoromethyl)-4,5-dihydroisoxazole (95); 3-{4-[1-(cyclopropylacetyl)-3-fluoroazetidin-3-yl]phenyl}-5-(3,4,5-trichlorophenyl)-5-(trifluoromethyl)-4,5-dihydroisoxazole (96); 3-[4-(1-butyryl-3-fluoroazetidin-3-yl)phenyl]-5-(3,4,5-trichlorophenyl)-5-(trifluoromethyl)-4,5-dihydroisoxazole (97); 3-[4-(3-fluoro-1-isobutyrylazetidin-3-yl)phenyl]-5-(3,4,5-trichlorophenyl)-5-(trifluoromethyl)-4,5-dihydroisoxazole (98); 3-[4-(3-fluoro-1-propionylazetidin-3-yl)phenyl]-5-(3,4,5-trichlorophenyl)-5-(trifluoromethyl)-4,5-dihydroisoxazole (99); 5-[3-chloro-5-(trifluoromethyl)phenyl]-3-[4-(3-fluoro-1-isobutyrylazetidin-3-yl)phenyl]-5-(trifluoromethyl)-4,5-dihydroisoxazole (100); 2-[3-(4-{5-[3-chloro-5-(trifluoromethyl)phenyl]-5-(trifluoromethyl)-4,5-dihydroisoxazol-3-yl}phenyl)-3-fluoroazetidin-1-yl]-2-oxoethanol (101); 5-[3-chloro-5-(trifluoromethyl)phenyl]-3-{4-[1-(cyclopentylcarbonyl)-3-fluoroazetidin-3-yl]phenyl}-5-(trifluoromethyl)-4,5-dihydroisoxazole (102); 3-[4-(1-butyryl-3-fluoroazetidin-3-yl)phenyl]-5-[3,4-dichloro-5-(trifluoromethyl)phenyl]-5-(trifluoromethyl)-4,5-dihydroisoxazole (103); 5-(3,5-dichlorophenyl)-3-[4-(1-propionylazetidin-3-yl)phenyl]-5-(trifluoromethyl)-4,5-dihydroisoxazole (104); 1-[(3-{4-[5-(3,5-dichlorophenyl)-5-(trifluoromethyl)-4,5-dihydroisoxazol-3-yl]phenyl}azetidin-1-yl)carbonyl]cyclopropanol (105); 5-(3,5-dichlorophenyl)-3-{4-[1-(methoxyacetyl)azetidin-3-yl]phenyl}-5-(trifluoromethyl)-4,5-dihydroisoxazole (106); 3-{4-[1-(cyclopropylacetyl)azetidin-3-yl]phenyl}-5-[3,4-dichloro-5-(trifluoromethyl)phenyl]-5-(trifluoromethyl)-4,5-dihydroisoxazole (107); 3-[4-(1-acetylazetidin-3-yl)phenyl]-5-[3,4-dichloro-5-(trifluoromethyl)phenyl]-5-(trifluoromethyl)-4,5-dihydroisoxazole (108); 5-[3,4-dichloro-5-(trifluoromethyl)phenyl]-3-[4-(1-propionylazetidin-3-yl)phenyl]-5-(trifluoromethyl)-4,5-dihydroisoxazole (109); 3-[4-(1-butyrylazetidin-3-yl)phenyl]-5-[3-chloro-5-(trifluoromethyl)phenyl]-5-(trifluoromethyl)-4,5-dihydroisoxazole (110); 3-[4-(1-butyrylazetidin-3-yl)phenyl]-5-[3,4-dichloro-5-(trifluoromethyl)phenyl]-5-(trifluoromethyl)-4,5-dihydroisoxazole (111); 2-[3-(4-{5-[3,4-dichloro-5-(trifluoromethyl)phenyl]-5-(trifluoromethyl)-4,5-dihydroisoxazol-3-yl}phenyl)azetidin-1-yl]-2-oxoethanol (112); 1-{[3-(4-{5-[3,4-dichloro-5-(trifluoromethyl)phenyl]-5-(trifluoromethyl)-4,5-dihydroisoxazol-3-yl}phenyl)azetidin-1-yl]carbonyl}cyclopropanol (113); 5-[3,4-dichloro-5-(trifluoromethyl)phenyl]-3-(4-{1-[(methylthio)acetyl]azetidin-3-yl}phenyl)-5-(trifluoromethyl)-4,5-dihydroisoxazole (114); 5-[3-chloro-5-(trifluoromethyl)phenyl]-3-{4-[1-(cyclopropylacetyl)azetidin-3-yl]phenyl}-5-(trifluoromethyl)-4,5-dihydroisoxazole (115); 5-[3-chloro-5-(trifluoromethyl)phenyl]-3-{4-[1-(methoxyacetyl)azetidin-3-yl]phenyl}-5-(trifluoromethyl)-4,5-dihydroisoxazole (116); 3-[3-(4-{5-[3,4-dichloro-5-(trifluoromethyl)phenyl]-5-(trifluoromethyl)-4,5-dihydroisoxazol-3-yl}phenyl)azetidin-1-yl]-3-oxopropanenitrile (117); 1-{[3-(4-{5-[3-chloro-5-(trifluoromethyl)phenyl]-5-(trifluoromethyl)-4,5-dihydroisoxazol-3-yl}phenyl)azetidin-1-yl]carbonyl}cyclopropanol (118); 5-[3,4-dichloro-5-(trifluoromethyl)phenyl]-3-{4-[1-(methoxyacetyl)azetidin-3-yl]phenyl}-5-(trifluoromethyl)-4,5-dihydroisoxazole (119); 5-[3-chloro-5-(trifluoromethyl)phenyl]-3-[4-(1-propionylazetidin-3-yl)phenyl]-5-(trifluoromethyl)-4,5-dihydroisoxazole (120); 3-[4-(1-butyrylazetidin-3-yl)phenyl]-5-(3,4,5-trichlorophenyl)-5-(trifluoromethyl)-4,5-dihydroisoxazole (121); 5-[3-chloro-5-(trifluoromethyl)phenyl]-3-[4-(1-isobutyrylazetidin-3-yl)phenyl]-5-(trifluoromethyl)-4,5-dihydroisoxazole (122); 1-[(3-{4-[5-(3,4,5-trichlorophenyl)-5-(trifluoromethyl)-4,5-dihydroisoxazol-3-yl]phenyl}azetidin-1-yl)carbonyl]cyclopropanol (123); 3-[4-(1-propionylazetidin-3-yl)phenyl]-5-(3,4,5-trichlorophenyl)-5-(trifluoromethyl)-4,5-dihydroisoxazole (124); 3-(4-{1-[(methylthio)acetyl]azetidin-3-yl}phenyl)-5-(3,4,5-trichlorophenyl)-5-(trifluoromethyl)-4,5-dihydroisoxazole (125); 3-{4-[1-(methoxyacetyl)azetidin-3-yl]phenyl}-5-(3,4,5-trichlorophenyl)-5-(trifluoromethyl)-4,5-dihydroisoxazole (126); 3-{4-[1-(cyclopropylacetyl)azetidin-3-yl]phenyl}-5-(3,4,5-trichlorophenyl)-5-(trifluoromethyl)-4,5-dihydroisoxazole (127); 5-(3,5-dichloro-4-fluorophenyl)-3-(4-{1-[(methylthio)acetyl]azetidin-3-yl}phenyl)-5-(trifluoromethyl)-4,5-dihydroisoxazole 128); 5-(3,5-dichloro-4-fluorophenyl)-3-{4-[1-(methoxyacetyl)azetidin-3-yl]phenyl}-5-(trifluoromethyl)-4,5-dihydroisoxazole (129); 1-[(3-{4-[5-(3,5-dichloro-4-fluorophenyl)-5-(trifluoromethyl)-4,5-dihydroisoxazol-3-yl]phenyl}azetidin-1-yl)carbonyl]cyclopropanol (130); 5-(3,5-dichloro-4-fluorophenyl)-3-[4-(1-propionylazetidin-3-yl)phenyl]-5-(trifluoromethyl)-4,5-dihydroisoxazole (131); 5-(3,5-dichloro-4-fluorophenyl)-3-[4-(1-isobutyrylazetidin-3-yl)phenyl]-5-(trifluoromethyl)-4,5-dihydroisoxazole (132); 5-(3,5-dichloro-4-fluorophenyl)-3-(4-{1-[(3,3-difluoroazetidin-1-yl)carbonyl]-3-fluoroazetidin-3-yl}phenyl)-5-(trifluoromethyl)-4,5-dihydroisoxazole (133); 3-{4-[5-(3,5-dichloro-4-fluorophenyl)-5-(trifluoromethyl)-4,5-dihydroisoxazol-3-yl]phenyl}-1-(3,3,3-trifluoropropanoyl)azetidin-3-ol (134); 5-[3,4-dichloro-5-(trifluoromethyl)phenyl]-3-{-4-[3-fluoro-1-(3,3,3-trifluoropropanoyl)azetidin-3-yl]phenyl}-5-(trifluoromethyl)-4,5-dihydroisoxazole (135); 5-(3,5-dichloro-4-fluorophenyl)-3-(4-{3-fluoro-1-[(4-methyl-1,3-oxazol-5-yl)carbonyl]azetidin-3-yl}phenyl)-5-(trifluoromethyl)-4,5-dihydroisoxazole (136); N-[2-(3-{4-[5-(3,5-dichloro-4-fluorophenyl)-5-(trifluoromethyl)-4,5-dihydroisoxazol-3-yl]phenyl}-3-fluoroazetidin-1-yl)-2-oxoethyl]formamide (137); 4-[(3-{4-[5-(3,5-dichloro-4-fluorophenyl)-5-(trifluoromethyl)-4,5-dihydroisoxazol-3-yl]phenyl}-3-fluoroazetidin-1-yl)carbonyl]pyridazine (138); 1-[2-(3-{4-[5-(3,5-dichloro-4-fluorophenyl)-5-(trifluoromethyl)-4,5-dihydroisoxazol-3-yl]phenyl}-3-fluoroazetidin-1-yl)-2-oxoethyl]-1H-1,2,4-triazole (139); 5-(3,5-dichloro-4-fluorophenyl)-3-(4-{3-fluoro-1-[(methylsulfonyl)acetyl]azetidin-3-yl}phenyl)-5-(trifluoromethyl)-4,5-dihydroisoxazole (140); 5-(3,5-dichloro-4-fluorophenyl)-3-{-4-[3-fluoro-1-(1H-pyrazol-1-ylacetyl)azetidin-3-yl]phenyl}-5-(trifluoromethyl)-4,5-dihydroisoxazole (141); 5-(3,5-dichloro-4-fluorophenyl)-3-{-4-[3-fluoro-1-(1,3-oxazol-5-ylcarbonyl)azetidin-3-yl]phenyl}-5-(trifluoromethyl)-4,5-dihydroisoxazole (142); 5-(3,5-dichloro-4-fluorophenyl)-3-{4-[1-(2,2-difluoropropanoyl)-3-fluoroazetidin-3-yl]phenyl}-5-(trifluoromethyl)-4,5-dihydroisoxazole (143); 1-{[3-(4-{5-[3,4-dichloro-5-(trifluoromethyl)phenyl]-5-(trifluoromethyl)-4,5-dihydroisoxazol-3-yl}phenyl)-3-fluoroazetidin-1-yl]carbonyl}azetidin-3-ol (144); 1-(3-{4-[5-(3,5-dichloro-4-fluorophenyl)-5-(trifluoromethyl)-4,5-dihydroisoxazol-3-yl]phenyl}-3-fluoroazetidin-1-yl)-2-methyl-1-oxopropan-2-ol (145); 3-[4-(1-but-3-enoyl-3-fluoroazetidin-3-yl)phenyl]-5-(3,5-dichloro-4-fluorophenyl)-5-(trifluoromethyl)-4,5-dihydroisoxazole (146); 2-(3-{4-[5-(3,5-dichloro-4- fluorophenyl)-5-(trifluoromethyl)-4,5-dihydroisoxazol-3-yl]phenyl}-3-fluoroazetidin-1-yl)-N,N-dimethyl-2-oxoethanesulfonamide (147); 5-(3,5-dichloro-4-fluorophenyl)-3-[4-(3-fluoro-1-{[(trifluoromethyl)thio]acetyl}azetidin-3-yl)phenyl-5-(trifluoromethyl)-4,5-dihydroisoxazole (148); 5-(3,5-dichloro-4-fluorophenyl)-3-{-4-[3-fluoro-1-(2-methoxypropanoyl)azetidin-3-yl]phenyl}-5-(trifluoromethyl)-4,5-dihydroisoxazole (149); 5-(3,5-dichloro-4-fluorophenyl)-3-(4-{1-[(2,2-difluorocyclopropyl)carbonyl]-3-fluoroazetidin-3-yl}phenyl)-5-(trifluoromethyl)-4,5-dihydroisoxazole (150); 3-(3-{4-[5-(3,5-dichloro-4-fluorophenyl)-5-(trifluoromethyl)-4,5-dihydroisoxazol-3-yl]phenyl}-3-fluoroazetidin-1-yl)-2-methyl-3-oxopropan-1-ol (151); (2S)-4-(3-{-4-[5-(3,5-dichloro-4-fluorophenyl)-5-(trifluoromethyl)-4,5-dihydroisoxazol-3-yl]phenyl}-3-fluoroazetidin-1-yl)-4-oxobutan-2-ol (152); 4-(3-{4-[5-(3,5-dichloro-4-fluorophenyl)-5-(trifluoromethyl)-4,5-dihydroisoxazol-3-yl]phenyl}-3-fluoroazetidin-1-yl)-4-oxobutan-2-ol (153); 3-{-4-[3-chloro-1-(cyclopropylcarbonyl)azetidin-3-yl]phenyl}-5-(3,5-dichloro-4-fluorophenyl)-5-(trifluoromethyl)-4,5-dihydroisoxazole (154); 3-{4-[3-chloro-1-(cyclopropylcarbonyl)azetidin-3-yl]phenyl}-5-[3,4-dichloro-5-(trifluoromethyl)phenyl]-5-(trifluoromethyl)-4,5-dihydroisoxazole (155); 5-(3-chlorophenyl)-3-{4-[1-(cyclopropylcarbonyl)-3-fluoroazetidin-3-yl]phenyl}-5-(trifluoromethyl)-4,5-dihydroisoxazole (156); 3-{4-[5-(3-chloro-4,5-difluorophenyl)-5-(trifluoromethyl)-4,5-dihydroisoxazol-3-yl]phenyl}-1-(cyclopropylcarbonyl)-azetidin-3-ol (157); 3-{4-[1-(cyclopropylcarbonyl)-3-fluoroazetidin-3-yl]phenyl}-5-[3,4-difluoro-5-(trifluoromethyl)phenyl]-5-(trifluoromethyl)-4,5-dihydroisoxazole (158); (2S)-1-(3-{4-[5-(3,5-dichloro-4-fluorophenyl)-5-(trifluoromethyl)-4,5-dihydroisoxazol-3-yl]phenyl}-3-fluoroazetidin-1-yl)-1-oxopropan-2-ol (159); (2R)-1-(3-{4-[5-(3,5-dichloro-4-fluorophenyl)-5-(trifluoromethyl)-4,5-dihydroisoxazol-3-yl]phenyl}-3-fluoroazetidin-1-yl)-1-oxopropan-2-ol (160); (2S)-4-(3-{4-[5-(3,5-dichloro-4-fluorophenyl)-5-(trifluoromethyl)-4,5-dihydroisoxazol-3-yl]phenyl}-3-fluoroazetidin-1-yl)-4-oxobutan-2-ol (161); 5-(3,5-dichloro-4-fluorophenyl)-3-(4-{3-fluoro-1-[(methylsulfinyl)acetyl]azetidin-3-yl}phenyl)-5-(trifluoromethyl)-4,5-dihydroisoxazole (162); 3-{-4-[3-azido-1-(cyclopropylcarbonyl)azetidin-3-yl]phenyl}-5-(3,4,5-trichlorophenyl)-5-(trifluoromethyl)-4,5-dihydroisoxazole (163); 3-[4-(3-azido-1-propionylazetidin-3-yl)phenyl]-5-(3,4,5-trichlorophenyl)-5-(trifluoromethyl)-4,5-dihydroisoxazole (164); S-[2-(3-{4-[5-(3,5-dichloro-4-fluorophenyl)-5-(trifluoromethyl)-4,5-dihydroisoxazol-3-yl]phenyl}-3-fluoroazetidin-1-yl)-2-oxoethyl]ethanethioate (165); 5-(3-fluorophenyl)-3-[4-(3-fluoro-1-propionylazetidin-3-yl)phenyl]-5-(trifluoromethyl)-4,5-dihydroisoxazole (166); 5-(3-chlorophenyl)-3-[4-(3-fluoro-1-propionylazetidin-3-yl)phenyl]-5-(trifluoromethyl)-4,5-dihydroisoxazole (167); 5-(3,4-dichlorophenyl)-3-[4-(3-fluoro-1-propionylazetidin-3-yl)phenyl]-5-(trifluoromethyl)-4,5-dihydroisoxazole (168); 3-{4-[1-(cyclopropylcarbonyl)-3-fluoroazetidin-3-yl]phenyl}-5-(trifluoromethyl)-5-[3-(trifluoromethyl)phenyl]-4,5-dihydroisoxazole (169); 5-(3-chloro-5-fluorophenyl)-3-{4-[1-(cyclopropylcarbonyl)-3-fluoroazetidin-3-yl]phenyl}-5-(trifluoromethyl)-4,5-dihydroisoxazole (170); 3-{4-[1-(cyclopropylcarbonyl)-3-fluoroazetidin-3-yl]phenyl}-5-(3,4-difluorophenyl)-5-(trifluoromethyl)-4,5-dihydroisoxazole (171); 1-(3-(4-(5-(3,5-dichloro-4-fluorophenyl)-5-(trifluoromethyl)-4,5-dihydroisoxazol-3-yl)phenyl)-3-fluoroazetidin-1-yl)-3,3,3-trifluoropropan-1-one (172); 3-{4[1-(azetidin-1-ylcarbonyl)-3-fluoroazetidin-3-yl]phenyl}-5-(3,5-dichlorophenyl)-5-(trifluoromethyl)-4,5-dihydroisoxazole (173); 3-{4-[1-(azetidin-1-ylcarbonyl)-3-fluoroazetidin-3-yl]phenyl}-5-(3,4,5-trichlorophenyl)-5-(trifluoromethyl)-4,5-dihydroisoxazole (174); 3-{4-[1-(azetidin-1-ylcarbonyl)-3-fluoroazetidin-3-yl]phenyl}-5-(3,5-dichloro-4-fluorophenyl)-5-(trifluoromethyl)-4,5-dihydroisoxazole (175); 1-(cyclopropylcarbonyl)-3-{4-[(5R)-5-[3,4-dichloro-5-(trifluoromethyl)phenyl]-5-(trifluoromethyl)-4,5-dihydroisoxazol-3-yl]phenyl}azetidin-3-ol (176); 5-(3,5-dichloro-4-fluorophenyl)-3-[4-(3-fluoro-1-isobutyrylazetidin-3-yl)phenyl]-5-(trifluoromethyl)-4,5-dihydroisoxazole (177); {[2-(3-{4-[5-(3,5-dichloro-4-fluorophenyl)-5-(trifluoromethyl)-4,5-dihydroisoxazol-3-yl]phenyl}-3-fluoroazetidin-1-yl)-2-oxoethyl]sulfonyl}acetonitrile (178), 1-(3-{4-[5-(3,5-Dichloro-4-fluoro-phenyl)-5-trifluoromethyl-4,5-dihydro-isoxazol-3-yl]-phenyl}-3-fluoro-azetidin-1-yl)-3-methanesulfonyl-propan-1-one (179), 1-(3-{4-[5-(3,5-Dichloro-4-fluoro-phenyl)-5-trifluoromethyl-4,5-dihydro-isoxazol-3-yl]-phenyl}-3-fluoro-azetidin-1-yl)-2-(2,2,2-trifluoro-ethanesulfonyl)-ethanone (180), 2-(3-{4-[5-(3,5-Dichloro-4-fluoro-phenyl)-205-trifluoromethyl-4,5-dihydro-isoxazol-3-yl]-phenyl}-3-fluoro-azetidin-1-yl)-2-oxo-ethanesulfonic acid dimethylamide (181), 2-Benzenesulfonyl-1-(3-{4-[5-(3,5-dichloro-4-fluoro-phenyl)-5-trifluoromethyl-4,5-dihydro-isoxazol-3-yl]-phenyl}-3-fluoro-azetidin-1-yl)-ethanone (182), 1-(3-{4-[5-(3,5-Dichloro-4-fluoro-phenyl)-5-trifluoromethyl-4,5-dihydro-isoxazol-3-yl]-phenyl}-3-fluoro-azetidin-1-yl)-2-methanesulfonyl-propan-1-one (183), cyclopropanecarboxylic acid (1-cyclopropanecarbonyl-3-{4-[5-(3,4-dichloro-5-trifluoromethyl-phenyl)-5-trifluoromethyl-4,5-dihydro-isoxazol-3-yl]-phenyl}-azetidin-3-yl)-amide (184), and (3-Amino-3-{4-[5-(3,4-dichloro-5-trifluoromethyl-phenyl)-5-trifluoromethyl-4,5-dihydro-isoxazol-3-yl]-phenyl}-azetidin-1-yl)-cyclopropyl-methanone (185).

Using procedures similarly described herein, compounds (Examples 186-205) of Formula (2d) were prepared and are presented in Table 3.

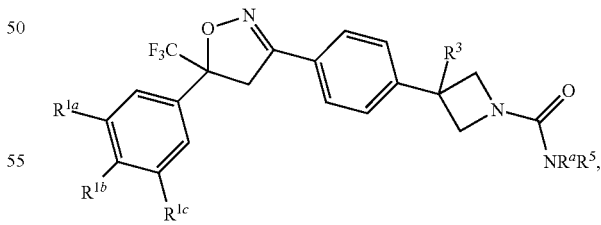

(2d)

TABLE 3

| Example No. | $R^{1a}$ | $R^{1b}$ | $R^{1c}$ | $R^a$ | $R^3$ | $R^5$ | m/z (ESI) [M + H]+ | Retention Time (minutes) |
|---|---|---|---|---|---|---|---|---|
| 186 | Cl | Cl | Cl | H | F | H | nd | nd a |
| 187 | Cl | Cl | Cl | H | H | cyclopropyl | 532 | 6.68d |
| 188 | Cl | H | Cl | H | H | cyclopropyl | 498.1 | 5.8d |

TABLE 3-continued

| Example No. | $R^{1a}$ | $R^{1b}$ | $R^{1c}$ | $R^a$ | $R^3$ | $R^5$ | m/z (ESI) [M + H]+ | Retention Time (minutes) |
|---|---|---|---|---|---|---|---|---|
| 189 | $CF_3$ | Cl | Cl | H | OH | propyl | nd | nd a |
| 190 | $CF_3$ | Cl | Cl | methyl | OH | methyl | 570 | 3.0a |
| 191 | Cl | Cl | Cl | H | H | ethyl | 520 | 6.69d |
| 192 | Cl | F | Cl | H | H | methyl | 490.1 | 5.32d |
| 193 | CF3 | Cl | Cl | H | H | methyl | 540.1 | 6.14d |
| 194 | Cl | H | Cl | H | H | ethyl | 486.1 | 5.8d |
| 195 | Cl | F | Cl | H | H | ethyl | 504.1 | 5.94d |
| 196 | $CF_3$ | H | Cl | H | H | methyl | 506.1 | 5.32d |
| 197 | $CF_3$ | H | Cl | H | H | cyclopropyl | 532.1 | 5.91d |
| 198 | Cl | F | Cl | H | H | cyclopropyl | 516.1 | 5.94d |
| 199 | $CF_3$ | Cl | Cl | H | H | cyclopropyl | 566.1 | 6.74d |
| 200 | $CF_3$ | Cl | Cl | H | F | $CH_2CF_3$ | 626 | 3.461a |
| 201 | Cl | Cl | Cl | methyl | F | methyl | 538 | 3.278a |
| 202 | $CF_3$ | Cl | Cl | methyl | F | methyl | 572 | 3.422a |
| 203 | $CF_3$ | Cl | Cl | H | F | $CH_2CH_2CF_3$ | 640 | 3.238a |
| 204 | $CF_3$ | Cl | Cl | H | F | ![oxetanyl] | 600 | 3.305a |
| 205 | Cl | Cl | Cl | methyl | $N_3$ | methyl | 561 | 3.724a |

∿∿∿ is the point of attachment
nd = not determined
HPLC methods a, b, c, d, and e are as defined herein The following IUPAC names for Examples (186-205) of Table 3 include: 3-fluoro-3-{4-[5-(3,4,5-trichlorophenyl)-5-(trifluoromethyl)-4,5-dihydroisoxazol-3-yl]phenyl}azetidine-1-carboxamide (186); N-cyclopropyl-3-{4-[5-(3,4,5-trichlorophenyl)-5-(trifluoromethyl)-4,5-dihydroisoxazol-3-yl]phenyl}azetidine-1-carboxamide (187); N-cyclopropyl-3-{4-[5-(3,5-dichlorophenyl)-5-(trifluoromethyl)-4,5-dihydroisoxazol-3-yl]phenyl}azetidine-1-carboxamide (188); 3-(4-{5-[3,4-dichloro-5-(trifluoromethyl)phenyl]-5-(trifluoromethyl)-4,5-dihydroisoxazol-3-yl}phenyl)-3-hydroxy-N-propylazetidine-1-carboxamide (189); 3-(4-{5-[3,4-dichloro-5-(trifluoromethyl)phenyl]-5-(trifluoromethyl)-4,5-dihydroisoxazol-3-yl}phenyl)-3-hydroxy-N,N-dimethylazetidine-1-carboxamide (190); N-ethyl-3-{-4-[5-(3,4,5-trichlorophenyl)-5-(trifluoromethyl)-4,5-dihydroisoxazol-3-yl]phenyl}azetidine-1-carboxamide (191); 3-{4-[5-(3,5-dichloro-4-fluorophenyl)-5-(trifluoromethyl)-4,5-dihydroisoxazol-3-yl]phenyl}-N-methylazetidine-1-carboxamide (192); 3-(4-{5-[3,4-dichloro-5-(trifluoromethyl)phenyl]-5-(trifluoromethyl)-4,5-dihydroisoxazol-3-yl}phenyl)-N-methylazetidine-1-carboxamide (193); 3-{4-[5-(3,5-dichlorophenyl)-5-(trifluoromethyl)-4,5-dihydroisoxazol-3-yl]phenyl}-N-ethylazetidine-1-carboxamide (194); 3-{4-[5-(3,5-dichloro-4-fluorophenyl)-5-(trifluoromethyl)-4,5-dihydroisoxazol-3-yl]phenyl}-N-ethylazetidine-1-carboxamide (195); 3-(4-{5-[3-chloro-5-(trifluoromethyl)phenyl]-5-(trifluoromethyl)-4,5-dihydroisoxazol-3-yl}phenyl)-N-methylazetidine-1-carboxamide (196); 3-(4-{5-[3-chloro-5-(trifluoromethyl)phenyl]-5-(trifluoromethyl)-4,5-dihydroisoxazol-3-yl}phenyl)-N-cyclopropylazetidine-1-carboxamide (197); N-cyclopropyl-3-{4-[5-(3,5-dichloro-4-fluorophenyl)-5-(trifluoromethyl)-4,5-dihydroisoxazol-3-yl]phenyl}azetidine-1-carboxamide (198); N-cyclopropyl-3-(4-{5-[3,4-dichloro-5-(trifluoromethyl)phenyl]-5-(trifluoromethyl)-4,5-dihydroisoxazol-3-yl}phenyl)azetidine-1-carboxamide (199); 3-(4-{5-[3,4-dichloro-5-(trifluoromethyl)phenyl]-5-(trifluoromethyl)-4,5-dihydroisoxazol-3-yl}phenyl)-3-fluoro-N-(2,2,2-trifluoroethyl)azetidine-1-carboxamide (200); 3-fluoro-N,N-dimethyl-3-{4-[5-(3,4,5-trichlorophenyl)-5-(trifluoromethyl)-4,5-dihydroisoxazol-3-yl]phenyl}azetidine-1-carboxamide (201); 3-(4-{5-[3,4-dichloro-5-(trifluoromethyl)phenyl]-5-(trifluoromethyl)-4,5-dihydroisoxazol-3-yl}phenyl)-3-fluoro-N,N-dimethylazetidine-1-carboxamide (202); 3-(4-{5-[3,4-dichloro-5-(trifluoromethyl)phenyl]-5-(trifluoromethyl)-4,5-dihydroisoxazol-3-yl}phenyl)-3-fluoro-N-(3,3,3-trifluoropropyl)azetidine-1-carboxamide (203); 3-(4-{5-[3,4-dichloro-5-(trifluoromethyl)phenyl]-5-(trifluoromethyl)-4,5-dihydroisoxazol-3-yl}phenyl)-3-fluoro-N-oxetan-3-ylazetidine-1-carboxamide (204); and 3-azido-N,N-dimethyl-3-{4-[5-(3,4,5-trichlorophenyl)-5-(trifluoromethyl)-4,5-dihydroisoxazol-3-yl]phenyl}azetidine-1-carboxamide (205).

Using procedures similarly described herein, compounds (Examples 206-218) of Formula (2e) were prepared and are presented in Table 4.

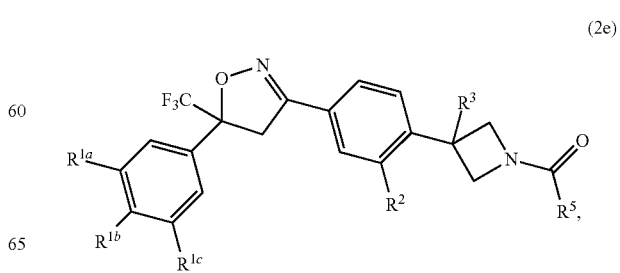

(2e)

TABLE 4

| Example No. | $R^{1a}$ | $R^{1b}$ | $R^{1c}$ | $R^2$ | $R^3$ | $R^5$ | m/z (ESI) [M + H]+ | Retention Time (minutes) |
|---|---|---|---|---|---|---|---|---|
| 206 | Cl | F | Cl | CN | F | cyclopropyl | 544 | 3.573a |
| 207 | Cl | F | Cl | CN | F | methyl | 518 | 3.046a |
| 208 | Cl | F | Cl | CN | F | $CH_2CF_3$ | 586 | 3.206a |
| 209 | Cl | F | Cl | CN | F | ethyl | 532 | 3.534a |
| 210 | Cl | F | Cl | CN | F | isopropyl | 546 | 3.657a |
| 211 | Cl | F | Cl | CN | F | $CH_2OH$ | 534 | 6.19d |
| 212 | Cl | F | Cl | CN | F | propyl | 546.1 | 7.17d |
| 213 | Cl | F | Cl | CN | F | cyclobutyl | 558.1 | 7.3d |
| 214 | Cl | F | Cl | CN | F | cyclopentyl | 572.1 | 7.54d |
| 215 | Cl | F | Cl | CN | F | $CH_2OCH_3$ | 548 | 6.74d |
| 216 | Cl | F | Cl | CN | F | $CH_2$-cyclopropyl | 558.1 | 7.15d |
| 217 | Cl | F | Cl | CN | F | n-butyl | 560.1 | 7.44d |
| 218 | Cl | F | Cl | CN | F | $CH_2SCH_3$ | 564 | 7.02d |

HPLC methods a, b, c, d, and e are as defined herein

The following IUPAC names for Examples (206-218) of Table 4 include: 2-[1-(cyclopropylcarbonyl)-3-fluoroazetidin-3-yl]-5-[5-(3,5-dichloro-4-fluorophenyl)-5-(trifluoromethyl)-4,5-dihydroisoxazol-3-yl]benzonitrile (206); 2-(1-acetyl-3-fluoroazetidin-3-yl)-5-[5-(3,5-dichloro-4-fluorophenyl)-5-(trifluoromethyl)-4,5-dihydroisoxazol-3-yl]benzonitrile (207); 5-[5-(3,5-dichloro-4-fluorophenyl)-5-(trifluoromethyl)-4,5-dihydroisoxazol-3-yl]-2-[3-fluoro-1-(3,3,3-trifluoropropanoyl)azetidin-3-yl]benzonitrile (208); 5-[5-(3,5-dichloro-4-fluorophenyl)-5-(trifluoromethyl)-4,5-dihydroisoxazol-3-yl]-2-(3-fluoro-1-propionylazetidin-3-yl)benzonitrile (209); 5-[5-(3,5-dichloro-4-fluorophenyl)-5-(trifluoromethyl)-4,5-dihydroisoxazol-3-yl]-2-(3-fluoro-1-isobutyrylazetidin-3-yl)benzonitrile (210); 5-[5-(3,5-dichloro-4-fluorophenyl)-5-(trifluoromethyl)-4,5-dihydroisoxazol-3-yl]-2-(3-fluoro-1-glycoloylazetidin-3-yl)benzonitrile (211); 2-(1-butyryl-3-fluoroazetidin-3-yl)-5-[5-(3,5-dichloro-4-fluorophenyl)-5-(trifluoromethyl)-4,5-dihydroisoxazol-3-yl]benzonitrile (212); 2-[1-(cyclobutylcarbonyl)-3-fluoroazetidin-3-yl]-5-[5-(3,5-dichloro-4-fluorophenyl)-5-(trifluoromethyl)-4,5-dihydroisoxazol-3-yl]benzonitrile (213); 2-[1-(cyclopentylcarbonyl)-3-fluoroazetidin-3-yl]-5-[5-(3,5-dichloro-4-fluorophenyl)-5-(trifluoromethyl)-4,5-dihydroisoxazol-3-yl]benzonitrile (214); 5-[5-(3,5-dichloro-4-fluorophenyl)-5-(trifluoromethyl)-4,5-dihydroisoxazol-3-yl]-2-[3-fluoro-1-(methoxyacetyl)azetidin-3-yl]benzonitrile (215); 2-[1-(cyclopropylacetyl)-3-fluoroazetidin-3-yl]-5-[5-(3,5-dichloro-4-fluorophenyl)-5-(trifluoromethyl)-4,5-dihydroisoxazol-3-yl]benzonitrile (216); 5-[5-(3,5-dichloro-4-fluorophenyl)-5-(trifluoromethyl)-4,5-dihydroisoxazol-3-yl]-2-(3-fluoro-1-pentanoylazetidin-3-yl)benzonitrile (217); and 5-[5-(3,5-dichloro-4-fluorophenyl)-5-(trifluoromethyl)-4,5-dihydroisoxazol-3-yl]-2-{3-fluoro-1-[(methylthio)acetyl]-azetidin-3-yl}benzonitrile (218).

Example 219

2-[1-(cyclopropylcarbonyl)-3-fluoroazetidin-3-yl]-5-[5-(3,4,5-trichlorophenyl)-5-(trifluoromethyl)-4,5-dihydroisoxazol-3-yl]pyridine

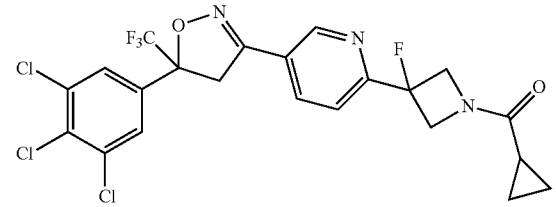 [SMILES: O=C(C1CC1)N1CC(F)(c2ccc(C3=NOC(c4cc(Cl)c(Cl)c(Cl)c4)(C(F)(F)F)C3)cn2)C1]

Using procedures described above, 2-[1-(cyclopropylcarbonyl)-3-fluoroazetidin-3-yl]-5-[5-(3,4,5-trichlorophenyl)-5-(trifluoromethyl)-4,5-dihydroisoxazol-3-yl]pyridine was prepared from 6-bromonicotinaldehyde and tert-butyl 3-oxoazetidine-1-carboxylate. ms 533.80[M−H], HPLC retention time 6.41 minutes. HPLC method "b". $^1$H NMR (400 MHz, CDCl$_3$) d 0.79-0.86 (m, 2H), 1.03-1.05 (m, 2H), 1.44-1.47 (m, 1H), 3.70 (d, J=16.88 Hz, 1H), 4.10 (d, J=17.28 Hz, 1H), 4.34-4.52 (m, 2H), 4.61 (dd, J=9.48, 22.36 Hz, 1H), 4.84 (dd, J=9.56, 20.32 Hz, 1H), 7.63 (s, 2H), 7.65 (s, 1H), 8.07-8.11 (m, 1H), 8.85 (s, 1H).

Example 220

(3-(4-(5-(3,5-dichloro-4-fluorophenyl)-5-(trifluoromethyl)-4,5-dihydroisoxazol-3-yl)phenyl)-3-fluoroazetidin-1-yl)(1-oxidothietan-3-yl)methanone

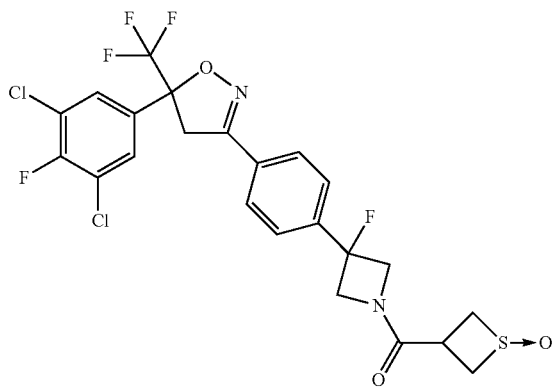 [SMILES: O=C(C1CS(=O)C1)N1CC(F)(c2ccc(C3=NOC(c4cc(Cl)c(F)c(Cl)c4)(C(F)(F)F)C3)cc2)C1]

The compound was prepared from the compound of Preparation 16 according to the method of Example 12 using thietane-3-carboxylic acid 1-oxide in place of butyric acid. Yield 133 mg (70%). $^1$H NMR (CDCl$_3$) δ 7.69 (d, 2H), 7.58 (d, 2H), 7.47 (m, 2H), 4.67-4.32 (m, 4H), 4.09 (d, 1H), 3.91-3.64 (m, 4H), 3.60-3.33 (m, 2H). LC/MS retention time=3.355 minutes, MS calculated for ($C_{23}H_{17}Cl_2F_5N_2O_3S$), 566.03; found 567.0 M+H+.

Example 221

(3-(4-(5-(3,5-dichloro-4-fluorophenyl)-5-(trifluoromethyl)-4,5-dihydroisoxazol-3-yl)phenyl)-3-fluoroazetidin-1-yl)(1,1-dioxidothietan-3-yl)methanone

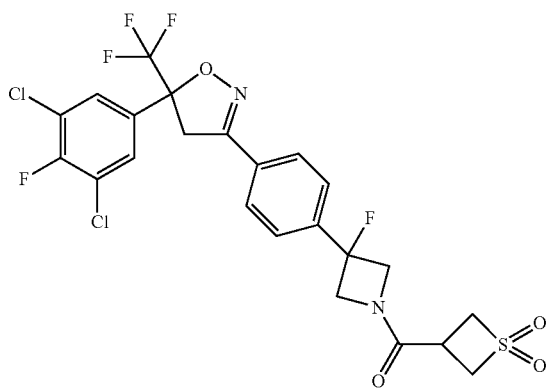 [SMILES: O=C(C1CS(=O)(=O)C1)N1CC(F)(c2ccc(C3=NOC(c4cc(Cl)c(F)c(Cl)c4)(C(F)(F)F)C3)cc2)C1]

A solution of (3-(4-(5-(3,5-dichloro-4-fluorophenyl)-5-(trifluoromethyl)-4,5-dihydroisoxazol-3-yl)phenyl)-3-fluoroazetidin-1-yl)(1-oxidothietan-3-yl)methanone (30 mg) in methanol (2 mL) was added to a solution of oxone (160 mg) in water (1 mL) cooled with an ice bath. Reaction allowed to warm slowly to ambient then stirred at ambient temperature for 16 hours. Majority of methanol removed under reduced pressure then remaining aqueous extracted with DCM (2×5 mL). Organic phase collected and condensed. The crude material was adsorbed on silica and chromatographed on a 4 g silica column, eluting with a gradient of 0% to 100% ethyl acetate in heptane. Fractions containing the desired material were combined and concentrated. Placing the flask on high vacuum overnight resulted in formation of a white foam. Yield 15.7 mg (51%). $^1$H NMR (DMSO-D6) δ 7.82 (m, 4H), 7.69 (m, 2H), 4.67 (d, 2H), 4.46-4.29 (m, 8H), 3.56-3.43 (m, 1H). LC/MS retention time=3.455 minutes, MS calculated for ($C_{23}H_{17}Cl_2F_5N_2O_4S$), 582.02; nd M+H+.

Example 222

1-(3-(4-(5-(3,5-dichloro-4-fluorophenyl)-5-(trifluoromethyl)-4,5-dihydroisoxazol-3-yl)phenyl)-3-fluoroazetidin-1-yl)-2-methylpropane-1-thione

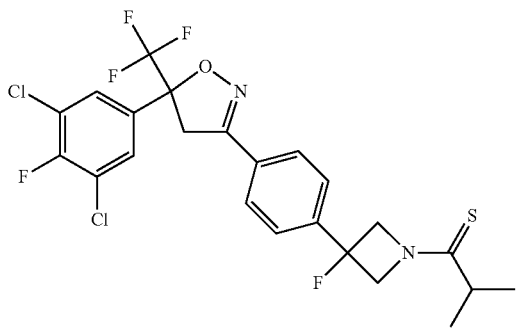 [SMILES: CC(C)C(=S)N1CC(F)(c2ccc(C3=NOC(c4cc(Cl)c(F)c(Cl)c4)(C(F)(F)F)C3)cc2)C1]

1-(3-(4-(5-(3,5-dichloro-4-fluorophenyl)-5-(trifluoromethyl)-4,5-dihydroisoxazol-3-yl)phenyl)-3-fluoroazetidin-1-yl)-2-methylpropan-1-one (500 mg, 1.9 mmol) was dissolved in toluene (35 mL). Lawesson's reagent (790 mg, 1.9 mmol) was added and the reaction mixture was heated to reflux for 2 hours, then cooled to room temperature and allowed to stir overnight. The reaction mixture was filtered and the filtrate was concentrated under vacuum. The crude residue from the filtrate was chromatographed (40 g Redi-Sep column) eluting from 100% heptane to 25:75 EtOAc:heptane to afford the product (415 mg, 80%) as a solid. $^1$HNMR (CDCl$_3$): 7.77 (2H), 7.61 (2H), 7.54 (2H), 4.68 (4H), 4.12 (1H), 3.72 (1H), 2.88 (1H), 1.28 (6H); m/z (Cl) 537 ([M+H]+.

Example 223

(1-(3-(4-(5-(3,5-dichloro-4-fluorophenyl)-5-(trifluoromethyl)-4,5-dihydroisoxazol-3-yl)phenyl)-3-fluoroazetidin-1-yl)-2-methylpropylidene)cyanamide

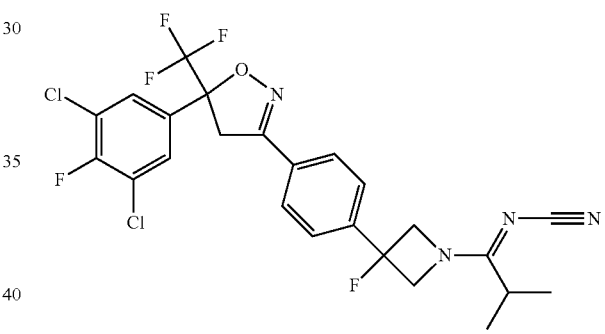

1-(3-(4-(5-(3,5-dichloro-4-fluorophenyl)-5-(trifluoromethyl)-4,5-dihydroisoxazol-3-yl)phenyl)-3-fluoroazetidin-1-yl)-2-methylpropane-1-thione (325 mg, 0.6 mmol) was dissolved in CH$_2$Cl$_2$ (15 mL) at 0° C. and methyl triflate (130 μL, 1.2 mmol) was added. The reaction was allowed to warm to room temperature and stirred for 3 hours. Next, the solution was cooled to 0° C. and a solution of cyanimide (54 mg, 1.2 mmol) and Hunig's base (220 μL, 1.2 mmol) in THF was added dropwise. The reaction was allowed to warm to room temperature and stirred for 1 hour. Water was added to the solution and the reaction was extracted with CH$_2$Cl$_2$. The organic phase was dried (Na$_2$SO$_4$) and concentrated under vacuum. The crude material was chromatographed (24 g Redi-Sep column) eluting from 100% heptane to 50:50 EtOAc:heptane to afford the product (104 mg, 31%) as a solid. $^1$HNMR (CDCl$_3$): 7.79 (2H), 7.61 (2H), 7.54 (2H), 4.68 (4H), 4.12 (1H), 3.72 (1H), 3.44 (1H), 1.38 (6H); m/z (Cl) 545 ([M+H]+.

Examples 224 and 225 were prepared according to the methods and schemes as described herein.

Example 224

(1-(3-Fluoro-3-{4-[5-(3,4,5-trichloro-phenyl)-5-trifluoromethyl-4,5-dihydro-isoxazol-3-yl]-phenyl}-azetidin-1-yl)-2-methanesulfonyl-ethanone

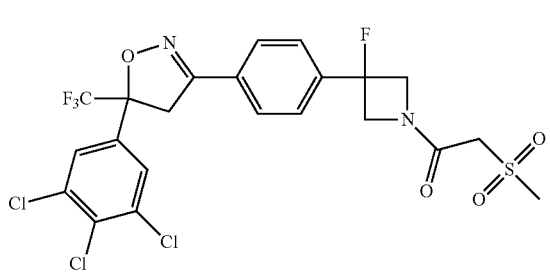 [SMILES: CS(=O)(=O)CC(=O)N1CC(F)(c2ccc(C3=NOC(c4cc(Cl)c(Cl)c(Cl)c4)(C(F)(F)F)C3)cc2)C1]

Example 225

1-(3-{4-[5-(3,4-Dichloro-5-trifluoromethyl-phenyl)-5-trifluoromethyl-4,5-dihydro-isoxazol-3-yl]-phenyl}-3-fluoro-azetidin-1-yl)-2-methanesulfonyl-ethanone

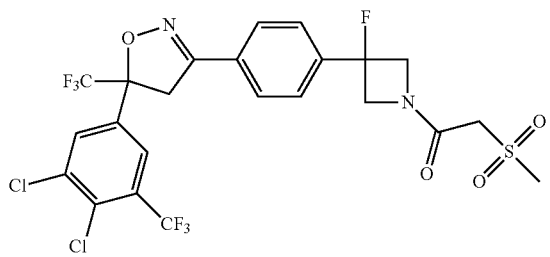 [SMILES: CS(=O)(=O)CC(=O)N1CC(F)(c2ccc(C3=NOC(c4cc(Cl)c(Cl)c(C(F)(F)F)c4)(C(F)(F)F)C3)cc2)C1]

NMR data for select compounds as described herein are presented in Table 5.

TABLE 5

NMR data for select compounds

| Compound No. | Solvent | $^1$H NMR (δ ppm) |
|---|---|---|
| 54 | CDCl$_3$ | 7.76 (d, 2 H), 7.61-7.52 (d, 4 H), 7.46 (t, 1 H), 5.17-4.18 (m, 4 H), 4.12 (d, 1 H), 3.73 (d, 1 H), 2.46 (s, 1 H), 1.43 (q, 2 H), 1.08 (q, 2 H) |
| 55 | CDCl$_3$ | 7.75 (d, 2 H), 7.61 (d, 2 H), 7.57 (m, 2 H), 5.15-4.20 (m, 4 H), 4.12 (d, 1 H), 3.72 (d, 1 H), 2.95 (s, 1 H), 1.41 (q, 2 H), 1.07 (q, 2 H) |
| 57 | CDCl$_3$ | 7.97 (d, 1 H), 7.87 (d, 1 H), 7.72 (m, 2 H), 7.61 (m, 2 H), 4.49-4.12 (m, 5 H), 3.84-3.69 (m, 2 H), 2.52 (m, 1 H), 1.15 (d, 6 H) |
| 58 | CDCl$_3$ | 7.97 (d, 1 H), 7.86 (d, 1 H), 7.72 (m, 2 H), 7.61 (m, 2 H), 4.46-4.12 (m, 5 H), 4.01 (d, 1 H), 3.74 (m, 1 H), 2.16 (t, 2 H), 1.68 (m, 2 H) 0.98 (t, 3 H) |
| 68 | DMSO-d$_6$ | 7.82 (d, 2 H), 7.74 (d, 2 H), 7.64 (d, 2 H), 6.53 (s, 1 H), 4.40-4.22 (m, 4 H), 4.03 (m, 2 H), 2.15 (q, 2 H), 1.00 (t, 2 H) |
| 133 | CDCl$_3$ | 7.75 (d, 2 H), 7.61 (d, 2 H), 7.55 (d, 2 H), 4.48 (m, 2 H), 4.38-4.24 (m, 6 H), 4.11 (d, 1 H), 3.72 (d, 1 H) |
| 134 | CDCl$_3$ | 7.72 (d, 2 H), 7.66-7.53 (m, 4 H), 4.56-4.28 (m, 4 H), 4.12 (d, 1 H), 3.90 (s, 1 H), 3.72 (d, 1 H), 3.07 (m, 2 H) |
| 135 | CDCl$_3$ | 7.97 (m, 1 H), 7.86 (m, 1 H), 7.78 (d, 2 H), 7.55 (d, 2 H), 4.78-4.66 (m, 1 H), 4.63-4.39 (m, 3 H), 4.17 (d, 1 H), 3.74 (d, 1 H), 3.11 (m, 2 H) |
| 137 | CDCl$_3$ | 8.29 (d, 1 H), 7.77 (d, 2 H), 7.61 (d, 2 H), 7.55 (d, 2 H), 6.58 (br s, 1 H), 4.73-4.39 (m, 4 H), 4.18-3.93 (m, 3 H), 3.72 (d, 1 H) |
| 140 | CDCl$_3$ | 7.77 (d, 2 H), 7.60 (m, 4H), 4.81 (d, 2 H), 4.57 (m, 1 H), 4.44 (m, 1 H), 4.11 (d, 1 H), 3.90 (s, 2 H), 3.72 (d, 1 H), 3.20 (s, 3 H) |
| 141 | CDCl$_3$ | 7.73 (d, 2 H), 7.64-7.57 (m, 4H), 7.50 (d, 2 H), 6.39 (m, 1 H), 4.96 (m, 2 H), 4.59-4.48 (m, 1 H), 4.46-4.33 (m, 2 H), 4.28-4.17 (m, 1 H), 4.14-4.07 (m, 1 H), 3.71 (d, 1 H) |
| 144 | CDCl$_3$ | 7.96 (m, 1 H), 7.85 (m, 1 H), 7.75 (d, 2 H), 7.58 (d, 2 H), 4.72-7.61 (m, 1 H), 4.49-4.38 (m, 2 H), 4.29-4.19 (m, 4 H), 4.15 (d, 1 H), 3.92-3.87 (m, 2 H), 3.72 (d, 1 H), 2.57 (m, 1 H) |
| 145 | CDCl$_3$ | 7.76 (d, 2 H), 7.61 (d, 2 H), 7.55 (d, 2 H), 4.95-4.33 (m, 4 H), 4.12 (d, 1 H), 3.72 (d, 1 H), 2.99 (s, 1 H), 1.50 (s, 6 H) |
| 153 | CDCl$_3$ | 7.76 (d, 2 H), 7.61 (d, 2 H), 7.55 (d, 2 H), 4.71-4.35 (m, 4 H), 4.34-4.23 (m, 1 H), 4.12 (d, 1 H), 3.72 (d, 2 H), 2.41-2.21 (m, 2 H), 1.28 (d, 3 H) |
| 165 | DMSO-d$_6$ | 7.85-7.79 (m, 4 H), 7.69 (d, 2 H), 4.82-4.69 (m, 2 H), 4.44-4.30 (m, 4 H), 3.70 (d, 2 H), 2.38 (s, 3 H) |
| 178 | CDCl$_3$ | 7.8 (2H), 7.5-7.7 (4H), 4.2-4.9 (6H), 4.0-4.2 (3H), 3.7 (1H) |
| 179 | CDCl$_3$ | 7.8 (2H), 7.6-7.7 (4H), 4.3-4.8 (4H), 4.0-4.2 (1H), 3.7-3.8 (1H), 3.3-3.6 (2H), 3.05 (3H), 2.7-2.9 (2H) |
| 180 | | 7.8 (2H), 7.5-7.7 (4H), 4.65-4.9 (2H), 4.3-4.65 (2H), (3.9-4.3 (5H), 3.6-3.8 (1H) |
| 181 | DMSO-d$_6$ | 7.8-7.9 (4H), 7.7 (2H), 4.7-4.9 (2H), 4.3-4.5 (4H), 4.15 (2H), 2.85 (6H) |
| 182 | CDCl$_3$ | 8.0 (2H), 7.7-7.8 (3H), 7.5-7.7 (6H), 4.7-4.9 (2H), 4.3-4.6 (2H), 3.9-4.2 (3H), 3.7-3.8 (1H) |
| 183 | CDCl$_3$ | 7.8 (2H), 7.5-7.7 (4H), 4.9-5.2 (1H), 4.3-4.8 (3H), 4.0-4.2 (1H), 3.6-3.9 (2H), 3.0 (3H), 1.7 (3H). |
| 187 | CDCl$_3$ | 7.69-7.64 (m, 4 H), 7.41 (d, 2 H), 4.43-4.34 (m, 3 H), 4.11 (d, 1 H), 3.98 (m, 2 H), 3.86-3.77 (m, 1 H), 3.70 (d, 1 H), 2.68-2.61 (m, 1 H), 0.76 (m, 2 H) 0.54 (m, 2 H) |

TABLE 5-continued

NMR data for select compounds

| Compound No. | Solvent | ¹H NMR (δ ppm) |
|---|---|---|
| 188 | CDCl₃ | 7.67 (m, 2 H), 7.54 (d, 2 H), 7.45 (t, 1 H), 7.41 (d, 2 H), 4.44-4.35 (m, 3 H), 4.10 (d, 1 H), 3.97 (m, 2 H), 3.85-3.76 (m, 1 H), 3.71 (d, 1 H), 2.68-2.60 (m, 1 H), 0.76 (m, 2 H) 0.54 (m, 2 H). |
| 190 | CDCl₃ | 7.98 (d, 1 H), 7.87 (d, 1 H), 7.70 (m, 4 H), 4.27 (m, 4 H), 4.17 (d, 1 H), 3.73 (d, 1 H), 3.62 (s, 1 H), 2.92 (s, 6 H) |
| 200 | CDCl₃ | 7.97 (s, 1 H), 7.86 (s, 1 H), 7.76 (d, 2 H), 7.56 (d, 2 H), 4.85 (m, 1 H), 4.60-4.43 (m, 2 H), 4.40-4.25 (m, 2 H), 4.18 (d, 1 H), 3.92 (m, 2 H), 3.75 (d, 1 H) |
| 201 | CDCl₃ | 7.72 (d, 2 H), 7.66 (s, 2 H), 7.57 (d, 2 H), 4.51-4.41 (m, 2 H), 4.31-4.21 (m, 2 H), 4.10 (d, 1 H), 3.70 (d, 1 H), 2.92 (s, 6 H) |
| 202 | CDCl₃ | 7.96 (m, 1 H), 7.85 (m, 1 H), 7.73 (d, 2 H), 7.58 (d, 2 H), 4.51-4.41 (m, 2 H), 4.31-4.21 (m, 2 H), 4.15 (d, 1 H), 3.72 (d, 1 H), 2.92 (s, 6 H) |
| 203 | CDCl₃ | 7.96 (m, 1 H), 7.85 (m, 1 H), 7.74 (d, 2 H), 7.56 (d, 2 H), 4.52-4.40 (m, 3 H), 4.29-4.20 (m, 2 H), 4.16 (d, 1 H), 3.72 (d, 1 H), 3.54 (m, 2 H), 2.46-2.33 (m, 2 H) |
| 204 | CDCl₃ | 7.96 (m, 1 H), 7.85 (m, 1 H), 7.75 (d, 2 H), 7.56 (d, 2 H), 5.05-4.92 (m, 3 H), 4.85 (d, 1 H), 4.54-4.47 (m, 3 H), 4.44 (d, 1 H), 4.32-4.22 (m, 2 H), 4.16 (d, 1 H), 3.73 (d, 1 H) |
| 213 | CDCl₃ | 8.07 (s, 1 H), 7.99 (m, 1H), 7.68 (m, 1H), 7.60 (d, 2 H), 4.74-4.47 (m, 4 H), 4.11 (d, 1 H),), 3.73 (d, 1 H). 3.14 (m, 1 H), 2.45-2.29 (m, 2 H), 2.27-1.86 (m, 4 H) |
| 216 | CDCl₃ | 8.06 (s, 1 H), 7.98 (m, 1 H), 7.68 (m, 1 H), 7.58 (d, 2 H), 4.80-4.48 (m, 4 H), 4.10 (d, 1 H), 3.72 (d, 1 H), 2.15 (d, 2 H), 1.12-1.02 (m, 1 H), 0.59 (m, 2 H), 0.18 (m, 2 H) |
| 224 | CDCl₃ | 7.77 (d, 2 H), 7.67 (s, 2 H), 7.59 (d, 2 H), 4.81 (d, 2 H), 4.63-4.38 (m, 2 H), 4.11 (d, 1 H), 3.90 (s, 2 H), 3.72 (d, 1 H), 3.20 (s, 3 H) |
| 225 | CDCl₃ | .97 (m, 1 H), 7.86 (m, 1 H), 7.77 (d, 2 H), 7.59 (d, 2 H), 4.81 (d, 2 H), 4.64-4.39 (m, 2 H), 4.17 (d, 1 H), 3.90 (s, 2 H), 3.73 (d, 1 H), 3.20 (s, 3 H) |

In addition to the previous 225 Examples, the following compounds can be prepared according to the aforementioned Schemes and preparations and are herein encompassed by the instant invention. These compounds of Formula (1) include: 2,2-dichloro-1-(3-(4-(5-(3,5-dichloro-4-fluorophenyl)-5-(trifluoromethyl)-4,5-dihydroisoxazol-3-yl)phenyl)-3-fluoroazetidin-1-yl)ethanone; 1-(3-(4-(5-(3,5-dichloro-4-fluorophenyl)-5-(trifluoromethyl)-4,5-dihydroisoxazol-3-yl)phenyl)-3-fluoroazetidin-1-yl)-2-fluoro-2-methylpropan-1-one; 1-(3-(4-(5-(3,5-dichloro-4-fluorophenyl)-5-(trifluoromethyl)-4,5-dihydroisoxazol-3-yl)phenyl)-3-fluoroazetidin-1-yl)-3-(methylthio)propan-1-one; 1-(3-(4-(5-(3,5-dichloro-4-fluorophenyl)-5-(trifluoromethyl)-4,5-dihydroisoxazol-3-yl)phenyl)-3-fluoroazetidin-1-yl)-3-(methylsulfonyl)propan-1-one; (3-(4-(5-(3,5-dichloro-4-fluorophenyl)-5-(trifluoromethyl)-4,5-dihydroisoxazol-3-yl)phenyl)-3-fluoroazetidin-1-yl)(thietan-3-yl)methanone; 1-(3-(4-(5-(3,5-dichloro-4-fluorophenyl)-5-(trifluoromethyl)-4,5-dihydroisoxazol-3-yl)phenyl)-3-fluoroazetidin-1-yl)-3,3,3-trifluoro-2-methylpropan-1-one; 1-(3-(4-(5-(3,5-dichloro-4-fluorophenyl)-5-(trifluoromethyl)-4,5-dihydroisoxazol-3-yl)phenyl)-3-fluoroazetidin-1-yl)-2-methyl-2-(methylsulfonyl)propan-1-one; 1-(3-(4-(5-(3,5-dichloro-4-fluorophenyl)-5-(trifluoromethyl)-4,5-dihydroisoxazol-3-yl)phenyl)-3-fluoroazetidin-1-yl)-2-(methylsulfonyl)propan-1-one; (3-(4-(5-(3,5-dichloro-4-fluorophenyl)-5-(trifluoromethyl)-4,5-dihydroisoxazol-3-yl)phenyl)-3-fluoroazetidin-1-yl)(1-(methylsulfonyl)cyclopropyl)methanone; 5-(3,5-dichloro-4-fluorophenyl)-3-(4-(3-fluoro-1-(1,1,1,3,3,3-hexafluoropropan-2-yl)azetidin-3-yl)phenyl)-5-(trifluoromethyl)-4,5-dihydroisoxazole; 1-(3-(4-(5-(3,5-dichloro-4-fluorophenyl)-5-(trifluoromethyl)-4,5-dihydroisoxazol-3-yl)phenyl)-3-fluoroazetidin-1-yl)-3,3-difluoropropan-1-one; 2-(3-(4-(5-(3,5-dichloro-4-fluorophenyl)-5-(trifluoromethyl)-4,5-dihydroisoxazol-3-yl)phenyl)-3-fluoroazetidin-1-yl)-N-methyl-2-oxoethanesulfonamide; 2-(3-(4-(5-(3,5-dichloro-4-fluorophenyl)-5-(trifluoromethyl)-4,5-dihydroisoxazol-3-yl)phenyl)-3-fluoroazetidin-1-yl)-N-isopropyl-2-oxoethanesulfonamide; 1-(3-(4-(5-(3,5-dichloro-4-fluorophenyl)-5-(trifluoromethyl)-4,5-dihydroisoxazol-3-yl)phenyl)-3-fluoroazetidin-1-yl)-2-(3-hydroxyazetidin-1-yl)ethanone; 1-(3-(4-(5-(3,5-dichloro-4-hydroxyphenyl)-5-(trifluoromethyl)-4,5-dihydroisoxazol-3-yl)phenyl)-3-fluoroazetidin-1-yl)-2-methylpropan-1-one;
(3-(4-(5-(3,5-dichloro-4-fluorophenyl)-5-(trifluoromethyl)-4,5-dihydroisoxazol-3-yl)phenyl)-3-fluoroazetidin-1-yl)(thietan-2-yl)methanone;
N-(1-(3-(4-(5-(3,5-dichloro-4-fluorophenyl)-5-(trifluoromethyl)-4,5-dihydroisoxazol-3-yl)phenyl)-3-fluoroazetidin-1-yl)-2-methyl-1-oxopropan-2-yl)acetamide;
1-(3-(4-(5-(3,5-dichloro-4-fluorophenyl)-5-(trifluoromethyl)-4,5-dihydroisoxazol-3-yl)phenyl)-3-fluoroazetidin-1-yl)-2-mercapto-2-methylpropan-1-one;
1-(3-(4-(5-(3,5-dichloro-4-fluorophenyl)-5-(trifluoromethyl)-4,5-dihydroisoxazol-3-yl)phenyl)-3-fluoroazetidin-1-yl)-3,3,3-trifluoro-2-hydroxy-2-methylpropan-1-one;
1-(3-(4-(5-(3,5-dichloro-4-fluorophenyl)-5-(trifluoromethyl)-4,5-dihydroisoxazol-3-yl)phenyl)-3-fluoroazetidin-1-yl)-3-hydroxy-2,2-dimethylpropan-1-one;
3-(3-(4-(5-(3,5-dichloro-4-fluorophenyl)-5-(trifluoromethyl)-4,5-dihydroisoxazol-3-yl)phenyl)-3-fluoroazetidin-1-yl)-2,2-dimethyl-3-oxopropanenitrile;
1-(3-(4-(5-(3,5-dichloro-4-fluorophenyl)-5-(trifluoromethyl)-4,5-dihydroisoxazol-3-yl)phenyl)-3-fluoroazetidin-1-yl)-3,3-difluoropropan-1-one;

S-(1-(3-(4-(5-(3,5-dichloro-4-fluorophenyl)-5-(trifluoromethyl)-4,5-dihydroisoxazol-3-yl)phenyl)-3-fluoroazetidin-1-yl)-2-methyl-1-oxopropan-2-yl)ethanethioate;
1-(3-(4-(5-(3,5-dichloro-4-fluorophenyl)-5-(trifluoromethyl)-4,5-dihydroisoxazol-3-yl)phenyl)-3-fluoroazetidin-1-yl)-2-methyl-2-(methylthio)propan-1-one;
1-(3-(4-(5-(3,5-dichloro-4-fluorophenyl)-5-(trifluoromethyl)-4,5-dihydroisoxazol-3-yl)phenyl)-3-fluoroazetidin-1-yl)-2-methyl-2-(methylsulfonyl)propan-1-one;
1-(3-(4-(5-(3,5-dichloro-4-fluorophenyl)-5-(trifluoromethyl)-4,5-dihydroisoxazol-3-yl)phenyl)-3-fluoroazetidin-1-yl)-2-methyl-1-oxopropane-2-sulfonamide;
1-(1-(3-(4-(5-(3,5-dichloro-4-fluorophenyl)-5-(trifluoromethyl)-4,5-dihydroisoxazol-3-yl)phenyl)-3-fluoroazetidin-1-yl)-2-methyl-1-oxopropan-2-yl)urea;
1-(3-(4-(5-(3,5-dichloro-4-fluorophenyl)-5-(trifluoromethyl)-4,5-dihydroisoxazol-3-yl)phenyl)-3-fluoroazetidin-1-yl)-2-(methylsulfinyl)ethanone;
1-(3-(4-(5-(3,5-dichloro-4-fluorophenyl)-5-(trifluoromethyl)-4,5-dihydroisoxazol-3-yl)phenyl)-3-fluoroazetidin-1-yl)-2-(methylsulfonyl)ethanone;
1-(3-(4-(5-(3,5-dichloro-4-fluorophenyl)-5-(trifluoromethyl)-4,5-dihydroisoxazol-3-yl)phenyl)-3-fluoroazetidin-1-yl)-2-(1H-pyrazol-1-yl)ethanone;
1-(3-(4-(5-(3,5-dichloro-4-fluorophenyl)-5-(trifluoromethyl)-4,5-dihydroisoxazol-3-yl)phenyl)-3-fluoroazetidin-1-yl)-2-hydroxy-2-methylpropan-1-one;
(3-{4-[5-(3,5-Dichloro-4-fluoro-phenyl)-5-trifluoromethyl-4,5-dihydro-isoxazol-3-yl]-phenyl}-3-fluoro-azetidin-1-yl)-thietan-3-yl-methanone
(E)-N-(1-(3-(4-(5-(3,5-dichloro-4-fluorophenyl)-5-(trifluoromethyl)-4,5-dihydroisoxazol-3-yl)phenyl)-3-fluoroazetidin-1-yl)-2-methylpropylidene)cyanamide;
1-(3-fluoro-3-(4-(5-(3,4,5-trichlorophenyl)-5-(trifluoromethyl)-4,5-dihydroisoxazol-3-yl)phenyl)azetidin-1-yl)-2-methylpropan-1-one;
3,3,3-trifluoro-1-(3-fluoro-3-(4-(5-(3,4,5-trichlorophenyl)-5-(trifluoromethyl)-4,5-dihydroisoxazol-3-yl)phenyl)azetidin-1-yl)propan-1-one;
1-(3-fluoro-3-(4-(5-(3,4,5-trichlorophenyl)-5-(trifluoromethyl)-4,5-dihydroisoxazol-3-yl)phenyl)azetidin-1-yl)-2-(methylthio)ethanone;
1-(3-fluoro-3-(4-(5-(3,4,5-trichlorophenyl)-5-(trifluoromethyl)-4,5-dihydroisoxazol-3-yl)phenyl)azetidin-1-yl)-2-(methylsulfinyl)ethanone;
1-(3-fluoro-3-(4-(5-(3,4,5-trichlorophenyl)-5-(trifluoromethyl)-4,5-dihydroisoxazol-3-yl)phenyl)azetidin-1-yl)-2-(methylsulfonyl)ethanone;
1-(3-fluoro-3-(4-(5-(3,4,5-trichlorophenyl)-5-(trifluoromethyl)-4,5-dihydroisoxazol-3-yl)phenyl)azetidin-1-yl)-2-(1H-pyrazol-1-yl)ethanone;
1-(3-fluoro-3-(4-(5-(3,4,5-trichlorophenyl)-5-(trifluoromethyl)-4,5-dihydroisoxazol-3-yl)phenyl)azetidin-1-yl)-2-hydroxy-2-methylpropan-1-one; (3-Fluoro-3-{4-[5-(3,4,5-trichloro-phenyl)-5-trifluoromethyl-4,5-dihydro-isoxazol-3-yl]-phenyl}-azetidin-1-yl)-thietan-3-yl-methanone;
(3-fluoro-3-(4-(5-(3,4,5-trichlorophenyl)-5-(trifluoromethyl)-4,5-dihydroisoxazol-3-yl)phenyl)azetidin-1-yl)(1-oxidothietan-3-yl)methanone;
(1,1-dioxidothietan-3-yl)(3-fluoro-3-(4-(5-(3,4,5-trichlorophenyl)-5-(trifluoromethyl)-4,5-dihydroisoxazol-3-yl)phenyl)azetidin-1-yl)methanone;
(E)-N-(1-(3-fluoro-3-(4-(5-(3,4,5-trichlorophenyl)-5-(trifluoromethyl)-4,5-dihydroisoxazol-3-yl)phenyl)azetidin-1-yl)-2-methylpropylidene)cyanamide;
1-(3-(4-(5-(3,4-dichloro-5-(trifluoromethyl)phenyl)-5-(trifluoromethyl)-4,5-dihydroisoxazol-3-yl)phenyl)-3-fluoroazetidin-1-yl)-2-methylpropan-1-one;
cyclopropyl(3-(4-(5-(3,4-dichloro-5-(trifluoromethyl)phenyl)-5-(trifluoromethyl)-4,5-dihydroisoxazol-3-yl)phenyl)-3-fluoroazetidin-1-yl)methanone;
1-(3-(4-(5-(3,4-dichloro-5-(trifluoromethyl)phenyl)-5-(trifluoromethyl)-4,5-dihydroisoxazol-3-yl)phenyl)-3-fluoroazetidin-1-yl)-3,3,3-trifluoropropan-1-one;
1-(3-(4-(5-(3,4-dichloro-5-(trifluoromethyl)phenyl)-5-(trifluoromethyl)-4,5-dihydroisoxazol-3-yl)phenyl)-3-fluoroazetidin-1-yl)-2-(methylthio)ethanone;
1-(3-(4-(5-(3,4-dichloro-5-(trifluoromethyl)phenyl)-5-(trifluoromethyl)-4,5-dihydroisoxazol-3-yl)phenyl)-3-fluoroazetidin-1-yl)-2-(methylsulfinyl)ethanone;
1-(3-(4-(5-(3,4-dichloro-5-(trifluoromethyl)phenyl)-5-(trifluoromethyl)-4,5-dihydroisoxazol-3-yl)phenyl)-3-fluoroazetidin-1-yl)-2-(methylsulfonyl)ethanone;
1-(3-(4-(5-(3,4-dichloro-5-(trifluoromethyl)phenyl)-5-(trifluoromethyl)-4,5-dihydroisoxazol-3-yl)phenyl)-3-fluoroazetidin-1-yl)-2-(1H-pyrazol-1-yl)ethanone;
1-(3-(4-(5-(3,4-dichloro-5-(trifluoromethyl)phenyl)-5-(trifluoromethyl)-4,5-dihydroisoxazol-3-yl)phenyl)-3-fluoroazetidin-1-yl)-2-hydroxy-2-methylpropan-1-one;
(3-{4-[5-(3,4-Dichloro-5-trifluoromethyl-phenyl)-5-trifluoromethyl-4,5-dihydro-isoxazol-3-yl]-phenyl}-3-fluoroazetidin-1-yl)-thietan-3-yl-methanone;
(3-(4-(5-(3,4-dichloro-5-(trifluoromethyl)phenyl)-5-(trifluoromethyl)-4,5-dihydroisoxazol-3-yl)phenyl)-3-fluoroazetidin-1-yl)(1-oxidothietan-3-yl)methanone;
(3-(4-(5-(3,4-dichloro-5-(trifluoromethyl)phenyl)-5-(trifluoromethyl)-4,5-dihydroisoxazol-3-yl)phenyl)-3-fluoroazetidin-1-yl)(1,1-dioxidothietan-3-yl)methanone;
(E)-N-(1-(3-(4-(5-(3,4-dichloro-5-(trifluoromethyl)phenyl)-5-(trifluoromethyl)-4,5-dihydroisoxazol-3-yl)phenyl)-3-fluoroazetidin-1-yl)-2-methylpropylidene)cyanamide;
1-(3-(4-(5-(4-chloro-3-(trifluoromethyl)phenyl)-5-(trifluoromethyl)-4,5-dihydroisoxazol-3-yl)phenyl)-3-fluoroazetidin-1-yl)-2-methylpropan-1-one;
(3-(4-(5-(4-chloro-3-(trifluoromethyl)phenyl)-5-(trifluoromethyl)-4,5-dihydroisoxazol-3-yl)phenyl)-3-fluoroazetidin-1-yl)(cyclopropyl)methanone;
1-(3-(4-(5-(4-chloro-3-(trifluoromethyl)phenyl)-5-(trifluoromethyl)-4,5-dihydroisoxazol-3-yl)phenyl)-3-fluoroazetidin-1-yl)-3,3,3-trifluoropropan-1-one;
1-(3-(4-(5-(4-chloro-3-(trifluoromethyl)phenyl)-5-(trifluoromethyl)-4,5-dihydroisoxazol-3-yl)phenyl)-3-fluoroazetidin-1-yl)-2-(methylthio)ethanone;
1-(3-(4-(5-(4-chloro-3-(trifluoromethyl)phenyl)-5-(trifluoromethyl)-4,5-dihydroisoxazol-3-yl)phenyl)-3-fluoroazetidin-1-yl)-2-(methylsulfinyl)ethanone;
1-(3-(4-(5-(4-chloro-3-(trifluoromethyl)phenyl)-5-(trifluoromethyl)-4,5-dihydroisoxazol-3-yl)phenyl)-3-fluoroazetidin-1-yl)-2-(methylsulfonyl)ethanone;
1-(3-(4-(5-(4-chloro-3-(trifluoromethyl)phenyl)-5-(trifluoromethyl)-4,5-dihydroisoxazol-3-yl)phenyl)-3-fluoroazetidin-1-yl)-2-(1H-pyrazol-1-yl)ethanone;
1-(3-(4-(5-(4-chloro-3-(trifluoromethyl)phenyl)-5-(trifluoromethyl)-4,5-dihydroisoxazol-3-yl)phenyl)-3-fluoroazetidin-1-yl)-2-hydroxy-2-methylpropan-1-one;
(3-{4-[5-(3-Chloro-4-trifluoromethyl-phenyl)-5-trifluoromethyl-4,5-dihydro-isoxazol-3-yl]-phenyl}-3-fluoro-azetidin-1-yl)-thietan-3-yl-methanone;
(3-(4-(5-(4-chloro-3-(trifluoromethyl)phenyl)-5-(trifluoromethyl)-4,5-dihydroisoxazol-3-yl)phenyl)-3-fluoroazetidin-1-yl)(1-oxidothietan-3-yl)methanone;

(3-(4-(5-(4-chloro-3-(trifluoromethyl)phenyl)-5-(trifluoromethyl)-4,5-dihydroisoxazol-3-yl)phenyl)-3-fluoroazetidin-1-yl)(1,1-dioxidothietan-3-yl)methanone;

(E)-N-(1-(3-(4-(5-(4-chloro-3-(trifluoromethyl)phenyl)-5-(trifluoromethyl)-4,5-dihydroisoxazol-3-yl)phenyl)-3-fluoroazetidin-1-yl)-2-methylpropylidene)cyanamide;

1-(3-fluoro-3-(4-(5-(trifluoromethyl)-5-(3-(trifluoromethyl)phenyl)-4,5-dihydroisoxazol-3-yl)phenyl)azetidin-1-yl)-2-methylpropan-1-one;

cyclopropyl(3-fluoro-3-(4-(5-(trifluoromethyl)-5-(3-(trifluoromethyl)phenyl)-4,5-dihydroisoxazol-3-yl)phenyl)azetidin-1-yl)methanone;

3,3,3-trifluoro-1-(3-fluoro-3-(4-(5-(trifluoromethyl)-5-(3-(trifluoromethyl)phenyl)-4,5-dihydroisoxazol-3-yl)phenyl)azetidin-1-yl)propan-1-one;

1-(3-fluoro-3-(4-(5-(trifluoromethyl)-5-(3-(trifluoromethyl)phenyl)-4,5-dihydroisoxazol-3-yl)phenyl)azetidin-1-yl)-2-(methylthio)ethanone;

1-(3-fluoro-3-(4-(5-(trifluoromethyl)-5-(3-(trifluoromethyl)phenyl)-4,5-dihydroisoxazol-3-yl)phenyl)azetidin-1-yl)-2-(methylsulfinyl)ethanone;

1-(3-fluoro-3-(4-(5-(trifluoromethyl)-5-(3-(trifluoromethyl)phenyl)-4,5-dihydroisoxazol-3-yl)phenyl)azetidin-1-yl)-2-(methylsulfonyl)ethanone;

1-(3-fluoro-3-(4-(5-(trifluoromethyl)-5-(3-(trifluoromethyl)phenyl)-4,5-dihydroisoxazol-3-yl)phenyl)azetidin-1-yl)-2-(1H-pyrazol-1-yl)ethanone;

1-(3-fluoro-3-(4-(5-(trifluoromethyl)-5-(3-(trifluoromethyl)phenyl)-4,5-dihydroisoxazol-3-yl)phenyl)azetidin-1-yl)-2-hydroxy-2-methylpropan-1-one;

(3-Fluoro-3-{-4-[5-trifluoromethyl-5-(4-trifluoromethyl-phenyl)-4,5-dihydro-isoxazol-3-yl]-phenyl}-azetidin-1-yl)-thietan-3-yl-methanone;

(3-fluoro-3-(4-(5-(trifluoromethyl)-5-(3-(trifluoromethyl)phenyl)-4,5-dihydroisoxazol-3-yl)phenyl)azetidin-1-yl)(1-oxidothietan-3-yl)methanone;

(1,1-dioxidothietan-3-yl)(3-fluoro-3-(4-(5-(trifluoromethyl)-5-(3-(trifluoromethyl)phenyl)-4,5-dihydroisoxazol-3-yl)phenyl)azetidin-1-yl)methanone;

(E)-N-(1-(3-fluoro-3-(4-(5-(trifluoromethyl)-5-(3-(trifluoromethyl)phenyl)-4,5-dihydroisoxazol-3-yl)phenyl)azetidin-1-yl)-2-methylpropylidene)cyanamide;

1-(3-(4-(5-(3,4-difluoro-5-(trifluoromethyl)phenyl)-5-(trifluoromethyl)-4,5-dihydroisoxazol-3-yl)phenyl)-3-fluoroazetidin-1-yl)-2-methylpropan-1-one;

cyclopropyl(3-(4-(5-(3,4-difluoro-5-(trifluoromethyl)phenyl)-5-(trifluoromethyl)-4,5-dihydroisoxazol-3-yl)phenyl)-3-fluoroazetidin-1-yl)methanone;

1-(3-(4-(5-(3,4-difluoro-5-(trifluoromethyl)phenyl)-5-(trifluoromethyl)-4,5-dihydroisoxazol-3-yl)phenyl)-3-fluoroazetidin-1-yl)-3,3,3-trifluoropropan-1-one;

1-(3-(4-(5-(3,4-difluoro-5-(trifluoromethyl)phenyl)-5-(trifluoromethyl)-4,5-dihydroisoxazol-3-yl)phenyl)-3-fluoroazetidin-1-yl)-2-(methylthio)ethanone;

1-(3-(4-(5-(3,4-difluoro-5-(trifluoromethyl)phenyl)-5-(trifluoromethyl)-4,5-dihydroisoxazol-3-yl)phenyl)-3-fluoroazetidin-1-yl)-2-(methylsulfinyl)ethanone;

1-(3-(4-(5-(3,4-difluoro-5-(trifluoromethyl)phenyl)-5-(trifluoromethyl)-4,5-dihydroisoxazol-3-yl)phenyl)-3-fluoroazetidin-1-yl)-2-(methylsulfonyl)ethanone;

1-(3-(4-(5-(3,4-difluoro-5-(trifluoromethyl)phenyl)-5-(trifluoromethyl)-4,5-dihydroisoxazol-3-yl)phenyl)-3-fluoroazetidin-1-yl)-2-(1H-pyrazol-1-yl)ethanone;

1-(3-(4-(5-(3,4-difluoro-5-(trifluoromethyl)phenyl)-5-(trifluoromethyl)-4,5-dihydroisoxazol-3-yl)phenyl)-3-fluoroazetidin-1-yl)-2-hydroxy-2-methylpropan-1-one;

(3-{4-[5-(3,4-Difluoro-5-trifluoromethyl-phenyl)-5-trifluoromethyl-4,5-dihydro-isoxazol-3-yl]-phenyl}-3-fluoro-azetidin-1-yl)-thietan-3-yl-methanone;

(3-(4-(5-(3,4-difluoro-5-(trifluoromethyl)phenyl)-5-(trifluoromethyl)-4,5-dihydroisoxazol-3-yl)phenyl)-3-fluoroazetidin-1-yl)(1-oxidothietan-3-yl)methanone;

(3-(4-(5-(3,4-difluoro-5-(trifluoromethyl)phenyl)-5-(trifluoromethyl)-4,5-dihydroisoxazol-3-yl)phenyl)-3-fluoroazetidin-1-yl)(1,1-dioxidothietan-3-yl)methanone;

(E)-N-(1-(3-(4-(5-(3,4-difluoro-5-(trifluoromethyl)phenyl)-5-(trifluoromethyl)-4,5-dihydroisoxazol-3-yl)phenyl)-3-fluoroazetidin-1-yl)-2-methylpropylidene)cyanamide;

1-(3-(4-(5-(3-chloro-4-fluorophenyl)-5-(trifluoromethyl)-4,5-dihydroisoxazol-3-yl)phenyl)-3-fluoroazetidin-1-yl)-2-methylpropan-1-one;

(3-(4-(5-(3-chloro-4-fluorophenyl)-5-(trifluoromethyl)-4,5-dihydroisoxazol-3-yl)phenyl)-3-fluoroazetidin-1-yl)(cyclopropyl)methanone;

1-(3-(4-(5-(3-chloro-4-fluorophenyl)-5-(trifluoromethyl)-4,5-dihydroisoxazol-3-yl)phenyl)-3-fluoroazetidin-1-yl)-3,3,3-trifluoropropan-1-one;

1-(3-(4-(5-(3-chloro-4-fluorophenyl)-5-(trifluoromethyl)-4,5-dihydroisoxazol-3-yl)phenyl)-3-fluoroazetidin-1-yl)-2-(methylthio)ethanone;

1-(3-(4-(5-(3-chloro-4-fluorophenyl)-5-(trifluoromethyl)-4,5-dihydroisoxazol-3-yl)phenyl)-3-fluoroazetidin-1-yl)-2-(methylsulfinyl)ethanone;

1-(3-(4-(5-(3-chloro-4-fluorophenyl)-5-(trifluoromethyl)-4,5-dihydroisoxazol-3-yl)phenyl)-3-fluoroazetidin-1-yl)-2-(methylsulfonyl)ethanone;

1-(3-(4-(5-(3-chloro-4-fluorophenyl)-5-(trifluoromethyl)-4,5-dihydroisoxazol-3-yl)phenyl)-3-fluoroazetidin-1-yl)-2-(1H-pyrazol-1-yl)ethanone;

1-(3-(4-(5-(3-chloro-4-fluorophenyl)-5-(trifluoromethyl)-4,5-dihydroisoxazol-3-yl)phenyl)-3-fluoroazetidin-1-yl)-2-hydroxy-2-methylpropan-1-one;

(3-{4-[5-(3-Chloro-4-fluoro-phenyl)-5-trifluoromethyl-4,5-dihydro-isoxazol-3-yl]-phenyl}-3-fluoro-azetidin-1-yl)-thietan-3-yl-methanone;

(3-(4-(5-(3-chloro-4-fluorophenyl)-5-(trifluoromethyl)-4,5-dihydroisoxazol-3-yl)phenyl)-3-fluoroazetidin-1-yl)(1-oxidothietan-3-yl)methanone;

(3-(4-(5-(3-chloro-4-fluorophenyl)-5-(trifluoromethyl)-4,5-dihydroisoxazol-3-yl)phenyl)-3-fluoroazetidin-1-yl)(1,1-dioxidothietan-3-yl)methanone;

(E)-N-(1-(3-(4-(5-(3-chloro-4-fluorophenyl)-5-(trifluoromethyl)-4,5-dihydroisoxazol-3-yl)phenyl)-3-fluoroazetidin-1-yl)-2-methylpropylidene)cyanamide;

1-(3-(4-(5-(3-chloro-5-fluorophenyl)-5-(trifluoromethyl)-4,5-dihydroisoxazol-3-yl)phenyl)-3-fluoroazetidin-1-yl)-2-methylpropan-1-one;

(3-(4-(5-(3-chloro-5-fluorophenyl)-5-(trifluoromethyl)-4,5-dihydroisoxazol-3-yl)phenyl)-3-fluoroazetidin-1-yl)(cyclopropyl)methanone;

1-(3-(4-(5-(3-chloro-5-fluorophenyl)-5-(trifluoromethyl)-4,5-dihydroisoxazol-3-yl)phenyl)-3-fluoroazetidin-1-yl)-3,3,3-trifluoropropan-1-one;

1-(3-(4-(5-(3-chloro-5-fluorophenyl)-5-(trifluoromethyl)-4,5-dihydroisoxazol-3-yl)phenyl)-3-fluoroazetidin-1-yl)-2-(methylthio)ethanone;

1-(3-(4-(5-(3-chloro-5-fluorophenyl)-5-(trifluoromethyl)-4,5-dihydroisoxazol-3-yl)phenyl)-3-fluoroazetidin-1-yl)-2-(methylsulfinyl)ethanone;

1-(3-(4-(5-(3-chloro-5-fluorophenyl)-5-(trifluoromethyl)-4,5-dihydroisoxazol-3-yl)phenyl)-3-fluoroazetidin-1-yl)-2-(methylsulfonyl)ethanone;

1-(3-(4-(5-(3-chloro-5-fluorophenyl)-5-(trifluoromethyl)-4,5-dihydroisoxazol-3-yl)phenyl)-3-fluoroazetidin-1-yl)-2-(1H-pyrazol-1-yl)ethanone;
1-(3-(4-(5-(3-chloro-5-fluorophenyl)-5-(trifluoromethyl)-4,5-dihydroisoxazol-3-yl)phenyl)-3-fluoroazetidin-1-yl)-2-hydroxy-2-methylpropan-1-one;
(3-{4-[5-(3-chloro-5-fluorophenyl)-5-trifluoromethyl-4,5-dihydro-isoxazol-3-yl]-phenyl}-3-fluoro-azetidin-1-yl)-thietan-3-yl-methanone;
(3-(4-(5-(3-chloro-5-fluorophenyl)-5-(trifluoromethyl)-4,5-dihydroisoxazol-3-yl)phenyl)-3-fluoroazetidin-1-yl)(1-oxidothietan-3-yl)methanone;
(3-(4-(5-(3-chloro-5-fluorophenyl)-5-(trifluoromethyl)-4,5-dihydroisoxazol-3-yl)phenyl)-3-fluoroazetidin-1-yl)(1,1-dioxidothietan-3-yl)methanone;
(E)-N-(1-(3-(4-(5-(3-chloro-5-fluorophenyl)-5-(trifluoromethyl)-4,5-dihydroisoxazol-3-yl)phenyl)-3-fluoroazetidin-1-yl)-2-methylpropylidene)cyanamide;
1-(3-fluoro-3-(4-(5-(trifluoromethyl)-5-(3,4,5-trifluorophenyl)-4,5-dihydroisoxazol-3-yl)phenyl)azetidin-1-yl)-2-methylpropan-1-one;
cyclopropyl(3-fluoro-3-(4-(5-(trifluoromethyl)-5-(3,4,5-trifluorophenyl)-4,5-dihydroisoxazol-3-yl)phenyl)azetidin-1-yl)methanone;
3,3,3-trifluoro-1-(3-fluoro-3-(4-(5-(trifluoromethyl)-5-(3,4,5-trifluorophenyl)-4,5-dihydroisoxazol-3-yl)phenyl)azetidin-1-yl)propan-1-one;
1-(3-fluoro-3-(4-(5-(trifluoromethyl)-5-(3,4,5-trifluorophenyl)-4,5-dihydroisoxazol-3-yl)phenyl)azetidin-1-yl)-2-(methylthio)ethanone;
1-(3-fluoro-3-(4-(5-(trifluoromethyl)-5-(3,4,5-trifluorophenyl)-4,5-dihydroisoxazol-3-yl)phenyl)azetidin-1-yl)-2-(methylsulfinyl)ethanone;
1-(3-fluoro-3-(4-(5-(trifluoromethyl)-5-(3,4,5-trifluorophenyl)-4,5-dihydroisoxazol-3-yl)phenyl)azetidin-1-yl)-2-(methylsulfonyl)ethanone;
1-(3-fluoro-3-(4-(5-(trifluoromethyl)-5-(3,4,5-trifluorophenyl)-4,5-dihydroisoxazol-3-yl)phenyl)azetidin-1-yl)-2-(1H-pyrazol-1-yl)ethanone;
1-(3-fluoro-3-(4-(5-(trifluoromethyl)-5-(3,4,5-trifluorophenyl)-4,5-dihydroisoxazol-3-yl)phenyl)azetidin-1-yl)-2-hydroxy-2-methylpropan-1-one;
(3-Fluoro-3-{-4-[5-trifluoromethyl-5-(3,4,5-trifluorophenyl)-4,5-dihydro-isoxazol-3-yl]-phenyl}-azetidin-1-yl)-thietan-3-yl-methanone;
(3-fluoro-3-(4-(5-(trifluoromethyl)-5-(3,4,5-trifluorophenyl)-4,5-dihydroisoxazol-3-yl)phenyl)azetidin-1-yl)(1-oxidothietan-3-yl)methanone;
(1,1-dioxidothietan-3-yl)(3-fluoro-3-(4-(5-(trifluoromethyl)-5-(3,4,5-trifluorophenyl)-4,5-dihydroisoxazol-3-yl)phenyl)azetidin-1-yl)methanone;
(E)-N-(1-(3-fluoro-3-(4-(5-(trifluoromethyl)-5-(3,4,5-trifluorophenyl)-4,5-dihydroisoxazol-3-yl)phenyl)azetidin-1-yl)-2-methylpropylidene)cyanamide;
2-(1-(cyclopropanecarbonyl)-3-fluoroazetidin-3-yl)-5-(5-(3,4,5-trichlorophenyl)-5-(trifluoromethyl)-4,5-dihydroisoxazol-3-yl)benzonitrile;
cyclopropyl(3-(4-(5-(3,4-dichloro-5-(trifluoromethyl)phenyl)-5-(trifluoromethyl)-4,5-dihydroisoxazol-3-yl)phenyl)-3-hydroxyazetidin-1-yl)methanone;
1-(3-(5-(5-(3,5-dichloro-4-fluorophenyl)-5-(trifluoromethyl)-4,5-dihydroisoxazol-3-yl)pyridin-2-yl)-3-fluoroazetidin-1-yl)-2-methylpropan-1-one;
cyclopropyl(3-(5-(5-(3,5-dichloro-4-fluorophenyl)-5-(trifluoromethyl)-4,5-dihydroisoxazol-3-yl)pyridin-2-yl)-3-fluoroazetidin-1-yl)methanone;
1-(3-(5-(5-(3,5-dichloro-4-fluorophenyl)-5-(trifluoromethyl)-4,5-dihydroisoxazol-3-yl)pyridin-2-yl)-3-fluoroazetidin-1-yl)-3,3,3-trifluoropropan-1-one;
1-(3-(5-(5-(3,5-dichloro-4-fluorophenyl)-5-(trifluoromethyl)-4,5-dihydroisoxazol-3-yl)pyridin-2-yl)-3-fluoroazetidin-1-yl)-2-(methylthio)ethanone;
1-(3-(5-(5-(3,5-dichloro-4-fluorophenyl)-5-(trifluoromethyl)-4,5-dihydroisoxazol-3-yl)pyridin-2-yl)-3-fluoroazetidin-1-yl)-2-(methylsulfinyl)ethanone;
1-(3-(5-(5-(3,5-dichloro-4-fluorophenyl)-5-(trifluoromethyl)-4,5-dihydroisoxazol-3-yl)pyridin-2-yl)-3-fluoroazetidin-1-yl)-2-(methylsulfonyl)ethanone;
1-(3-(5-(5-(3,5-dichloro-4-fluorophenyl)-5-(trifluoromethyl)-4,5-dihydroisoxazol-3-yl)pyridin-2-yl)-3-fluoroazetidin-1-yl)-2-(1H-pyrazol-1-yl)ethanone;
1-(3-(5-(5-(3,5-dichloro-4-fluorophenyl)-5-(trifluoromethyl)-4,5-dihydroisoxazol-3-yl)pyridin-2-yl)-3-fluoroazetidin-1-yl)-2-hydroxy-2-methylpropan-1-one;
(3-{5-[5-(3,5-Dichloro-4-fluoro-phenyl)-5-trifluoromethyl-4,5-dihydro-isoxazol-3-yl]-pyridin-2-yl}-3-fluoro-azetidin-1-yl)-thietan-3-yl-methanone;
(3-(5-(5-(3,5-dichloro-4-fluorophenyl)-5-(trifluoromethyl)-4,5-dihydroisoxazol-3-yl)pyridin-2-yl)-3-fluoroazetidin-1-yl)(1-oxidothietan-3-yl)methanone;
(3-(5-(5-(3,5-dichloro-4-fluorophenyl)-5-(trifluoromethyl)-4,5-dihydroisoxazol-3-yl)pyridin-2-yl)-3-fluoroazetidin-1-yl)(1,1-dioxidothietan-3-yl)methanone;
(E)-N-(1-(3-(5-(5-(3,5-dichloro-4-fluorophenyl)-5-(trifluoromethyl)-4,5-dihydroisoxazol-3-yl)pyridin-2-yl)-3-fluoroazetidin-1-yl)-2-methylpropylidene)cyanamide;
1-(3-fluoro-3-(5-(5-(3,4,5-trichlorophenyl)-5-(trifluoromethyl)-4,5-dihydroisoxazol-3-yl)pyridin-2-yl)azetidin-1-yl)-2-methylpropan-1-one;
cyclopropyl(3-fluoro-3-(5-(5-(3,4,5-trichlorophenyl)-5-(trifluoromethyl)-4,5-dihydroisoxazol-3-yl)pyridin-2-yl)azetidin-1-yl)methanone;
3,3,3-trifluoro-1-(3-fluoro-3-(5-(5-(3,4,5-trichlorophenyl)-5-(trifluoromethyl)-4,5-dihydroisoxazol-3-yl)pyridin-2-yl)azetidin-1-yl)propan-1-one;
1-(3-fluoro-3-(5-(5-(3,4,5-trichlorophenyl)-5-(trifluoromethyl)-4,5-dihydroisoxazol-3-yl)pyridin-2-yl)azetidin-1-yl)-2-(methylthio)ethanone;
1-(3-fluoro-3-(5-(5-(3,4,5-trichlorophenyl)-5-(trifluoromethyl)-4,5-dihydroisoxazol-3-yl)pyridin-2-yl)azetidin-1-yl)-2-(methylsulfinyl)ethanone;
1-(3-fluoro-3-(5-(5-(3,4,5-trichlorophenyl)-5-(trifluoromethyl)-4,5-dihydroisoxazol-3-yl)pyridin-2-yl)azetidin-1-yl)-2-(methylsulfonyl)ethanone;
1-(3-fluoro-3-(5-(5-(3,4,5-trichlorophenyl)-5-(trifluoromethyl)-4,5-dihydroisoxazol-3-yl)pyridin-2-yl)azetidin-1-yl)-2-(1H-pyrazol-1-yl)ethanone;
1-(3-fluoro-3-(5-(5-(3,4,5-trichlorophenyl)-5-(trifluoromethyl)-4,5-dihydroisoxazol-3-yl)pyridin-2-yl)azetidin-1-yl)-2-hydroxy-2-methylpropan-1-one;
(3-Fluoro-3-{5-[5-(3,4,5-trichloro-phenyl)-5-trifluoromethyl-4,5-dihydro-isoxazol-3-yl]-pyridin-2-yl}-azetidin-1-yl)-thietan-3-yl-methanone;
(3-fluoro-3-(5-(5-(3,4,5-trichlorophenyl)-5-(trifluoromethyl)-4,5-dihydroisoxazol-3-yl)pyridin-2-yl)azetidin-1-yl)(1-oxidothietan-3-yl)methanone;
(1,1-dioxidothietan-3-yl)(3-fluoro-3-(5-(5-(3,4,5-trichlorophenyl)-5-(trifluoromethyl)-4,5-dihydroisoxazol-3-yl)pyridin-2-yl)azetidin-1-yl)methanone;
(E)-N-(1-(3-fluoro-3-(5-(5-(3,4,5-trichlorophenyl)-5-(trifluoromethyl)-4,5-dihydroisoxazol-3-yl)pyridin-2-yl)azetidin-1-yl)-2-methylpropylidene)cyanamide;

1-(3-(5-(5-(3,4-dichloro-5-(trifluoromethyl)phenyl)-5-(trifluoromethyl)-4,5-dihydroisoxazol-3-yl)pyridin-2-yl)-3-fluoroazetidin-1-yl)-2-methylpropan-1-one;
cyclopropyl(3-(5-(5-(3,4-dichloro-5-(trifluoromethyl)phenyl)-5-(trifluoromethyl)-4,5-dihydroisoxazol-3-yl)pyridin-2-yl)-3-fluoroazetidin-1-yl)methanone;
1-(3-(5-(5-(3,4-dichloro-5-(trifluoromethyl)phenyl)-5-(trifluoromethyl)-4,5-dihydroisoxazol-3-yl)pyridin-2-yl)-3-fluoroazetidin-1-yl)-3,3,3-trifluoropropan-1-one;
1-(3-(5-(5-(3,4-dichloro-5-(trifluoromethyl)phenyl)-5-(trifluoromethyl)-4,5-dihydroisoxazol-3-yl)pyridin-2-yl)-3-fluoroazetidin-1-yl)-2-(methylthio)ethanone;
1-(3-(5-(5-(3,4-dichloro-5-(trifluoromethyl)phenyl)-5-(trifluoromethyl)-4,5-dihydroisoxazol-3-yl)pyridin-2-yl)-3-fluoroazetidin-1-yl)-2-(methylsulfinyl)ethanone;
1-(3-(5-(5-(3,4-dichloro-5-(trifluoromethyl)phenyl)-5-(trifluoromethyl)-4,5-dihydroisoxazol-3-yl)pyridin-2-yl)-3-fluoroazetidin-1-yl)-2-(methylsulfonyl)ethanone;
1-(3-(5-(5-(3,4-dichloro-5-(trifluoromethyl)phenyl)-5-(trifluoromethyl)-4,5-dihydroisoxazol-3-yl)pyridin-2-yl)-3-fluoroazetidin-1-yl)-2-(1H-pyrazol-1-yl)ethanone;
1-(3-(5-(5-(3,4-dichloro-5-(trifluoromethyl)phenyl)-5-(trifluoromethyl)-4,5-dihydroisoxazol-3-yl)pyridin-2-yl)-3-fluoroazetidin-1-yl)-2-hydroxy-2-methylpropan-1-one;
(3-{5-[5-(3,4-Dichloro-5-trifluoromethyl-phenyl)-5-trifluoromethyl-4,5-dihydro-isoxazol-3-yl]-pyridin-2-yl}-3-fluoro-azetidin-1-yl)-thietan-3-yl-methanone;
(3-(5-(5-(3,4-dichloro-5-(trifluoromethyl)phenyl)-5-(trifluoromethyl)-4,5-dihydroisoxazol-3-yl)pyridin-2-yl)-3-fluoroazetidin-1-yl)(1-oxidothietan-3-yl)methanone;
(3-(5-(5-(3,4-dichloro-5-(trifluoromethyl)phenyl)-5-(trifluoromethyl)-4,5-dihydroisoxazol-3-yl)pyridin-2-yl)-3-fluoroazetidin-1-yl)(1,1-dioxidothietan-3-yl)methanone;
(E)-N-(1-(3-(5-(5-(3,4-dichloro-5-(trifluoromethyl)phenyl)-5-(trifluoromethyl)-4,5-dihydroisoxazol-3-yl)pyridin-2-yl)-3-fluoroazetidin-1-yl)-2-methylpropylidene)cyanamide;
1-(3-(5-(5-(4-chloro-3-(trifluoromethyl)phenyl)-5-(trifluoromethyl)-4,5-dihydroisoxazol-3-yl)pyridin-2-yl)-3-fluoroazetidin-1-yl)-2-methylpropan-1-one;
(3-(5-(5-(4-chloro-3-(trifluoromethyl)phenyl)-5-(trifluoromethyl)-4,5-dihydroisoxazol-3-yl)pyridin-2-yl)-3-fluoroazetidin-1-yl)(cyclopropyl)methanone;
1-(3-(5-(5-(4-chloro-3-(trifluoromethyl)phenyl)-5-(trifluoromethyl)-4,5-dihydroisoxazol-3-yl)pyridin-2-yl)-3-fluoroazetidin-1-yl)-3,3,3-trifluoropropan-1-one;
1-(3-(5-(5-(4-chloro-3-(trifluoromethyl)phenyl)-5-(trifluoromethyl)-4,5-dihydroisoxazol-3-yl)pyridin-2-yl)-3-fluoroazetidin-1-yl)-2-(methylthio)ethanone;
1-(3-(5-(5-(4-chloro-3-(trifluoromethyl)phenyl)-5-(trifluoromethyl)-4,5-dihydroisoxazol-3-yl)pyridin-2-yl)-3-fluoroazetidin-1-yl)-2-(methylsulfinyl)ethanone;
1-(3-(5-(5-(4-chloro-3-(trifluoromethyl)phenyl)-5-(trifluoromethyl)-4,5-dihydroisoxazol-3-yl)pyridin-2-yl)-3-fluoroazetidin-1-yl)-2-(methylsulfonyl)ethanone;
1-(3-(5-(5-(4-chloro-3-(trifluoromethyl)phenyl)-5-(trifluoromethyl)-4,5-dihydroisoxazol-3-yl)pyridin-2-yl)-3-fluoroazetidin-1-yl)-2-(1H-pyrazol-1-yl)ethanone;
1-(3-(5-(5-(4-chloro-3-(trifluoromethyl)phenyl)-5-(trifluoromethyl)-4,5-dihydroisoxazol-3-yl)pyridin-2-yl)-3-fluoroazetidin-1-yl)-2-hydroxy-2-methylpropan-1-one;
(3-{5-[5-(4-Chloro-3-trifluoromethyl-phenyl)-5-trifluoromethyl-4,5-dihydro-isoxazol-3-yl]-pyridin-2-yl}-3-fluoro-azetidin-1-yl)-thietan-3-yl-methanone;
(3-(5-(5-(4-chloro-3-(trifluoromethyl)phenyl)-5-(trifluoromethyl)-4,5-dihydroisoxazol-3-yl)pyridin-2-yl)-3-fluoroazetidin-1-yl)(1-oxidothietan-3-yl)methanone;
(3-(5-(5-(4-chloro-3-(trifluoromethyl)phenyl)-5-(trifluoromethyl)-4,5-dihydroisoxazol-3-yl)pyridin-2-yl)-3-fluoroazetidin-1-yl)(1,1-dioxidothietan-3-yl)methanone;
(E)-N-(1-(3-(5-(5-(4-chloro-3-(trifluoromethyl)phenyl)-5-(trifluoromethyl)-4,5-dihydroisoxazol-3-yl)pyridin-2-yl)-3-fluoroazetidin-1-yl)-2-methylpropylidene)cyanamide;
1-(3-fluoro-3-(5-(5-(trifluoromethyl)-5-(3-(trifluoromethyl)phenyl)-4,5-dihydroisoxazol-3-yl)pyridin-2-yl)azetidin-1-yl)-2-methylpropan-1-one;
cyclopropyl(3-fluoro-3-(5-(5-(trifluoromethyl)-5-(3-(trifluoromethyl)phenyl)-4,5-dihydroisoxazol-3-yl)pyridin-2-yl)azetidin-1-yl)methanone;
3,3,3-trifluoro-1-(3-fluoro-3-(5-(5-(trifluoromethyl)-5-(3-(trifluoromethyl)phenyl)-4,5-dihydroisoxazol-3-yl)pyridin-2-yl)azetidin-1-yl)propan-1-one;
1-(3-fluoro-3-(5-(5-(trifluoromethyl)-5-(3-(trifluoromethyl)phenyl)-4,5-dihydroisoxazol-3-yl)pyridin-2-yl)azetidin-1-yl)-2-(methylthio)ethanone;
1-(3-fluoro-3-(5-(5-(trifluoromethyl)-5-(3-(trifluoromethyl)phenyl)-4,5-dihydroisoxazol-3-yl)pyridin-2-yl)azetidin-1-yl)-2-(methylsulfinyl)ethanone;
1-(3-fluoro-3-(5-(5-(trifluoromethyl)-5-(3-(trifluoromethyl)phenyl)-4,5-dihydroisoxazol-3-yl)pyridin-2-yl)azetidin-1-yl)-2-(methylsulfonyl)ethanone;
1-(3-fluoro-3-(5-(5-(trifluoromethyl)-5-(3-(trifluoromethyl)phenyl)-4,5-dihydroisoxazol-3-yl)pyridin-2-yl)azetidin-1-yl)-2-(1H-pyrazol-1-yl)ethanone;
1-(3-fluoro-3-(5-(5-(trifluoromethyl)-5-(3-(trifluoromethyl)phenyl)-4,5-dihydroisoxazol-3-yl)pyridin-2-yl)azetidin-1-yl)-2-hydroxy-2-methylpropan-1-one;
(3-Fluoro-3-{5-[5-trifluoromethyl-5-(3-trifluoromethyl-phenyl)-4,5-dihydro-isoxazol-3-yl]-pyridin-2-yl}-azetidin-1-yl)-thietan-3-yl-methanone;
(3-fluoro-3-(5-(5-(trifluoromethyl)-5-(3-(trifluoromethyl)phenyl)-4,5-dihydroisoxazol-3-yl)pyridin-2-yl)azetidin-1-yl)(1-oxidothietan-3-yl)methanone;
(1,1-dioxidothietan-3-yl)(3-fluoro-3-(5-(5-(trifluoromethyl)-5-(3-(trifluoromethyl)phenyl)-4,5-dihydroisoxazol-3-yl)pyridin-2-yl)azetidin-1-yl)methanone;
(E)-N-(1-(3-fluoro-3-(5-(5-(trifluoromethyl)-5-(3-(trifluoromethyl)phenyl)-4,5-dihydroisoxazol-3-yl)pyridin-2-yl)azetidin-1-yl)-2-methylpropylidene)cyanamide;
1-(3-(5-(5-(3,4-difluoro-5-(trifluoromethyl)phenyl)-5-(trifluoromethyl)-4,5-dihydroisoxazol-3-yl)pyridin-2-yl)-3-fluoroazetidin-1-yl)-2-methylpropan-1-one;
cyclopropyl(3-(5-(5-(3,4-difluoro-5-(trifluoromethyl)phenyl)-5-(trifluoromethyl)-4,5-dihydroisoxazol-3-yl)pyridin-2-yl)-3-fluoroazetidin-1-yl)methanone;
1-(3-(5-(5-(3,4-difluoro-5-(trifluoromethyl)phenyl)-5-(trifluoromethyl)-4,5-dihydroisoxazol-3-yl)pyridin-2-yl)-3-fluoroazetidin-1-yl)-3,3,3-trifluoropropan-1-one;
1-(3-(5-(5-(3,4-difluoro-5-(trifluoromethyl)phenyl)-5-(trifluoromethyl)-4,5-dihydroisoxazol-3-yl)pyridin-2-yl)-3-fluoroazetidin-1-yl)-2-(methylthio)ethanone;
1-(3-(5-(5-(3,4-difluoro-5-(trifluoromethyl)phenyl)-5-(trifluoromethyl)-4,5-dihydroisoxazol-3-yl)pyridin-2-yl)-3-fluoroazetidin-1-yl)-2-(methylsulfinyl)ethanone;
1-(3-(5-(5-(3,4-difluoro-5-(trifluoromethyl)phenyl)-5-(trifluoromethyl)-4,5-dihydroisoxazol-3-yl)pyridin-2-yl)-3-fluoroazetidin-1-yl)-2-(methylsulfonyl)ethanone;
1-(3-(5-(5-(3,4-difluoro-5-(trifluoromethyl)phenyl)-5-(trifluoromethyl)-4,5-dihydroisoxazol-3-yl)pyridin-2-yl)-3-fluoroazetidin-1-yl)-2-(1H-pyrazol-1-yl)ethanone;
1-(3-(5-(5-(3,4-difluoro-5-(trifluoromethyl)phenyl)-5-(trifluoromethyl)-4,5-dihydroisoxazol-3-yl)pyridin-2-yl)-3-fluoroazetidin-1-yl)-2-hydroxy-2-methylpropan-1-one;

(3-{5-[5-(3,4-Difluoro-5-trifluoromethyl-phenyl)-5-trifluoromethyl-4,5-dihydro-isoxazol-3-yl]-pyridin-2-yl}-3-fluoro-azetidin-1-yl)-thietan-3-yl-methanone;
(3-(5-(5-(3,4-difluoro-5-(trifluoromethyl)phenyl)-5-(trifluoromethyl)-4,5-dihydroisoxazol-3-yl)pyridin-2-yl)-3-fluoroazetidin-1-yl)(1-oxidothietan-3-yl)methanone;
(3-(5-(5-(3,4-difluoro-5-(trifluoromethyl)phenyl)-5-(trifluoromethyl)-4,5-dihydroisoxazol-3-yl)pyridin-2-yl)-3-fluoroazetidin-1-yl)(1,1-dioxidothietan-3-yl)methanone;
(E)-N-(1-(3-(5-(5-(3,4-difluoro-5-(trifluoromethyl)phenyl)-5-(trifluoromethyl)-4,5-dihydroisoxazol-3-yl)pyridin-2-yl)-3-fluoroazetidin-1-yl)-2-methylpropylidene)cyanamide;
1-(3-(5-(5-(3-chloro-4-fluorophenyl)-5-(trifluoromethyl)-4,5-dihydroisoxazol-3-yl)pyridin-2-yl)-3-fluoroazetidin-1-yl)-2-methylpropan-1-one;
(3-(5-(5-(3-chloro-4-fluorophenyl)-5-(trifluoromethyl)-4,5-dihydroisoxazol-3-yl)pyridin-2-yl)-3-fluoroazetidin-1-yl)(cyclopropyl)methanone;
1-(3-(5-(5-(3-chloro-4-fluorophenyl)-5-(trifluoromethyl)-4,5-dihydroisoxazol-3-yl)pyridin-2-yl)-3-fluoroazetidin-1-yl)-3,3,3-trifluoropropan-1-one;
1-(3-(5-(5-(3-chloro-4-fluorophenyl)-5-(trifluoromethyl)-4,5-dihydroisoxazol-3-yl)pyridin-2-yl)-3-fluoroazetidin-1-yl)-2-(methylthio)ethanone;
1-(3-(5-(5-(3-chloro-4-fluorophenyl)-5-(trifluoromethyl)-4,5-dihydroisoxazol-3-yl)pyridin-2-yl)-3-fluoroazetidin-1-yl)-2-(methylsulfinyl)ethanone;
1-(3-(5-(5-(3-chloro-4-fluorophenyl)-5-(trifluoromethyl)-4,5-dihydroisoxazol-3-yl)pyridin-2-yl)-3-fluoroazetidin-1-yl)-2-(methylsulfonyl)ethanone;
1-(3-(5-(5-(3-chloro-4-fluorophenyl)-5-(trifluoromethyl)-4,5-dihydroisoxazol-3-yl)pyridin-2-yl)-3-fluoroazetidin-1-yl)-2-(1H-pyrazol-1-yl)ethanone;
1-(3-(5-(5-(3-chloro-4-fluorophenyl)-5-(trifluoromethyl)-4,5-dihydroisoxazol-3-yl)pyridin-2-yl)-3-fluoroazetidin-1-yl)-2-hydroxy-2-methylpropan-1-one;
(3-{5-[5-(3-Chloro-4-fluoro-phenyl)-5-trifluoromethyl-4,5-dihydro-isoxazol-3-yl]-pyridin-2-yl}-3-fluoro-azetidin-1-yl)-thietan-3-yl-methanone;
(3-(5-(5-(3-chloro-4-fluorophenyl)-5-(trifluoromethyl)-4,5-dihydroisoxazol-3-yl)pyridin-2-yl)-3-fluoroazetidin-1-yl)(1-oxidothietan-3-yl)methanone;
(3-(5-(5-(3-chloro-4-fluorophenyl)-5-(trifluoromethyl)-4,5-dihydroisoxazol-3-yl)pyridin-2-yl)-3-fluoroazetidin-1-yl)(1,1-dioxidothietan-3-yl)methanone;
(E)-N-(1-(3-(5-(5-(3-chloro-4-fluorophenyl)-5-(trifluoromethyl)-4,5-dihydroisoxazol-3-yl)pyridin-2-yl)-3-fluoroazetidin-1-yl)-2-methylpropylidene)cyanamide;
1-(3-(5-(5-(3-chloro-5-fluorophenyl)-5-(trifluoromethyl)-4,5-dihydroisoxazol-3-yl)pyridin-2-yl)-3-fluoroazetidin-1-yl)-2-methylpropan-1-one;
(3-(5-(5-(3-chloro-5-fluorophenyl)-5-(trifluoromethyl)-4,5-dihydroisoxazol-3-yl)pyridin-2-yl)-3-fluoroazetidin-1-yl)(cyclopropyl)methanone;
1-(3-(5-(5-(3-chloro-5-fluorophenyl)-5-(trifluoromethyl)-4,5-dihydroisoxazol-3-yl)pyridin-2-yl)-3-fluoroazetidin-1-yl)-3,3,3-trifluoropropan-1-one;
1-(3-(5-(5-(3-chloro-5-fluorophenyl)-5-(trifluoromethyl)-4,5-dihydroisoxazol-3-yl)pyridin-2-yl)-3-fluoroazetidin-1-yl)-2-(methylthio)ethanone;
1-(3-(5-(5-(3-chloro-5-fluorophenyl)-5-(trifluoromethyl)-4,5-dihydroisoxazol-3-yl)pyridin-2-yl)-3-fluoroazetidin-1-yl)-2-(methylsulfinyl)ethanone;
1-(3-(5-(5-(3-chloro-5-fluorophenyl)-5-(trifluoromethyl)-4,5-dihydroisoxazol-3-yl)pyridin-2-yl)-3-fluoroazetidin-1-yl)-2-(methylsulfonyl)ethanone;
1-(3-(5-(5-(3-chloro-5-fluorophenyl)-5-(trifluoromethyl)-4,5-dihydroisoxazol-3-yl)pyridin-2-yl)-3-fluoroazetidin-1-yl)-2-(1H-pyrazol-1-yl)ethanone;
1-(3-(5-(5-(3-chloro-5-fluorophenyl)-5-(trifluoromethyl)-4,5-dihydroisoxazol-3-yl)pyridin-2-yl)-3-fluoroazetidin-1-yl)-2-hydroxy-2-methylpropan-1-one;
(3-{5-[5-(3-Chloro-5-fluorophenyl)-5-trifluoromethyl-4,5-dihydro-isoxazol-3-yl]-pyridin-2-yl}-3-fluoro-azetidin-1-yl)-thietan-3-yl-methanone;
(3-(5-(5-(3-chloro-5-fluorophenyl)-5-(trifluoromethyl)-4,5-dihydroisoxazol-3-yl)pyridin-2-yl)-3-fluoroazetidin-1-yl)(1-oxidothietan-3-yl)methanone;
(3-(5-(5-(3-chloro-5-fluorophenyl)-5-(trifluoromethyl)-4,5-dihydroisoxazol-3-yl)pyridin-2-yl)-3-fluoroazetidin-1-yl)(1,1-dioxidothietan-3-yl)methanone;
(E)-N-(1-(3-(5-(5-(3-chloro-5-fluorophenyl)-5-(trifluoromethyl)-4,5-dihydroisoxazol-3-yl)pyridin-2-yl)-3-fluoroazetidin-1-yl)-2-methylpropylidene)cyanamide;
1-(3-fluoro-3-(5-(5-(trifluoromethyl)-5-(3,4,5-trifluorophenyl)-4,5-dihydroisoxazol-3-yl)pyridin-2-yl)azetidin-1-yl)-2-methylpropan-1-one;
cyclopropyl(3-fluoro-3-(5-(5-(trifluoromethyl)-5-(3,4,5-trifluorophenyl)-4,5-dihydroisoxazol-3-yl)pyridin-2-yl)azetidin-1-yl) methanone;
3,3,3-trifluoro-1-(3-fluoro-3-(5-(5-(trifluoromethyl)-5-(3,4,5-trifluorophenyl)-4,5-dihydroisoxazol-3-yl)pyridin-2-yl)azetidin-1-yl)propan-1-one;
1-(3-fluoro-3-(4-(5-(trifluoromethyl)-5-(3,4,5-trifluorophenyl)-4,5-dihydroisoxazol-3-yl)phenyl)-1,2-diazetidin-1-yl)-2-(methylthio)ethanone;
1-(3-fluoro-3-(5-(5-(trifluoromethyl)-5-(3,4,5-trifluorophenyl)-4,5-dihydroisoxazol-3-yl)pyridin-2-yl)azetidin-1-yl)-2-(methylsulfinyl)ethanone;
1-(3-fluoro-3-(5-(5-(trifluoromethyl)-5-(3,4,5-trifluorophenyl)-4,5-dihydroisoxazol-3-yl)pyridin-2-yl)azetidin-1-yl)-2-(methylsulfonyl)ethanone;
1-(3-fluoro-3-(5-(5-(trifluoromethyl)-5-(3,4,5-trifluorophenyl)-4,5-dihydroisoxazol-3-yl)pyridin-2-yl)azetidin-1-yl)-2-(1H-pyrazol-1-yl)ethanone;
1-(3-fluoro-3-(5-(5-(trifluoromethyl)-5-(3,4,5-trifluorophenyl)-4,5-dihydroisoxazol-3-yl)pyridin-2-yl)azetidin-1-yl)-2-hydroxy-2-methylpropan-1-one;
(3-fluoro-3-{5-[5-trifluoromethyl-5-(3,4,5-trifluorophenyl)-4,5-dihydro-isoxazol-3-yl]-pyridin-2-yl}-azetidin-1-yl)-thietan-3-yl-methanone;
(3-fluoro-3-(5-(5-(trifluoromethyl)-5-(3,4,5-trifluorophenyl)-4,5-dihydroisoxazol-3-yl)pyridin-2-yl)azetidin-1-yl)(1-oxidothietan-3-yl)methanone;
(1,1-dioxidothietan-3-yl)(3-fluoro-3-(5-(5-(trifluoromethyl)-5-(3,4,5-trifluorophenyl)-4,5-dihydroisoxazol-3-yl)pyridin-2-yl)azetidin-1-yl)methanone; and
(E)-N-(1-(3-fluoro-3-(5-(5-(trifluoromethyl)-5-(3,4,5-trifluorophenyl)-4,5-dihydroisoxazol-3-yl)pyridin-2-yl)azetidin-1-yl)-2-methyl propylidene)cyanamide, stereoisomers thereof, pharmaceutical or veterinarily acceptable salts thereof.

Biological Assays

The biological activity of the compounds of the present invention were tested against fleas, ticks, flies, and or sea lice using the test methods described below.

Horn Fly (*Haematobia irritans*) Feed Assay

Formula (1) compounds were dissolved in DMSO and aliquots were added to citrated bovine blood in a membrane covered Petri dish. Approximately ten horn flies were placed onto each Petri dish and covered. The flies were allowed to feed on the treated blood cell. Flies were held at approximately 80° F. with a minimum of approximately 50% relative humidity. Flies were examined for knockdown and mortality at approximately 2 and 24 hours. Endpoint data were recorded as a lethal dose 90% ($LD^{90}$) in µg/mL. In this assay, Examples 8-10, 28, 32-34, 36, 38, 54, 160, 168-69, 171, 209, and 221 demonstrated an $LD^{90}$ of ≦0.3 µg/mL. Further in this assay, Examples 3-5, 11, 13-16, 20-22, 26-27, 31, 37, 40, 42, 45, 56, 59, 84-85, 87, 95, 99, 117, 137, 141, 145, 148, 152-53, 158, 162, 200, 206-07, 220, and 224 demonstrated an $LD^{90}$ of ≦1 µg/mL. Further in this assay, Examples 1, 2, 6, 12, 46, 60, 65, 69, 77, 98, 108, 112, 133, 135, 138, 140, 142-44, 147, 154, 163, 170, 179, 187, 193, 197, 199, 201-02, 204, 216, 219, 222, and 225 demonstrated an $LD^{90}$ of ≦3 µg/mL.

Stable Fly (*Stomoxys calcitrans*) Topical Assay

Formula (1) compounds were dissolved in acetone, and 1 µL was placed on the thorax of an anesthetized fly (n=10). The flies were allowed to recover, and were incubated for 24 hours at room temperature. Flies were examined for knockdown and mortality at 2 and 24 hours. Endpoint data was recorded as lethal dose 90% ($LD^{90}$) in µg/fly. In this assay, Examples 1 and 11 demonstrated an $LD^{90}$ of ≦0.01 µg/fly. Further in this assay, Examples 2, 9, 12, and 99 demonstrated an $LD^{90}$ of ≦0.03 µg/fly. Further in this assay, Examples 6, 16, 26, 28, 33, 36, 37, and 98 demonstrated an $LD^{90}$ of ≦0.1 µg/fly. Further in this assay, Examples 3, 14, 19, 27, 46, 84, 91, and 188 demonstrated an $LD^{90}$ of ≦1 µg/fly.

Flea (*Ctenocephalides felis*) Membrane Feed Assay-Adult

Formula (1) compounds were dissolved in DMSO and aliquots were added to citrated bovine blood in a membrane covered Petri dish pre-warmed to 37° C. Feeding tubes containing approximately 30-35 adult fleas were placed onto the Petri dishes. The fleas were allowed to feed for approximately 2 hours. Fleas were observed for knockdown and/or death at approximately 2 and 24 hours. Endpoint data were recorded as a lethal dose 90% ($LD^{90}$) in µg/mL. In this assay, Example 10 demonstrated an $LD^{90}$ of ≦0.03 µg/mL. Further in this assay, Examples 27 and 36 demonstrated an $LD^{90}$ of ≦0.1 µg/mL. Further in this assay, Examples 4-5, 11, 19, 23, 28, 32-33, 38, 84, 104, 117, 131, 137, 141, 160-161, 167-169, 175, 215-216, and 221 demonstrated an $LD^{90}$ of ≦0.3 µg/mL. Further, in this assay, Examples 1-3, 6-8, 12-16, 20-22, 26, 31, 37, 40-41, 43, 45-56, 59-60, 68, 72-77, 82, 91, 95-101, 103, 106-107, 109-110, 113, 116, 119-121, 123-126, 128-130, 132-133, 135, 138, 140, 145-146, 148, 152-153, 158, 162-164, 170, 173-174, 176, 197-199, 201-202, 205-210, 212-213, 218-220, and 222-223 demonstrated an $LD^{90}$ of ≦1 µg/mL. Further, in this assay, Examples 17, 24-25, 29-30, 34-35, 39, 42, 44, 57-58, 61-65, 67, 69-70, 79-81, 87, 89, 94, 102, 105, 108, 111-112, 114-115, 118, 122, 127, 134, 136, 139, 142-144, 147, 154-157, 165-166, 171, 179, 186-196, 200, 203-204, 211, 214-215, 217, and 224-225 demonstrated an $LD^{90}$ of ≦3 µg/mL.

Soft Tick (*Ornithidorus turicata*) Blood Feed Assay

Formula (1) compounds were dissolved in dimethylsulfoxide (DMSO) and aliquots were added to citrated bovine blood in a membrane covered Petri dish. The Petri dish was then placed on a warming tray. Approximately 5 nymph stage ticks were placed onto the membrane, covered, and left to feed. Fed ticks were removed and placed into a Petri dish with sand. Fed ticks were observed at approximately 24, 48 and 72 hours for paralysis and/or death. Endpoint data was recorded as an $ED^{100}$ and/or an $LD^{100}$ in µg/mL. Positive control was fipronil and DMSO was used for the negative control. In this assay, Examples 11, 19, 40, 169, and 175 demonstrated an $ED^{100}$ of ≦0.003 µg/cm². Further, In this assay, Examples 2-8, 10-17, 20-21, 26-28, 32-34, 36-38, 41-48, 50-54, 56, 59-60, 65-66, 68, 70, 72-74, 76, 84, 95-99, 103, 131, 133, 135, 141-143, 145-146, 155, 158, 165, 168, 171, 173-174, 202, 206, 209-210, 212-213, 215-216, 218-219, and 221 demonstrated an $ED^{100}$ of ≦0.03 µg/cm². In this assay, Examples 1, 9, 22,-25, 29-31, 35, 39, 49, 55, 57-58, 67, 69, 71, 75, 77, 82, 87, 104, 117, 136-140, 144, 148, 152-154, 160, 170, 187-188, 203-204, 207, 211, 214, 217, 220, and 223 demonstrated an $ED^{100}$ of ≦0.3 µg/cm². Further, in this assay, Examples 18, 89, and 91 demonstrated an $ED^{100}$ of ≦1 µg/cm². Further, in this assay, Example 86 demonstrated an $ED^{100}$ of ≦3 µg/cm².

Copepod (*Lepeophtheirus salmonis*) BioAssay

Two Formula (1) compounds were dissolved in sea water. Negative control was sea water and positive control was emamectin benzoate. Ten pre-adult/adult salmon lice were exposed for 24 hours. Lice were monitored for motility and endpoint data was recorded as an Effective Concentration 100% ($EC^{100}$) based on immotility. In this assay, Examples 19 and 177 had an $EC^{100}$ value of 50 ppb.

Comparative Data: Flea Feed Assay

Comparator compounds T1 and T2 were tested in the flea feed assay, as described above, and are compared to Examples 39 and 43, respectively. The compounds T1 (WO2008/122375) and T2 (US2009/0156643) represent the closet exemplified art. The data represents the 24 hour time period. Endpoint data were recorded as an lethal dose 90% ($LD^{90}$) in µg/mL. In this assay, Example 39 and 43 had an $LD^{90}$ of ≦3 and ≦1 µg/cm², respectively. Comparator compounds T1 and T2 both had $LD^{90}$ values of >30 µg/cm².

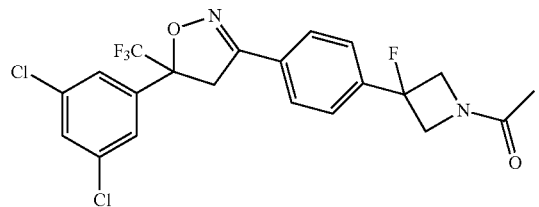

Example 39

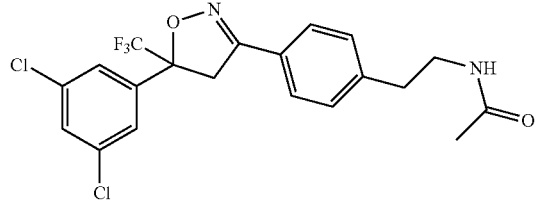

T1

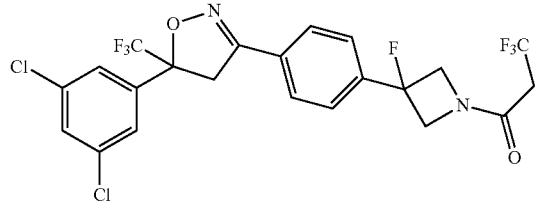

Example 43

-continued

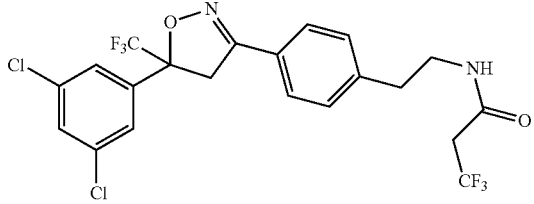

T2

We claim:

1. A compound of Formula (1)

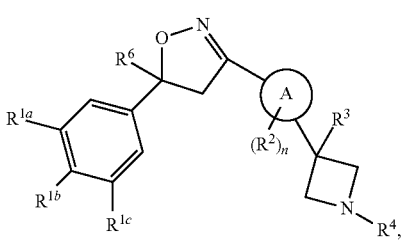

(1)

wherein
A is phenyl, naphthyl, or heteroaryl where said heteroaryl contains 1 to 4 heteroatoms each independently selected from N, O and S;
$R^{1a}$, $R^{1b}$, and $R^{1c}$ are each independently hydrogen, halo, hydroxyl, cyano, nitro, $C_1$-$C_6$alkyl, $C_1$-$C_6$haloalkyl, $C_1$-$C_6$alkoxy, $C_0$-$C_3$alkyl$C_3$-$C_6$cycloalkyl, $C_1$-$C_6$haloalkoxy, —C(O)NH$_2$, —SF$_5$, or —S(O)$_p$R;
$R^2$ is halo, cyano, $C_1$-$C_6$alkyl, $C_1$-$C_6$haloalkyl, nitro, hydroxyl, —C(O)NR$^a$R$^b$, $C_2$-$C_6$alkenyl, $C_2$-$C_6$alkynyl, —S(O)$_p$R, or —OR;
$R^3$ is hydrogen, halo, hydroxyl, cyano, $C_1$-$C_6$alkyl, $C_1$-$C_6$haloalkyl, $C_0$-$C_3$alkyl$C_3$-$C_6$cycloalkyl, —C(O)NH$_2$, nitro, —SC(O)R, —C(O)NR$^a$R$^b$, $C_0$-$C_3$alkylNR$^a$R$^4$, —NR$^a$NR$^b$R$^4$, —NR$^a$OR$^b$, —ONR$^a$R$^b$, N$_3$, —NHR$^4$, —OR, or —S(O)$_p$R;
$R^4$ is hydrogen, $C_1$-$C_6$alkyl, $C_0$-$C_6$alkyl$C_3$-$C_6$cycloalkyl, —C(O)R$^5$, —C(S)R$^5$, —C(O)NR$^a$R$^5$, —C(O)C(O)NR$^a$R$^5$, —S(O)$_p$R$^c$, —S(O)$_2$NR$^a$R$^5$, —C(NR$^7$)R$^5$, —C(NR$^7$)NR$^a$R$^5$, $C_0$-$C_6$alkylphenyl, $C_0$-$C_6$alkylheteroaryl, or $C_0$-$C_6$alkylheterocycle;
$R^5$ is hydrogen, $C_1$-$C_6$alkyl, $C_2$-$C_6$alkenyl, $C_0$-$C_6$alkyl$C_3$-$C_6$cycloalkyl, $C_0$-$C_6$alkylphenyl, $C_0$-$C_6$alkylheteroaryl, or $C_0$-$C_6$alkylheterocycle;
$R^6$ is cyano, $C_1$-$C_6$alkyl, $C_1$-$C_6$haloalkyl, —C(O)NR$^a$R$^b$, $C_2$-$C_6$alkenyl, $C_2$-$C_6$alkynyl, $C_2$-$C_6$haloalkenyl, or $C_2$-$C_6$haloalkynyl;
$R^7$ is hydrogen, $C_1$-$C_6$alkyl, hydroxyl, cyano, nitro, —S(O)$_p$R$^c$, or $C_1$-$C_6$alkoxy;
R is $C_1$-$C_6$alkyl or $C_3$-$C_6$cycloalkyl each optionally substituted by at least one halo;
$R^a$ is hydrogen, $C_1$-$C_6$alkyl, or $C_0$-$C_3$alkyl$C_3$-$C_6$cycloalkyl; wherein the alkyl and alkylcycloalkyl is optionally substituted by cyano or at least one halo substituent;
$R^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each optionally substituted, where chemically possible, with at least one substituent selected from hydroxyl, cyano, halo, or —S(O)$_p$R;

$R^c$ is $C_1$-$C_6$alkyl, $C_1$-$C_6$haloalkyl, $C_1$-$C_6$haloalkyl$C_3$-$C_6$cycloalkyl, $C_0$-$C_3$alkyl$C_3$-$C_6$cycloalkyl, $C_0$-$C_3$alkylphenyl, $C_0$-$C_3$alkylheteroaryl, or $C_0$-$C_3$alkylheterocycle each optionally substituted with at least one substituent selected from cyano, halo, hydroxyl, oxo, $C_1$-$C_6$alkoxy, $C_1$-$C_6$haloalkoxy, $C_1$-$C_6$haloalkyl, —S(O)$_p$R, —SH, —S(O)$_p$NR$^a$R$^b$, —NR$^a$R$^b$, —NR$^a$C(O)R$^b$, —SC(O)R$^b$, —SCN, or —C(O)NR$^a$R$^b$;
each of $R^4$ and $R^5$ $C_1$-$C_6$alkyl or $C_0$-$C_6$alkyl$C_3$-$C_6$cycloalkyl can be optionally and independently substituted by at least one substituent selected from cyano, halo, hydroxyl, oxo, $C_1$-$C_6$alkoxy, $C_1$-$C_6$haloalkoxy, $C_1$-$C_6$haloalkyl, —S(O)$_p$R$^c$, —SH, —S(O)$_p$NR$^a$R$^b$, —NR$^a$R$^b$, —NR$^a$C(O)R$^b$, —SC(O)R$^c$, —SCN, or —C(O)NR$^a$R$^b$; and
wherein $R^4$ and $R^5$ $C_0$-$C_6$alkylphenyl, $C_0$-$C_6$alkylheteroaryl, or $C_0$-$C_6$alkylheterocycle moiety can be further optionally substituted with at least one substituent selected from cyano, halo, oxo, =S, =NR$^7$, hydroxyl, $C_1$-$C_6$alkoxy, $C_1$-$C_6$alkyl, $C_1$-$C_6$haloalkyl, —SH, —S(O)$_p$R, and $C_1$-$C_6$haloalkoxy;
n is the integer 0, 1, or 2, and when n is 2, each $R^2$ may be identical or different from each other; and
p is the integer 0, 1, or 2;
and pharmaceutically or veterinarily acceptable salts thereof.

2. The compound of claim 1 having Formula (2a), (2b), or (6a)

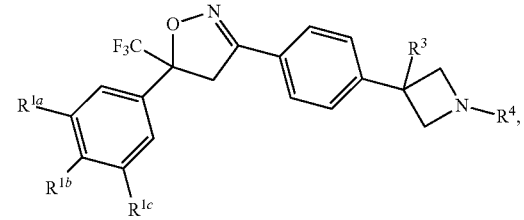

(2a)

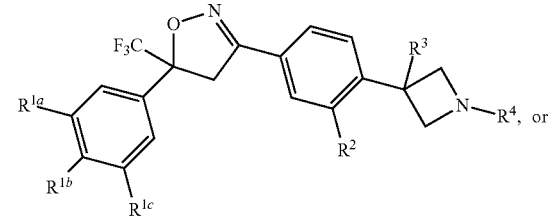

(2b)

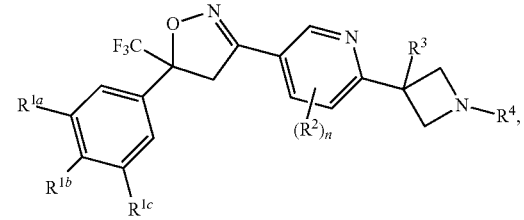

(6a)

wherein
$R^{1a}$, $R^{1b}$, and $R^{1c}$ are each independently selected from hydrogen, halo, hydroxyl, and $C_1$-$C_6$haloalkyl;
$R^2$ is halo, cyano, hydroxyl, —C(O)NR$^a$R$^b$, or —OR; and
$R^3$ is hydrogen, halo, hydroxyl, N$_3$, or cyano;
and pharmaceutically or veterinarily acceptable salts thereof.

3. The compound of claim 2 wherein
$R^{1a}$, $R^{1b}$, and $R^{1c}$ are each independently selected from hydrogen, fluoro, chloro, bromo, and —$CF_3$;
$R^2$ is halo, cyano, hydroxyl, or —C(O)$NR^aR^b$;
$R^3$ is hydrogen, fluoro, chloro, hydroxyl, $N_3$, or cyano; and
$R^4$ is —C(O)$R^5$, —C(O)$NR^aR^5$, —S(O)$_pR^c$, —C(S)$R^5$, —S(O)$_2NR^aR^5$, —C($NR^7$)$R^5$, or —C($NR^7$)$NR^aR^5$, and veterinary salts thereof.

4. The compound of claim 3 wherein
$R^2$ is cyano or —C(O)$NR^aR^b$;
$R^3$ is hydrogen, fluoro, hydroxyl, $N_3$, or cyano;
$R^4$ is —C(O)$R^5$, —C(O)$NR^aR^5$, or —C($NR^7$)$R^5$; and
pharmaceutically or veterinarily acceptable salts thereof.

5. A compound of claim 1 selected from the group consisting of:
- 1-(3-fluoro-3-(4-(5-(3,4,5-trichlorophenyl)-5-(trifluoromethyl)-4,5-dihydroisoxazol-3-yl)phenyl)azetidin-1-yl)ethanone;
- cyclopropyl(3-fluoro-3-(4-(5-(3,4,5-trichlorophenyl)-5-(trifluoromethyl)-4,5-dihydroisoxazol-3-yl)phenyl)azetidin-1-yl)methanone;
- 3-fluoro-N-methyl-3-(4-(5-(3,4,5-trichlorophenyl)-5-(trifluoromethyl)-4,5-dihydroisoxazol-3-yl)phenyl)azetidine-1-carboxamide;
- N-ethyl-3-fluoro-3-(4-(5-(3,4,5-trichlorophenyl)-5-(trifluoromethyl)-4,5-dihydroisoxazol-3-yl)phenyl)azetidine-1-carboxamide;
- N-cyclopropyl-3-fluoro-3-(4-(5-(3,4,5-trichlorophenyl)-5-(trifluoromethyl)-4,5-dihydroisoxazol-3-yl)phenyl)azetidine-1-carboxamide;
- cyclopropyl(3-(4-(5-(3,5-dichlorophenyl)-5-(trifluoromethyl)-4,5-dihydroisoxazol-3-yl)phenyl)-3-fluoroazetidin-1-yl)methanone;
- 1-(3-(4-(5-(3,5-dichlorophenyl)-5-(trifluoromethyl)-4,5-dihydroisoxazol-3-yl)phenyl)-3-fluoroazetidin-1-yl)-2-methylpropan-1-one;
- 3-(4-(5-(3,5-dichlorophenyl)-5-(trifluoromethyl)-4,5-dihydroisoxazol-3-yl)phenyl)-3-fluoro-N-methylazetidine-1-carboxamide;
- 3-(4-(5-(3,5-dichlorophenyl)-5-(trifluoromethyl)-4,5-dihydroisoxazol-3-yl)phenyl)-N-ethyl-3-fluoroazetidine-1-carboxamide;
- N-cyclopropyl-3-(4-(5-(3,5-dichlorophenyl)-5-(trifluoromethyl)-4,5-dihydroisoxazol-3-yl)phenyl)-3-fluoroazetidine-1-carboxamide;
- 1-(3-(4-(5-(3,5-dichloro-4-fluorophenyl)-5-(trifluoromethyl)-4,5-dihydroisoxazol-3-yl)phenyl)-3-fluoroazetidin-1-yl)propan-1-one;
- 1-(3-(4-(5-(3,5-dichloro-4-fluorophenyl)-5-(trifluoromethyl)-4,5-dihydroisoxazol-3-yl)phenyl)-3-fluoroazetidin-1-yl)butan-1-one;
- 2-cyclopropyl-1-(3-(4-(5-(3,5-dichloro-4-fluorophenyl)-5-(trifluoromethyl)-4,5-dihydroisoxazol-3-yl)phenyl)-3-fluoroazetidin-1-yl)ethanone;
- 3-(3-(4-(5-(3,5-dichloro-4-fluorophenyl)-5-(trifluoromethyl)-4,5-dihydroisoxazol-3-yl)phenyl)-3-fluoroazetidin-1-yl)-3-oxopropanenitrile;
- 1-(3-(4-(5-(3,5-dichloro-4-fluorophenyl)-5-(trifluoromethyl)-4,5-dihydroisoxazol-3-yl)phenyl)-3-fluoroazetidin-1-yl)-2-(methylthio)ethanone;
- 1-(3-(4-(5-(3,5-dichloro-4-fluorophenyl)-5-(trifluoromethyl)-4,5-dihydroisoxazol-3-yl)phenyl)-3-fluoroazetidin-1-yl)-2-methoxyethanone;
- cyclobutyl(3-(4-(5-(3,5-dichloro-4-fluorophenyl)-5-(trifluoromethyl)-4,5-dihydroisoxazol-3-yl)phenyl)-3-fluoroazetidin-1-yl)methanone;
- 1-(3-(4-(5-(3,5-dichloro-4-fluorophenyl)-5-(trifluoromethyl)-4,5-dihydroisoxazol-3-yl)phenyl)-3-fluoroazetidin-1-yl)-2-methylpropan-1-one;
- 1-(3-(4-(5-(3,5-dichloro-4-fluorophenyl)-5-(trifluoromethyl)-4,5-dihydroisoxazol-3-yl)phenyl)-3-fluoroazetidin-1-yl)-3,3,3-trifluoropropan-1-one;
- N-cyclopropyl-3-(4-(5-(3,5-dichloro-4-fluorophenyl)-5-(trifluoromethyl)-4,5-dihydroisoxazol-3-yl)phenyl)-3-fluoroazetidine-1-carboxamide;
- 3-(4-(5-(3,5-dichloro-4-fluorophenyl)-5-(trifluoromethyl)-4,5-dihydroisoxazol-3-yl)phenyl)-3-fluoro-N-methylazetidine-1-carboxamide;
- 3-(4-(5-(3,5-dichloro-4-fluorophenyl)-5-(trifluoromethyl)-4,5-dihydroisoxazol-3-yl)phenyl)-N-ethyl-3-fluoroazetidine-1-carboxamide;
- 3-(4-(5-(3,5-dichloro-4-fluorophenyl)-5-(trifluoromethyl)-4,5-dihydroisoxazol-3-yl)phenyl)-3-fluoroazetidine-1-carboxamide;
- cyclopropyl(3-(4-(5-(3,4-dichloro-5-(trifluoromethyl)phenyl)-5-(trifluoromethyl)-4,5-dihydroisoxazol-3-yl)phenyl)-3-hydroxyazetidin-1-yl)methanone;
- cyclobutyl(3-(4-(5-(3,4-dichloro-5-(trifluoromethyl)phenyl)-5-(trifluoromethyl)-4,5-dihydroisoxazol-3-yl)phenyl)-3-hydroxyazetidin-1-yl)methanone;
- 3-(4-(5-(3,4-dichloro-5-(trifluoromethyl)phenyl)-5-(trifluoromethyl)-4,5-dihydroisoxazol-3-yl)phenyl)-3-fluoro-N-methylazetidine-1-carboxamide;
- 3-(4-(5-(3,4-dichloro-5-(trifluoromethyl)phenyl)-5-(trifluoromethyl)-4,5-dihydroisoxazol-3-yl)phenyl)-N-ethyl-3-fluoroazetidine-1-carboxamide;
- N-cyclopropyl-3-(4-(5-(3,4-dichloro-5-(trifluoromethyl)phenyl)-5-(trifluoromethyl)-4,5-dihydroisoxazol-3-yl)phenyl)-3-fluoroazetidine-1-carboxamide;
- 3-(4-(5-(3,4-dichloro-5-(trifluoromethyl)phenyl)-5-(trifluoromethyl)-4,5-dihydroisoxazol-3-yl)phenyl)-N-ethyl-3-hydroxyazetidine-1-carboxamide;
- N-cyclopropyl-3-(4-(5-(3,4-dichloro-5-(trifluoromethyl)phenyl)-5-(trifluoromethyl)-4,5-dihydroisoxazol-3-yl)phenyl)-3-hydroxyazetidine-1-carboxamide;
- 3-(4-(5-(3,5-bis(trifluoromethyl)phenyl)-5-(trifluoromethyl)-4,5-dihydroisoxazol-3-yl)phenyl)-3-fluoro-N-methylazetidine-1-carboxamide;
- 3-(4-(5-(3,5-bis(trifluoromethyl)phenyl)-5-(trifluoromethyl)-4,5-dihydroisoxazol-3-yl)phenyl)-N-ethyl-3-fluoroazetidine-1-carboxamide;
- 3-(4-(5-(3,5-bis(trifluoromethyl)phenyl)-5-(trifluoromethyl)-4,5-dihydroisoxazol-3-yl)phenyl)-N-cyclopropyl-3-fluoroazetidine-1-carboxamide;
- 3-(4-(5-(3,5-bis(trifluoromethyl)phenyl)-5-(trifluoromethyl)-4,5-dihydroisoxazol-3-yl)phenyl)-N-cyclopropyl-3-hydroxyazetidine-1-carboxamide;
- 3-(4-(5-(3-chloro-5-(trifluoromethyl)phenyl)-5-(trifluoromethyl)-4,5-dihydroisoxazol-3-yl)phenyl)-N-ethyl-3-hydroxyazetidine-1-carboxamide;
- 3-(4-(5-(3-chloro-5-(trifluoromethyl)phenyl)-5-(trifluoromethyl)-4,5-dihydroisoxazol-3-yl)phenyl)-N-ethyl-3-fluoroazetidine-1-carboxamide;
- 3-(4-(5-(3-chloro-5-(trifluoromethyl)phenyl)-5-(trifluoromethyl)-4,5-dihydroisoxazol-3-yl)phenyl)-N-cyclopropyl-3-fluoroazetidine-1-carboxamide;
- 3-(4-(5-(3-chloro-5-(trifluoromethyl)phenyl)-5-(trifluoromethyl)-4,5-dihydroisoxazol-3-yl)phenyl)-3-fluoro-N-methylazetidine-1-carboxamide;
- 1-(3-(4-(5-(3,5-Dichlorophenyl)-5-(trifluoromethyl)-4,5-dihydroisoxazol-3-yl)phenyl)-3-fluoroazetidin-1-yl)ethanone;

cyclopropyl(3-(4-(5-(3,5-dichloro-4-fluorophenyl)-5-(trifluoromethyl)-4,5-dihydroisoxazol-3-yl)phenyl)-3-fluoroazetidin-1-yl)methanone;
2-Cyclopropyl-1-(3-(4-(5-(3,5-dichlorophenyl)-5-(trifluoromethyl)-4,5-dihydroisoxazol-3-yl)phenyl)-3-fluoroazetidin-1-yl)ethanone;
3-(3-(4-(5-(3,5-Dichlorophenyl)-5-(trifluoromethyl)-4,5-dihydroisoxazol-3-yl)phenyl)-3-fluoroazetidin-1-yl)-3-oxopropanenitrile;
1-(3-(4-(5-(3,5-Dichlorophenyl)-5-(trifluoromethyl)-4,5-dihydroisoxazol-3-yl)phenyl)-3-fluoroazetidin-1-yl)-3,3,3-trifluoropropan-1-one;
1-(3-(4-(5-(3,5-Dichlorophenyl)-5-(trifluoromethyl)-4,5-dihydroisoxazol-3-yl)phenyl)-3-fluoroazetidin-1-yl)-2-methoxyethanone;
1-(3-(4-(5-(3,5-Dichlorophenyl)-5-(trifluoromethyl)-4,5-dihydroisoxazol-3-yl)phenyl)-3-fluoroazetidin-1-yl)propan-1-one;
1-(3-(4-(5-(3,5-Dichlorophenyl)-5-(trifluoromethyl)-4,5-dihydroisoxazol-3-yl)phenyl)-3-fluoroazetidin-1-yl)butan-1-one;
5-[3,5-bis(trifluoromethyl)phenyl]-3-{4-[1-(cyclobutylcarbonyl)-3-fluoroazetidin-3-yl]phenyl}-5-(trifluoromethyl)-4,5-dihydroisoxazole;
5-[3,5-bis(trifluoromethyl)phenyl]-3-{4-[1-(cyclopropylcarbonyl)-3-fluoroazetidin-3-yl]phenyl}-5-(trifluoromethyl)-4,5-dihydroisoxazole;
5-[3,5-bis(trifluoromethyl)phenyl]-3-[4-(3-fluoro-1-isobutyrylazetidin-3-yl)phenyl]-5-(trifluoromethyl)-4,5-dihydroisoxazole;
3-[4-(1-butyryl-3-fluoroazetidin-3-yl)phenyl]-5-[3-chloro-5-(trifluoromethyl)phenyl]-5-(trifluoromethyl)-4,5-dihydroisoxazole;
5-[3-chloro-5-(trifluoromethyl)phenyl]-3-[4-(3-fluoro-1-propionylazetidin-3-yl)phenyl]-5-(trifluoromethyl)-4,5-dihydroisoxazole;
3-[4-(1-acetyl-3-fluoroazetidin-3-yl)phenyl]-5-[3-chloro-5-(trifluoromethyl)phenyl]-5-(trifluoromethyl)-4,5-dihydroisoxazole;
3-[3-(4-{5-[3-chloro-5-(trifluoromethyl)phenyl]-5-(trifluoromethyl)-4,5-dihydroisoxazol-3-yl}phenyl)-3-fluoroazetidin-1-yl]-3-oxopropanenitrile;
1-[(3-{4-[5-(3,5-dichlorophenyl)-5-(trifluoromethyl)-4,5-dihydroisoxazol-3-yl]phenyl}-3-fluoroazetidin-1-yl)carbonyl]cyclopropanol;
1-[(3-{4-[5-(3,5-dichloro-4-fluorophenyl)-5-(trifluoromethyl)-4,5-dihydroisoxazol-3-yl]phenyl}-3-fluoroazetidin-1-yl)carbonyl]cyclopropanol;
3-{-4-[3-fluoro-1-(methoxyacetyl)azetidin-3-yl]phenyl}-5-(3,4,5-trichlorophenyl)-5-(trifluoromethyl)-4,5-dihydroisoxazole;
3-(4-{5-[3,4-dichloro-5-(trifluoromethyl)phenyl]-5-(trifluoromethyl)-4,5-dihydroisoxazol-3-yl}phenyl)-1-isobutyrylazetidin-3-ol;
1-butyryl-3-(4-{5-[3,4-dichloro-5-(trifluoromethyl)phenyl]-5-(trifluoromethyl)-4,5-dihydroisoxazol-3-yl}phenyl)azetidin-3-ol;
5-[3,5-bis(trifluoromethyl)phenyl]-3-{4-[1-(cyclopropylacetyl)-3-fluoroazetidin-3-yl]phenyl}-5-(trifluoromethyl)-4,5-dihydroisoxazole;
2-[3-(4-{5-[3,5-bis(trifluoromethyl)phenyl]-5-(trifluoromethyl)-4,5-dihydroisoxazol-3-yl}phenyl)-3-fluoroazetidin-1-yl]-2-oxoethanol;
5-[3-chloro-5-(trifluoromethyl)phenyl]-3-(4-{3-fluoro-1-[(methylthio)acetyl]azetidin-3-yl}phenyl)-5-(trifluoromethyl)-4,5-dihydroisoxazole;
5-[3-chloro-5-(trifluoromethyl)phenyl]-3-{4-[1-(cyclobutylcarbonyl)-3-fluoroazetidin-3-yl]phenyl}-5-(trifluoromethyl)-4,5-dihydroisoxazole;
3-[3-(4-{5-[3,4-dichloro-5-(trifluoromethyl)phenyl]-5-(trifluoromethyl)-4,5-dihydroisoxazol-3-yl}phenyl)-3-fluoroazetidin-1-yl]-3-oxopropanamide;
3-[3-(4-{5-[3,4-dichloro-5-(trifluoromethyl)phenyl]-5-(trifluoromethyl)-4,5-dihydroisoxazol-3-yl}phenyl)-3-fluoroazetidin-1-yl]-3-oxopropanamide;
1-[(3-fluoro-3-{4-[5-(3,4,5-trichlorophenyl)-5-(trifluoromethyl)-4,5-dihydroisoxazol-3-yl]phenyl}azetidin-1-yl)carbonyl]cyclopropanol;
5-(3,5-dichlorophenyl)-3-{-4-[3-fluoro-1-(3-methylbutanoyl)azetidin-3-yl]phenyl}-5-(trifluoromethyl)-4,5-dihydroisoxazole;
3-(4-{3-fluoro-1-[(methylthio)acetyl]azetidin-3-yl}phenyl)-5-(3,4,5-trichlorophenyl)-5-(trifluoromethyl)-4,5-dihydroisoxazole;
3-{4-[5-(3,5-dichloro-4-fluorophenyl)-5-(trifluoromethyl)-4,5-dihydroisoxazol-3-yl]phenyl}-1-propionylazetidin-3-ol;
5-[3-chloro-5-(trifluoromethyl)phenyl]-3-{4-[1-(cyclopropylcarbonyl)-3-fluoroazetidin-3-yl]phenyl}-5-(trifluoromethyl)-4,5-dihydroisoxazole;
5-(3,5-dichloro-4-fluorophenyl)-3-{-4-[3-fluoro-1-(1H-pyrazol-3-ylcarbonyl)azetidin-3-yl]phenyl}-5-(trifluoromethyl)-4,5-dihydroisoxazole;
4-{2-[3-(4-{5-[3,5-bis(trifluoromethyl)phenyl]-5-(trifluoromethyl)-4,5-dihydroisoxazol-3-yl}phenyl)-3-fluoroazetidin-1-yl]-2-oxoethyl}pyridine;
5-[3-chloro-5-(trifluoromethyl)phenyl]-3-{4-[1-(cyclopropylacetyl)-3-fluoroazetidin-3-yl]phenyl}-5-(trifluoromethyl)-4,5-dihydroisoxazole;
5-[3,4-dichloro-5-(trifluoromethyl)phenyl]-3-[4-(3-fluoro-1-propionylazetidin-3-yl)phenyl]-5-(trifluoromethyl)-4,5-dihydroisoxazole;
3-{4-[1-(cyclopropylcarbonyl)-3-fluoroazetidin-3-yl]phenyl}-5-[3,4-dichloro-5-(trifluoromethyl)phenyl]-5-(trifluoromethyl)-4,5-dihydroisoxazole;
3-[4-(1-acetyl-3-fluoroazetidin-3-yl)phenyl]-5-[3,4-dichloro-5-(trifluoromethyl)phenyl]-5-(trifluoromethyl)-4,5-dihydroisoxazole;
5-[3,4-dichloro-5-(trifluoromethyl)phenyl]-3-[4-(3-fluoro-1-isobutyrylazetidin-3-yl)phenyl]-5-(trifluoromethyl)-4,5-dihydroisoxazole;
3-[3-(4-{5-[3,4-dichloro-5-(trifluoromethyl)phenyl]-5-(trifluoromethyl)-4,5-dihydroisoxazol-3-yl}phenyl)-3-fluoroazetidin-1-yl]-3-oxopropanenitrile;
4-[(3-fluoro-3-{4-[5-(3,4,5-trichlorophenyl)-5-(trifluoromethyl)-4,5-dihydroisoxazol-3-yl]phenyl}azetidin-1-yl)carbonyl]pyridine;
5-[3,5-bis(trifluoromethyl)phenyl]-3-[4-(3-fluoro-1-propionylazetidin-3-yl)phenyl]-5-(trifluoromethyl)-4,5-dihydroisoxazole;
3-{4-[1-(cyclopentylcarbonyl)-3-fluoroazetidin-3-yl]phenyl}-5-[3,4-dichloro-5-(trifluoromethyl)phenyl]-5-(trifluoromethyl)-4,5-dihydroisoxazole;
5-[3,4-dichloro-5-(trifluoromethyl)phenyl]-3-(4-{3-fluoro-1-[(methylthio)acetyl]azetidin-3-yl}phenyl)-5-(trifluoromethyl)-4,5-dihydroisoxazole;
1-(cyclopropylcarbonyl)-3-{4-[5-(3,5-dichloro-4-fluorophenyl)-5-(trifluoromethyl)-4,5-dihydroisoxazol-3-yl]phenyl}azetidin-3-ol;
(3-(2-bromo-4-(5-(3,4,5-trichlorophenyl)-5-(trifluoromethyl)-4,5-dihydroisoxazol-3-yl)phenyl)-3-fluoroazetidin-1-yl)(cyclopropyl)methanone;

2-(1-(cyclopropanecarbonyl)-3-fluoroazetidin-3-yl)-5-(5-(3,4,5-trichlorophenyl)-5-(trifluoromethyl)-4,5-dihydroisoxazol-3-yl)benzonitrile;

5-(3-chloro-5-(trifluoromethyl)phenyl)-3-(4-(3-fluoro-1-(methylsulfonyl)azetidin-3-yl)phenyl)-5-(trifluoromethyl)-4,5-dihydroisoxazole;

3-(2-bromo-4-(5-(3,4,5-trichlorophenyl)-5-(trifluoromethyl)-4,5-dihydroisoxazol-3-yl)phenyl)-1-(cyclopropanecarbonyl)azetidine-3-carbonitrile;

1-(cyclopropanecarbonyl)-3-(4-(5-(3,4,5-trichlorophenyl)-5-(trifluoromethyl)-4,5-dihydroisoxazol-3-yl)phenyl)azetidine-3-carbonitrile;

1-(3-(4-(5-(3,5-dichlorophenyl)-5-(trifluoromethyl)-4,5-dihydroisoxazol-3-yl)phenyl)azetidin-1-yl)-2-methylpropan-1-one;

2-methyl-1-(3-(4-(5-(3,4,5-trichlorophenyl)-5-(trifluoromethyl)-4,5-dihydroisoxazol-3-yl)phenyl)azetidin-1-yl)propan-1-one;

Cyclopropyl(3-(4-(5-(3,5-dichlorophenyl)-5-(trifluoromethyl)-4,5-dihydroisoxazol-3-yl)phenyl)azetidin-1-yl)methanone;

Cyclopropyl(3-(4-(5-(3,4,5-trichlorophenyl)-5-(trifluoromethyl)-4,5-dihydroisoxazol-3-yl)phenyl)azetidin-1-yl)methanone;

1-(3-(4-(5-(3,5-dichlorophenyl)-5-(trifluoromethyl)-4,5-dihydroisoxazol-3-yl)phenyl)azetidin-1-yl)ethanone;

1-(3-(4-(5-(3,4,5-trichlorophenyl)-5-(trifluoromethyl)-4,5-dihydroisoxazol-3-yl)phenyl)azetidin-1-yl)ethanone;

1-isobutyryl-3-{4-[5-(3,4,5-trichlorophenyl)-5-(trifluoromethyl)-4,5-dihydroisoxazol-3-yl]phenyl}azetidin-3-ol;

3-{4-[3-fluoro-1-(3,3,3-trifluoropropanoyl)azetidin-3-yl]phenyl}-5-(3,4,5-trichlorophenyl)-5-(trifluoromethyl)-4,5-dihydroisoxazole;

3-{4-[1-(cyclopropylacetyl)-3-fluoroazetidin-3-yl]phenyl}-5-(3,4,5-trichlorophenyl)-5-(trifluoromethyl)-4,5-dihydroisoxazole;

3-[4-(1-butyryl-3-fluoroazetidin-3-yl)phenyl]-5-(3,4,5-trichlorophenyl)-5-(trifluoromethyl)-4,5-dihydroisoxazole;

3-[4-(3-fluoro-1-isobutyrylazetidin-3-yl)phenyl]-5-(3,4,5-trichlorophenyl)-5-(trifluoromethyl)-4,5-dihydroisoxazole;

3-[4-(3-fluoro-1-propionylazetidin-3-yl)phenyl]-5-(3,4,5-trichlorophenyl)-5-(trifluoromethyl)-4,5-dihydroisoxazole;

5-[3-chloro-5-(trifluoromethyl)phenyl]-3-[4-(3-fluoro-1-isobutyrylazetidin-3-yl)phenyl]-5-(trifluoromethyl)-4,5-dihydroisoxazole;

2-[3-(4-{5-[3-chloro-5-(trifluoromethyl)phenyl]-5-(trifluoromethyl)-4,5-dihydroisoxazol-3-yl}phenyl)-3-fluoroazetidin-1-yl]-2-oxoethanol;

5-[3-chloro-5-(trifluoromethyl)phenyl]-3-{4-[1-(cyclopentylcarbonyl)-3-fluoroazetidin-3-yl]phenyl}-5-(trifluoromethyl)-4,5-dihydroisoxazole;

3-[4-(1-butyryl-3-fluoroazetidin-3-yl)phenyl]-5-[3,4-dichloro-5-(trifluoromethyl)phenyl]-5-(trifluoromethyl)-4,5-dihydroisoxazole;

5-(3,5-dichlorophenyl)-3-[4-(1-propionylazetidin-3-yl)phenyl]-5-(trifluoromethyl)-4,5-dihydroisoxazole;

1-[(3-{4-[5-(3,5-dichlorophenyl)-5-(trifluoromethyl)-4,5-dihydroisoxazol-3-yl]phenyl}azetidin-1-yl)carbonyl]cyclopropanol;

5-(3,5-dichlorophenyl)-3-{4[1-(methoxyacetyl)azetidin-3-yl]phenyl}-5-(trifluoromethyl)-4,5-dihydroisoxazole;

3-{4-[1-(cyclopropylacetyl)azetidin-3-yl]phenyl}-5-[3,4-dichloro-5-(trifluoromethyl)phenyl]-5-(trifluoromethyl)-4,5-dihydroisoxazole;

3-[4-(1-acetylazetidin-3-yl)phenyl]-5-[3,4-dichloro-5-(trifluoromethyl)phenyl]-5-(trifluoromethyl)-4,5-dihydroisoxazole;

5-[3,4-dichloro-5-(trifluoromethyl)phenyl]-3-[4-(1-propionylazetidin-3-yl)phenyl]-5-(trifluoromethyl)-4,5-dihydroisoxazole;

3-[4-(1-butyrylazetidin-3-yl)phenyl]-5-[3-chloro-5-(trifluoromethyl)phenyl]-5-(trifluoromethyl)-4,5-dihydroisoxazole;

3-[4-(1-butyrylazetidin-3-yl)phenyl]-5-[3,4-dichloro-5-(trifluoromethyl)phenyl]-5-(trifluoromethyl)-4,5-dihydroisoxazole;

2-[3-(4-{5-[3,4-dichloro-5-(trifluoromethyl)phenyl]-5-(trifluoromethyl)-4,5-dihydroisoxazol-3-yl}phenyl)azetidin-1-yl]-2-oxoethanol;

1-{[3-(4-{5-[3,4-dichloro-5-(trifluoromethyl)phenyl]-5-(trifluoromethyl)-4,5-dihydroisoxazol-3-yl}phenyl)azetidin-1-yl]carbonyl}cyclopropanol;

5-[3,4-dichloro-5-(trifluoromethyl)phenyl]-3-(4-{1-[(methylthio)acetyl]azetidin-3-yl}phenyl)-5-(trifluoromethyl)-4,5-dihydroisoxazole;

5-[3-chloro-5-(trifluoromethyl)phenyl]-3-{4-[1-(cyclopropylacetyl)azetidin-3-yl]phenyl}-5-(trifluoromethyl)-4,5-dihydroisoxazole;

5-[3-chloro-5-(trifluoromethyl)phenyl]-3-{4-[1-(methoxyacetyl)azetidin-3-yl]phenyl}-5-(trifluoromethyl)-4,5-dihydroisoxazole;

3-[3-(4-{5-[3,4-dichloro-5-(trifluoromethyl)phenyl]-5-(trifluoromethyl)-4,5-dihydroisoxazol-3-yl}phenyl)azetidin-1-yl]-3-oxopropanenitrile;

1-{[3-(4-{5-[3-chloro-5-(trifluoromethyl)phenyl]-5-(trifluoromethyl)-4,5-dihydroisoxazol-3-yl}phenyl)azetidin-1-yl]carbonyl}cyclopropanol;

5-[3,4-dichloro-5-(trifluoromethyl)phenyl]-3-{4-[1-(methoxyacetyl)azetidin-3-yl]phenyl}-5-(trifluoromethyl)-4,5-dihydroisoxazole;

5-[3-chloro-5-(trifluoromethyl)phenyl]-3-[4-(1-propionylazetidin-3-yl)phenyl]-5-(trifluoromethyl)-4,5-dihydroisoxazole;

3-[4-(1-butyrylazetidin-3-yl)phenyl]-5-(3,4,5-trichlorophenyl)-5-(trifluoromethyl)-4,5-dihydroisoxazole;

5-[3-chloro-5-(trifluoromethyl)phenyl]-3[4-(1-isobutyrylazetidin-3-yl)phenyl]-5-(trifluoromethyl)-4,5-dihydroisoxazole;

1-[(3-{4-[5-(3,4,5-trichlorophenyl)-5-(trifluoromethyl)-4,5-dihydroisoxazol-3-yl]phenyl}azetidin-1-yl)carbonyl]cyclopropanol;

3-[4-(1-propionylazetidin-3-yl)phenyl]-5-(3,4,5-trichlorophenyl)-5-(trifluoromethyl)-4,5-dihydroisoxazole;

3-(4-{1-[(methylthio)acetyl]azetidin-3-yl}phenyl)-5-(3,4,5-trichlorophenyl)-5-(trifluoromethyl)-4,5-dihydroisoxazole;

3-{4-[1-(methoxyacetyl)azetidin-3-yl]phenyl}-5-(3,4,5-trichlorophenyl)-5-(trifluoromethyl)-4,5-dihydroisoxazole;

3-{4-[1-(cyclopropylacetyl)azetidin-3-yl]phenyl}-5-(3,4,5-trichlorophenyl)-5-(trifluoromethyl)-4,5-dihydroisoxazole;

5-(3,5-dichloro-4-fluorophenyl)-3-(4-{1-[(methylthio)acetyl]azetidin-3-yl}phenyl)-5-(trifluoromethyl)-4,5-dihydroisoxazole;

5-(3,5-dichloro-4-fluorophenyl)-3-{4-[1-(methoxyacetyl)azetidin-3-yl]phenyl}-5-(trifluoromethyl)-4,5-dihydroisoxazole;

1-[(3-{4-[5-(3,5-dichloro-4-fluorophenyl)-5-(trifluoromethyl)-4,5-dihydroisoxazol-3-yl]phenyl}azetidin-1-yl)carbonyl]cyclopropanol;

5-(3,5-dichloro-4-fluorophenyl)-3-[4-(1-propionylazetidin-3-yl)phenyl]-5-(trifluoromethyl)-4,5-dihydroisoxazole;

5-(3,5-dichloro-4-fluorophenyl)-3-[4-(1-isobutyrylazetidin-3-yl)phenyl]-5-(trifluoromethyl)-4,5-dihydroisoxazole;

5-(3,5-dichloro-4-fluorophenyl)-3-(4-{1-[(3,3-difluoroazetidin-1-yl)carbonyl]-3-fluoroazetidin-3-yl}phenyl)-5-(trifluoromethyl)-4,5-dihydroisoxazole;

3-{4-[5-(3,5-dichloro-4-fluorophenyl)-5-(trifluoromethyl)-4,5-dihydroisoxazol-3-yl]phenyl}-1-(3,3,3-trifluoropropanoyl)azetidin-3-ol;

5-[3,4-dichloro-5-(trifluoromethyl)phenyl]-3-{-4-[3-fluoro-1-(3,3,3-trifluoropropanoyl)azetidin-3-yl]phenyl}-5-(trifluoromethyl)-4,5-dihydroisoxazole;

5-(3,5-dichloro-4-fluorophenyl)-3-(4-{3-fluoro-1-[(4-methyl-1,3-oxazol-5-yl)carbonyl]azetidin-3-yl}phenyl)-5-(trifluoromethyl)-4,5-dihydroisoxazole;

N-[2-(3-{4-[5-(3,5-dichloro-4-fluorophenyl)-5-(trifluoromethyl)-4,5-dihydroisoxazol-3-yl]phenyl}-3-fluoroazetidin-1-yl)-2-oxoethyl]formamide;

4-[(3-{4-[5-(3,5-dichloro-4-fluorophenyl)-5-(trifluoromethyl)-4,5-dihydroisoxazol-3-yl]phenyl}-3-fluoroazetidin-1-yl)carbonyl]pyridazine;

1-[2-(3-{4-[5-(3,5-dichloro-4-fluorophenyl)-5-(trifluoromethyl)-4,5-dihydroisoxazol-3-yl]phenyl}-3-fluoroazetidin-1-yl)-2-oxoethyl]-1H-1,2,4-triazole;

5-(3,5-dichloro-4-fluorophenyl)-3-(4-{3-fluoro-1-[(methylsulfonyl)acetyl]azetidin-3-yl}phenyl)-5-(trifluoromethyl)-4,5-dihydroisoxazole;

5-(3,5-dichloro-4-fluorophenyl)-3-{-4-[3-fluoro-1-(1H-pyrazol-1-ylacetyl)azetidin-3-yl]phenyl}-5-(trifluoromethyl)-4,5-dihydroisoxazole;

5-(3,5-dichloro-4-fluorophenyl)-3-{-4-[3-fluoro-1-(1,3-oxazol-5-ylcarbonyl)azetidin-3-yl]phenyl}-5-(trifluoromethyl)-4,5-dihydroisoxazole;

5-(3,5-dichloro-4-fluorophenyl)-3-{4-[1-(2,2-difluoropropanoyl)-3-fluoroazetidin-3-yl]phenyl}-5-(trifluoromethyl)-4,5-dihydroisoxazole;

1-{[3-(4-{5-[3,4-dichloro-5-(trifluoromethyl)phenyl]-5-(trifluoromethyl)-4,5-dihydroisoxazol-3-yl}phenyl)-3-fluoroazetidin-1-yl]carbonyl}azetidin-3-ol;

1-(3-{4-[5-(3,5-dichloro-4-fluorophenyl)-5-(trifluoromethyl)-4,5-dihydroisoxazol-3-yl]phenyl}-3-fluoroazetidin-1-yl)-2-methyl-1-oxopropan-2-ol;

3-[4-(1-but-3-enoyl-3-fluoroazetidin-3-yl)phenyl]-5-(3,5-dichloro-4-fluorophenyl)-5-(trifluoromethyl)-4,5-dihydroisoxazole;

2-(3-{4-[5-(3,5-dichloro-4-fluorophenyl)-5-(trifluoromethyl)-4,5-dihydroisoxazol-3-yl]phenyl}-3-fluoroazetidin-1-yl)-N,N-dimethyl-2-oxoethanesulfonamide;

5-(3,5-dichloro-4-fluorophenyl)-3-[4-(3-fluoro-1-{[(trifluoromethyl)thio]acetyl}azetidin-3-yl)phenyl]-5-(trifluoromethyl)-4,5-dihydroisoxazole;

5-(3,5-dichloro-4-fluorophenyl)-3-{-4-[3-fluoro-1-(2-methoxypropanoyl)azetidin-3-yl]phenyl}-5-(trifluoromethyl)-4,5-dihydroisoxazole;

5-(3,5-dichloro-4-fluorophenyl)-3-(4-{1-[(2,2-difluorocyclopropyl)carbonyl]-3-fluoroazetidin-3-yl}phenyl)-5-(trifluoromethyl)-4,5-dihydroisoxazole;

3-(3-{4-[5-(3,5-dichloro-4-fluorophenyl)-5-(trifluoromethyl)-4,5-dihydroisoxazol-3-yl]phenyl}-3-fluoroazetidin-1-yl)-2-methyl-3-oxopropan-1-ol;

(2S)-4-(3-{4-[5-(3,5-dichloro-4-fluorophenyl)-5-(trifluoromethyl)-4,5-dihydroisoxazol-3-yl]phenyl}-3-fluoroazetidin-1-yl)-4-oxobutan-2-ol;

4-(3-{4-[5-(3,5-dichloro-4-fluorophenyl)-5-(trifluoromethyl)-4,5-dihydroisoxazol-3-yl]phenyl}-3-fluoroazetidin-1-yl)-4-oxobutan-2-ol;

3-{-4-[3-chloro-1-(cyclopropylcarbonyl)azetidin-3-yl]phenyl}-5-(3,5-dichloro-4-fluorophenyl)-5-(trifluoromethyl)-4,5-dihydroisoxazole;

3-{-4-[3-chloro-1-(cyclopropylcarbonyl)azetidin-3-yl]phenyl}-5-[3,4-dichloro-5-(trifluoromethyl)phenyl]-5-(trifluoromethyl)-4,5-dihydroisoxazole;

5-(3-chlorophenyl)-3-{4[1-(cyclopropylcarbonyl)-3-fluoroazetidin-3-yl]phenyl}-5-(trifluoromethyl)-4,5-dihydroisoxazole;

3-{4-[5-(3-chloro-4,5-difluorophenyl)-5-(trifluoromethyl)-4,5-dihydroisoxazol-3-yl]phenyl}-1-(cyclopropylcarbonyl)-azetidin-3-ol;

3-{4-[1-(cyclopropylcarbonyl)-3-fluoroazetidin-3-yl]phenyl}-5-[3,4-difluoro-5-(trifluoromethyl)phenyl]-5-(trifluoromethyl)-4,5-dihydroisoxazole;

(2S)-1-(3-{4-[5-(3,5-dichloro-4-fluorophenyl)-5-(trifluoromethyl)-4,5-dihydroisoxazol-3-yl]phenyl}-3-fluoroazetidin-1-yl)-1-oxopropan-2-ol;

(2R)-1-(3-{4-[5-(3,5-dichloro-4-fluorophenyl)-5-(trifluoromethyl)-4,5-dihydroisoxazol-3-yl]phenyl}-3-fluoroazetidin-1-yl)-1-oxopropan-2-ol;

(2S)-4-(3-{4-[5-(3,5-dichloro-4-fluorophenyl)-5-(trifluoromethyl)-4,5-dihydroisoxazol-3-yl]phenyl}-3-fluoroazetidin-1-yl)-4-oxobutan-2-ol;

5-(3,5-dichloro-4-fluorophenyl)-3-(4-{3-fluoro-1-[(methylsulfinyl)acetyl]azetidin-3-yl}phenyl)-5-(trifluoromethyl)-4,5-dihydroisoxazole;

3-{-4-[3-azido-1-(cyclopropylcarbonyl)azetidin-3-yl]phenyl}-5-(3,4,5-trichlorophenyl)-5-(trifluoromethyl)-4,5-dihydroisoxazole;

3-[4-(3-azido-1-propionylazetidin-3-yl)phenyl]-5-(3,4,5-trichlorophenyl)-5-(trifluoromethyl)-4,5-dihydroisoxazole;

S-[2-(3-{4-[5-(3,5-dichloro-4-fluorophenyl)-5-(trifluoromethyl)-4,5-dihydroisoxazol-3-yl]phenyl}-3-fluoroazetidin-1-yl)-2-oxoethyl]ethanethioate;

5-(3-fluorophenyl)-3-[4-(3-fluoro-1-propionylazetidin-3-yl)phenyl]-5-(trifluoromethyl)-4,5-dihydroisoxazole;

5-(3-chlorophenyl)-3-[4-(3-fluoro-1-propionylazetidin-3-yl)phenyl]-5-(trifluoromethyl)-4,5-dihydroisoxazole;

5-(3,4-dichlorophenyl)-3-[4-(3-fluoro-1-propionylazetidin-3-yl)phenyl]-5-(trifluoromethyl)-4,5-dihydroisoxazole;

3-{4-[1-(cyclopropylcarbonyl)-3-fluoroazetidin-3-yl]phenyl}-5-(trifluoromethyl)-5-[3-(trifluoromethyl)phenyl]-4,5-dihydroisoxazole;

5-(3-chloro-5-fluorophenyl)-3-{4-[1-(cyclopropylcarbonyl)-3-fluoroazetidin-3-yl]phenyl}-5-(trifluoromethyl)-4,5-dihydroisoxazole;

3-{4-[1-(cyclopropylcarbonyl)-3-fluoroazetidin-3-yl]phenyl}-5-(3,4-difluorophenyl)-5-(trifluoromethyl)-4,5-dihydroisoxazole;

1-(3-(4-(5-(3,5-dichloro-4-fluorophenyl)-5-(trifluoromethyl)-4,5-dihydroisoxazol-3-yl)phenyl)-3-fluoroazetidin-1-yl)-3,3,3-trifluoropropan-1-one;

3-{4-[1-(azetidin-1-ylcarbonyl)-3-fluoroazetidin-3-yl]phenyl}-5-(3,5-dichlorophenyl)-5-(trifluoromethyl)-4,5-dihydroisoxazole;

3-{4-[1-(azetidin-1-ylcarbonyl)-3-fluoroazetidin-3-yl]phenyl}-5-(3,4,5-trichlorophenyl)-5-(trifluoromethyl)-4,5-dihydroisoxazole;

3-{4-[1-(azetidin-1-ylcarbonyl)-3-fluoroazetidin-3-yl]phenyl}-5-(3,5-dichloro-4-fluorophenyl)-5-(trifluoromethyl)-4,5-dihydroisoxazole;

1-(cyclopropylcarbonyl)-3-{4-[(5R)-5-[3,4-dichloro-5-(trifluoromethyl)phenyl]-5-(trifluoromethyl)-4,5-dihydroisoxazol-3-yl]phenyl}azetidin-3-ol;

5-(3,5-dichloro-4-fluorophenyl)-3-[4-(3-fluoro-1-isobutyrylazetidin-3-yl)phenyl]-5-(trifluoromethyl)-4,5-dihydroisoxazole;

{[2-(3-{4-[5-(3,5-dichloro-4-fluorophenyl)-5-(trifluoromethyl)-4,5-dihydroisoxazol-3-yl]phenyl}-3-fluoroazetidin-1-yl)-2-oxoethyl]sulfonyl}acetonitrile;

1-(3-{4-[5-(3,5-Dichloro-4-fluoro-phenyl)-5-trifluoromethyl-4,5-dihydro-isoxazol-3-yl]-phenyl}-3-fluoroazetidin-1-yl)-3-methanesulfonyl-propan-1-one;

1-(3-{4-[5-(3,5-Dichloro-4-fluoro-phenyl)-5-trifluoromethyl-4,5-dihydro-isoxazol-3-yl]-phenyl}-3-fluoroazetidin-1-yl)-2-(2,2,2-trifluoro-ethanesulfonyl)-ethanone;

2-(3-{4-[5-(3,5-Dichloro-4-fluoro-phenyl)-5-trifluoromethyl-4,5-dihydro-isoxazol-3-yl]-phenyl}-3-fluoroazetidin-1-yl)-2-oxo-ethanesulfonic acid dimethylamide;

2-Benzenesulfonyl-1-(3-{4-[5-(3,5-dichloro-4-fluorophenyl)-5-trifluoromethyl-4,5-dihydro-isoxazol-3-yl]-phenyl}-3-fluoro-azetidin-1-yl)-ethanone;

1-(3-{4-[5-(3,5-Dichloro-4-fluoro-phenyl)-5-trifluoromethyl-4,5-dihydro-isoxazol-3-yl]-phenyl}-3-fluoroazetidin-1-yl)-2-methanesulfonyl-propan-1-one;

cyclopropanecarboxylic acid (1-cyclopropanecarbonyl-3-{4-[5-(3,4-dichloro-5-trifluoromethyl-phenyl)-5-trifluoromethyl-4,5-dihydro-isoxazol-3-yl]-phenyl}-azetidin-3-yl)-amide;

(3-Amino-3-{4-[5-(3,4-dichloro-5-trifluoromethyl-phenyl)-5-trifluoromethyl-4,5-dihydro-isoxazol-3-yl]-phenyl}-azetidin-1-yl)-cyclopropyl-methanone;

3-fluoro-3-{4-[5-(3,4,5-trichlorophenyl)-5-(trifluoromethyl)-4,5-dihydroisoxazol-3-yl]phenyl}azetidine-1-carboxamide;

N-cyclopropyl-3-{4-[5-(3,4,5-trichlorophenyl)-5-(trifluoromethyl)-4,5-dihydroisoxazol-3-yl]phenyl}azetidine-1-carboxamide;

N-cyclopropyl-3-{4-[5-(3,5-dichlorophenyl)-5-(trifluoromethyl)-4,5-dihydroisoxazol-3-yl]phenyl}azetidine-1-carboxamide;

3-(4-{5-[3,4-dichloro-5-(trifluoromethyl)phenyl]-5-(trifluoromethyl)-4,5-dihydroisoxazol-3-yl}phenyl)-3-hydroxy-N-propylazetidine-1-carboxamide;

3-(4-{5-[3,4-dichloro-5-(trifluoromethyl)phenyl]-5-(trifluoromethyl)-4,5-dihydroisoxazol-3-yl}phenyl)-3-hydroxy-N,N-dimethylazetidine-1-carboxamide;

N-ethyl-3-{4-[5-(3,4,5-trichlorophenyl)-5-(trifluoromethyl)-4,5-dihydroisoxazol-3-yl]phenyl}azetidine-1-carboxamide;

3-{4-[5-(3,5-dichloro-4-fluorophenyl)-5-(trifluoromethyl)-4,5-dihydroisoxazol-3-yl]phenyl}-N-methylazetidine-1-carboxamide;

3-(4-{5-[3,4-dichloro-5-(trifluoromethyl)phenyl]-5-(trifluoromethyl)-4,5-dihydroisoxazol-3-yl}phenyl)-N-methylazetidine-1-carboxamide;

3-{4-[5-(3,5-dichlorophenyl)-5-(trifluoromethyl)-4,5-dihydroisoxazol-3-yl]phenyl}-N-ethylazetidine-1-carboxamide;

3-{4-[5-(3,5-dichloro-4-fluorophenyl)-5-(trifluoromethyl)-4,5-dihydroisoxazol-3-yl]phenyl}-N-ethylazetidine-1-carboxamide;

3-(4-{5-[3-chloro-5-(trifluoromethyl)phenyl]-5-(trifluoromethyl)-4,5-dihydroisoxazol-3-yl}phenyl)-N-methylazetidine-1-carboxamide;

3-(4-{5-[3-chloro-5-(trifluoromethyl)phenyl]-5-(trifluoromethyl)-4,5-dihydroisoxazol-3-yl}phenyl)-N-cyclopropylazetidine-1-carboxamide;

N-cyclopropyl-3-{4-[5-(3,5-dichloro-4-fluorophenyl)-5-(trifluoromethyl)-4,5-dihydroisoxazol-3-yl]phenyl}azetidine-1-carboxamide;

N-cyclopropyl-3-(4-{5-[3,4-dichloro-5-(trifluoromethyl)phenyl]-5-(trifluoromethyl)-4,5-dihydroisoxazol-3-yl}phenyl)azetidine-1-carboxamide;

3-(4-{5-[3,4-dichloro-5-(trifluoromethyl)phenyl]-5-(trifluoromethyl)-4,5-dihydroisoxazol-3-yl}phenyl)-3-fluoro-N-(2,2,2-trifluoroethyl)azetidine-1-carboxamide;

3-fluoro-N,N-dimethyl-3-{4-[5-(3,4,5-trichlorophenyl)-5-(trifluoromethyl)-4,5-dihydroisoxazol-3-yl]phenyl}azetidine-1-carboxamide;

3-(4-{5-[3,4-dichloro-5-(trifluoromethyl)phenyl]-5-(trifluoromethyl)-4,5-dihydroisoxazol-3-yl}phenyl)-3-fluoro-N,N-dimethylazetidine-1-carboxamide;

3-(4-{5-[3,4-dichloro-5-(trifluoromethyl)phenyl]-5-(trifluoromethyl)-4,5-dihydroisoxazol-3-yl}phenyl)-3-fluoro-N-(3,3,3-trifluoropropyl)azetidine-1-carboxamide;

3-(4-{5-[3,4-dichloro-5-(trifluoromethyl)phenyl]-5-(trifluoromethyl)-4,5-dihydroisoxazol-3-yl}phenyl)-3-fluoro-N-oxetan-3-ylazetidine-1-carboxamide;

3-azido-N,N-dimethyl-3-{4-[5-(3,4,5-trichlorophenyl)-5-(trifluoromethyl)-4,5-dihydroisoxazol-3-yl]phenyl}azetidine-1-carboxamide;

2-[1-(cyclopropylcarbonyl)-3-fluoroazetidin-3-yl]-5-[5-(3,5-dichloro-4-fluorophenyl)-5-(trifluoromethyl)-4,5-dihydroisoxazol-3-yl]benzonitrile;

2-(1-acetyl-3-fluoroazetidin-3-yl)-5-[5-(3,5-dichloro-4-fluorophenyl)-5-(trifluoromethyl)-4,5-dihydroisoxazol-3-yl]benzonitrile;

5-[5-(3,5-dichloro-4-fluorophenyl)-5-(trifluoromethyl)-4,5-dihydroisoxazol-3-yl]-2-[3-fluoro-1-(3,3,3-trifluoropropanoyl)azetidin-3-yl]benzonitrile;

5-[5-(3,5-dichloro-4-fluorophenyl)-5-(trifluoromethyl)-4,5-dihydroisoxazol-3-yl]-2-(3-fluoro-1-propionylazetidin-3-yl)benzonitrile;

5-[5-(3,5-dichloro-4-fluorophenyl)-5-(trifluoromethyl)-4,5-dihydroisoxazol-3-yl]-2-(3-fluoro-1-isobutyrylazetidin-3-yl)benzonitrile;

5-[5-(3,5-dichloro-4-fluorophenyl)-5-(trifluoromethyl)-4,5-dihydroisoxazol-3-yl]-2-(3-fluoro-1-glycoloylazetidin-3-yl)benzonitrile;

2-(1-butyryl-3-fluoroazetidin-3-yl)-5-[5-(3,5-dichloro-4-fluorophenyl)-5-(trifluoromethyl)-4,5-dihydroisoxazol-3-yl]benzonitrile;

2-[1-(cyclobutylcarbonyl)-3-fluoroazetidin-3-yl]-5-[5-(3,5-dichloro-4-fluorophenyl)-5-(trifluoromethyl)-4,5-dihydroisoxazol-3-yl]benzonitrile;

2-[1-(cyclopentylcarbonyl)-3-fluoroazetidin-3-yl]-5-[5-(3,5-dichloro-4-fluorophenyl)-5-(trifluoromethyl)-4,5-dihydroisoxazol-3-yl]benzonitrile;

5-[5-(3,5-dichloro-4-fluorophenyl)-5-(trifluoromethyl)-4,5-dihydroisoxazol-3-yl]-2-[3-fluoro-1-(methoxyacetyl)azetidin-3-yl]benzonitrile;

2-[1-(cyclopropylacetyl)-3-fluoroazetidin-3-yl]-5-[5-(3,5-dichloro-4-fluorophenyl)-5-(trifluoromethyl)-4,5-dihydroisoxazol-3-yl]benzonitrile;

5-[5-(3,5-dichloro-4-fluorophenyl)-5-(trifluoromethyl)-4,5-dihydroisoxazol-3-yl]-2-(3-fluoro-1-pentanoylazetidin-3-yl)benzonitrile;

5-[5-(3,5-dichloro-4-fluorophenyl)-5-(trifluoromethyl)-4,5-dihydroisoxazol-3-yl]-2-{3-fluoro-1-[(methylthio)acetyl]-azetidin-3-yl}benzonitrile;

2-[1-(cyclopropylcarbonyl)-3-fluoroazetidin-3-yl]-5-[5-(3,4,5-trichlorophenyl)-5-(trifluoromethyl)-4,5-dihydroisoxazol-3-yl]pyridine;

(3-(4-(5-(3,5-dichloro-4-fluorophenyl)-5-(trifluoromethyl)-4,5-dihydroisoxazol-3-yl)phenyl)-3-fluoroazetidin-1-yl)(1-oxidothietan-3-yl)methanone;

(3-(4-(5-(3,5-dichloro-4-fluorophenyl)-5-(trifluoromethyl)-4,5-dihydroisoxazol-3-yl)phenyl)-3-fluoroazetidin-1-yl)(1,1-dioxidothietan-3-yl)methanone;

1-(3-(4-(5-(3,5-dichloro-4-fluorophenyl)-5-(trifluoromethyl)-4,5-dihydroisoxazol-3-yl)phenyl)-3-fluoroazetidin-1-yl)-2-methylpropane-1-thione;

(1-(3-(4-(5-(3,5-dichloro-4-fluorophenyl)-5-(trifluoromethyl)-4,5-dihydroisoxazol-3-yl)phenyl)-3-fluoroazetidin-1-yl)-2-methylpropylidene)cyanamide;

(1-(3-Fluoro-3-{4-[5-(3,4,5-trichloro-phenyl)-5-trifluoromethyl-4,5-dihydro-isoxazol-3-yl]-phenyl}-azetidin-1-yl)-2-methanesulfonyl-ethanone; and 1-(3-{4-[5-(3,4-Dichloro-5-trifluoromethyl-phenyl)-5-trifluoromethyl-4,5-dihydro-isoxazol-3-yl]-phenyl}-3-fluoro-azetidin-1-yl)-2-methanesulfonyl-ethanone, stereoisomers thereof, pharmaceutical and veterinarily acceptable salts thereof.

6. A pharmaceutical or veterinary composition comprising a therapeutic amount of a compound of Formula (1)

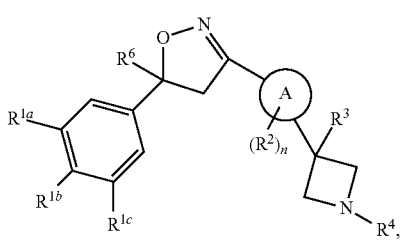

(1)

wherein

A is phenyl, naphthyl, or heteroaryl where said heteroaryl contains 1 to 4 heteroatoms each independently selected from N, O and S;

$R^{1a}$, $R^{1b}$, and $R^{1c}$ are each independently hydrogen, halo, hydroxyl, cyano, nitro, $C_1$-$C_6$alkyl, $C_1$-$C_6$haloalkyl, $C_1$-$C_6$alkoxy, $C_0$-$C_3$alkyl$C_3$-$C_6$cycloalkyl, $C_1$-$C_6$haloalkoxy, —C(O)NH$_2$, —SF$_5$, or —S(O)$_p$R;

$R^2$ is halo, cyano, $C_1$-$C_6$alkyl, $C_1$-$C_6$haloalkyl, nitro, hydroxyl, —C(O)NR$^a$R$^b$, $C_2$-$C_6$alkenyl, $C_2$-$C_6$alkynyl, —S(O)$_p$R, or —OR;

$R^3$ is hydrogen, halo, hydroxyl, cyano, $C_1$-$C_6$alkyl, $C_1$-$C_6$haloalkyl, $C_0$-$C_3$alkyl$C_3$-$C_6$cycloalkyl, —C(O)NH$_2$, nitro, —SC(O)R, —C(O)NR$^a$R$^b$, $C_0$-$C_3$alkylNR$^a$R$^4$, —NR$^a$NR$^b$R$^4$, —NR$^a$OR$^b$, —ONR$^a$R$^b$, N$_3$, —NHR$^4$, —OR, or —S(O)$_p$R;

$R^4$ is hydrogen, $C_1$-$C_6$alkyl, $C_0$-$C_3$alkyl$C_3$-$C_6$cycloalkyl, —C(O)R$^5$, —C(S)R$^5$, —C(O)C(O)NR$^a$R$^5$, —S(O)$_p$R$^c$, —S(O)$_2$NR$^a$R$^5$, —C(NR$^7$)R$^5$, —C(NR$^7$)NR$^a$R$^5$, $C_0$-$C_6$alkylphenyl, $C_0$-$C_6$alkylheteroaryl, or $C_0$-$C_6$alkylheterocycle;

$R^5$ is hydrogen, $C_1$-$C_6$alkyl, $C_2$-$C_6$alkenyl, $C_0$-$C_6$alkyl$C_3$-$C_6$cycloalkyl, $C_0$-$C_6$alkylphenyl, $C_0$-$C_6$alkylheteroaryl, or $C_0$-$C_6$alkylheterocycle;

$R^6$ is cyano, $C_1$-$C_6$alkyl, $C_1$-$C_6$haloalkyl, —C(O)NR$^a$R$^b$, $C_2$-$C_6$alkenyl, $C_2$-$C_6$alkynyl, $C_2$-$C_6$haloalkenyl, or $C_2$-$C_6$haloalkynyl;

$R^7$ is hydrogen, $C_1$-$C_6$alkyl, hydroxyl, cyano, nitro, —S(O)$_p$R$^c$, or $C_1$-$C_6$alkoxy;

R is $C_1$-$C_6$alkyl or $C_3$-$C_6$cycloalkyl each optionally substituted by at least one halo;

$R^a$ is hydrogen, $C_1$-$C_6$alkyl, or $C_0$-$C_3$alkyl$C_3$-$C_6$cycloalkyl; wherein the alkyl and alkylcycloalkyl is optionally substituted by cyano or at least one halo substituent;

$R^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each optionally substituted, where chemically possible, with at least one substituent selected from hydroxyl, cyano, halo, or —S(O)$_p$R;

$R^c$ is $C_1$-$C_6$alkyl, $C_1$-$C_6$haloalkyl, $C_1$-$C_6$haloalkyl$C_3$-$C_6$cycloalkyl, $C_0$-$C_3$alkyl$C_3$-$C_6$cycloalkyl, $C_0$-$C_3$alkylphenyl, $C_0$-$C_3$alkylheteroaryl, or $C_0$-$C_3$alkylheterocycle each optionally substituted with at least one substituent selected from cyano, halo, hydroxyl, oxo, $C_1$-$C_6$alkoxy, $C_1$-$C_6$haloalkoxy, $C_1$-$C_6$haloalkyl, —S(O)$_p$R, —SH, —S(O)$_p$NR$^a$R$^b$, —NR$^a$R$^b$, —NR$^a$C(O)R$^b$, —SC(O)R$^b$, —SCN, or —C(O)NR$^a$R$^b$;

each of $R^4$ and $R^5$ $C_1$-$C_6$alkyl or $C_0$-$C_6$alkyl$C_3$-$C_6$cycloalkyl can be optionally and independently substituted by at least one substituent selected from cyano, halo, hydroxyl, oxo, $C_1$-$C_6$alkoxy, $C_1$-$C_6$haloalkoxy, $C_1$-$C_6$haloalkyl, —S(O)$_p$R$^c$, —SH, —S(O)$_p$NR$^a$R$^b$, —NR$^a$R$^b$, —NR$^a$C(O)R$^b$, —SC(O)R$^c$, —SCN, or —C(O)NR$^a$R$^b$; and wherein $R^4$ and $R^5$ $C_0$-$C_6$alkylphenyl, $C_0$-$C_6$alkylheteroaryl, or $C_0$-$C_6$alkylheterocycle moiety can be further optionally substituted with at least one substituent selected from cyano, halo, oxo, =S, =NR$^7$, hydroxyl, $C_1$-$C_6$alkoxy, $C_1$-$C_6$alkyl, $C_1$-$C_6$haloalkyl, —SH, —S(O)$_p$R, and $C_1$-$C_6$haloalkoxy;

n is the integer 0, 1, or 2, and when n is 2, each $R^2$ may be identical or different from each other; and p is the integer 0, 1, or 2;

and pharmaceutically or veterinarily acceptable salts thereof.

7. The pharmaceutical or veterinary composition of claim 6 further comprising a pharmaceutically or veterinarily acceptable excipient, diluent, or carrier.

8. The pharmaceutical or veterinary composition of claim 7 further comprising at least one additional veterinary agent.

9. The pharmaceutical or veterinary composition of claim 8 wherein said additional veterinary agent is selected from the group consisting of abamectin, ivermectin, avermectin, moxidectin, emamectin, eprinomectin, selamectin, doramectin, nemadectin, albendazole, cambendazole, fenbendazole, flubendazole, mebendazole, oxfenbendazole, oxibendazole, parbendazole, tetramisole, levamisole, pyrantel pamoate, oxantel, morantel, indoxacarb, closantel, triclabendazole, clorsulon, refoxanide, niclosamide, praziquantel, epsiprantel, 2-desoxoparaherquamide, pyripole, pyrafluprole, lufenuron, spiromesifen, tebufenozide, spinosad, spinetoram, imidacloprid, dinotefuran, metaflumizone, thibendiamide, chlorantraniliprole, indoxacarb, pyridalyl, pyrimidifen, pyrifluquinazon, milbemycin oxime, milbemycin, DEET, demiditraz, amitraz, fipronil, insect growth regulator, permethrin, and pyrethrin, or mixtures thereof.

10. The pharmaceutical or veterinary composition of claim 9 wherein said additional veterinary agent is milbemycin oxime.

11. The pharmaceutical or veterinary composition of claim 9 wherein said additional veterinary agent is moxidectin.

12. A method for the treatment of parasites in an animal comprising administering to said animal an effective amount of a compound of Formula (1)

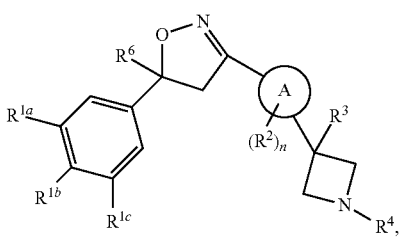

(1)

wherein
A is phenyl, naphthyl, or heteroaryl where said heteroaryl contains 1 to 4 heteroatoms each independently selected from N, O and S;

$R^{1a}$, $R^{1b}$, and $R^{1c}$ are each independently hydrogen, halo, hydroxyl, cyano, nitro, $C_1$-$C_6$alkyl, $C_1$-$C_6$haloalkyl, $C_1$-$C_6$alkoxy, $C_0$-$C_3$alkyl$C_3$-$C_6$cycloalkyl, $C_1$-$C_6$haloalkoxy, —C(O)NH$_2$, —SF$_5$, or —S(O)$_p$R;

$R^2$ is halo, cyano, $C_1$-$C_6$alkyl, $C_1$-$C_6$haloalkyl, nitro, hydroxyl, —C(O)NR$^a$R$^b$, $C_2$-$C_6$alkenyl, $C_2$-$C_6$alkynyl, —S(O)$_p$R, or —OR;

$R^3$ is hydrogen, halo, hydroxyl, cyano, $C_1$-$C_6$alkyl, $C_1$-$C_6$haloalkyl, $C_0$-$C_3$alkyl$C_3$-$C_6$cycloalkyl, —C(O)NH$_2$, nitro, —SC(O)R, —C(O)NR$^a$R$^b$, $C_0$-$C_3$alkylNR$^a$R$^4$, —NR$^a$NR$^b$R$^4$, —NR$^a$OR$^b$, —ONR$^a$R$^b$, N$_3$, —NHR$^4$, —OR, or —S(O)$_p$R;

$R^4$ is hydrogen, $C_1$-$C_6$alkyl, $C_0$-$C_3$alkyl$C_3$-$C_6$cycloalkyl, —C(O)R$^5$, —C(S)R$^5$, —C(O)NR$^a$R$^5$, —C(O)C(O)NR$^a$R$^5$, —S(O)$_p$R$^c$, —S(O)$_2$NR$^a$R$^5$, —C(NR$^7$)R$^5$, —C(NR$^7$)NR$^a$R$^5$, $C_0$-$C_6$alkylphenyl, $C_0$-$C_6$alkylheteroaryl, or $C_0$-$C_6$alkylheterocycle;

$R^5$ is hydrogen, $C_1$-$C_6$alkyl, $C_2$-$C_6$alkenyl, $C_0$-$C_6$alkyl$C_3$-$C_6$cycloalkyl, $C_0$-$C_6$alkylphenyl, $C_0$-$C_6$alkylheteroaryl, or $C_0$-$C_6$alkylheterocycle;

$R^6$ is cyano, $C_1$-$C_6$alkyl, $C_1$-$C_6$haloalkyl, —C(O)NR$^a$R$^b$, $C_2$-$C_6$alkenyl, $C_2$-$C_6$alkynyl, $C_2$-$C_6$haloalkenyl, or $C_2$-$C_6$haloalkynyl;

$R^7$ is hydrogen, $C_1$-$C_6$alkyl, hydroxyl, cyano, nitro, —S(O)$_p$R$^c$, or $C_1$-$C_6$alkoxy;

R is $C_1$-$C_6$alkyl or $C_3$-$C_6$cycloalkyl each optionally substituted by at least one halo;

$R^a$ is hydrogen, $C_1$-$C_6$alkyl, or $C_0$-$C_3$alkyl$C_3$-$C_6$cycloalkyl; wherein the alkyl and alkylcycloalkyl is optionally substituted by cyano or at least one halo substituent;

$R^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each optionally substituted, where chemically possible, with at least one substituent selected from hydroxyl, cyano, halo, or —S(O)$_p$R;

$R^c$ is $C_1$-$C_6$alkyl, $C_1$-$C_6$haloalkyl, $C_1$-$C_6$haloalkyl$C_3$-$C_6$cycloalkyl, $C_0$-$C_3$alkyl$C_3$-$C_6$cycloalkyl, $C_0$-$C_3$alkylphenyl, $C_0$-$C_3$alkylheteroaryl, or $C_0$-$C_3$alkylheterocycle each optionally substituted with at least one substituent selected from cyano, halo, hydroxyl, oxo, $C_1$-$C_6$alkoxy, $C_1$-$C_6$haloalkoxy, $C_1$-$C_6$haloalkyl, —S(O)$_p$R, —SH, —S(O)$_p$NR$^a$R$^b$, —NR$^a$R$^b$, —NR$^a$C(O)R$^b$, —SC(O)R$^b$, —SCN, or —C(O)NR$^a$R$^b$;

each of $R^4$ and $R^5$ $C_1$-$C_6$alkyl or $C_0$-$C_6$alkyl$C_3$-$C_6$cycloalkyl can be optionally and independently substituted by at least one substituent selected from cyano, halo, hydroxyl, oxo, $C_1$-$C_6$alkoxy, $C_1$-$C_6$haloalkoxy, $C_1$-$C_6$haloalkyl, —S(O)$_p$R$^c$, —SH, —S(O)$_p$NR$^a$R$^b$, —NR$^a$R$^b$, —NR$^a$C(O)R$^b$, —SC(O)R$^c$, —SCN, or —C(O)NR$^a$R$^b$; and wherein $R^4$ and $R^5$ $C_0$-$C_6$alkylphenyl, $C_0$-$C_6$alkylheteroaryl, or $C_0$-$C_6$alkylheterocycle moiety can be further optionally substituted with at least one substituent selected from cyano, halo, oxo, =S, =NR$^7$, hydroxyl, $C_1$-$C_6$alkoxy, $C_1$-$C_6$alkyl, $C_1$-$C_6$haloalkyl, —SH, —S(O)$_p$R, and $C_1$-$C_6$haloalkoxy;

n is the integer 0, 1, or 2, and when n is 2, each $R^2$ may be identical or different from each other; and p is the integer 0, 1, or 2;

and pharmaceutically or veterinarily acceptable salts thereof.

13. The method of claim 12 wherein the animal is a companion animal or livestock.

14. The method of claim 13 wherein the companion animal is dog.

15. The method of claim 13 wherein livestock is cattle.

16. The method of claim 12 wherein the animal is a bird.

17. The method of claim 16 wherein the bird is a chicken or turkey.

18. The method of claim 12 wherein the animal is a fish.

19. The method of claim 12 wherein the compound is administered topically, orally, or by injection.

* * * * *